United States Patent
Sahin et al.

(10) Patent No.: US 10,428,149 B2
(45) Date of Patent: Oct. 1, 2019

(54) SINGLE-CHAIN TUMOR NECROSIS FACTOR (TNF) LIGAND FAMILY MOLECULES, FUSION PROTEINS AND DERIVATIVES THEREOF

(71) Applicants: UNIVERSITÄT STUTTGART, Stuttgart (DE); BIONTECH AG, Mainz (DE)

(72) Inventors: Ugur Sahin, Mainz (DE); Roland Kontermann, Nürtingen (DE); Klaus Pfizenmaier, Tiefenbronn (DE); Martin Siegemund, Stuttgart (DE); Meike Hutt, Stuttgart (DE); Oliver Seifert, Stuttgart (DE)

(73) Assignee: UNIVERSITAT STUTTGART, Stuttgart (DE)

( * ) Notice: Subject to any disclaimer, the term of this patent is extended or adjusted under 35 U.S.C. 154(b) by 0 days.

(21) Appl. No.: 15/558,372

(22) PCT Filed: Mar. 18, 2016

(86) PCT No.: PCT/EP2016/055974
§ 371 (c)(1),
(2) Date: Sep. 14, 2017

(87) PCT Pub. No.: WO2016/146818
PCT Pub. Date: Sep. 22, 2016

(65) Prior Publication Data
US 2018/0094059 A1 Apr. 5, 2018

(30) Foreign Application Priority Data
Mar. 18, 2015 (EP) .................................... 15159703

(51) Int. Cl.
C07K 16/32 (2006.01)
C07K 16/28 (2006.01)
C07K 14/705 (2006.01)

(52) U.S. Cl.
CPC .... C07K 16/2863 (2013.01); C07K 14/70575 (2013.01); C07K 16/32 (2013.01); C07K 2317/622 (2013.01); C07K 2317/626 (2013.01); C07K 2319/00 (2013.01); C07K 2319/01 (2013.01); C07K 2319/91 (2013.01)

(58) Field of Classification Search
CPC ............... C07K 16/2863; C07K 16/32; C07K 14/70575; C07K 2319/00; C07K 2319/01; C07K 2319/91; C07K 2317/622; C07K 2317/626
See application file for complete search history.

(56) References Cited

FOREIGN PATENT DOCUMENTS

WO    WO 2010/010051 A1    1/2010

OTHER PUBLICATIONS

Siegennund M, et al. (Apr. 1, 2012). Cell Death and Disease. 3(4):e295. DOI:10.1038/cddis.2012.29.*
Siegemund M, et al. (2012). Cell Death and Disease. 3:e295. (doi: 10.1038/cddis.2012.29).*
Holliger et al., "Diabodies: Small Bivalent and Bispecific Antibody Fragments" PNAS, 90:6444-48 (Jul. 1993).
Seifert et al., "Tetravalent Antibody-scTRAIL Fusion Proteins with Improved Properties" Molecular Cancer Therapeutics, 13(1)101-11 (Jan. 2014).
Siegemund et al., "Superior antitumoral activity of dimerized targeted single-chain TRAIL fusion proteins under retention of tumor selectivity" Cell Death and Disease 3(4):e295 (Apr. 2012).

* cited by examiner

*Primary Examiner* — Robert S Landsman
(74) *Attorney, Agent, or Firm* — McDonnell Boehnen Hulbert & Berghoff LLP

(57) ABSTRACT

The present invention relates to a polypeptide comprising a component A with at least three tumor necrosis factor (TNF) homology domains of TNF-ligand family members (THD) in which C-terminal and N-terminal reference points are defined by consensus sequences and which are connected through short stretches of additional C-terminal and/or N-terminal amino acids of the THD or variants thereof, and a component B comprising a dimerization domain. Further, the present invention relates to a polypeptide comprising at least three THDs in which C-terminal and N-terminal reference points are defined by consensus sequences and which are connected through short stretches of additional C-terminal and/or N-terminal amino acids of the THD or variants thereof. Further, the invention relates to a nucleic acid comprising said polypeptides, a vector comprising said nucleic acid and a pharmaceutical composition comprising said polypeptides, or said nucleic acids or said vector. Further, the present invention relates to said polypeptides, said nucleic acid or said vector for the use as a medicament or for the use in the diagnosis, prophylaxis or treatment of hyperproliferative disorders and inflammatory disorders.

Figure 2:
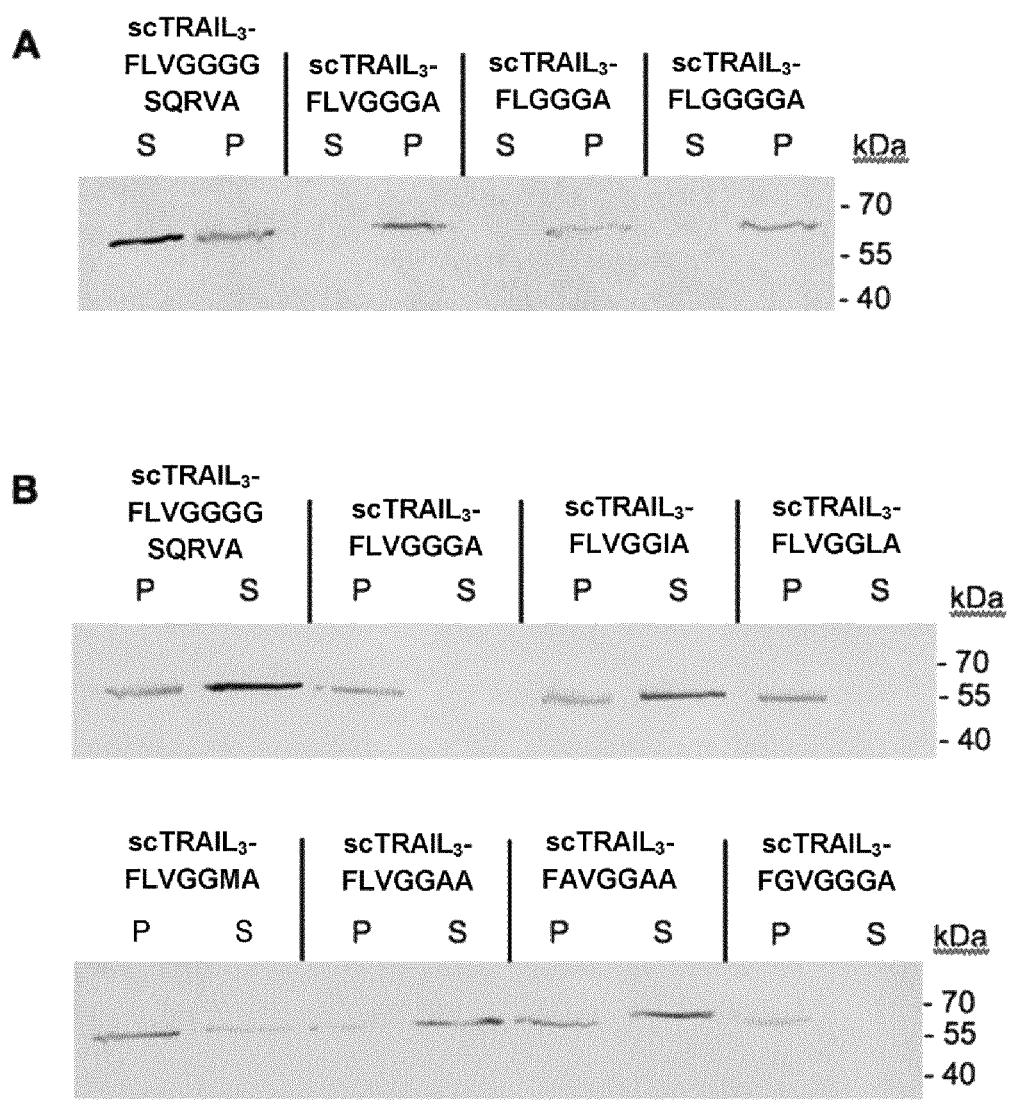

23 Claims, 54 Drawing Sheets
Specification includes a Sequence Listing.

Fig. 1
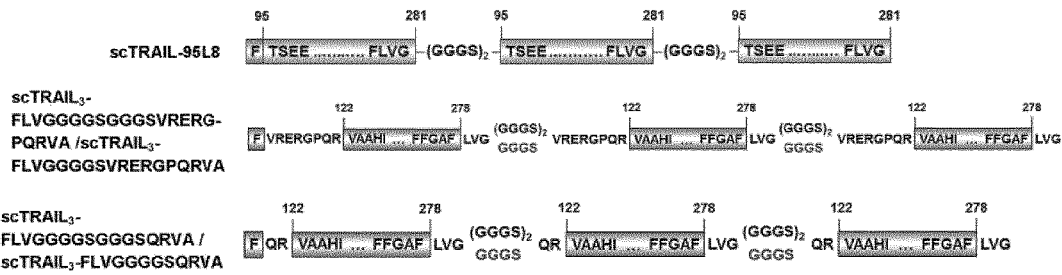
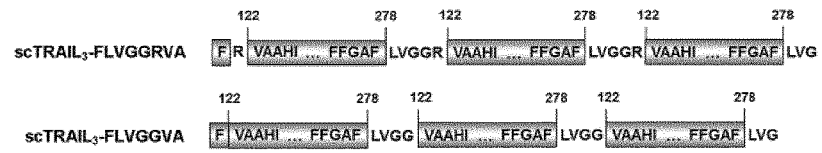
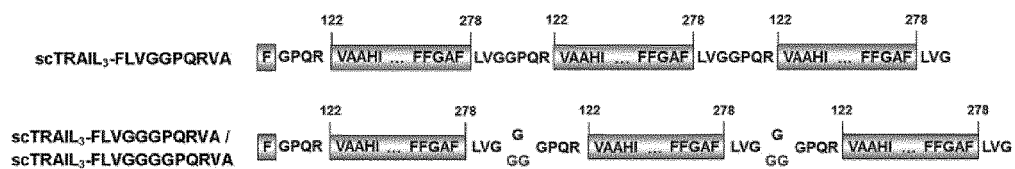
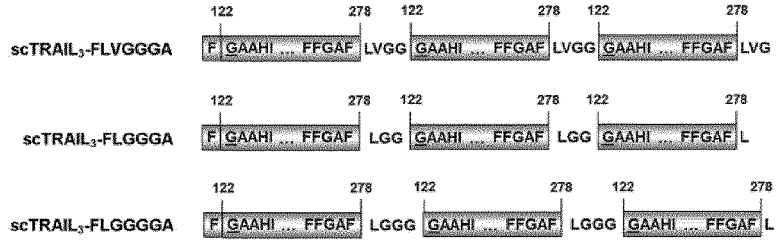

Fig. 1
E
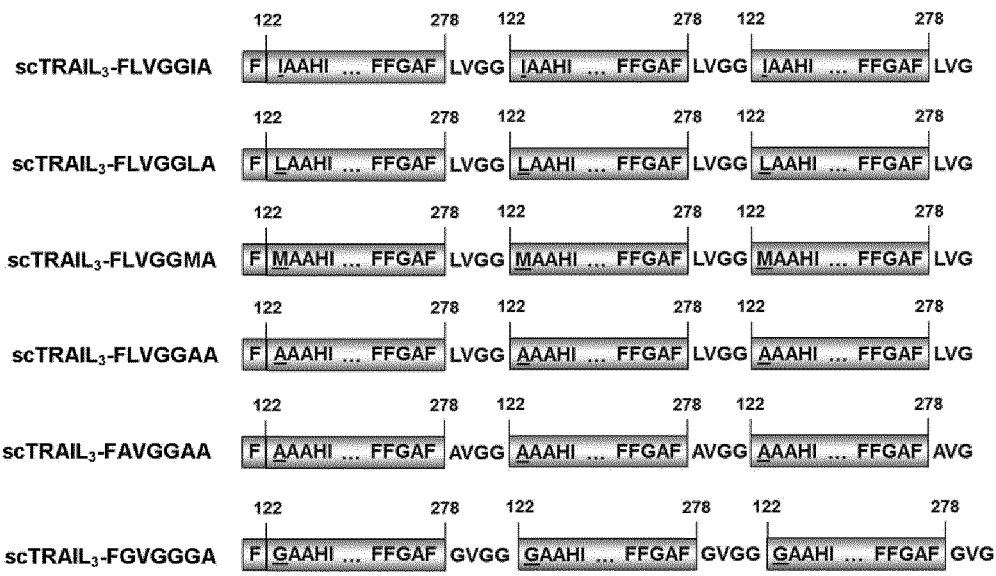
F
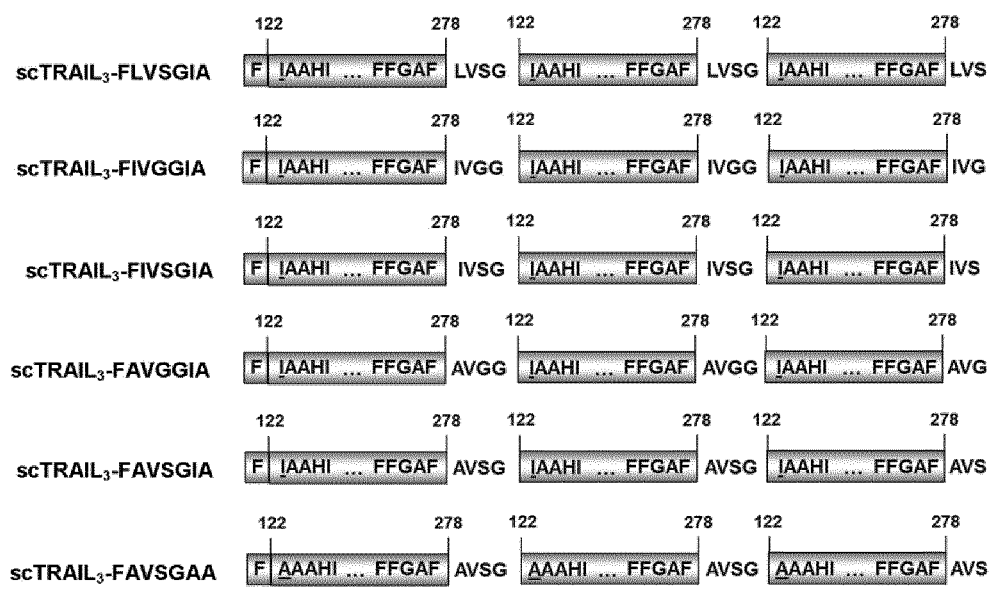

cont.

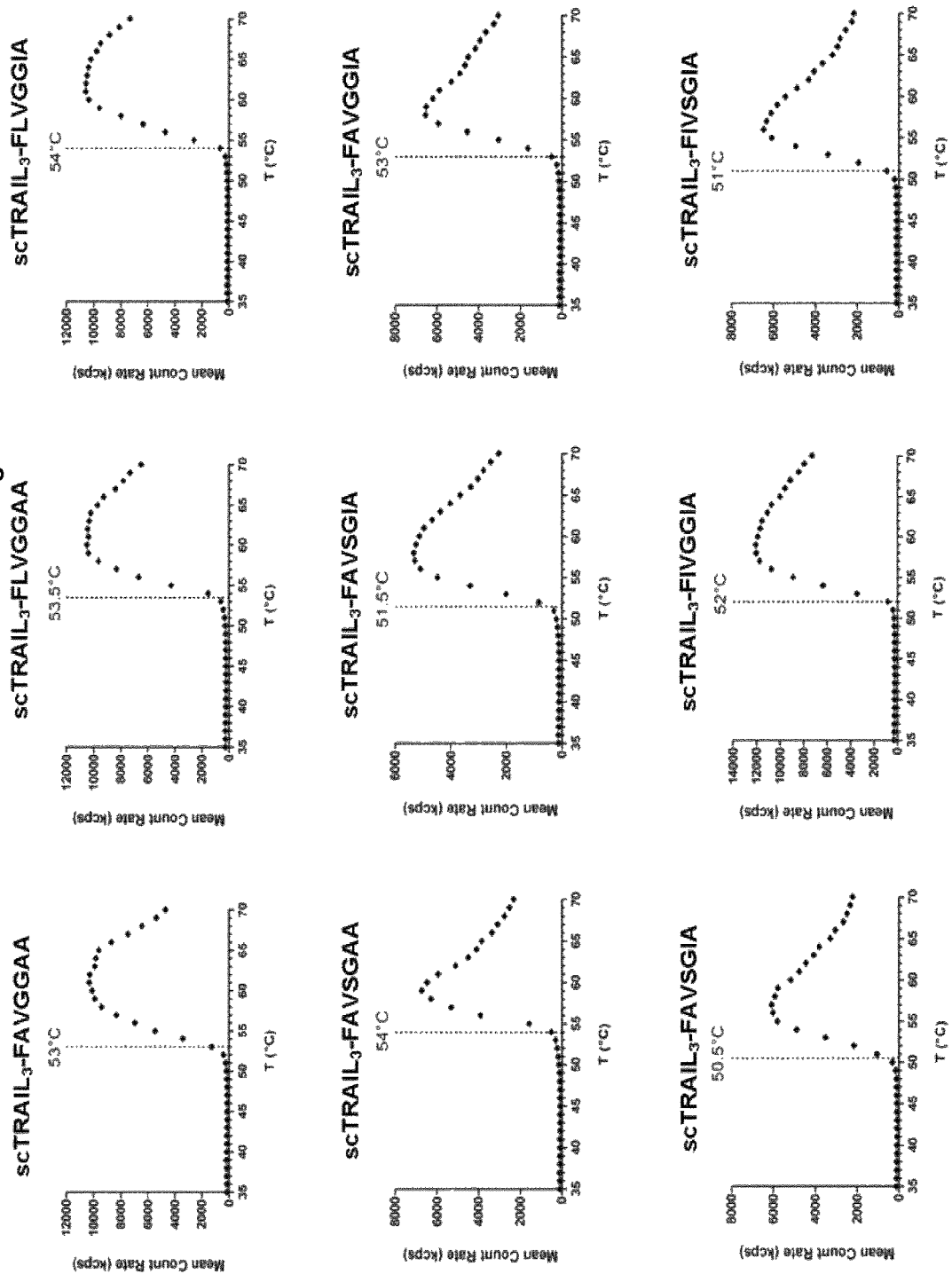

cont.

cont.

cont.

Fig. 5
A
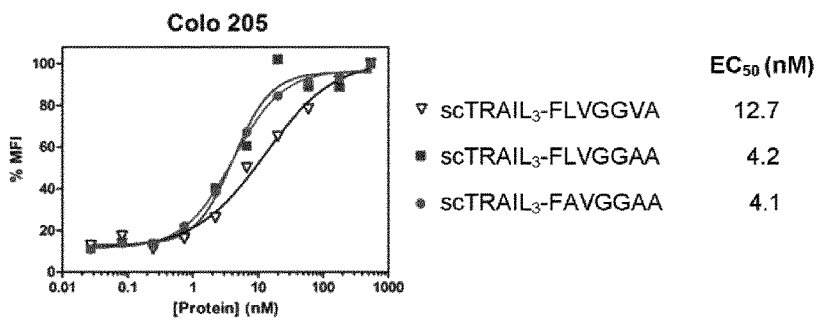
B
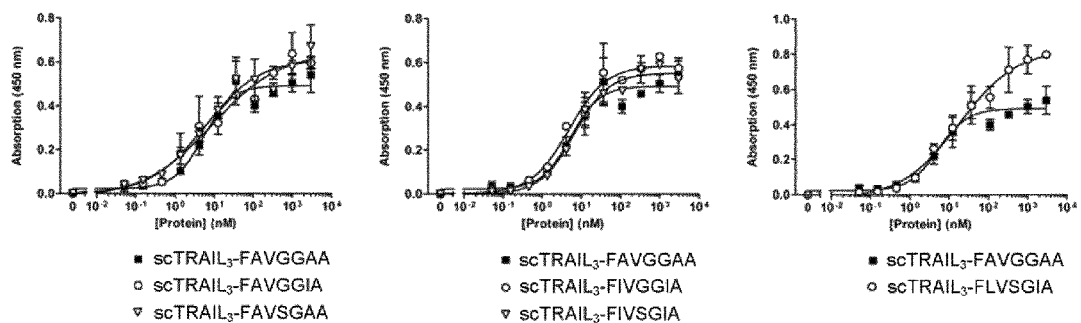
| scTRAIL | EC$_{50}$ (nM) |
|---|---|
| scTRAIL$_3$-FAVGGAA | 5.25 |
| scTRAIL$_3$-FAVGGIA | 8.82 |
| scTRAIL$_3$-FAVSGAA | 5.69 |
| scTRAIL$_3$-FIVGGIA | 4.82 |
| scTRAIL$_3$-FIVSGIA | 6.70 |
| scTRAIL$_3$-FLVSGIA | 17.54 | cont.

cont.

Fig. 8
A
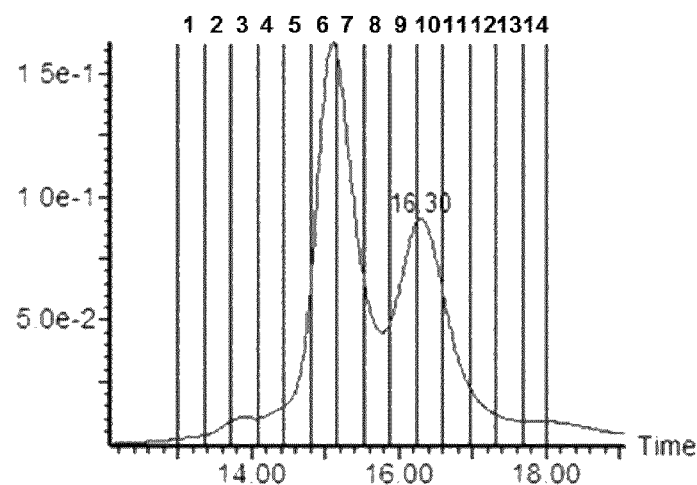
B
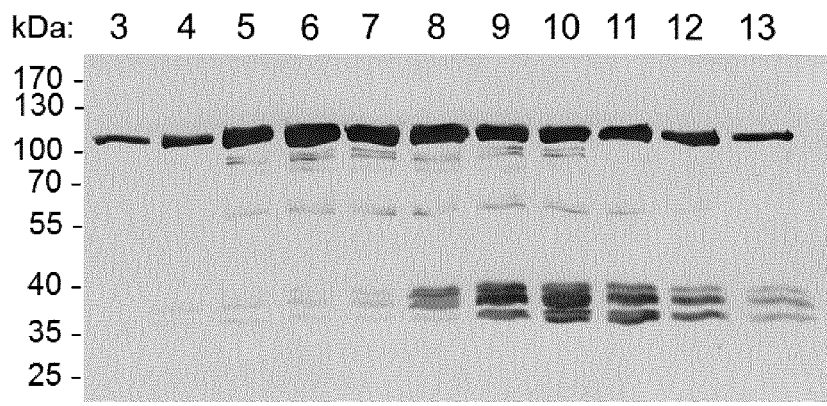
(anti-FLAG M2)

Fig. 9
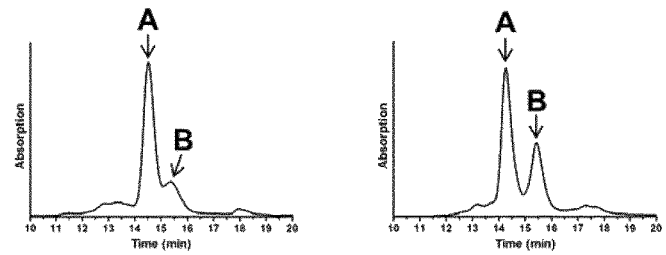
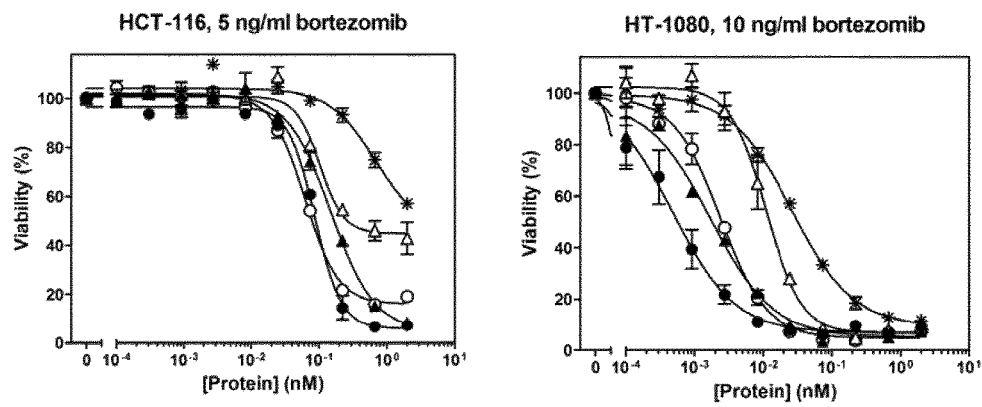
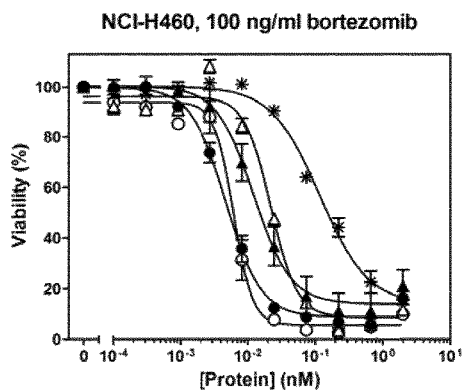
- ● Db-Glyco-scTRAIL₃-FAVSGAA, form A
- ▲ Db-Glyco-scTRAIL₃-FAVSGAA, form B
- ○ Db-scTRAIL-95L8, form A
- △ Db-scTRAIL-95L8, form B
- ∗ scFv-Glyco-scTRAIL₃-FAVSGAA Fig. 10
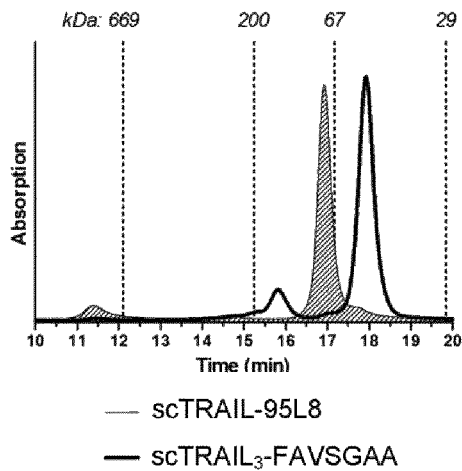
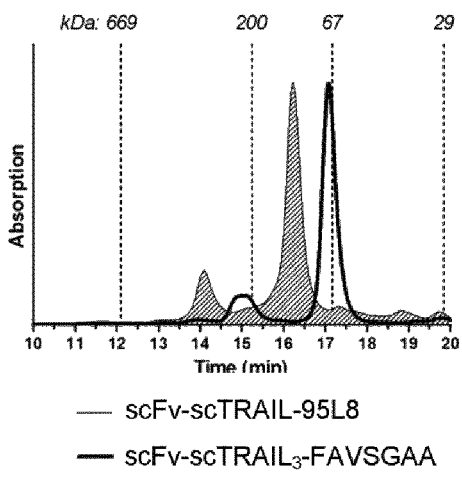
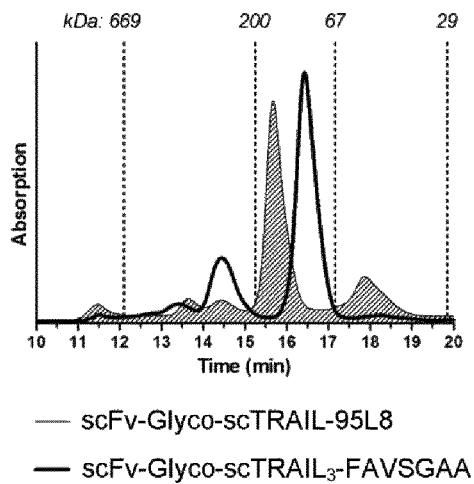
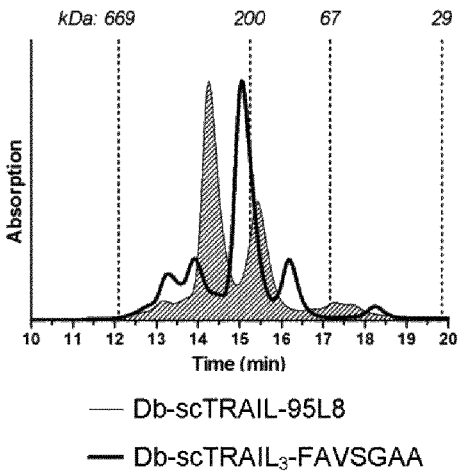
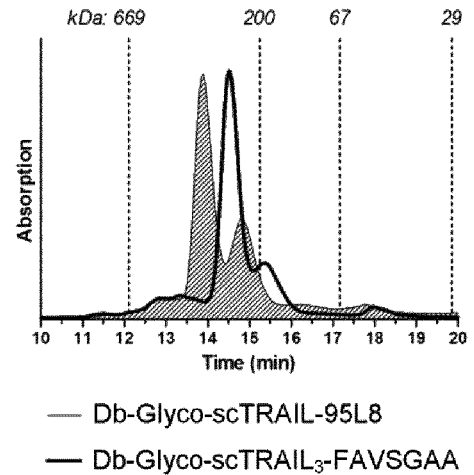

Fig. 12
A
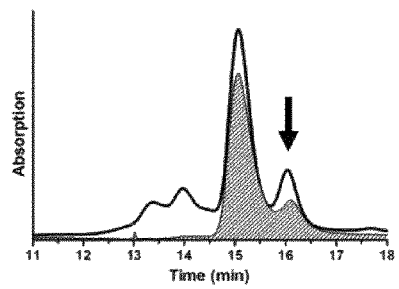
— Db-scTRAIL$_3$-FAVSGAA
--- Db-scTRAIL$_3$-FLVGGGPQRVA
B
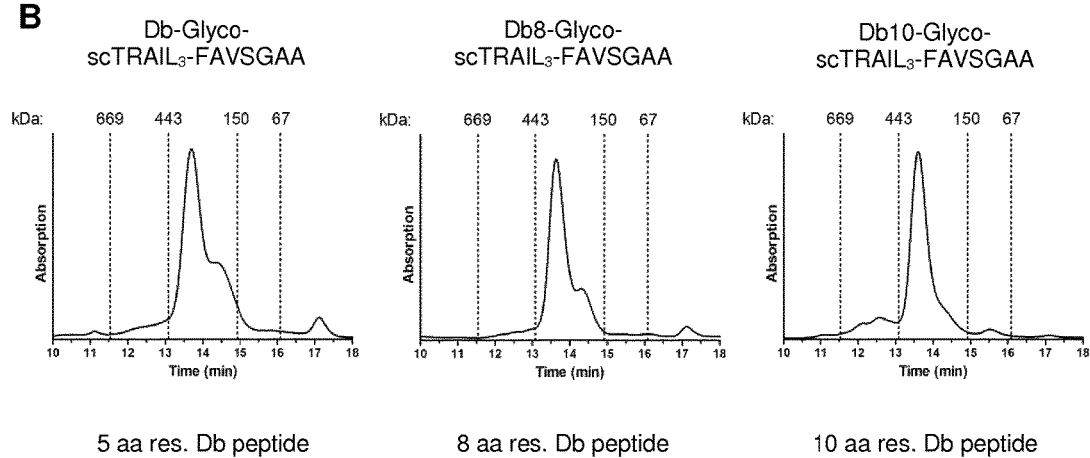
Db-Glyco-scTRAIL$_3$-FAVSGAA   Db8-Glyco-scTRAIL$_3$-FAVSGAA   Db10-Glyco-scTRAIL$_3$-FAVSGAA
5 aa res. Db peptide    8 aa res. Db peptide    10 aa res. Db peptide
C
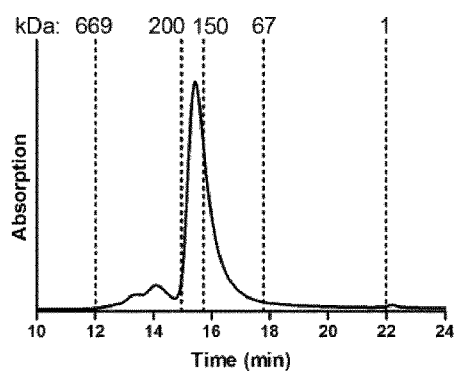

Fig. 14

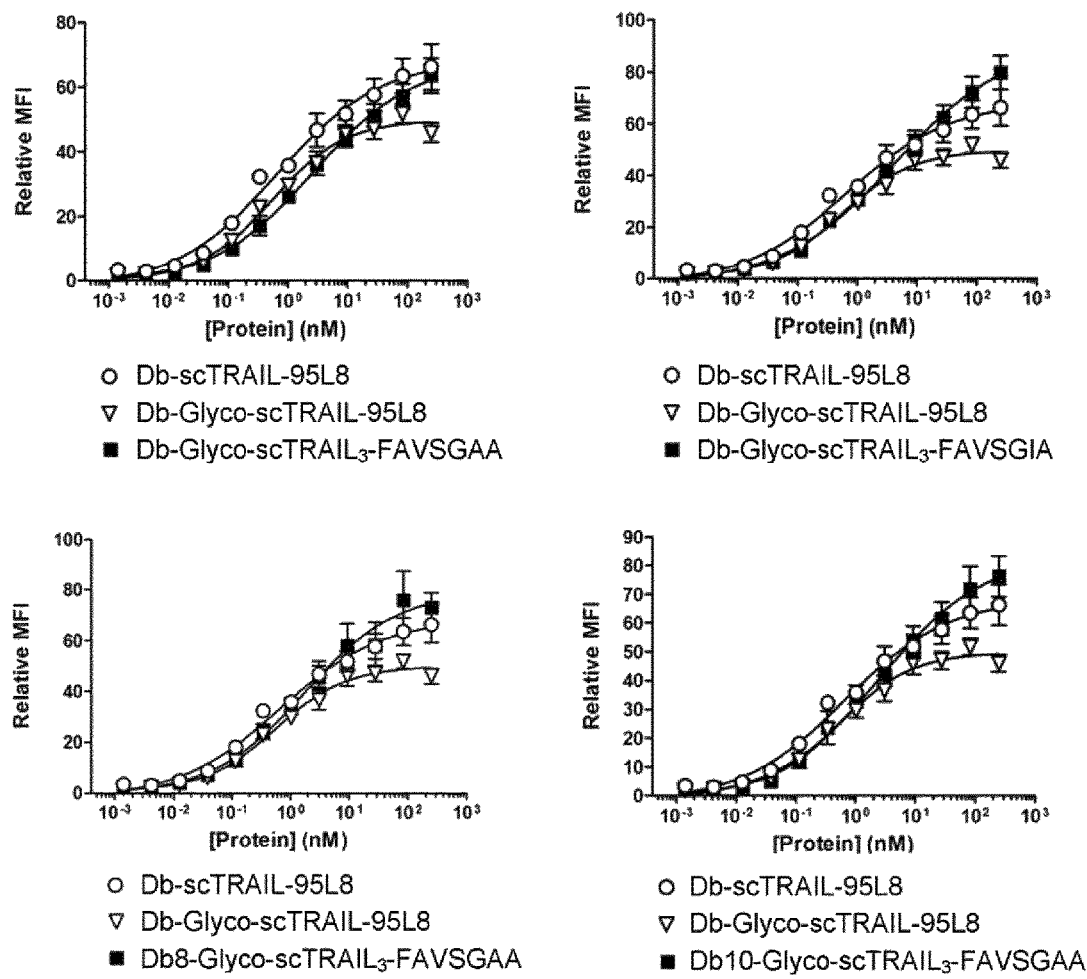

○ Db-scTRAIL-95L8
▽ Db-Glyco-scTRAIL-95L8
■ Db-Glyco-scTRAIL$_3$-FAVSGAA

○ Db-scTRAIL-95L8
▽ Db-Glyco-scTRAIL-95L8
■ Db-Glyco-scTRAIL$_3$-FAVSGIA

○ Db-scTRAIL-95L8
▽ Db-Glyco-scTRAIL-95L8
■ Db8-Glyco-scTRAIL$_3$-FAVSGAA

○ Db-scTRAIL-95L8
▽ Db-Glyco-scTRAIL-95L8
■ Db10-Glyco-scTRAIL$_3$-FAVSGAA

| HT1080 | EC$_{50}$ (nM) |
|---|---|
| Db-scTRAIL-95L8 | 0.7 ± 0.3 |
| Db-Glyco-scTRAIL-95L8 | 0.6 ± 0.1 |
| Db-Glyco-scTRAIL$_3$-FAVSGAA | 2.6 ± 0.9 |
| Db-Glyco-scTRAIL$_3$-FAVSGIA | 4.3 ± 1.4 |
| Db8-Glyco-scTRAIL$_3$-FAVSGAA | 1.9 ± 0.9 |
| Db10-Glyco-scTRAIL$_3$-FAVSGAA | 3.0 ± 1.3 |

Fig. 15

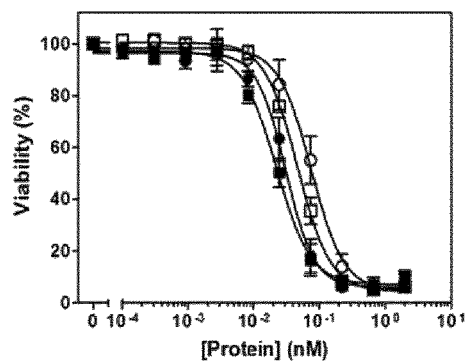

- ● Db-Glyco-scTRAIL$_3$-FAVSGAA
- ○ Db-Glyco-scTRAIL$_3$-FAVSGAA + Cet.
- ■ Db-scTRAIL-95L8
- □ Db-scTRAIL-95L8 + Cetuximab

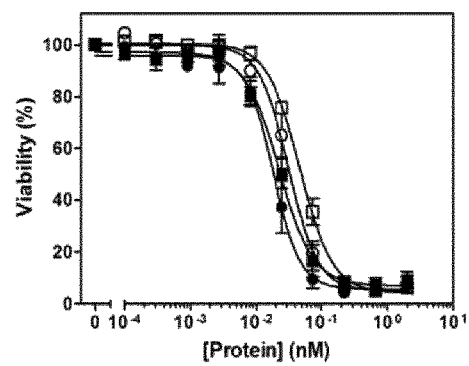

- ● Db-Glyco-scTRAIL$_3$-FAVSGIA
- ○ Db-Glyco-scTRAIL$_3$-FAVSGIA + Cet.
- ■ Db-scTRAIL-95L8
- □ Db-scTRAIL-95L8 + Cetuximab

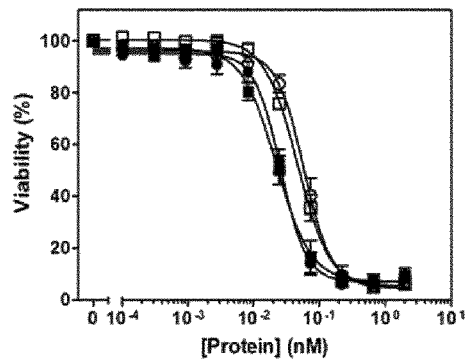

- ● Db8-Glyco-scTRAIL$_3$-FAVSGAA
- ○ Db8-Glyco-scTRAIL$_3$-FAVSGAA + Cet.
- ■ Db-scTRAIL-95L8
- □ Db-scTRAIL-95L8 + Cetuximab

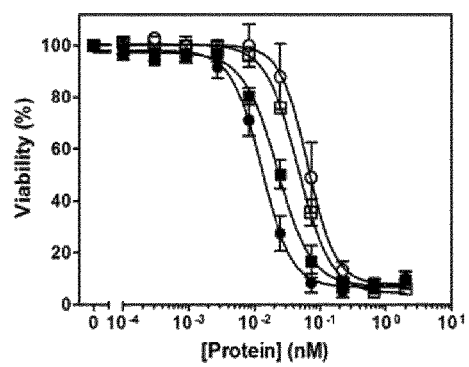

- ● Db10-Glyco-scTRAIL$_3$-FAVSGAA
- ○ Db10-Glyco-scTRAIL$_3$-FAVSGAA + Cet.
- ■ Db-scTRAIL-95L8
- □ Db-scTRAIL-95L8 + Cetuximab

Fig. 17

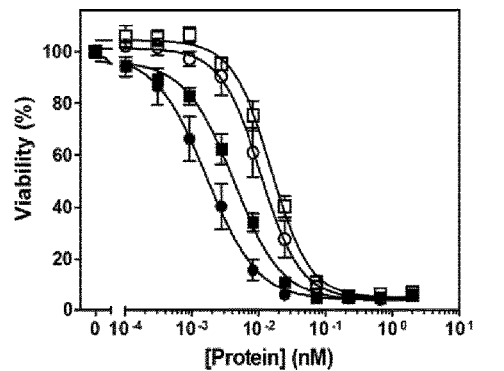

- ● Db-Glyco-scTRAIL₃-FAVSGAA
- ○ Db-Glyco-scTRAIL₃-FAVSGAA + Cet.
- ■ Db-scTRAIL-95L8
- □ Db-scTRAIL-95L8 + Cetuximab

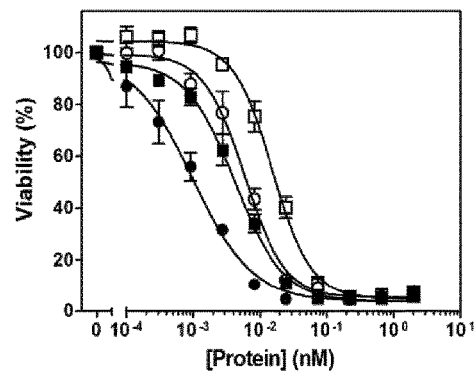

- ● Db-Glyco-scTRAIL₃-FAVSGIA
- ○ Db-Glyco-scTRAIL₃-FAVSGIA + Cet.
- ■ Db-scTRAIL-95L8
- □ Db-scTRAIL-95L8 + Cetuximab

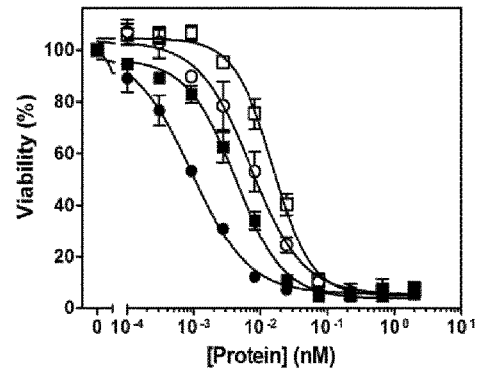

- ● Db8-Glyco-scTRAIL₃-FAVSGAA
- ○ Db8-Glyco-scTRAIL₃-FAVSGAA + Cet.
- ■ Db-scTRAIL-95L8
- □ Db-scTRAIL-95L8 + Cetuximab

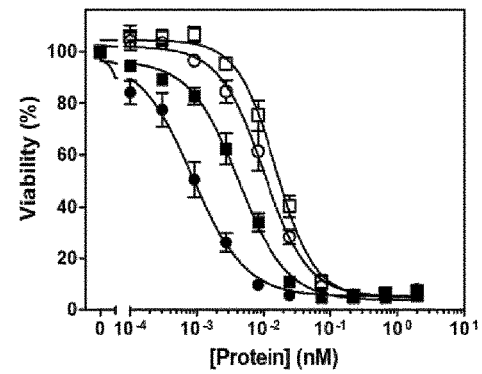

- ● Db10-Glyco-scTRAIL₃-FAVSGAA
- ○ Db10-Glyco-scTRAIL₃-FAVSGAA + Cet.
- ■ Db-scTRAIL-95L8
- □ Db-scTRAIL-95L8 + Cetuximab (reducing)

Fig. 31
A
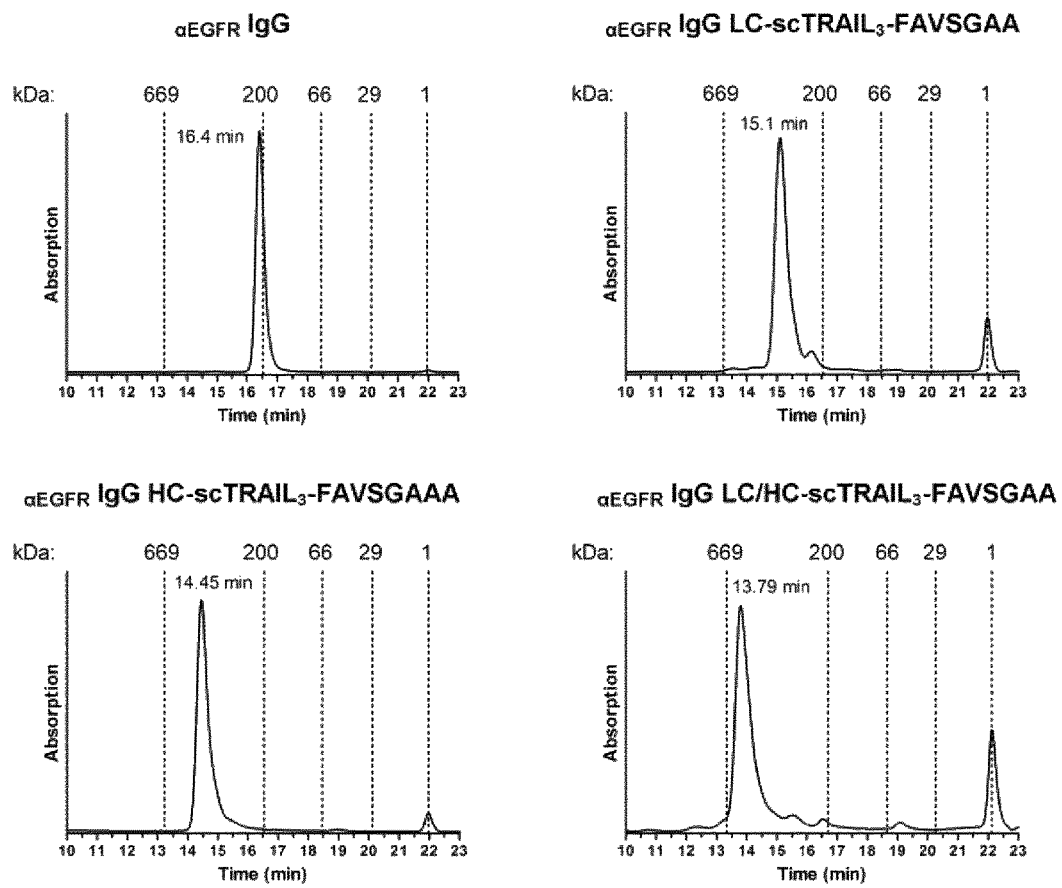
B
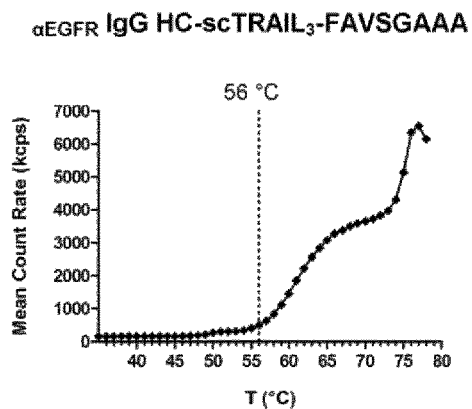

Fig. 32
A
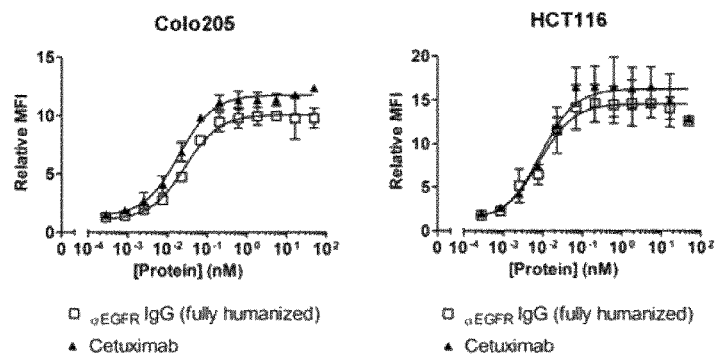
B
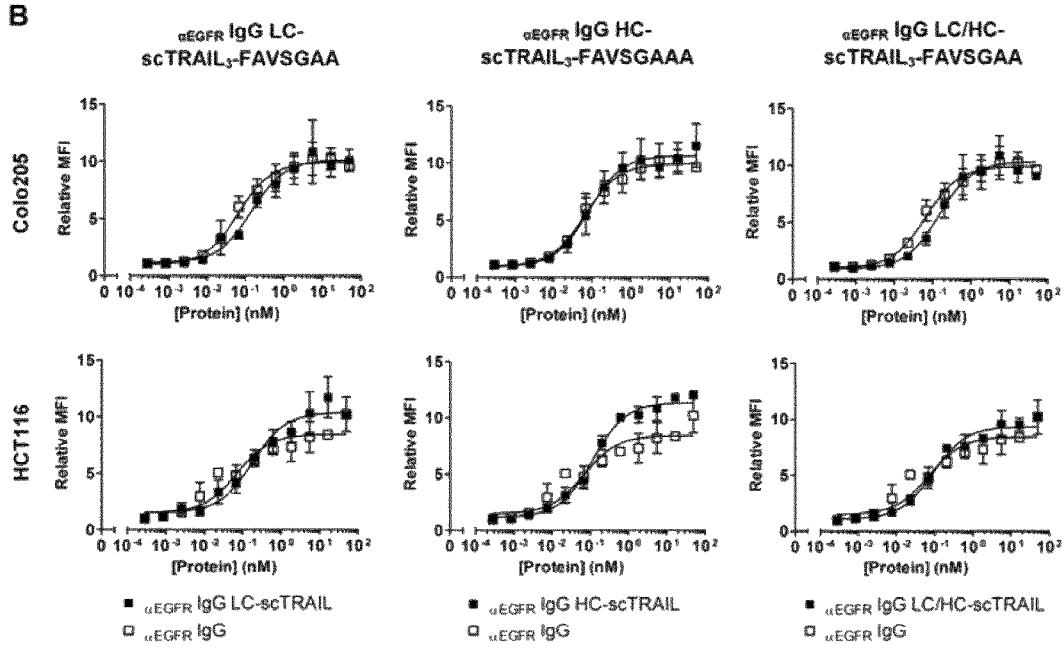
C
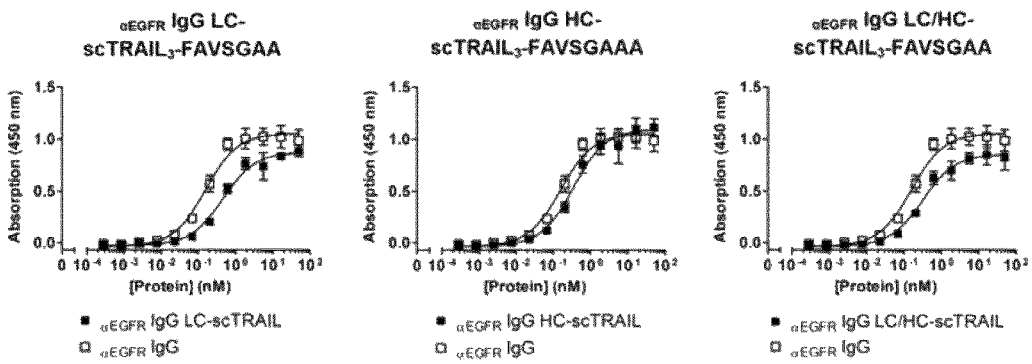

Fig. 37
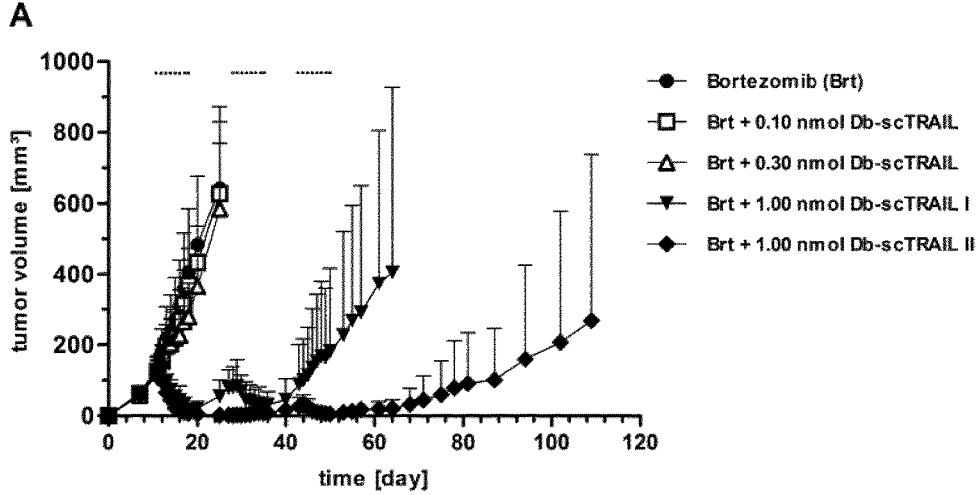
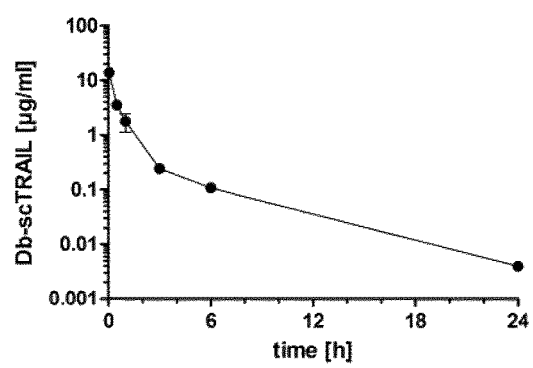
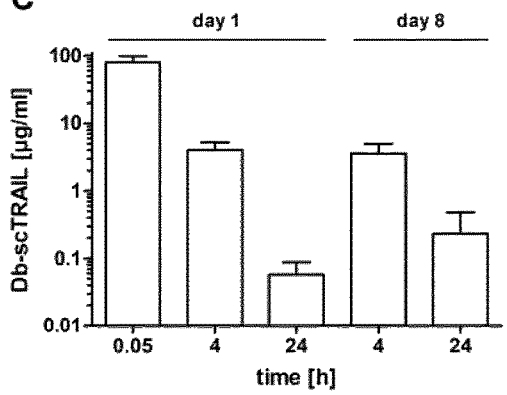
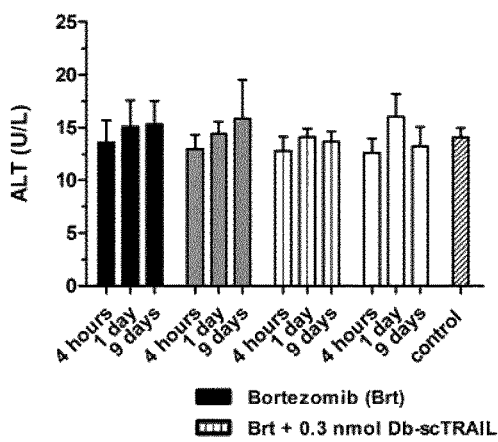
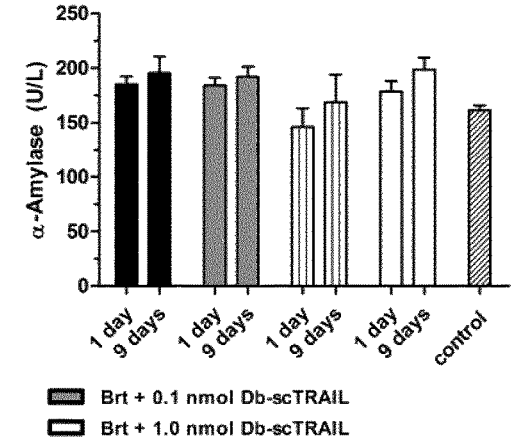

Fig. 38
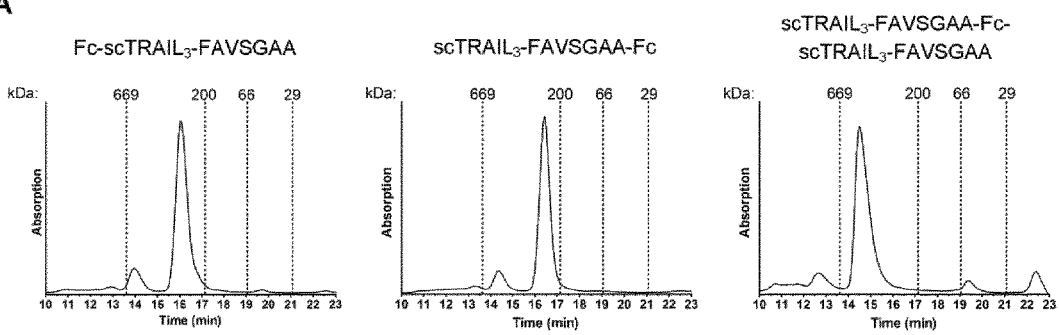
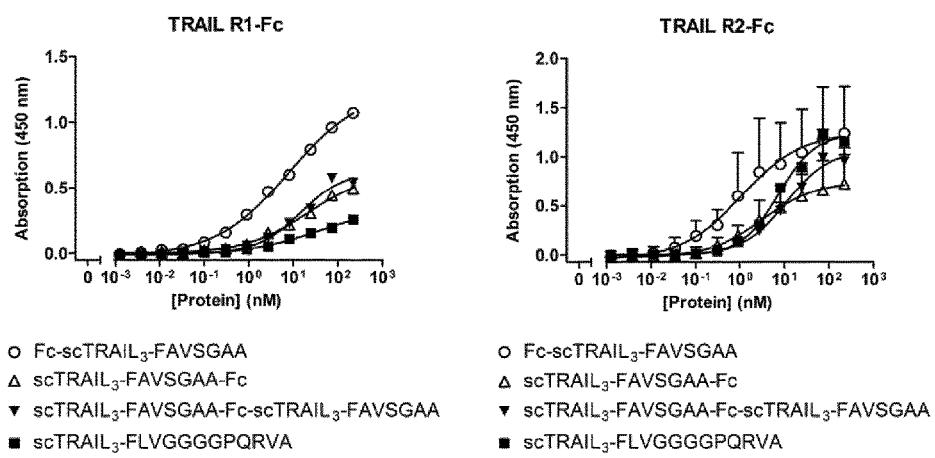
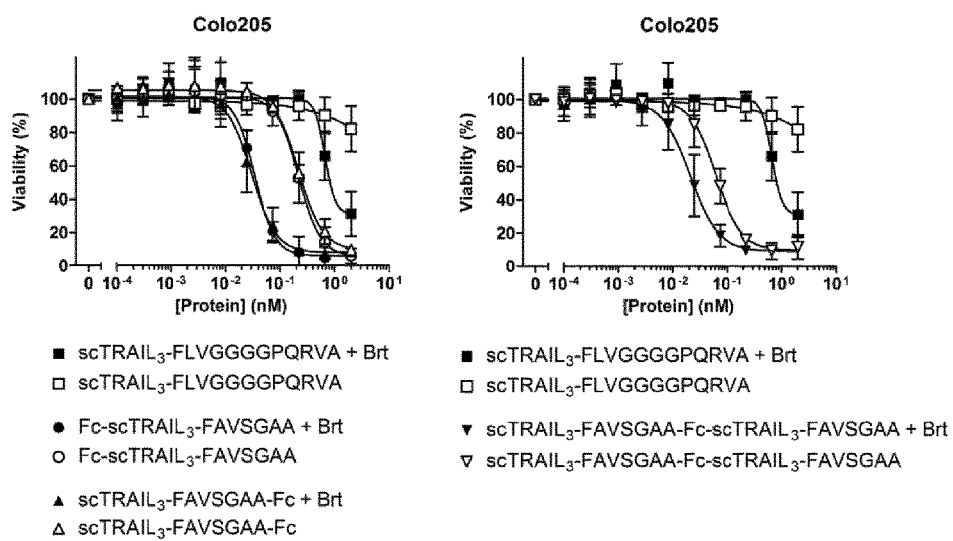

Fig. 39
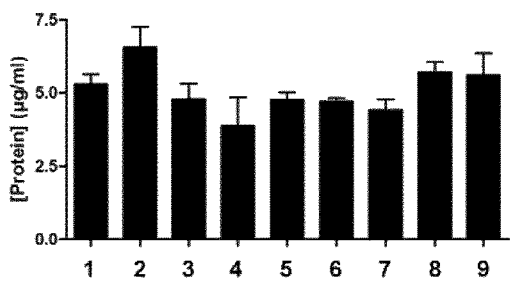
1. scTRAIL$_3$-FAVSGAA-0-Fc
2. scTRAIL$_3$-FAVSGAA-5 G/S-Fc
3. scTRAIL$_3$-FAVSGAA-10 G/S-Fc
4. scTRAIL$_3$-FAVSGAA-15 G/S-Fc
5. scTRAIL$_3$-FAVSGAA-20 G/S-Fc
6. scTRAIL$_3$-FAVSGAA-25 G/S-Fc
7. scTRAIL$_3$-FAVSGAA-"W"-Fc
8. scTRAIL$_3$-FAVSGAA-Fc
9. Fc-scTRAIL$_3$-FAVSGAA
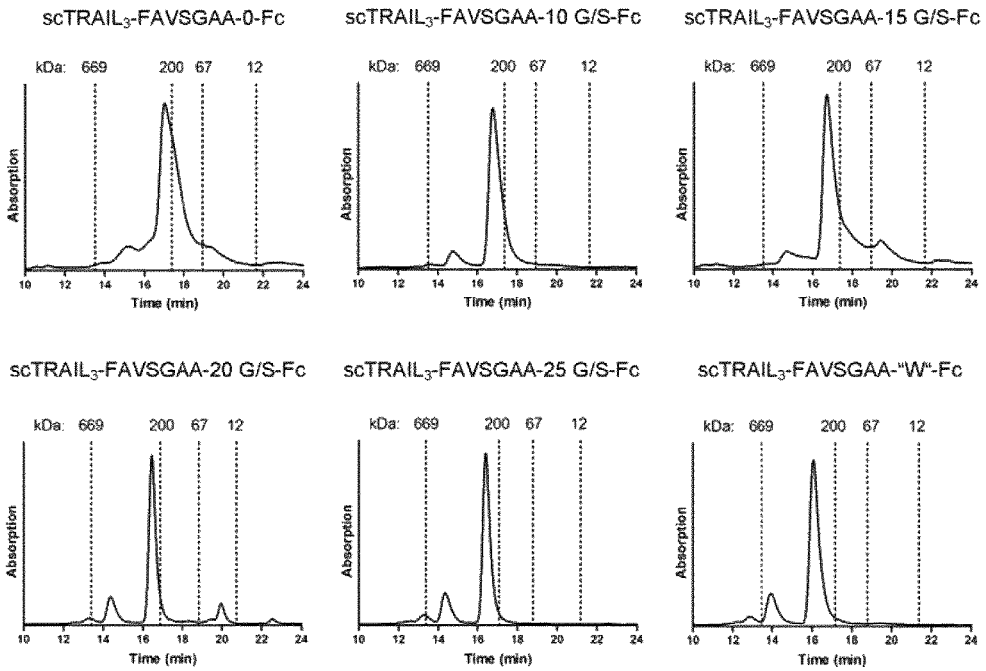
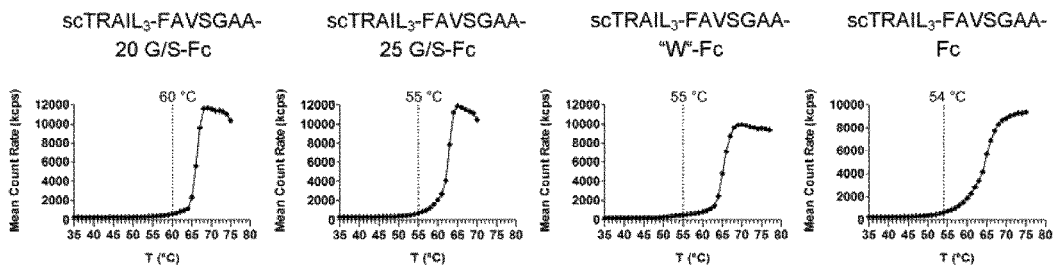

SINGLE-CHAIN TUMOR NECROSIS FACTOR (TNF) LIGAND FAMILY MOLECULES, FUSION PROTEINS AND DERIVATIVES THEREOF

CROSS-REFERENCE TO RELATED APPLICATION

This application is a U.S. national phase of International Application No. PCT/EP2016/055974, filed on Mar. 18, 2016, which claims priority to European Patent Application No. 15159703.6, filed Mar. 18, 2015, both of which are incorporated by reference herein in their entirety.

The present invention relates to a polypeptide comprising a component A with at least three tumor necrosis factor (TNF) homology domains of TNF-ligand family members (THD) in which C-terminal and N-terminal reference points are defined by consensus sequences and which are connected through short stretches of additional C-terminal and/or N-terminal amino acids of the THD or variants thereof, and a component B comprising a dimerization domain. Further, the present invention relates to a polypeptide comprising at least three THDs in which C-terminal and N-terminal reference points are defined by consensus sequences and which are connected through short stretches of additional C-terminal and/or N-terminal amino acids of the THD or variants thereof. Further, the invention relates to a nucleic acid comprising said polypeptides, a vector comprising said nucleic acid and a pharmaceutical composition comprising said polypeptides, or said nucleic acids or said vector. Further, the present invention relates to said polypeptides, said nucleic acid or said vector for the use as a medicament or for the use in the diagnosis, prophylaxis or treatment of hyperproliferative disorders and inflammatory disorder.

BACKGROUND OF THE INVENTION

The cytokine TRAIL is capable of specifically inducing apoptosis in tumor cells without affecting non-transformed cells and, thus is considered as a valuable effector molecule for therapy of cancer and other diseases. Unlike other members of the tumor necrosis factor (TNF) superfamily, e.g. TNF or CD95L, TRAIL is well tolerated upon systemic application, which facilitates the development of TRAIL-based biopharmaceuticals. TRAIL activates the extrinsic apoptotic pathway via binding to death receptors (DR) 4 and 5 which leads to cell death of tumor cells. Nevertheless, effective tumor eradication upon triggering of death receptors is hampered by intracellular resistance mechanisms and low bioactivity of conventional TRAIL biopharmaceuticals. Different therapeutic strategies dealing with DR activation have been developed. Agonistic monoclonal antibodies directed against either DR4, such as Mapatumumab or DR5, e.g. Conatumumab and Lexatumumab have been tested in phase I or phase II clinical studies with ambiguous results (for review see Holland et al. 2014; Micheau et al., 2013). Furthermore, soluble forms of TRAIL such as dulanermin (Herbst et al., 2010 a, b) and a circularly permuted TRAIL (CPT, Chen et al., 2012a) have been studied in several clinical trials. Although the combination of recombinant TRAIL with chemotherapeutics, e.g. thalidomide (Chen et al., 2012b) has led to more promising results than the monotherapy with the recombinant product, current forms of TRAIL are still associated with disadvantages, particularly a short half-life in the blood circulation, which does not exceed one hour. Thus, as a first step to overcome TRAIL-associated limitations, a single-chain format featuring three TRAIL modules (amino acid residues 95-281) connected by Gly/Ser peptides of 16, respectively 8 residues was developed, which has been shown to be more stable compared with soluble TRAIL (unpublished data; Schneider et al., 2010; Siegemund et al., 2012). Moreover, single-chain TRAIL can also be used for generation of antibody TRAIL fusion proteins. The homotrimeric TRAIL is naturally expressed as a membrane protein, which can also be present in a proteolytically cleaved, soluble form. This soluble form can induce apoptosis in tumor cells mainly via triggering the death receptor 4 (DR4) mediated extrinsic pathway, while a full activation of the apoptosis machinery involving an activation of death receptor 5 (DR5) still demands an oligomeric presence or localization of TRAIL at the plasma membrane. Since a therapeutic application of TRAIL should be based on a soluble protein, additional strategies are needed to mimic the bioactivity of membrane-localized TRAIL. The fusion of TRAIL or single-chain TRAIL to recombinant antibody formats, e.g. scFvs or diabodies, is an appropriate way to achieve a cell surface targeting, taking tumor specific markers into account (for review see de Bruyn et al., 2013)). Such TRAIL fusion proteins have been shown to express higher tumor specificity and an increased serum half-life compared with soluble TRAIL (Schneider et al., 2010). However, even the single-chain variants of TRAIL described so far exhibit a rather low thermal stability, with melting points of approximately 46-47° C. as determined by dynamic light scattering, which can affect therapeutic activity and stability during production and storage. In particular, evidence has been found that higher protein thermostability can directly correlate with an increased serum half-life time, actually representing one of the most requested properties in view of therapeutic applications for recombinant proteins (Gao et al., 2009). Therefore, the development of derivatives of single-chain THDs (scTHDs), in particular single chain TRAILs (scTRAILs) with improved thermal stability and solubility is currently challenging. It has surprisingly been shown by the present inventors that the use of THDs with additional N- and/or C-terminal deletions and distinct mutations at the N- and C-terminus of the THD, in particular TRAIL provides several advantages including inter alia increased solubility of the proteins, increased thermal stability, higher recombinant production rate and higher molecular integrity, e.g. less degradation/chain termination. The use of these improved scTHDs in the diabody-scTHD format, in particular diabody-scTRAIL format provides further benefits for the therapeutic suitability of this format. This format has been further enhanced by including redesigned connecting peptides between $V_H$ and $V_L$ of the diabody as well as improving the connecting peptides between the diabody and the improved scTHD variants, in particular scTRAIL variants.

SUMMARY OF THE INVENTION

In a first aspect the present invention provides a polypeptide comprising:
(i) component A comprising:
at least three THDs, wherein the C-terminus of the first and second THD, respectively, which is in each case defined by the C-terminal consensus sequence (SEQ ID NO: 1)
-S/T/V-F/Y/S-F-G-A/L/V/I-X$_1$, is linked to the N-terminus of the second and third THD, respectively, which is in each case defined by the N-terminal consensus sequence $X_2$-V/A/F-A-H-V/L/I/Y (SEQ ID NO: 2)
or
$X_3$-V/W/F/C-A/L-E/Y/Q/H-L, (SEQ ID NO: 3)

through a peptide $X_a$, which is in each case independently selected and has a length of 3 to 8 amino acids,
wherein $X_1$ is a non-polar/hydrophob or polar/neutral amino acid, preferably selected from the group consisting of F, V, Q, A, I, L, and Y;
wherein $X_2$ is selected from the group consisting of P, K, V, I, and A;
wherein $X_3$ is selected from the group consisting of D, S, M, and I;
(ii) component B comprising
a dimerization domain consisting of an antibody $V_L$ and $V_H$ region linked directly to each other with a peptide that has a length of between 7 and 11 amino acids.

In a second aspect the present invention provides a polypeptide comprising:
component C comprising:
at least three THDs, wherein the C-terminus of the first and second THD, respectively, which is in each case defined by the C-terminal consensus sequence

-S/T/V-F/Y/S-F-G-A/L/V/I-$X_1$, (SEQ ID NO: 1)

is linked to the N-terminus of the second and third THD, respectively, which is in each case defined by the N-terminal consensus sequence $X_2$-V/A/F-A-H-V/L/I/Y (SEQ ID NO: 2)
or
$X_3$-V/W/F/C-A/L-E/Y/Q/H-L, (SEQ ID NO: 3)

through a peptide $X_c$, which is in each case independently selected and has a length of 3 to 5 amino acids,
wherein $X_1$ is a non-polar/hydrophob or neutral/polar, amino acid, preferably selected from the group consisting of F, V, Q, A, I, L, and Y;
wherein $X_2$ is selected from the group consisting of P, K, V, I, and A; and
wherein $X_3$ is selected from the group consisting of D, S, M, and I.

In a third aspect the present invention provides a nucleic acid encoding the polypeptides of the first and second aspect of the present invention.

In a fourth aspect the present invention provides a vector comprising the nucleic acids of the third aspect of the present invention.

In a fifth aspect the present invention provides a pharmaceutical composition comprising the polypeptides of the first or second aspect of the present invention or the nucleic acid of the third aspect of the present invention or the vector of the fourth aspect of the present invention.

In a sixth aspect the present invention relates to a polypeptide of the first or the second aspect, a nucleic acid of the third aspect or a vector of the fourth aspect for use as a medicament.

In a seventh aspect the present invention relates to a polypeptide of the first or the second aspect, a nucleic acid of the third aspect or a vector of the fourth aspect for use in the diagnosis, prophylaxis or treatment of proliferative disorders and anti-inflammatory disorders.

LIST OF FIGURES

In the following, the content of the figures comprised in this specification is described. In this context please also refer to the detailed description of the invention above and/or below.

FIG. 1: ScTRAIL molecules of this invention

Schematic representations of scTRAIL molecules described in the present application. With the exception of scTRAIL-95L8, THDs of human TRAIL spanning the amino acid positions 122 to 278 are depicted as boxes. Amino acid substitutions within the THDs are underlined. (TSEE is SEQ ID NO:265; FLVG is SEQ ID NO:264; GGGS2 is SEQ ID NO:261; VRERGPQR is SEQ ID NO:266; VAAHI is SEQ ID NO:25; FFGAF is SEQ ID NO:267; GGGS is SEQ ID NO:263; LVGGR is SEQ ID NO:268; LVGG is SEQ ID NO:159; GPQR is SEQ ID NO:166; GAAHI is SEQ ID NO:270; IAAHI is SEQ ID NO:271; LAAHI is SEQ ID NO:272; MAAHI is SEQ ID NO:273; AAAHI is SEQ ID NO:274; AVGG is SEQ ID NO:162; GVGG is SEQ ID NO:269; LVSG is SEQ ID NO:161; IVGG is SEQ ID NO:164; IVSG is SEQ ID NO:165; AVSG is SEQ ID NO:163).

FIG. 2: Western Blot analysis of selected scTRAIL molecules

The solubility of selected scTRAIL molecules with crucial amino acid deletions or substitutions at (A) positions 280, 281 and 122 or (B) positions 279 and 122 was tested in an anti-FLAG western blot. To this, HEK293 cells were transiently transfected with equal amounts of plasmid DNA and cultivated for three days in OptiMEM I medium supplemented with 50 µM zinc chloride, followed by collecting of supernatants (S) and cell pellet samples (P) for reducing SDS-PAGE/western blotting. Underlined constructs produced soluble protein by the majority and were used for further characterization.

Figure 3:
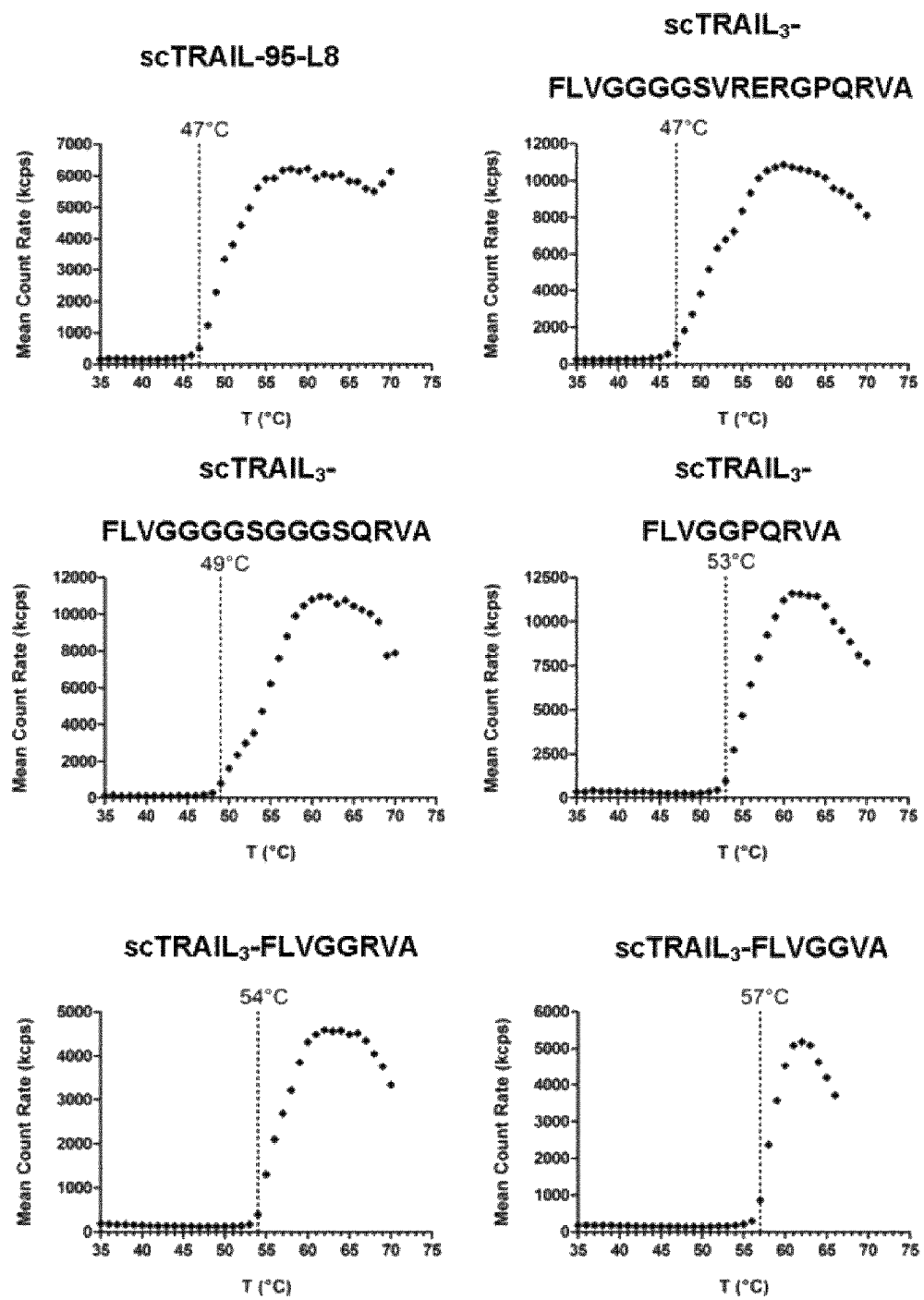
Figure 3:
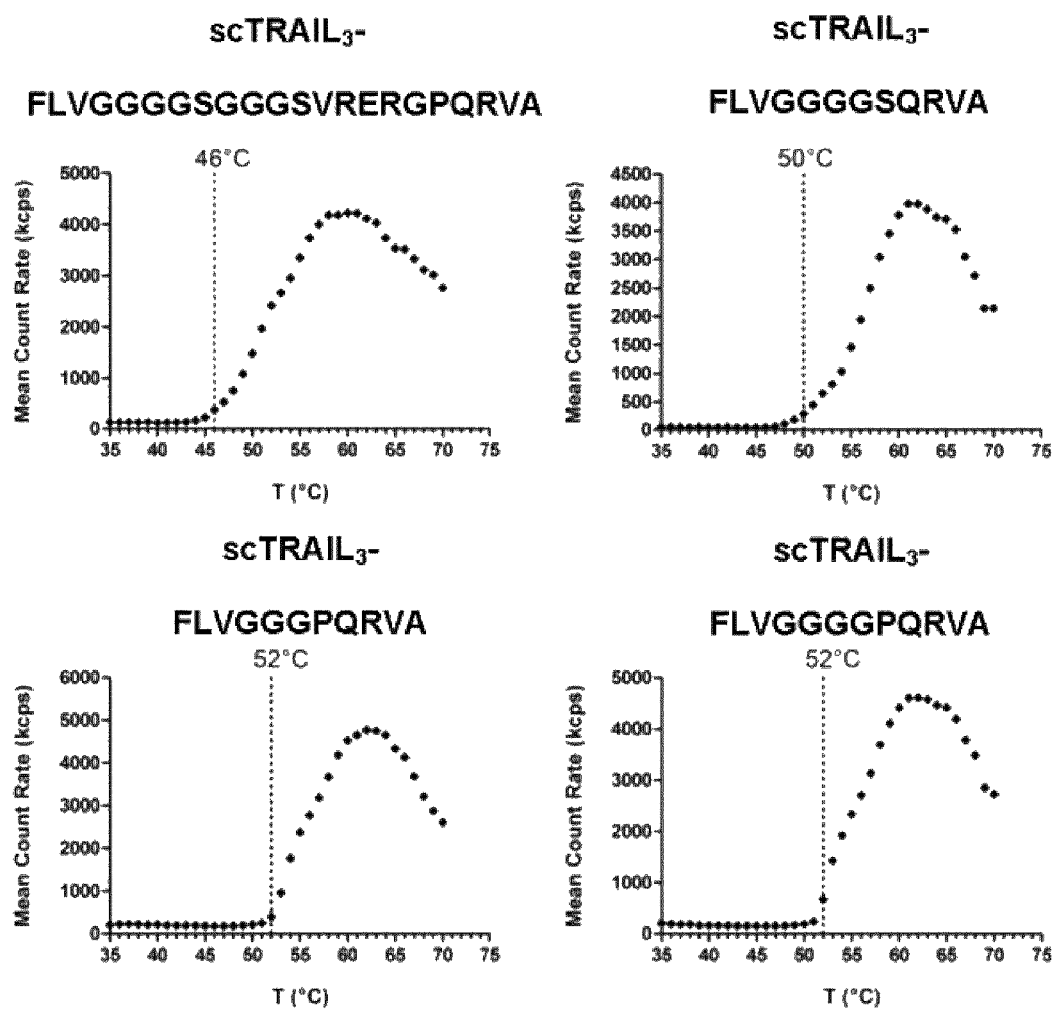

FIG. 3: Melting point analysis of scTRAILs

The melting points of scTRAIL molecules were analyzed by dynamic light scattering using a zetasizer instrument.

Figure 4:
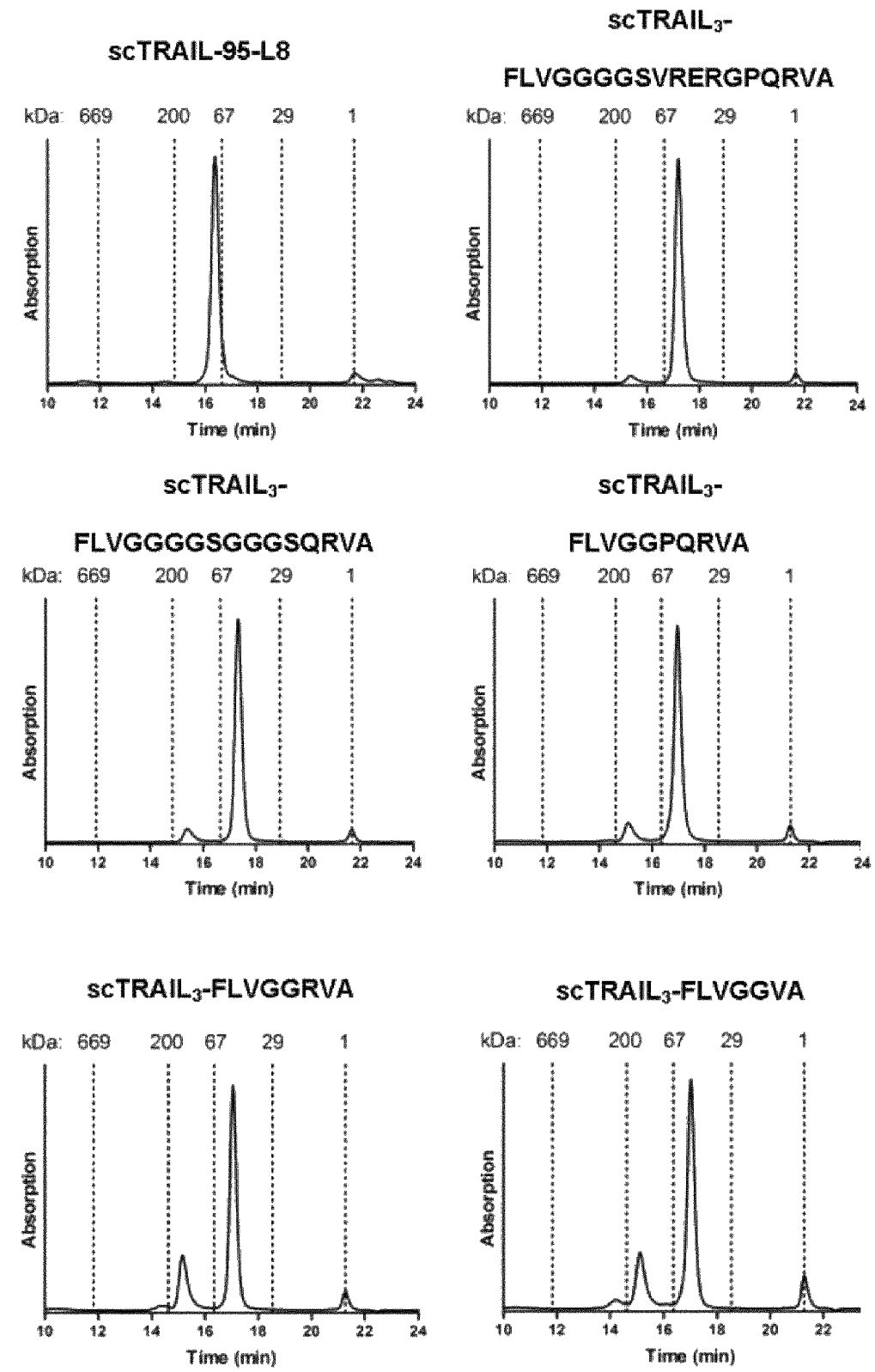
Figure 4:
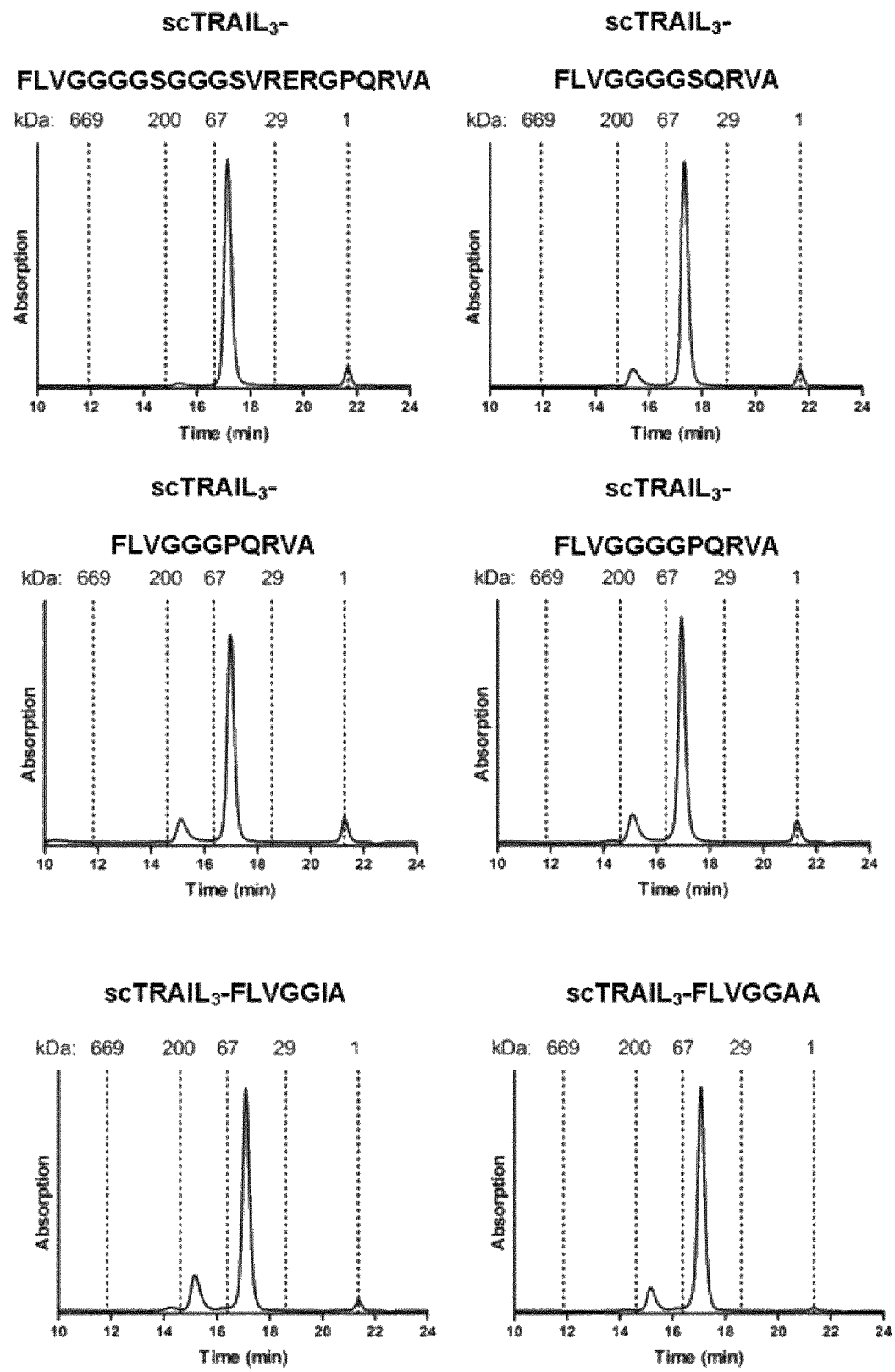
Figure 4:
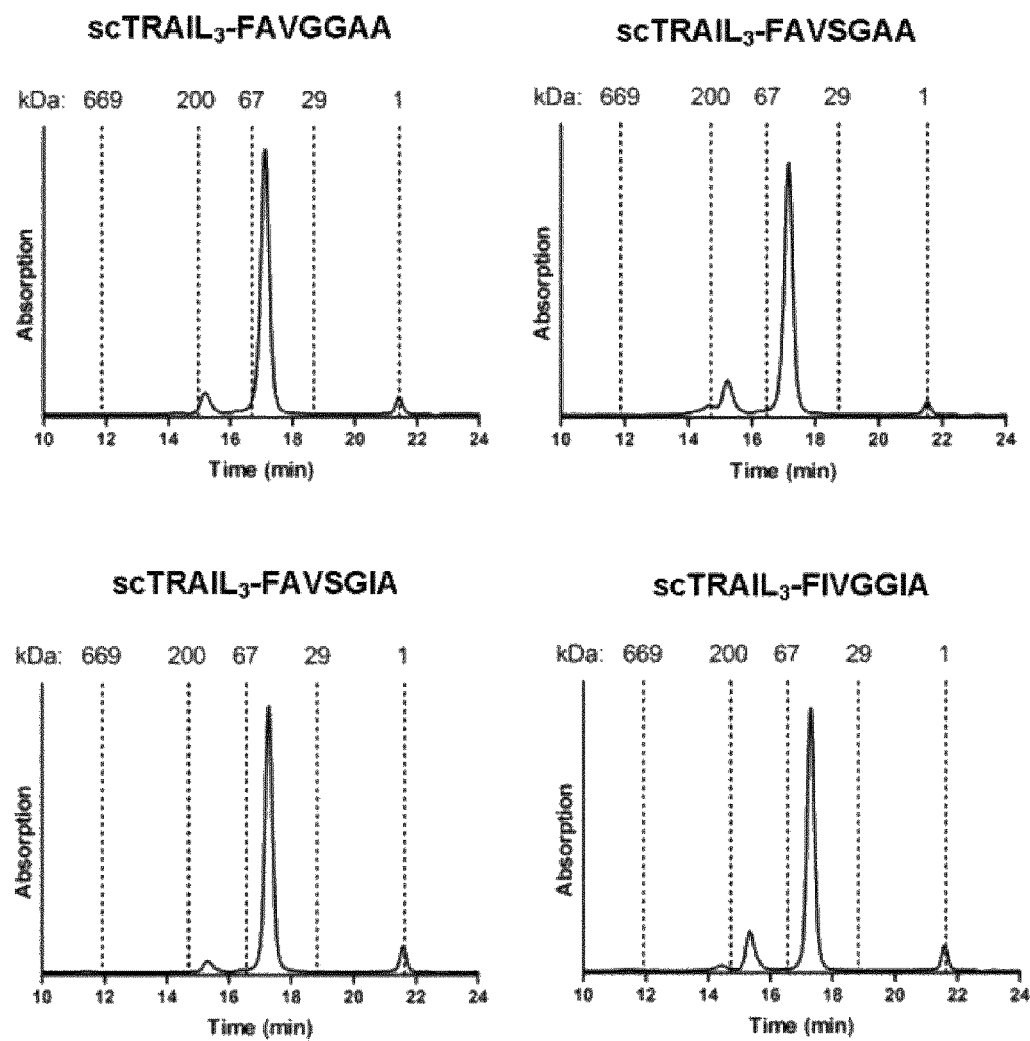
Figure 4:
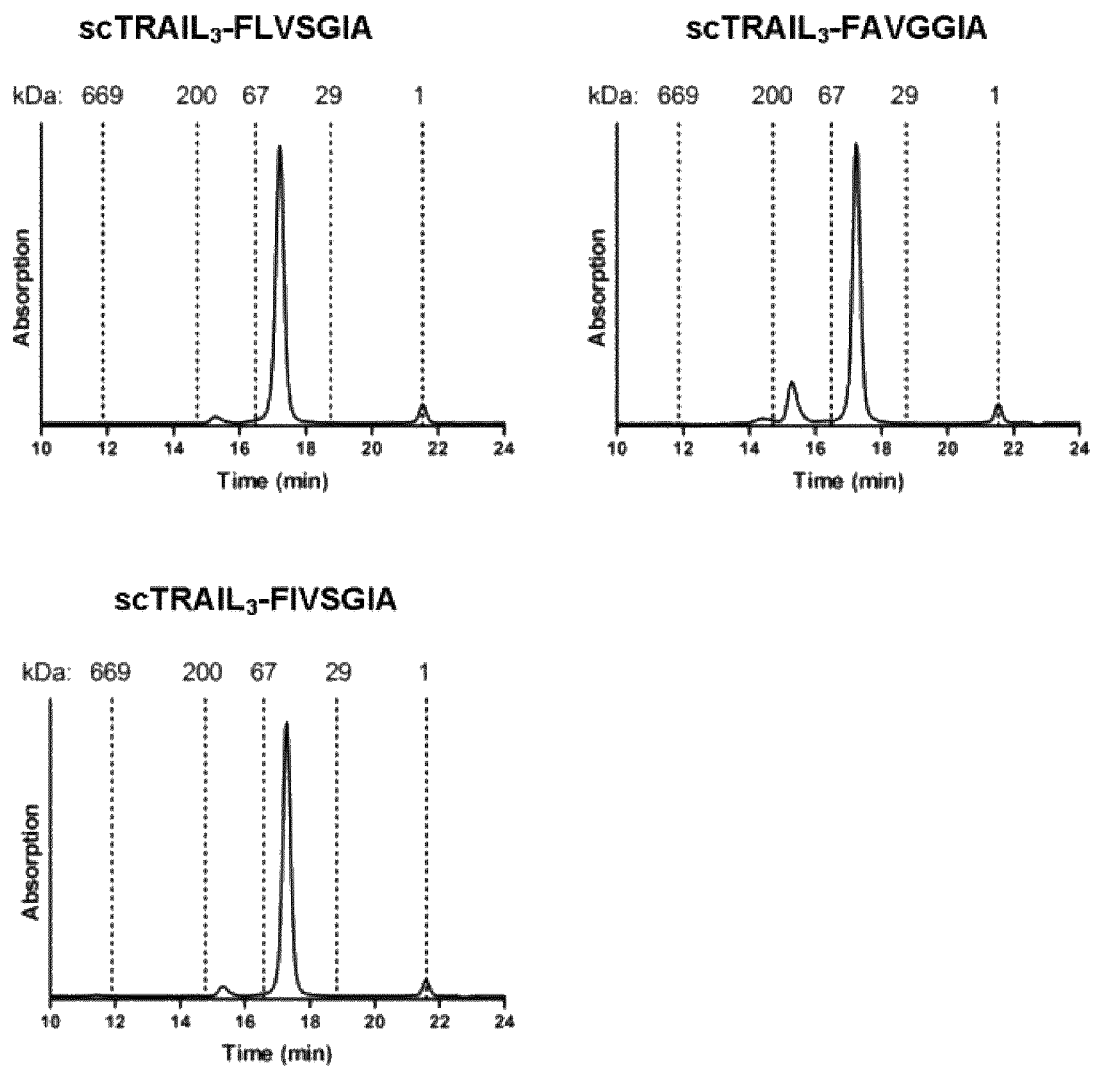

FIG. 4: Size exclusion chromatography of scTRAILs

Affinity-purified scTRAIL molecules were analyzed by size exclusion chromatography for their molecular constitution. The retention times of the standard proteins thyroglobulin (669 kDa), beta-amylase (200 kDa), bovine serum albumin (67 kDa), carboanhydrase (29 kDa) and FLAG peptide are indicated by lines.

FIG. 5: Binding studies of scTRAILs

Selected scTRAIL molecules were tested for their binding to either (A) Colo205 cells using flow cytometry, or to (B) immobilized DR5-Fc fusion protein using an ELISA approach. Data points were fitted with curves and values of half-maximum binding (EC50) were determined.

Figure 6:
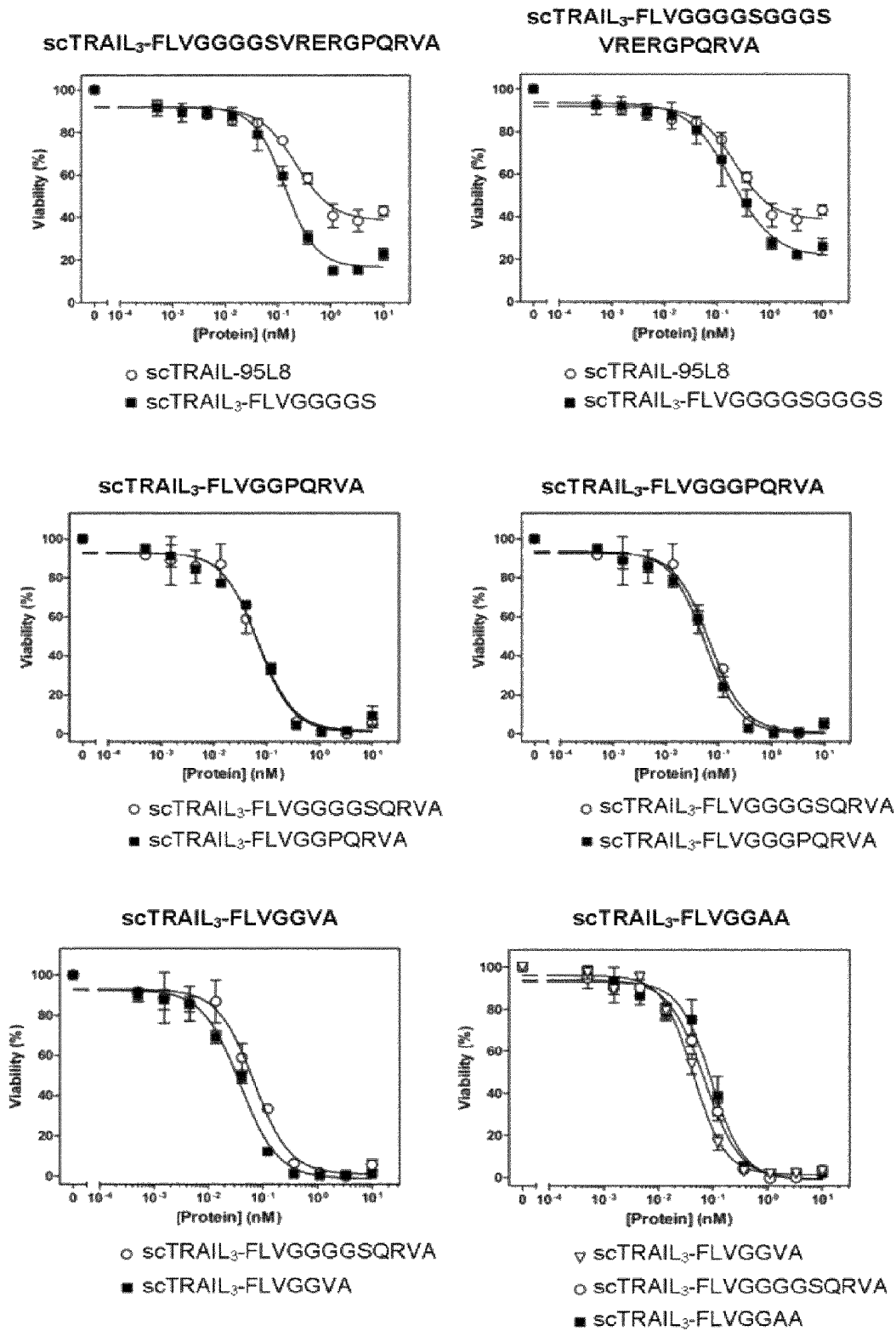
Figure 6:
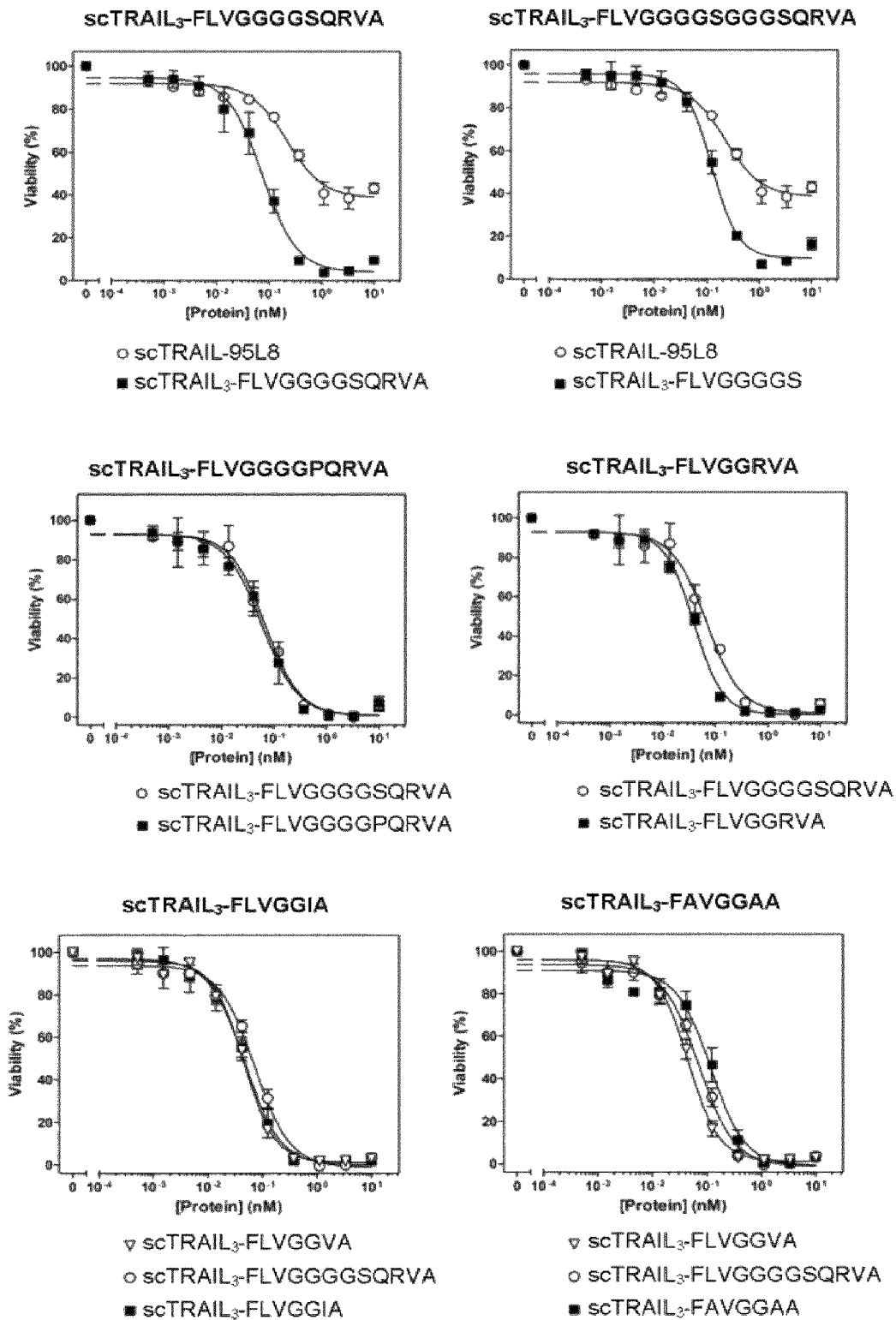
Figure 6:
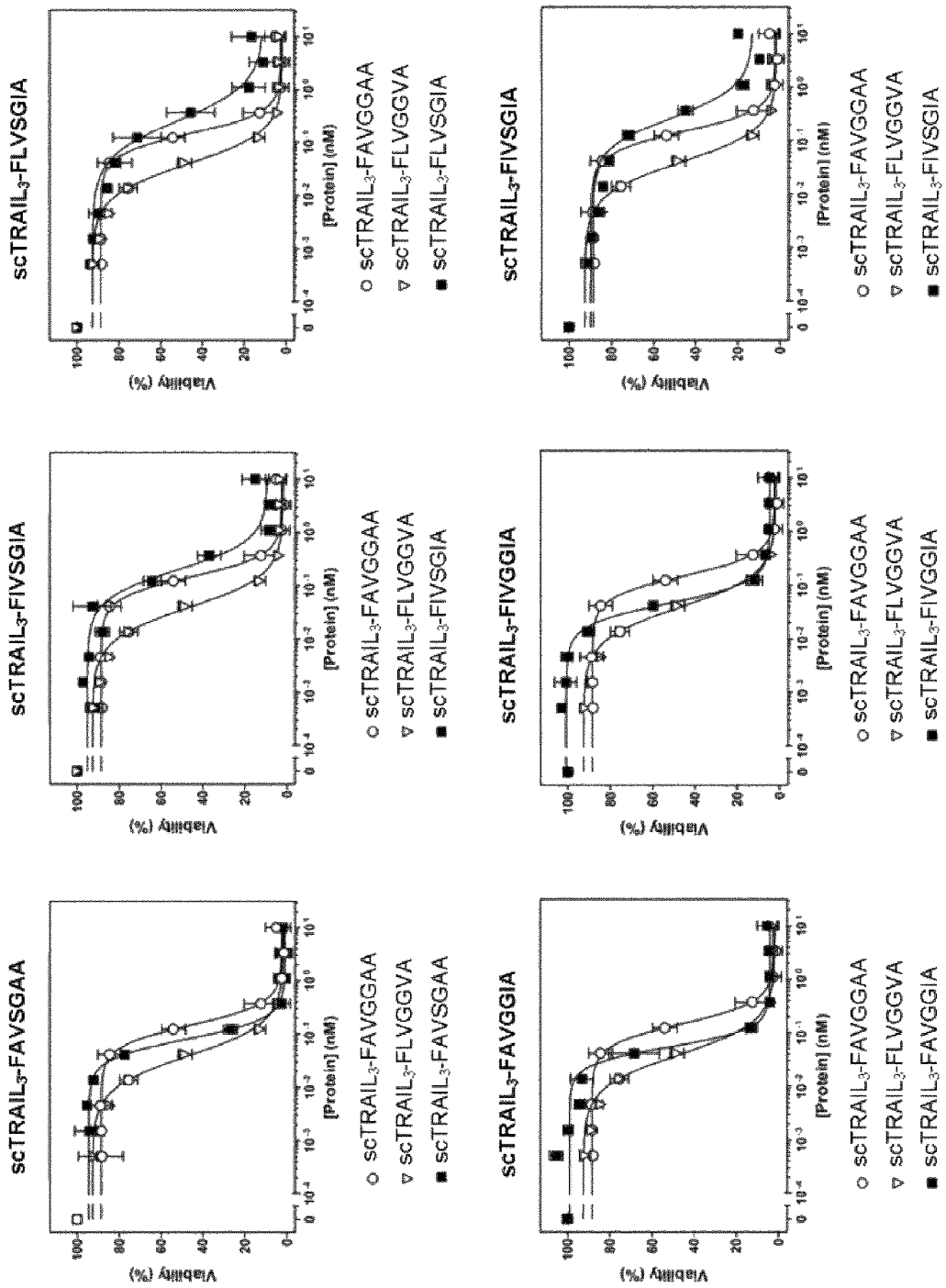

FIG. 6: Cytotoxicity test

The cytotoxic activity of the scTRAIL molecules was assayed in vitro on Colo205 colon cancer cells in presence of 250 ng/ml Bortezomib. The percentage of surviving cells was measured by crystal violet staining. Data points: mean±S.E.M (n=3).

Figure 7:
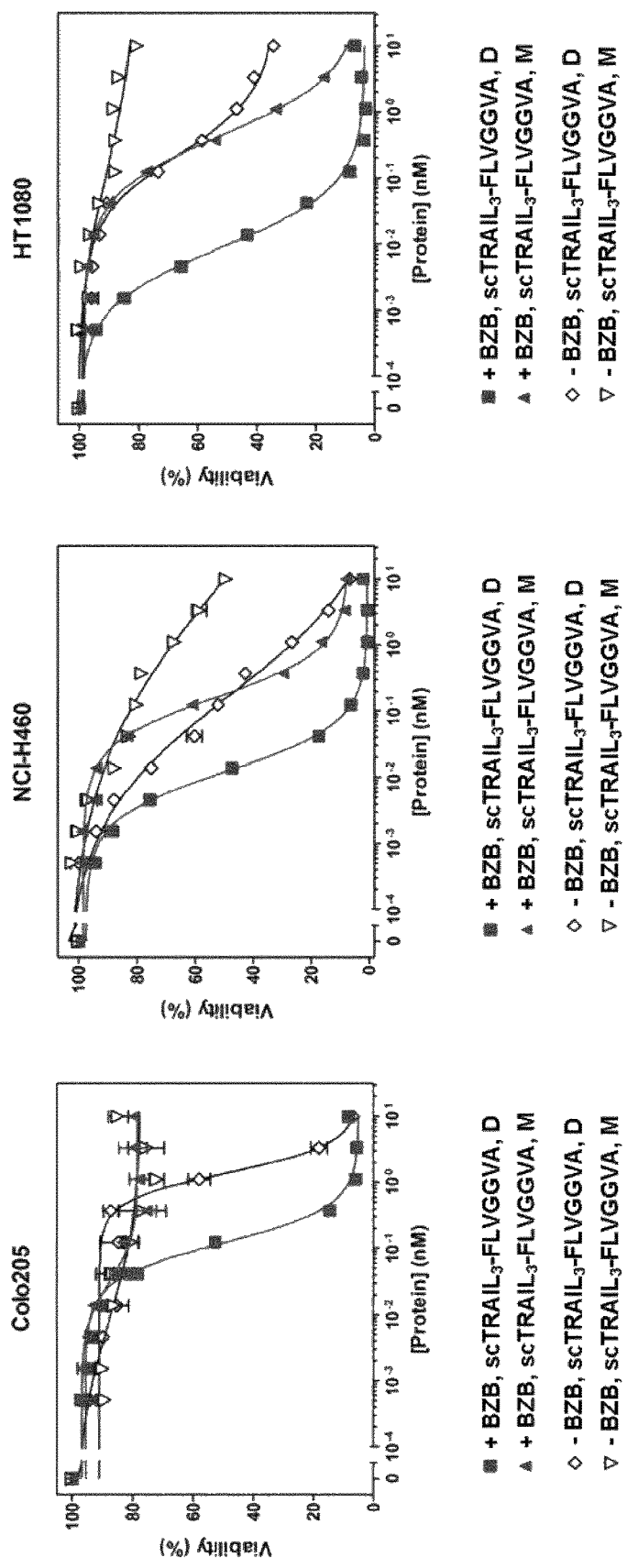

FIG. 7: SEC and cytotoxicity test of scTRAIL$_3$-FLVG-GVA

Purified scTRAIL$_3$-FLVGGVA was separated via size exclusion chromatography and fractions of the eluate were collected in order to separate the putative dimeric/aggregate (D) from the monomeric (M) form. After measuring the protein content of the fractions, equimolar concentrations of both species were subjected to a cytotoxicity assay using the cell lines Colo205, NCI-H460 and HT1080 with or without Bortezomib sensitization. Dependent on the specific cell line, the bioactivities of monomeric and dimeric scTRAIL were found to differ significantly.

FIG. 8: SEC of Db-scTRAIL-95L8

Db-scTRAIL-95L8 was separated by SEC (A) and fractions were blotted followed by detection with anti-FLAG M2 antibody (B). The peak represented by the fractions 6 and 7 is due to intact dimeric fusion protein. The peak involving the fractions 9 to 11 is characterized by signals from a full-length polypeptide chain and a ~40 kDa fragment comprising FLAG tag, VH, VL and a part of the first TRAIL monomer. This fragment likely forms a dimer with a full-length polypeptide chain yielding a partially fragmented dimer.

FIG. 9: SEC and bioactivity analysis of Db-scTRAIL variants (A) Different molecular forms of Db-scTRAIL-95L8 and Db-Glyco-scTRAIL$_3$-FAVSGAA were separated preparatively by SEC. (B) The molecular forms "A" and "B" were analyzed for their bioactivity in a cell viability assay on HCT-116, HT1080 and NCI-H460 cells with the indicated concentrations of the proteasome inhibitor Bortezomib.

FIG. 10: Comparison of scTRAIL variants

Previously generated scTRAIL-95L8 (Siegemund et al., 2012) and new scTRAIL$_3$-FAVSGAA (SEQ ID NO: 227) were compared by SEC. In addition, scFv or diabody fusion proteins comprising both versions of scTRAIL, respectively scTRAIL$_3$ are shown.

Figure 11:
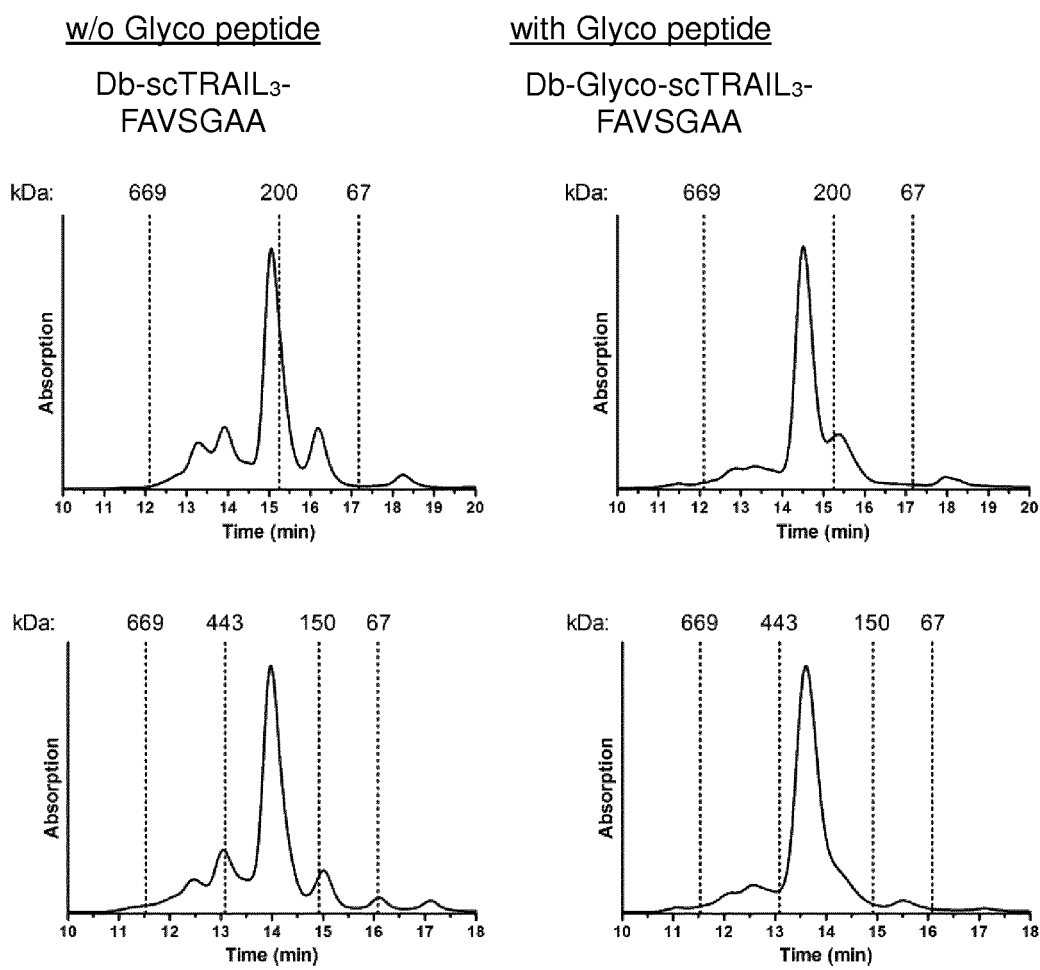

FIG. 11: SEC of scTRAIL variants

Db-scTRAIL$_3$-FAVSGAA (upper left), Db-Glyco-scTRAIL$_3$-FAVSGAA (upper right), Db10-scTRAIL$_3$-FAVSGAA (lower left) and Db10-Glyco-scTRAIL$_3$-FAVSGAA (lower right) were analyzed by size exclusion chromatography (SEC) to demonstrate the effect of the glycosylated connecting peptide on protein quality.

FIG. 12: Dimerization analysis of Db-scTRAIL$_3$ variants (A) SEC analysis revealed the occurrence of a second molecular form in preparations of several Db-scTRAIL variants which could be identified as a dimer with a truncation in one polypeptide chain (arrow). Additionally, aggregates were observed for example in a preparation of Db-scTRAIL$_3$-FAVSGAA. (B) A combination of a glycosylated peptide between the V$_L$ domain and the scTRAIL moiety together with an extension of the diabody connecting peptide to 8 or 10 residues has been proven to successfully reduce aggregation and fragmentation of the protein. The SEC analysis confirmed the quantitative dimerization of Db-Glyco-scTRAIL$_3$-FAVSGAA, Db8-Glyco-scTRAIL$_3$-FAVSGAA and Db10-Glyco-scTRAIL$_3$-FAVSGAA. (C) SEC analysis of Db-Glyco-scTRAIL$_3$-FAVSGIA.

Figure 13:
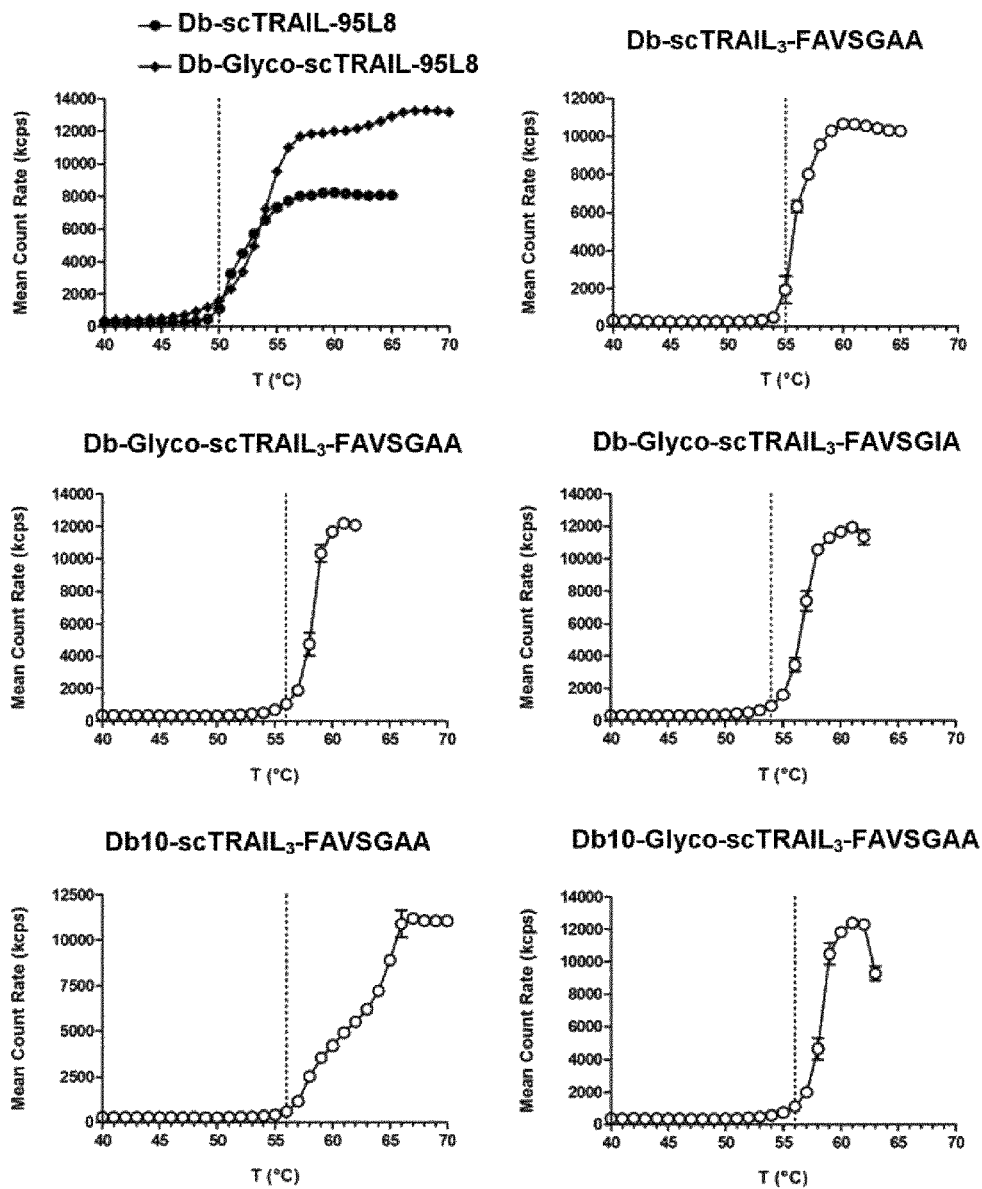

FIG. 13: Thermal stability of Db-scTRAIL$_3$ variants

Purified Db-scTRAIL-95L8, Db-Glyco-scTRAIL-95L8, Db-scTRAIL$_3$-FAVSGAA, Db-Glyco-scTRAIL$_3$-FAVSGAA, Db-Glyco-scTRAIL$_3$-FAVSGIA, Db10-scTRAIL$_3$-FAVSGAA and Db10-Glyco-scTRAIL$_3$-FAVSGAA were analyzed for their melting temperatures (Tm) by dynamic light scattering.

FIG. 14: Binding to cells (A) Db-scTRAIL-95L8, Db-Glyco-scTRAIL-95L8, Db-Glyco-scTRAIL$_3$-FAVSGAA, Db-Glyco-scTRAIL$_3$-FAVSGIA, Db8-Glyco-scTRAIL$_3$-FAVSGAA and Db10-Glyco-scTRAIL$_3$-FAVSGAA were analyzed for their binding abilities to EGFR+ TRAILR+HT1080 cells using flow cytometry. The differences in the EC$_{50}$ values between the different Db variants are statistically not significant (P=0.11, n=3).

FIG. 15: Cell viability assay in Colo 205 cells

Preparations of Db-scTRAIL-95L8, Db-Glyco-scTRAIL$_3$-FAVSGAA, Db-Glyco-scTRAIL$_3$-FAVSGIA, Db8-Glyco-scTRAIL$_3$-FAVSGAA and Db10-Glyco-scTRAIL$_3$-FAVSGAA were analyzed for their bioactivity in a cell viability assay using Colo 205 sensitized with 250 ng/ml of the proteasome inhibitor Bortezomib (mean±SEM, n=4). Where indicated, 10 µg/ml of the anti-EGFR antibody Cetuximab was added prior to fusion protein incubation for EGFR competition studies.

Figure 16:
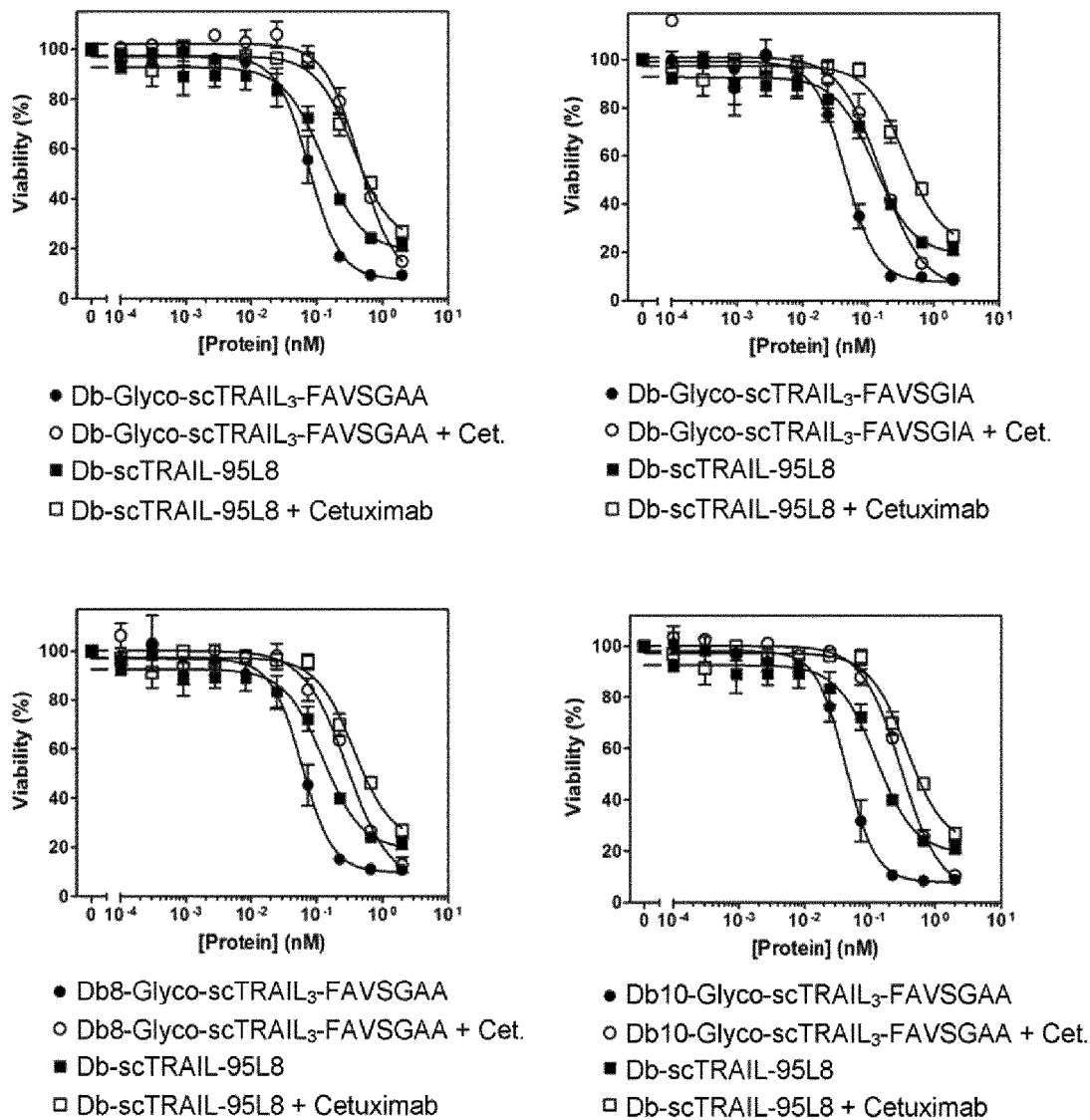

FIG. 16: Cell viability assay in HCT-116 cells

Preparations of Db-scTRAIL-95L8, Db-Glyco-scTRAIL$_3$-FAVSGAA, Db-Glyco-scTRAIL$_3$-FAVSGIA, Db8-Glyco-scTRAIL$_3$-FAVSGAA and Db10-Glyco-scTRAIL$_3$-FAVSGAA were analyzed for their bioactivity in a cell viability assay using HCT-116 sensitized with 5 ng/ml of the proteasome inhibitor Bortezomib (mean±SEM, n=2). Where indicated, 10 µg/ml of the anti-EGFR antibody Cetuximab was added prior to fusion protein incubation for EGFR competition studies.

FIG. 17: Cell viability assay in HT 1080 cells

Preparations of Db-scTRAIL-95L8, Db-Glyco-scTRAIL$_3$-FAVSGAA, Db-Glyco-scTRAIL$_3$-FAVSGIA, Db8-Glyco-scTRAIL$_3$-FAVSGAA and Db10-Glyco-scTRAIL$_3$-FAVSGAA were analyzed for their bioactivity in a cell viability assay using HT1080 sensitized with 10 ng/ml of the proteasome inhibitor Bortezomib (mean±SEM, n=2). Where indicated, 10 µg/ml of the anti-EGFR antibody Cetuximab was added prior to fusion protein incubation for EGFR competition studies.

Figure 18:
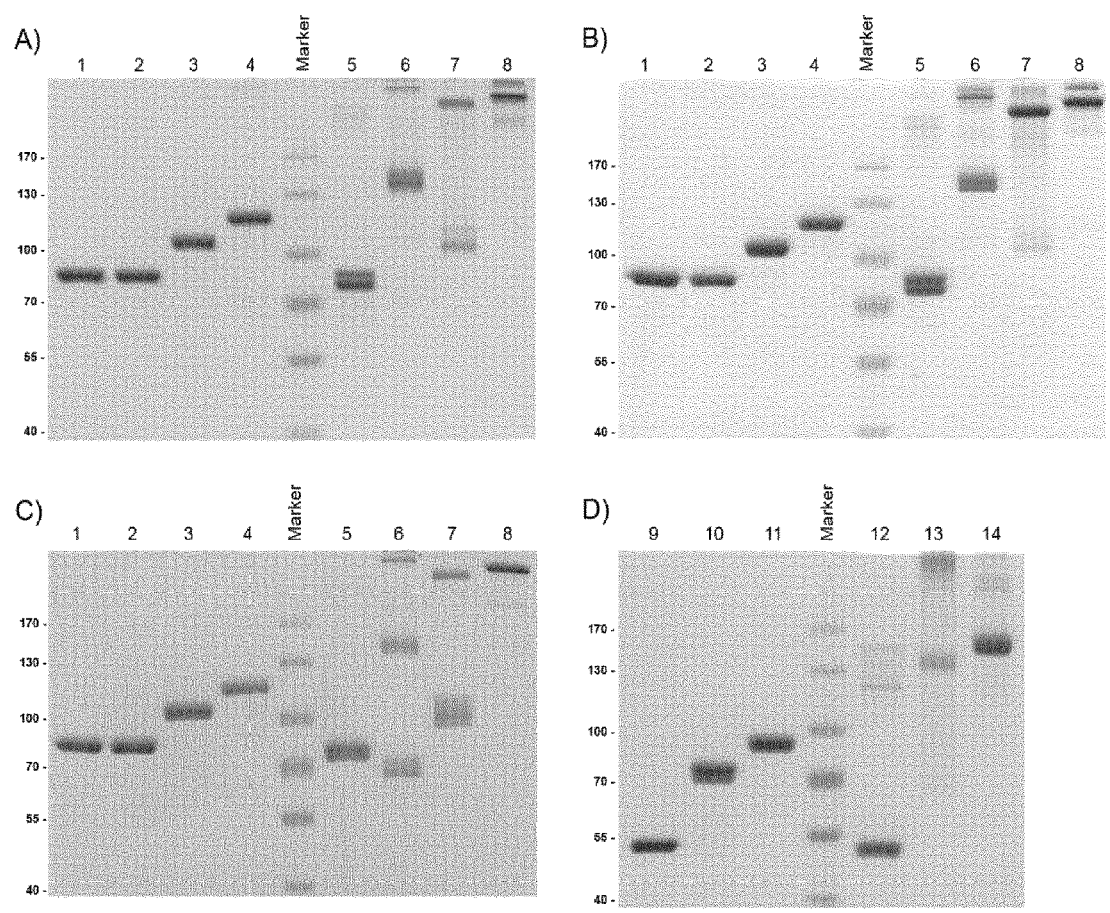

FIG. 18: SDS-PAGE analysis

SDS-PAGE analysis (8% PAA, Coomassie stained) of Db-scTRAIL$_3$-FLVGGGPQRVA, dsDb-scTRAIL$_3$-FLVGGGPQRVA, scFv-EHD2-scTRAIL$_3$-FLVGGGPQRVA and scFv-Fc-scTRAIL$_3$-FLVGGGPQRVA under reducing (1, 2, 3, 4) and non-reducing (5, 6, 7, 8) conditions for fusion proteins targeting EGFR (A), HER2 (B), and HER3 (C). D) SDS-PAGE analysis of non-targeted constructs scTRAIL$_3$-FLVGGGPQRVA, EHD2-scTRAIL$_3$-FLVGGGPQRVA and Fc-scTRAIL$_3$-FLVGGGPQRVA under reducing (9, 10, 11) and non-reducing conditions (12, 13, 14).

Figure 19:
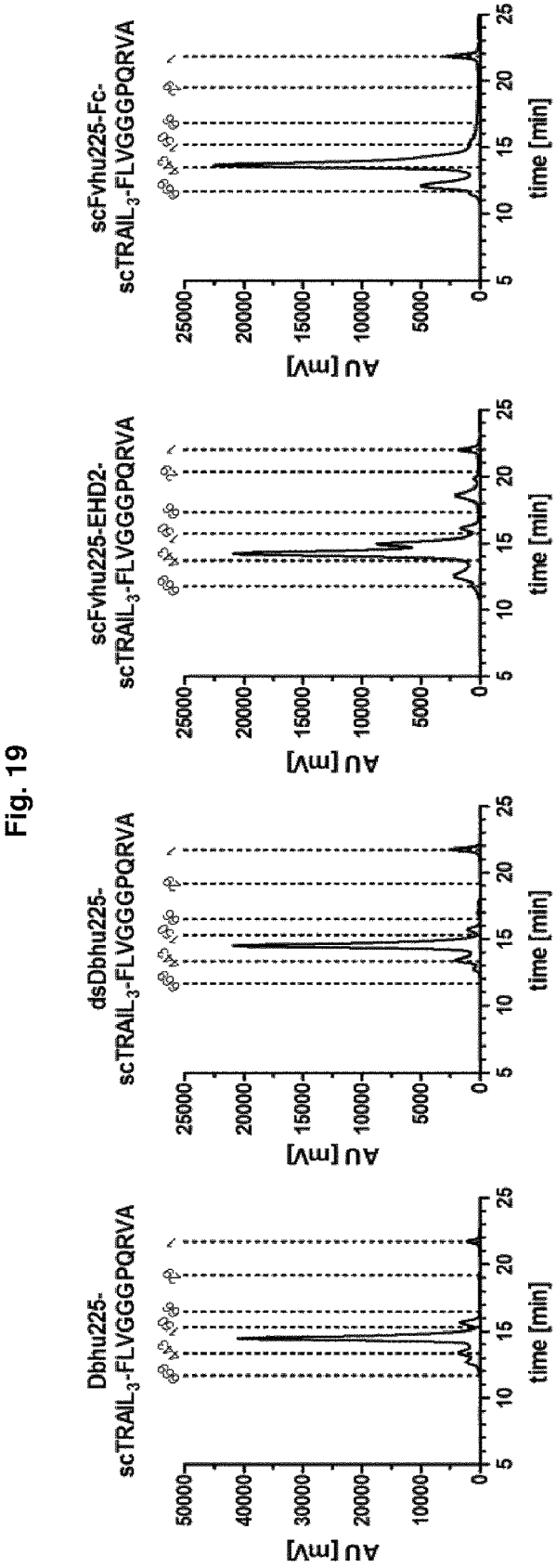

FIG. 19: SEC of EGFR-scTRAIL fusion protein

Size exclusion chromatography of EGFR-targeting dimeric scTRAIL$_3$-FLVGGGPQRVA fusion proteins.

Figure 20:
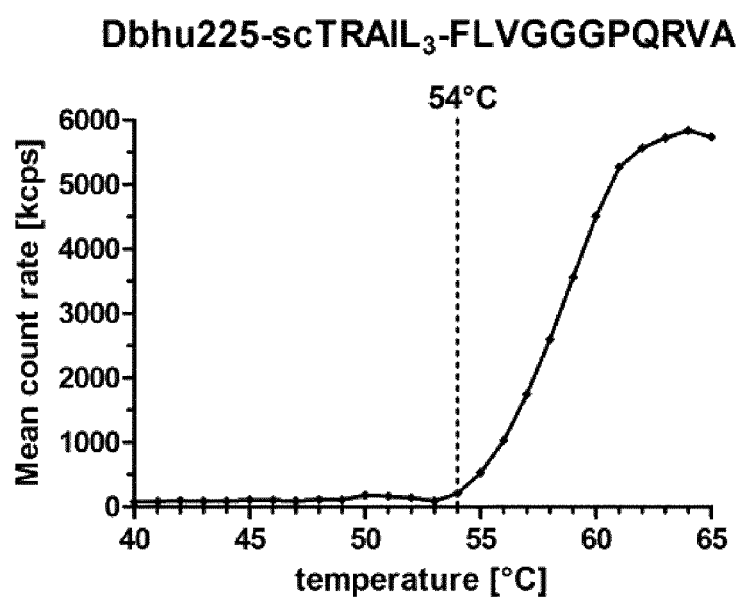

FIG. 20: Thermal stability analysis of Dbhu225-scTRAIL$_3$

Melting point of Dbhu225-scTRAIL$_3$-FLVGGGPQRVA was determined by dynamic light scattering.

Figure 21:
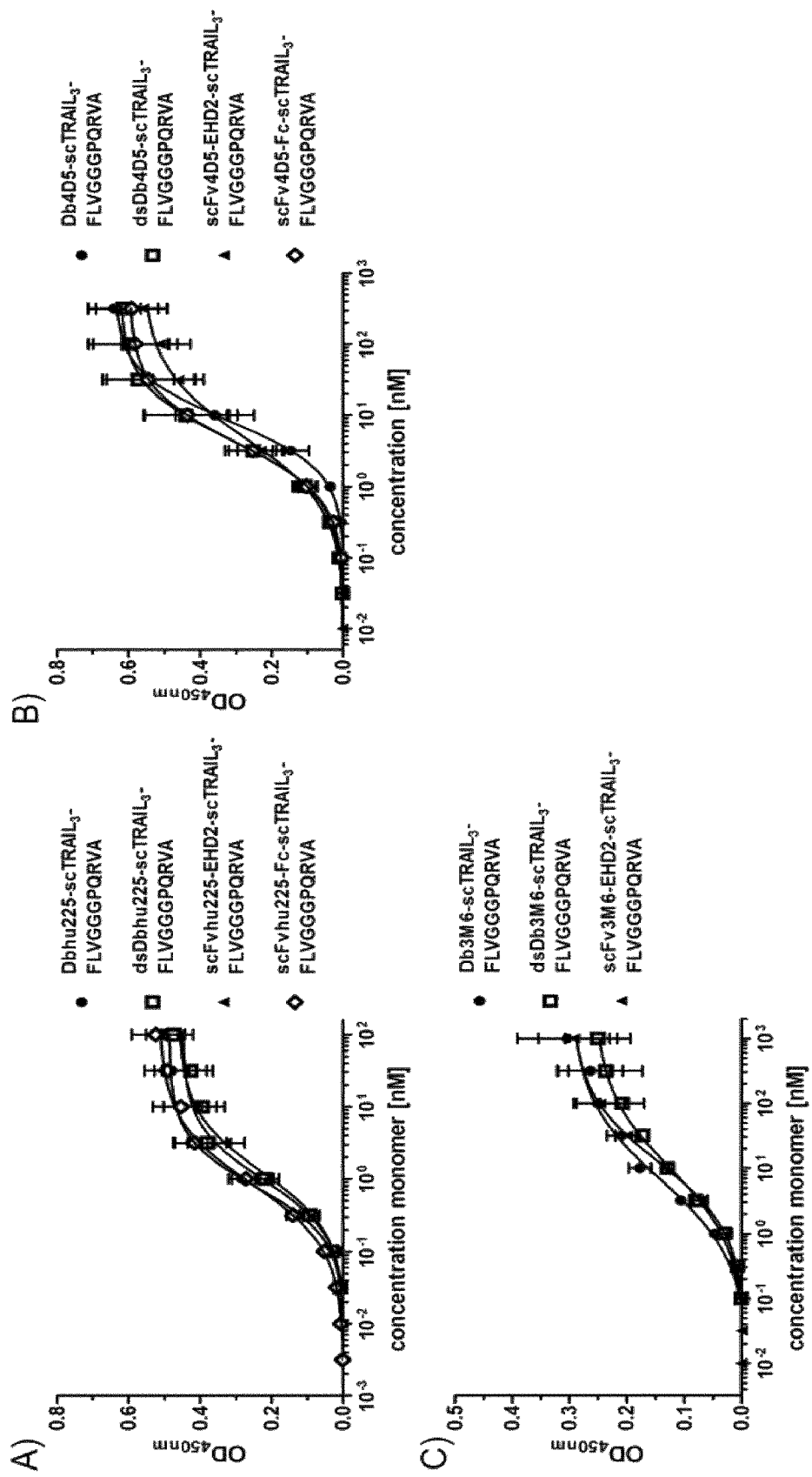

FIG. 21: Target antigen binding analysis (ELISA)

Binding of targeted dimeric scTRAIL$_3$-FLVGGGPQRVA fusion proteins to EGFR-Fc (A), HER2-Fc (B), and HER3-Fc (C) was analyzed by ELISA. Optical density was measured at 450 nm. Data are represented as mean±S.D. (n=3).

Figure 22:
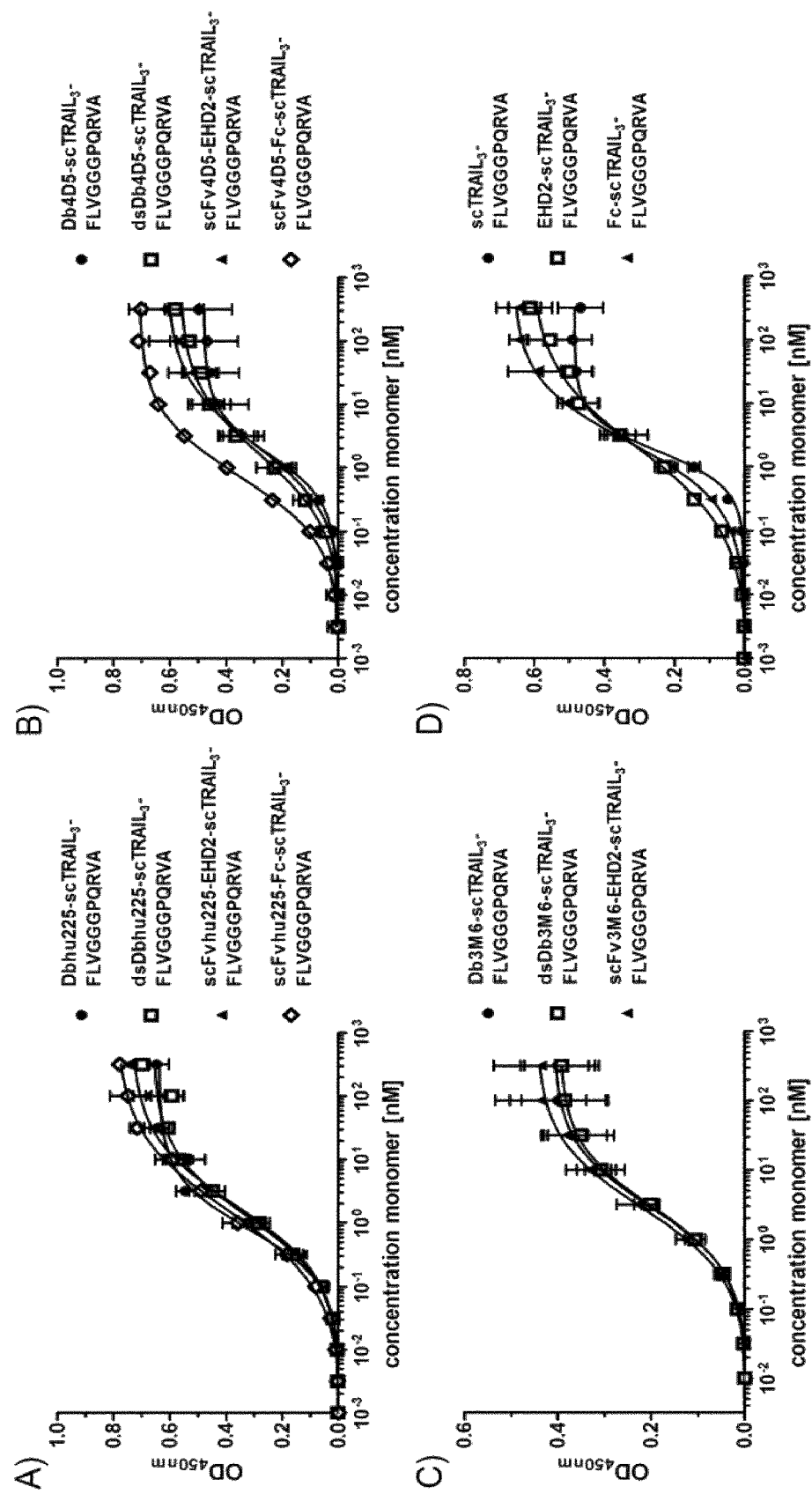

FIG. 22: TRAILR2 binding studies (ELISA)

Binding of scTRAIL$_3$-FLVGGGPQRVA fusion proteins targeting EGFR (A), HER2 (B), HER3 (C) and non-targeted constructs (D) to TRAIL-R2-Fc was analyzed by ELISA. Optical density was measured at 450 nm. Data are represented as mean±S.D. (n=3).

Figure 23:
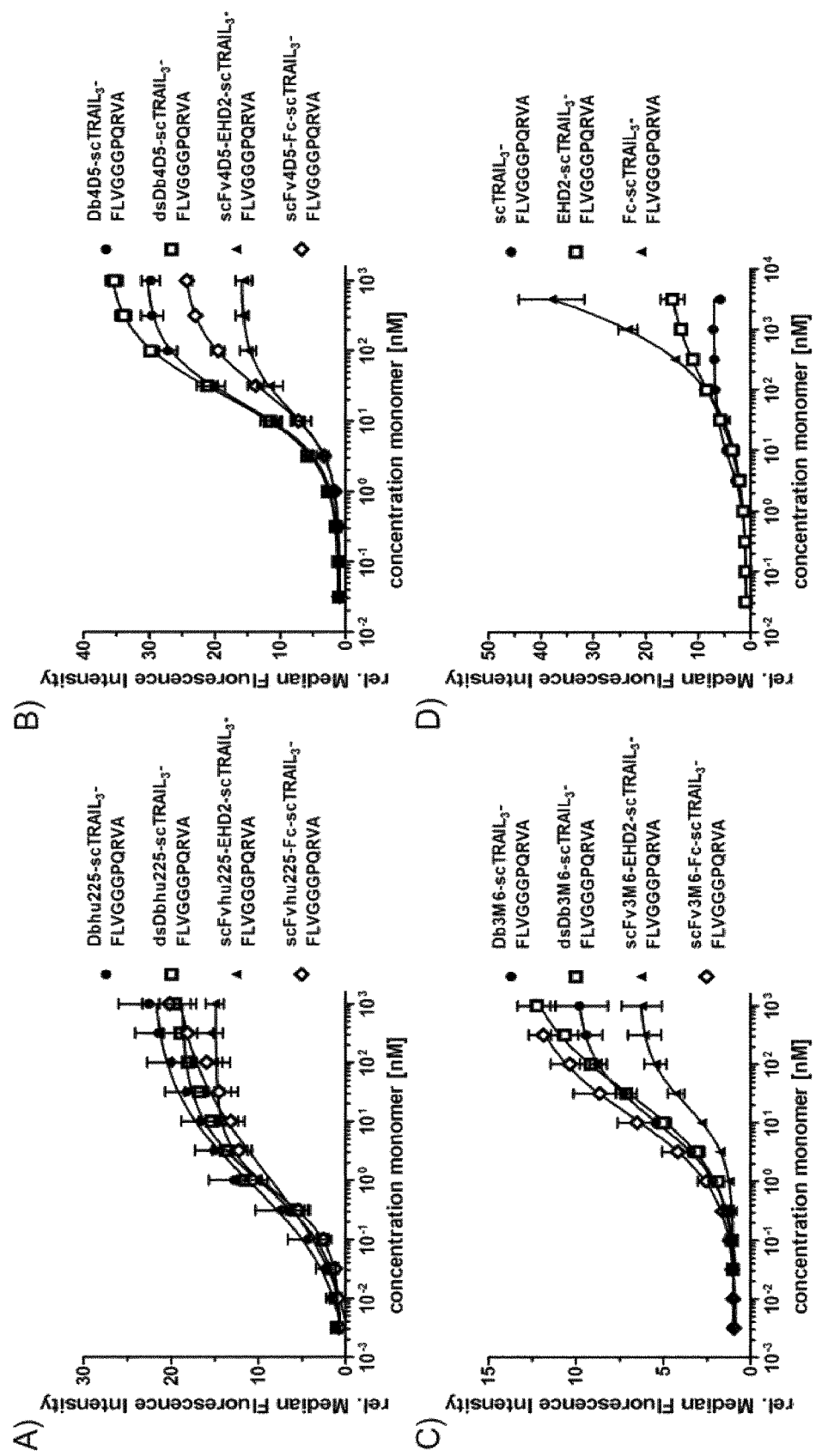

FIG. 23: Binding studies to intact Colo205 cells

Binding of scTRAIL$_3$-FLVGGGPQRVA fusion proteins targeting EGFR (A), HER2 (B), HER3 (C) and non-targeted constructs (D) to Colo205 cells was analyzed by flow cytometry. Data are represented as mean±S.D. (n=3).

Figure 24:
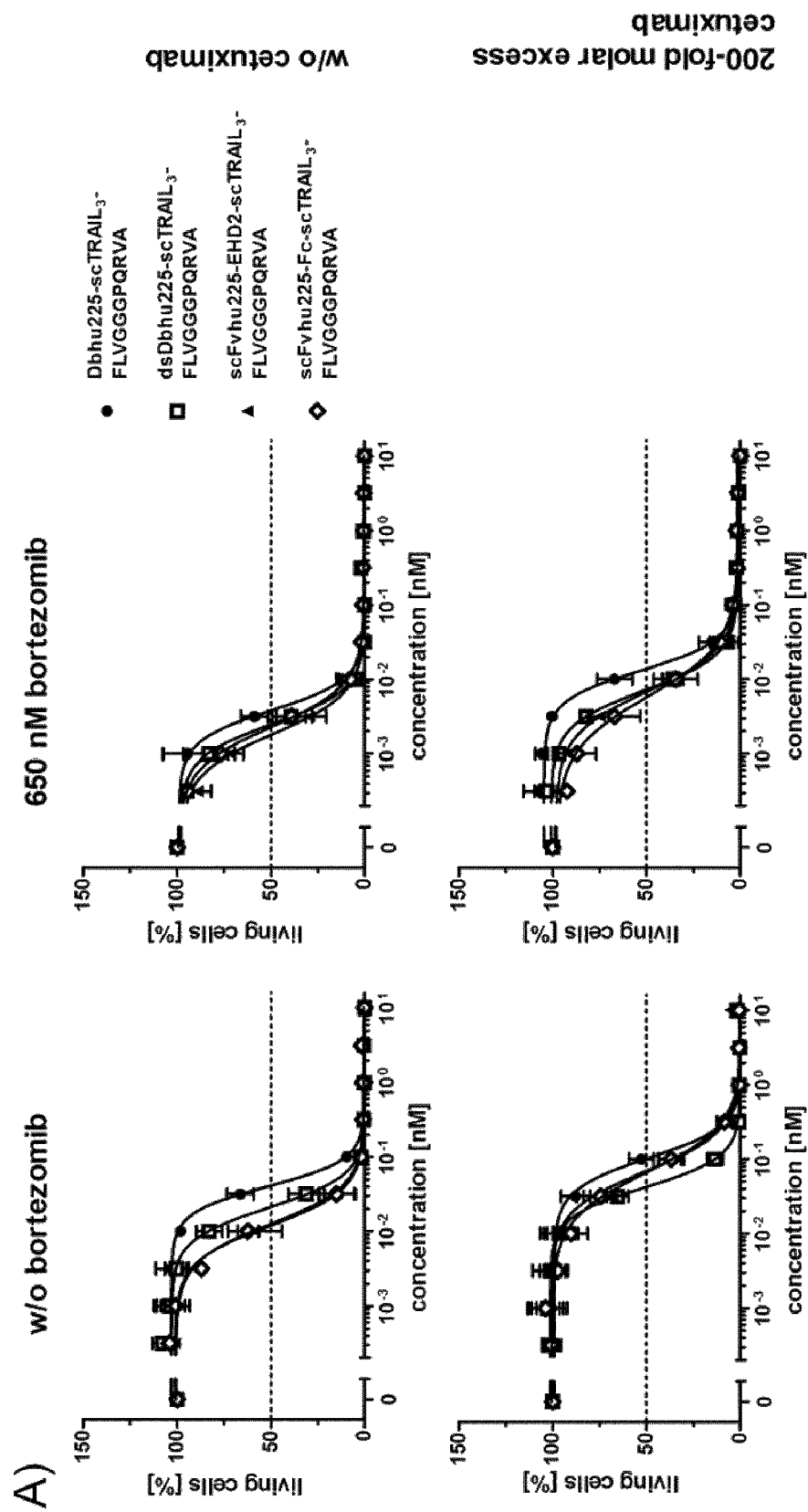
Figure 24:
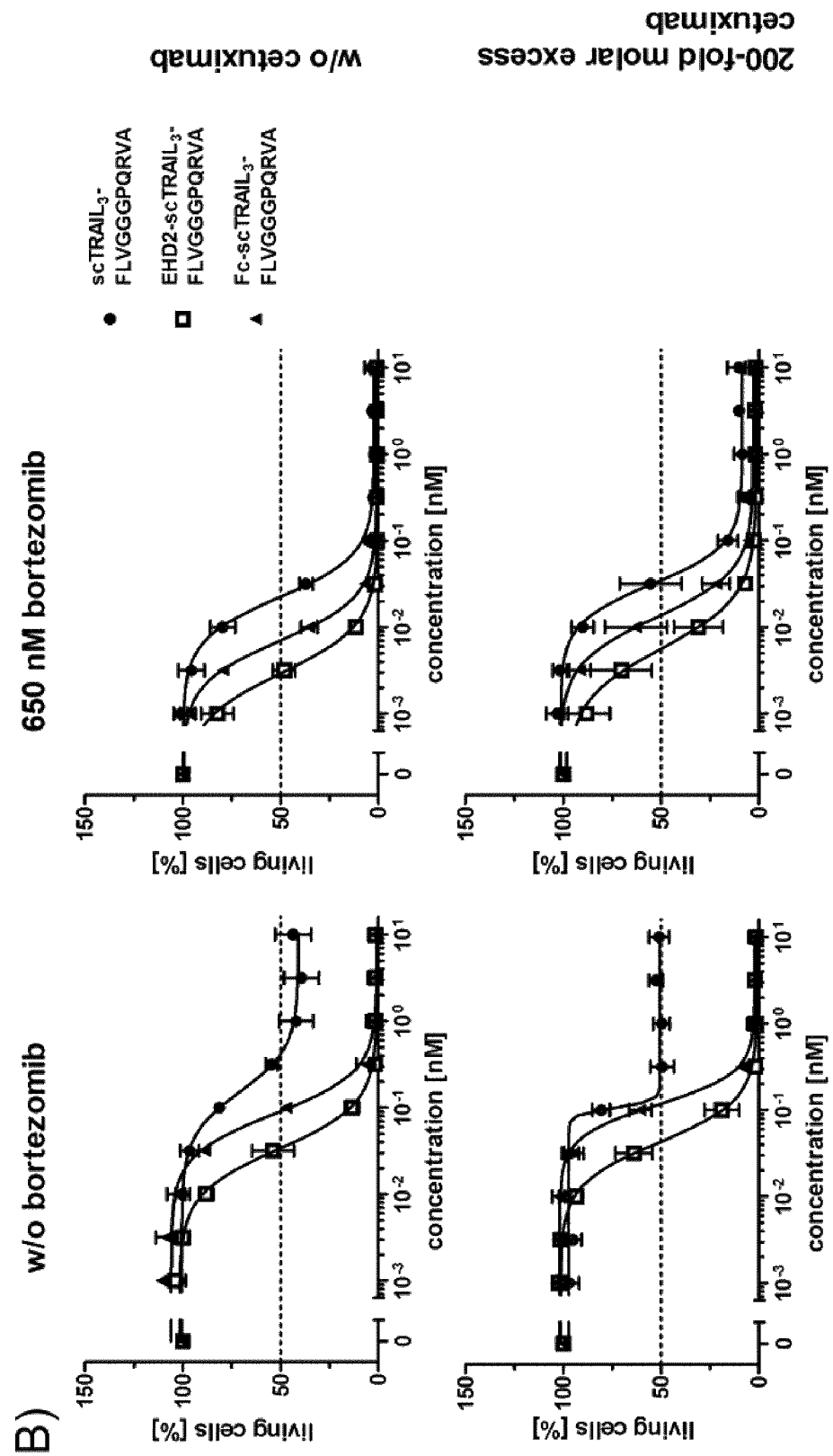

FIG. 24: Cytotoxicity induction in Colo205 cells by TRAIL variants: effects of sensitizers and EGFR targeting Induction of cell death of EGFR-targeting (A) and non-targeted (B) scTRAIL$_3$-FLVGGGPQRVA fusion proteins on Colo205 cells was analyzed in the absence and presence of Bortezomib (650 nM, 250 ng/ml). Effects of targeting were investigated by preincubation with Cetuximab (200-fold molar excess). Data are represented as mean±S.D. (n=3).

Figure 25:
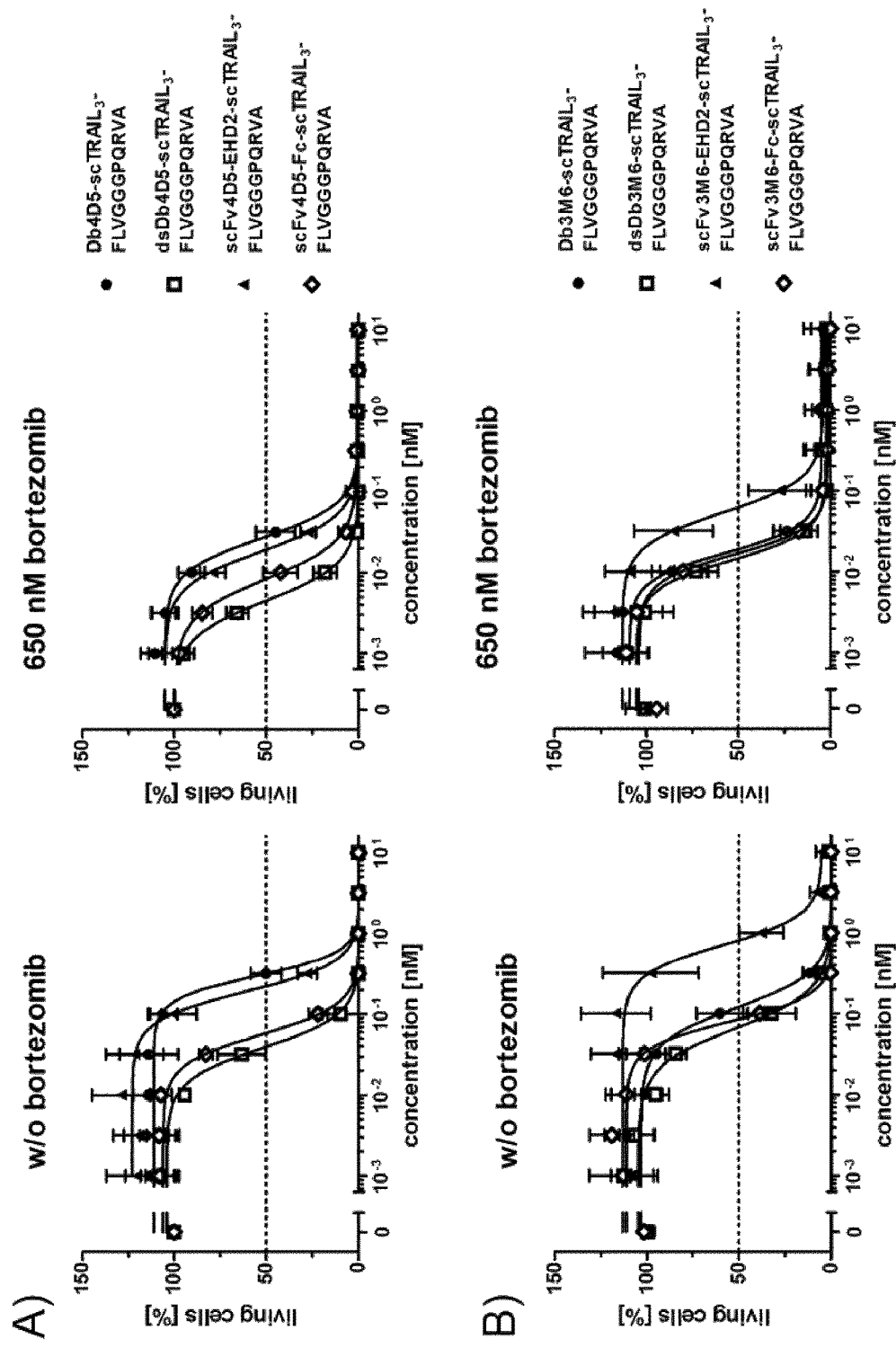

FIG. 25: Cytotoxicity induction in Colo205 cells upon HER2 and HER3 targeting targeting Induction of cell death of HER2-(A) and HER3-targeting (B) scTRAIL$_3$-FLVGGG-PQRVA fusion proteins on Colo205 cells was analyzed in the absence and presence of Bortezomib (650 nM, 250 ng/ml). Data are represented as mean±S.D. (n=3).

Figure 26:
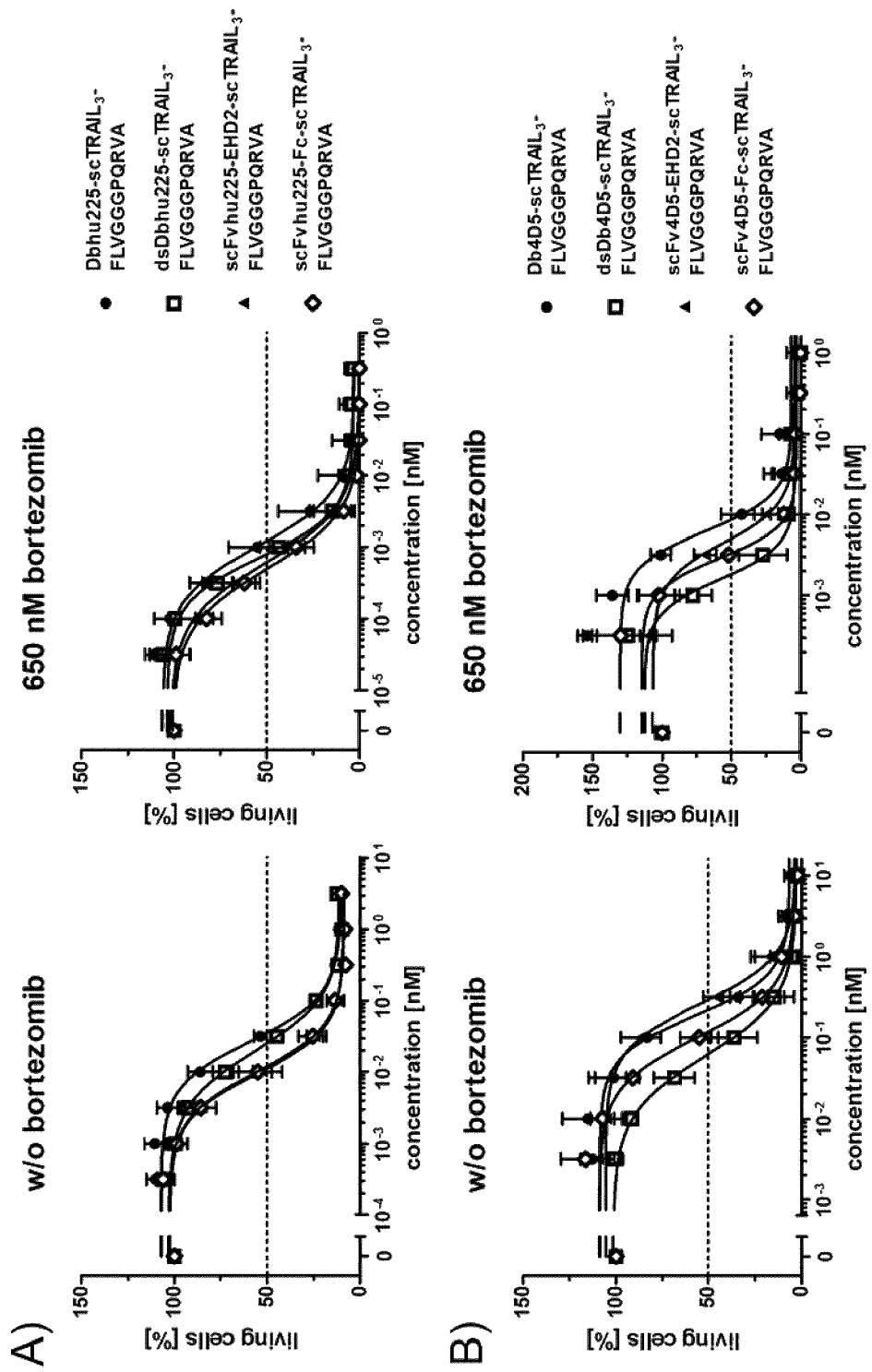
Figure 26:
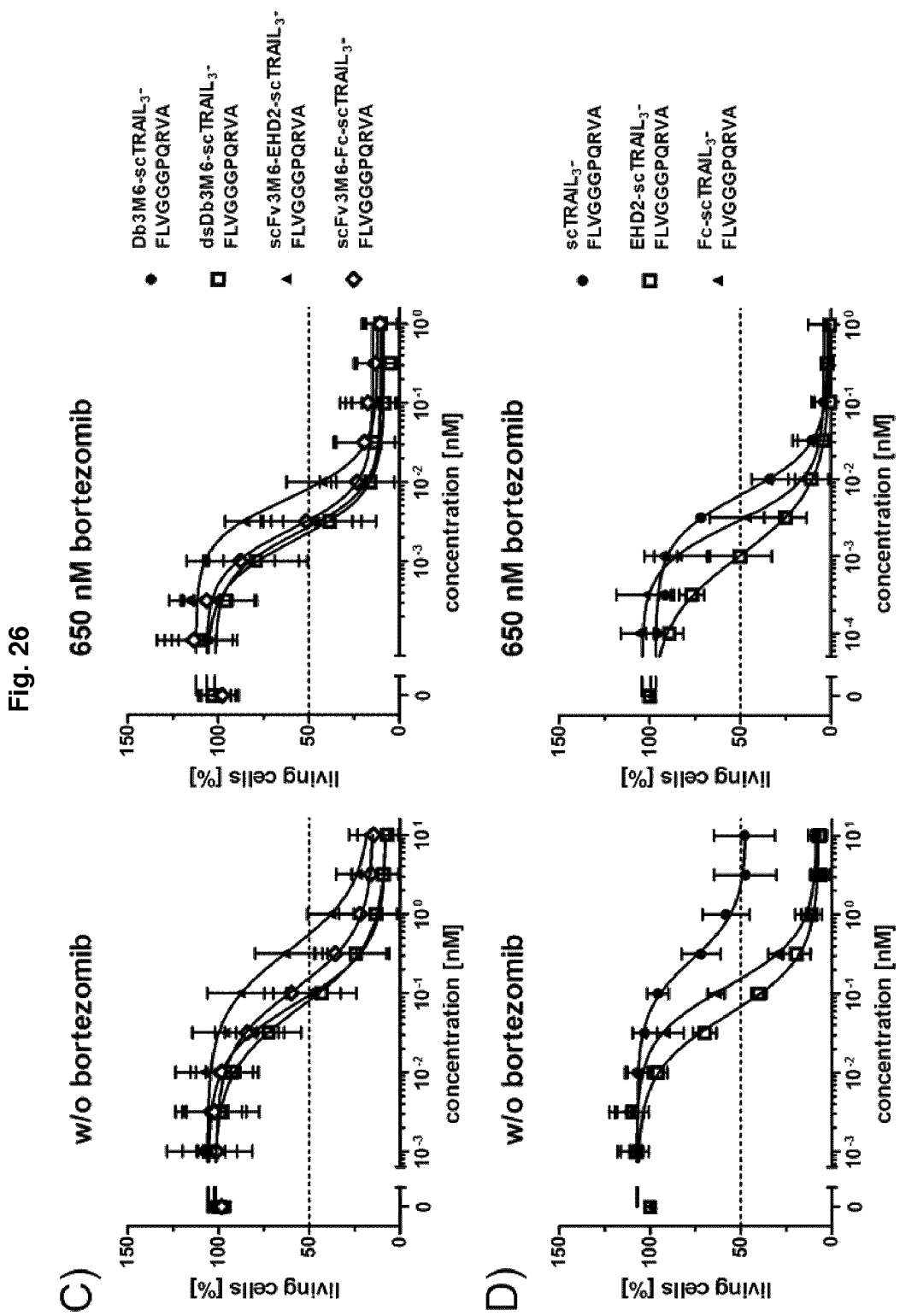

FIG. 26: Cytotoxicity assay with HCT-116 cells

Induction of cell death of EGFR-(A), HER2-(B), and HER3-targeting (C) and non-targeted (D) scTRAIL$_3$-FLVGGGPQRVA constructs on HCT-116 cells was analyzed in the absence and presence of Bortezomib (650 nM, 250 ng/ml). Data are represented as mean±S.D. (n=3).

Figure 27:
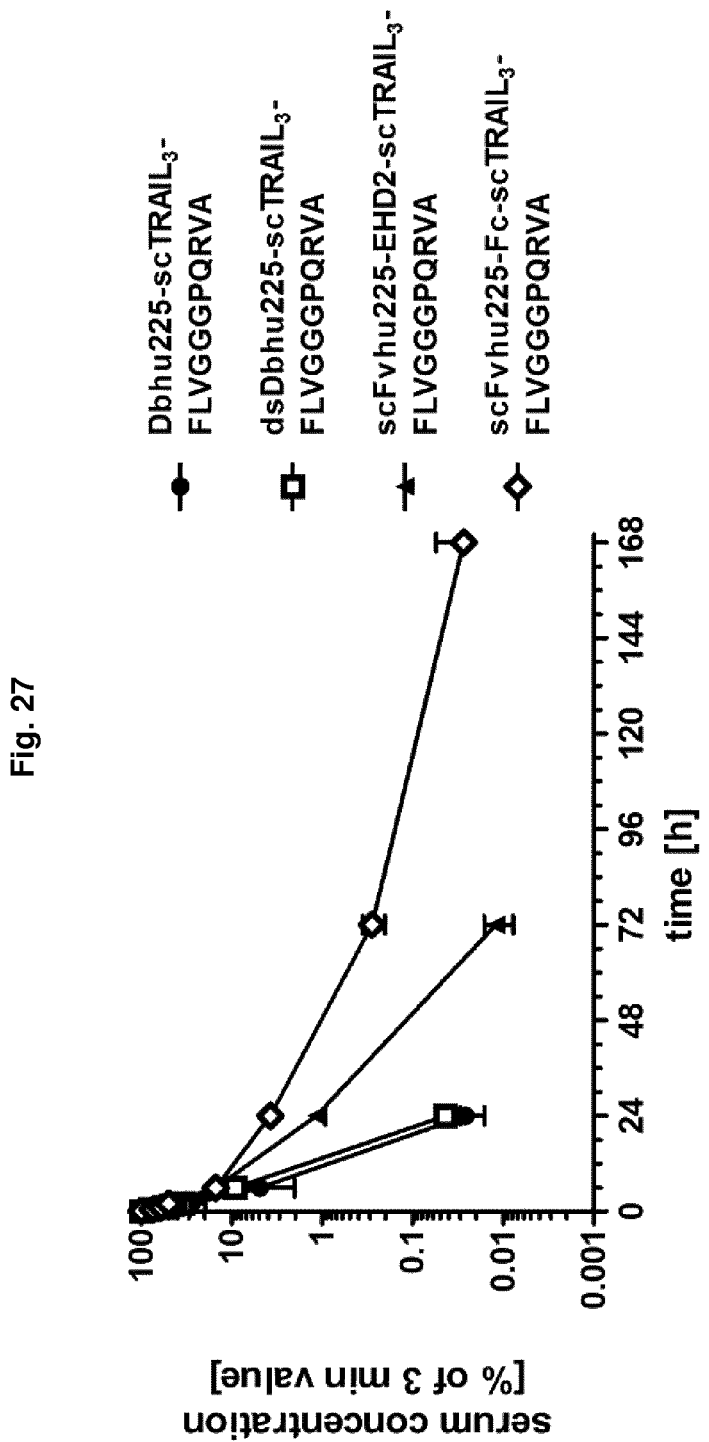

FIG. 27: Pharmacokinetic analyses

Pharmacokinetic properties of EGFR-targeting scTRAIL$_3$-FLVGGGPQRVA fusion proteins were analyzed in CD1 mice. 25 µg protein was i.v. injected into the tail vein. Protein concentrations in blood samples were determined at time points indicated by ELISA and normalized to the 3 min value. Data are represented as mean±S.D. (n=3).

Figure 28:
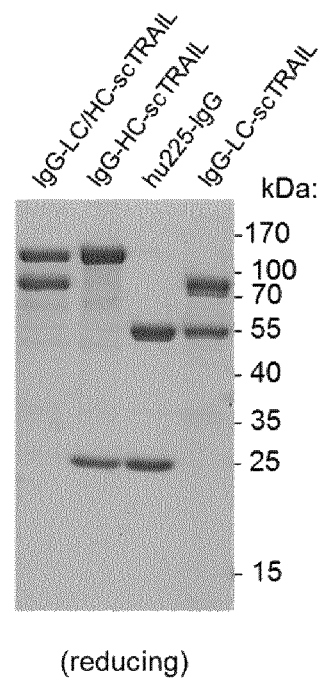

FIG. 28: Generation of IgG-scTRAIL$_3$ fusion proteins

Anti-EGFR IgG and anti-EGFR IgG-scTRAIL$_3$ fusion proteins were affinity purified from tissue culture supernatant obtained from transiently transfected HEK293 cells using anti-FLAG M2 agarose, and analyzed by reducing SDS-PAGE and Coomassie staining. Samples representing IgG-LC/HC-scTRAIL$_3$ (lane 1), IgG-heavy chain (HC)-scTRAIL$_3$ (lane 2), hu225 (anti-EGFR) IgG (lane 3) and IgG-light chain (LC)-scTRAIL$_3$ (lane 4) are shown.

Figure 29:
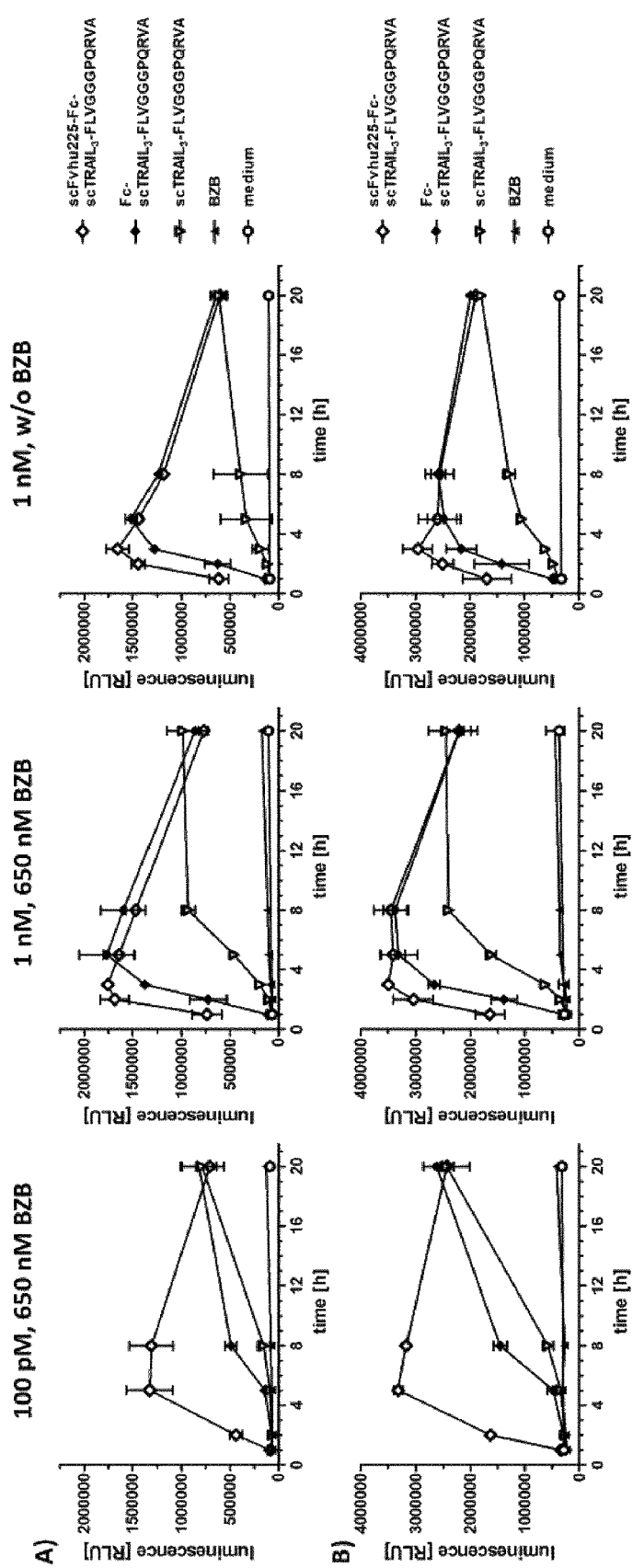

FIG. 29: Time-dependent caspase-8 (A) and -3/7 (B) activation in Colo205 cells

Caspase-8 (A) and -3/7 (B) activity was analyzed after treatment of the cells with scFvhu225-Fc-scTRAIL$_3$-FLVGGGPQRVA, Fc-scTRAIL$_3$-FLVGGGPQRVA, and scTRAIL$_3$-FLVGGGPQRVA at concentrations of 100 pM and 1 nM scTRAIL units in combination with bortezomib (BZB, 650 nM) or alone for 1 h, 2 h, 3 h, 5 h, 8 h, and 20 h. As controls, cells were treated either with bortezomib or with medium alone.

Figure 30:
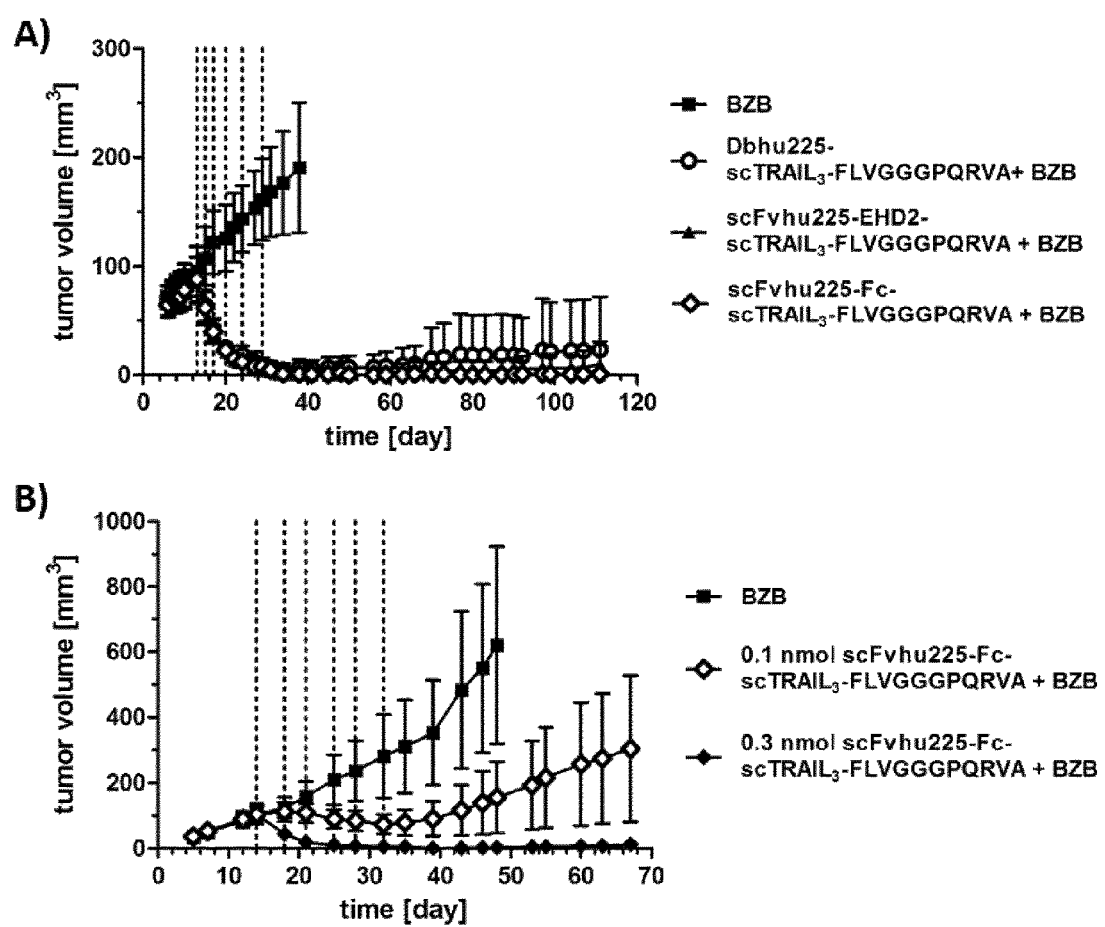

FIG. 30: Effects of EGFR-targeting scTRAIL$_3$-FLVGGG-PQRVA fusion proteins in Colo205 xenograft models NMRI nu/nu mice bearing Colo205 tumors with a size of ~100 mm$^3$ received six treatments with scTRAIL$_3$-FLVGGGPQRVA constructs in combination with bortezomib (5 µg BZB per treatment) or BZB alone. Points of treatment are indicated with dotted lines. A) 0.5 nmol dimeric EGFR-targeting scTRAIL$_3$-FLVGGGPQRVA molecules of different formats were analyzed. B) Effects of 0.1 nmol and 0.3 nmol scFvhu225-Fc-scTRAIL$_3$-FLVGGG-PQRVA were compared.

FIG. 31: Size exclusion chromatography and melting point of IgG-scTRAIL$_3$ (A) Affinity-purified preparations of anti-EGFR IgG, anti-EGFR IgG LC-scTRAIL$_3$-FAVSGAA, anti-EGFR IgG HC-scTRAIL3-FAVSGAA and anti-EGFR IgG LC/HC-scTRAIL$_3$-FAVSGAA were analyzed by size exclusion chromatography for their molecular constitution. The retention times of the standard proteins thyroglobulin (669 kDa), beta-amylase (200 kDa), bovine serum albumin (66 kDa), carboanhydrase (29 kDa) and FLAG peptide (1 kDa) are indicated by lines. (B) The melting point of anti-EGFR IgG HC-scTRAIL$_3$-FAVSGAA was analyzed by dynamic light scattering using a zetasizer instrument.

FIG. 32: EGFR-specific binding of IgG-scTRAIL$_3$ fusion proteins (A) The anti-EGFR human IgG1 scaffold antibody for IgG scTRAIL$_3$ fusion proteins was tested for binding to EGFR+ tumor cell lines Colo205 (mean±SEM, n=3) and HCT116 (mean±SEM, n=2) via flow cytometry, compared with the parental antibody cetuximab. (B) anti-EGFR IgG LC-scTRAIL$_3$-FAVSGAA, anti-EGFR IgG HC-scTRAIL$_3$-FAVSGAA and anti-EGFR IgG LC/HC-scTRAIL$_3$-FAVS-GAA were tested for binding to Colo205 and HCT116 cells via flow cytometry together with the scaffold antibody anti-EGFR IgG serving as a reference (mean±SEM, n=3). (C) Anti-EGFR IgG LC-scTRAIL$_3$-FAVSGAA, anti-EGFR IgG HC-scTRAIL$_3$-FAVSGAA and anti-EGFR IgG LC/HC-scTRAIL$_3$-FAVSGAA were tested for binding to purified EGFR-Fc via ELISA together with the scaffold antibody anti-EGFR IgG serving as a reference (mean±SEM, n=3).

Figure 33:
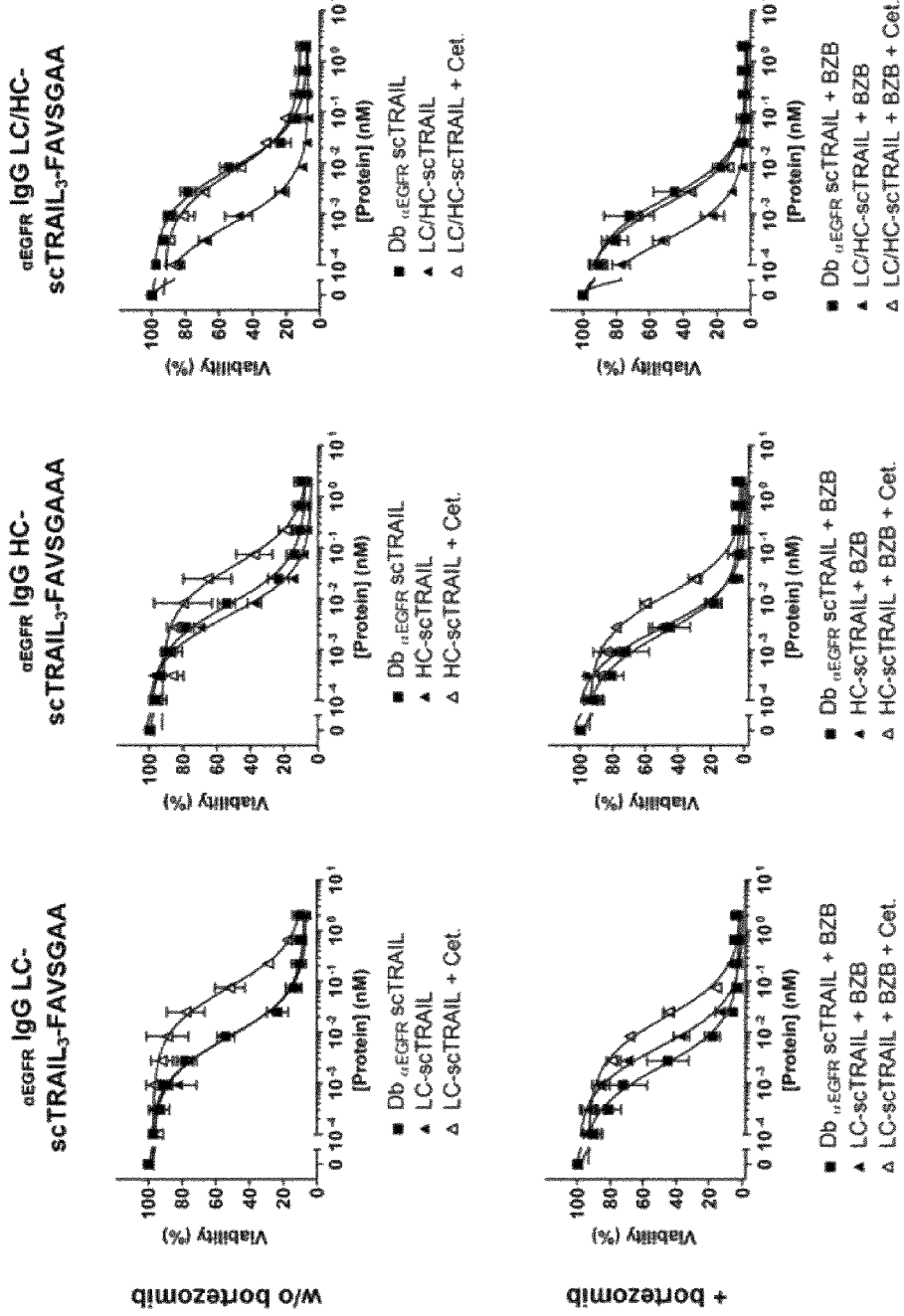

FIG. 33: Cell viability assay in HCT116 cells applying IgG-scTRAIL$_3$ fusion proteins Preparations of anti-EGFR IgG LC-scTRAIL$_3$-FAVS-GAA, anti-EGFR IgG HC-scTRAIL$_3$-FAVSGAA and anti-EGFR IgG LC/HC-scTRAIL$_3$-FAVSGAA were analyzed for their bioactivity in a cell viability assay using HCT116 cells sensitized with 5 ng/ml of the proteasome inhibitor bortezomib or without sensitization (mean±SEM, n=3). Where indicated, 10 µg/ml of the anti-EGFR antibody cetuximab was added prior to fusion protein incubation for EGFR competition studies.

Figure 34:
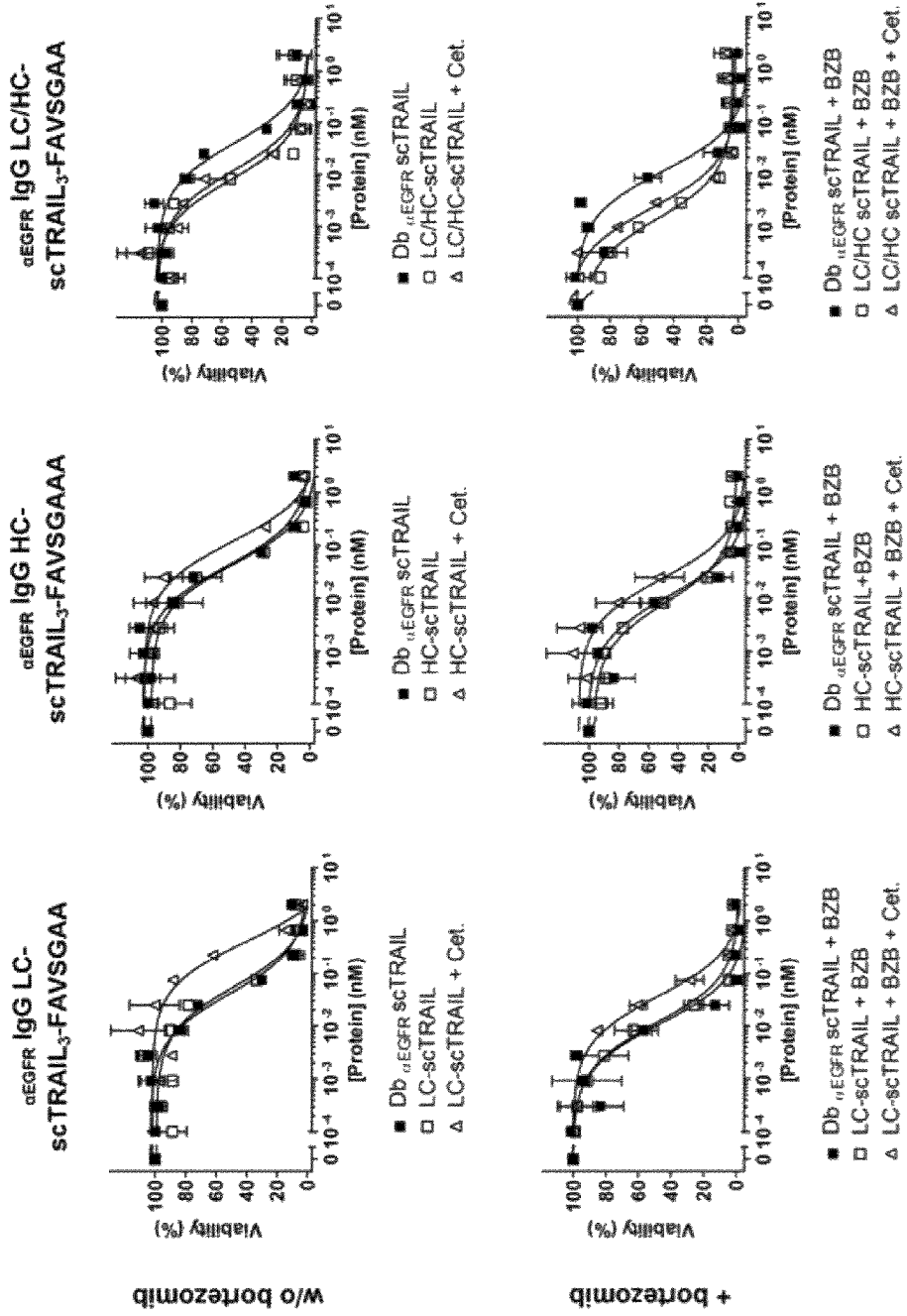

FIG. 34: Cell viability assay in Colo205 cells applying IgG-scTRAIL$_3$ fusion proteins Preparations of anti-EGFR IgG LC-scTRAIL$_3$-FAVS-GAA, anti-EGFR IgG HC-scTRAIL$_3$-FAVSGAA and anti-EGFR IgG LC/HC-scTRAIL$_3$-FAVSGAA were analyzed for their bioactivity in a cell viability assay using Colo205 cells sensitized with 250 ng/ml of the proteasome inhibitor bortezomib or without sensitization (mean±SEM, n=2). Where indicated, 10 µg/ml of the anti-EGFR antibody cetuximab was added prior to fusion protein incubation for EGFR competition studies.

Figure 35:
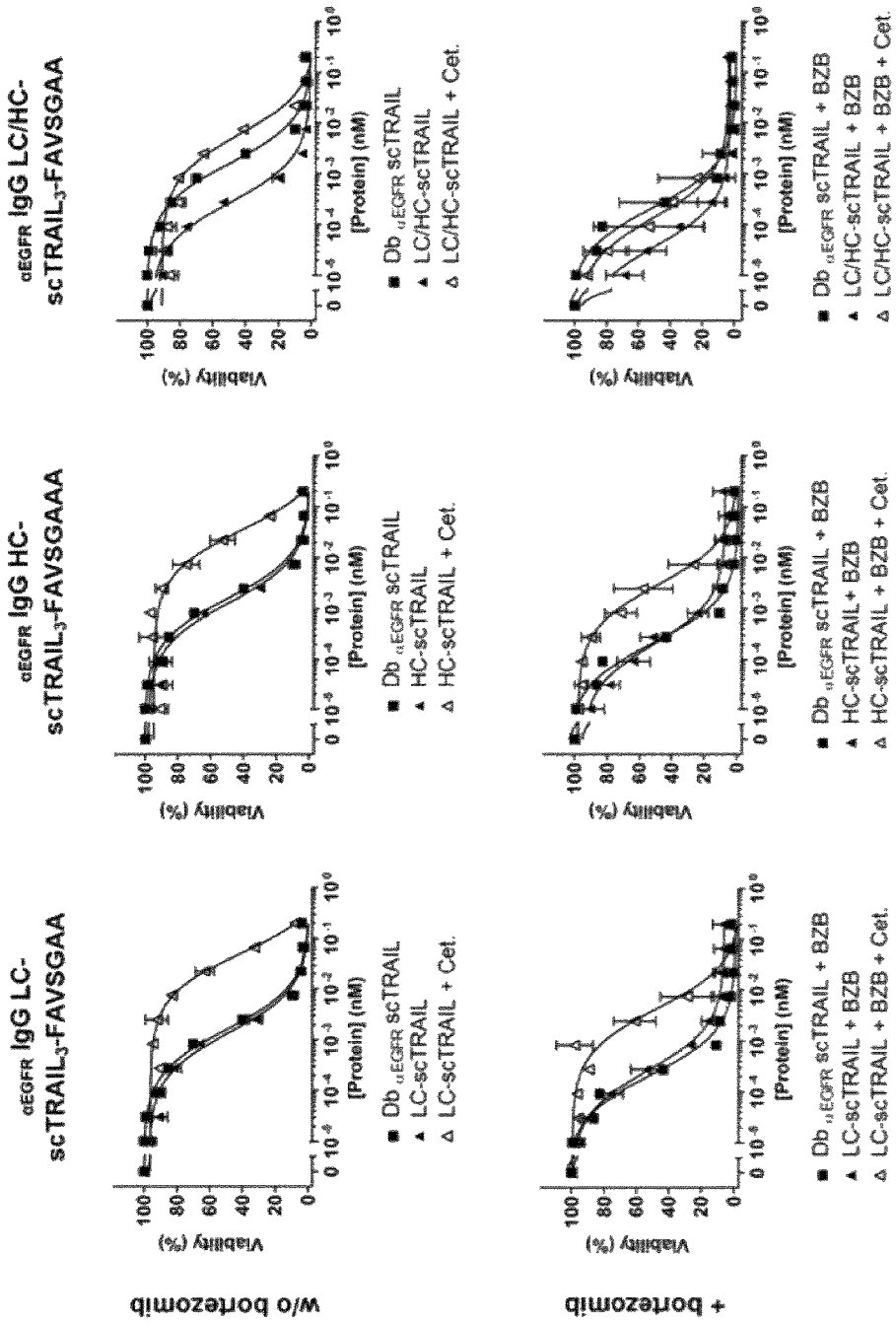

FIG. 35: Cell viability assay in HT1080 cells applying IgG-scTRAIL$_3$ fusion proteins Preparations of anti-EGFR IgG LC-scTRAIL$_3$-FAVS-GAA, anti-EGFR IgG HC-scTRAIL$_3$-FAVSGAA and anti-EGFR IgG LC/HC-scTRAIL$_3$-FAVSGAA were analyzed for their bioactivity in a cell viability assay using HT1080 cells sensitized with 10 ng/ml of the proteasome inhibitor bortezomib or without sensitization (mean±SEM, n=2). Where indicated, 10 µg/ml of the anti-EGFR antibody cetuximab was added prior to fusion protein incubation for EGFR competition studies.

Figure 36:
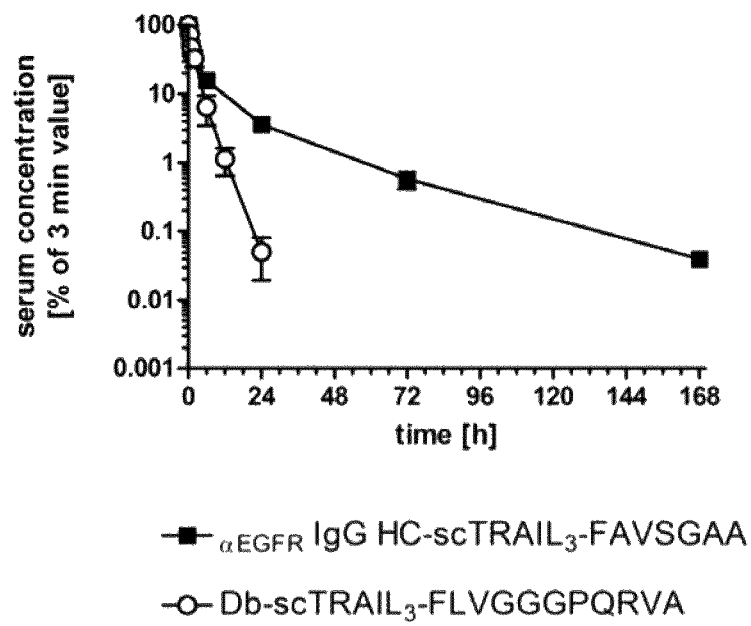

FIG. 36: Pharmacokinetics of anti-EGFR IgG HC-sc-TRAIL$_3$-FAVSGAA

Pharmacokinetic properties of EGFR-targeting IgG HC-scTRAIL$_3$-FAVSGAA were analyzed in CD1 mice.

Data points from Db-scTRAIL$_3$-FLVGGGPQRVA were plotted for reasons of comparison. 25 µg protein was i.v. injected into the tail vein. Protein concentrations in blood samples were determined at time points indicated by ELISA and normalized to the 3 min value. Data are represented as mean±S.D. (n=3).

FIG. 37: In vivo antitumor activity, pharmacokinetics and compatibility of Db10-Glyco-scTRAIL$_3$-FAVSGAA (A) Colo205-bearing nude mice received eight intravenous (i.v.) injections of the Db10-Glyco-scTRAIL$_3$-FAVSGAA fusion protein (0.1 nmol, 0.3 nmol, or 1.0 nmol) in combination with eight intraperitoneal (i.p.) injections of bortezomib (Brt; 5 µg per injection) every day indicated by dots. Mean±95% CI (n=12 tumors per group). The 1.0 nmol-treated group received an identical regime of Db10-Glyco-scTRAIL$_3$-FAVSGAA and bortezomib after regrowth of tumors (volume approximately 100 mm$^3$). Therefore, animals were divided into two subgroups of fast (I) and slow (II) regrowth. (B, C) Db10-Glyco-scTRAIL$_3$-FAVSGAA (168 µg per animal in B/25 µg per animal in C) was injected i.v. into Colo205-bearing nude mice (B) or CD-1 mice (C). The serum concentrations of the fusion protein were analyzed via ELISA. Mean±SD (n=3). (D, E) Activity of alanine aminotransferase (ALT, D) and α-amylase (E) was measured after 4 hours (only for D), 1 day, and 9 days after the first of total eight injections (every day) of Db10-Glyco-scTRAIL$_3$-FAVSGAA (0.1 nmol, 0.3 nmol, or 1.0 nmol; i.v.) and/or bortezomib (Brt, 5 µg; i.p.). Control mice were non-treated. Mean±SD (n=3).

FIG. 38: scTRAIL$_3$-FAVSGAA fusion proteins with Fc comprising a glycosylated peptide linker (A) Affinity-purified preparations of Fc-scTRAIL$_3$-FAVSGAA (SEQ ID NO: 246), scTRAIL$_3$-FAVSGAA-Fc (SEQ ID NO: 245) and scTRAIL$_3$-FAVSGAA-Fc-scTRAIL$_3$-FAVSGAA (SEQ ID NO: 247) were analyzed by size exclusion chromatography. (B) The same proteins were tested in ELISA for binding to TRAIL R1-Fc (n=1) and TRAIL R2-Fc (mean±S.D., n=4). Monomeric scTRAIL$_3$-FLVGGGPQRVA was used as a reference. (C) Fc-scTRAIL$_3$-FAVSGAA, scTRAIL$_3$-FAVSGAA-Fc and scTRAIL$_3$-FAVSGAA-Fc-scTRAIL$_3$-FAVSGAA were analyzed for their cytotoxic activity on Colo205 cells in presence or without 250 ng/ml bortezomib (Brt). Monomeric scTRAIL$_3$-FLVGGGPQRVA served as a reference (mean±S.D., n=3).

FIG. 39: scTRAIL$_3$-FAVSGAA fusion proteins with Fc comprising a glycine/serine, glycosylated or alpha-helical peptide linker (A) 1.3×10$^6$ HEK293 cells per 6-well were transiently transfected with 4 µg plasmid DNA and 12 µg polyethylene imine for expression of the listed scTRAIL$_3$-FAVSGAA Fc fusion proteins. 24 h after transfection, medium was replaced by 3 ml OptiMEM I+50 µM zinc chloride and cells were cultivated for three days at 37° C., 5% CO$_2$. The yields of produced protein in supernatants were assayed by TRAIL ELISA (BD Biosciences) (mean±S.D., n=3). (B) Affinity-purified preparations of the indicated scTRAIL$_3$-FAVSGAA Fc fusion proteins were analyzed by size exclusion chromatography. (C) Melting points of scTRAIL$_3$-FAVSGAA fusion proteins with Fc were determined by dynamic light scattering.

Figure 40:
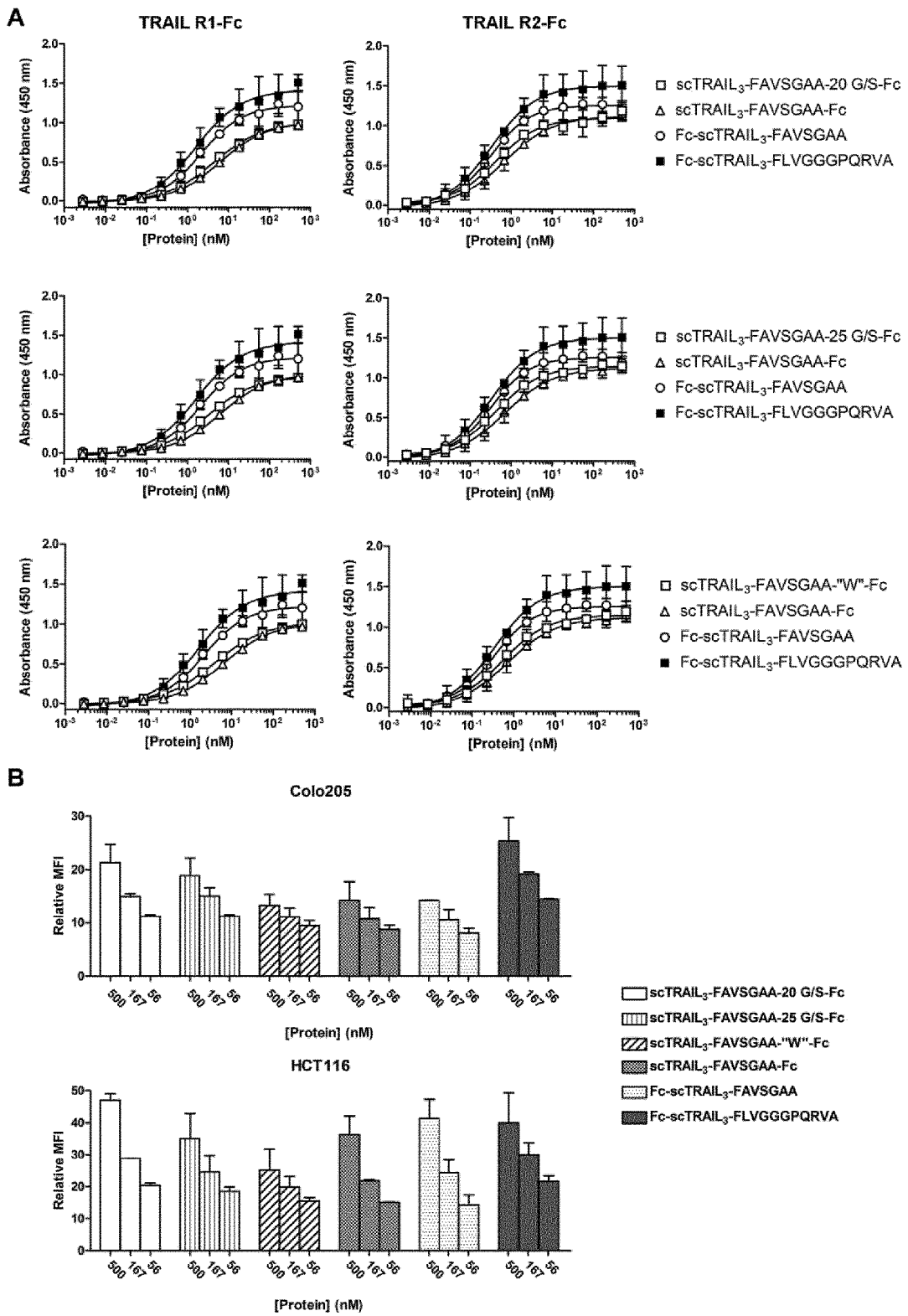

FIG. 40: Comparison of binding properties of scTRAIL$_3$ fusion proteins with Fc comprising a glycine/serine, glycosylated or alpha-helical peptide linker (A) Binding of scTRAIL$_3$-FAVSGAA-20 G/S-Fc (SEQ ID NO: 252), scTRAIL$_3$-FAVSGAA-25 G/S-Fc (SEQ ID NO: 253), scTRAIL$_3$-FAVSGAA-"W"-Fc (SEQ ID NO: 254), scTRAIL$_3$-FAVSGAA-Fc (SEQ ID NO: 245), Fc-scTRAIL$_3$-FAVSGAA (SEQ ID NO: 246) and Fc-scTRAIL$_3$-FLVGGGPQRVA to TRAIL-R1-Fc (left) or TRAIL-R2-Fc (right) in ELISA (mean±S.D., n=3). (B) Binding of scTRAIL$_3$-FAVSGAA-20 G/S-Fc, scTRAIL$_3$-FAVSGAA-25 G/S-Fc, scTRAIL$_3$-FAVSGAA-"W"-Fc, scTRAIL$_3$-FAVSGAA-Fc, Fc-scTRAIL$_3$-FAVSGAA and Fc-scTRAIL$_3$-FLVGGGPQRVA to Colo205 and HCT116 cells in flow cytometry (mean±S.D., n=3).

Figure 41:
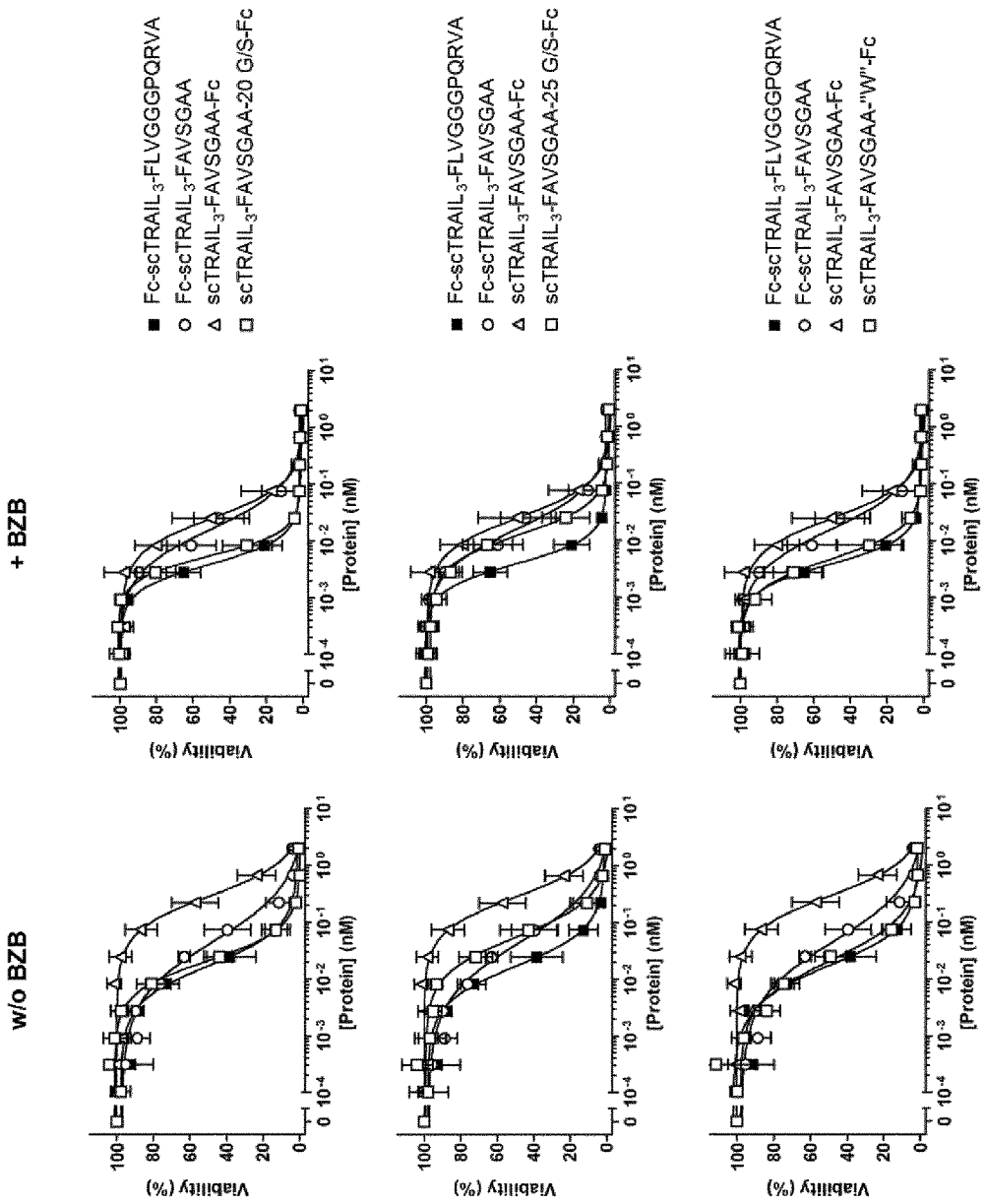

FIG. 41: Cell viability assay in Colo205 cells applying scTRAIL$_3$ Fc fusion proteins Preparations of scTRAIL$_3$-FAVSGAA-20 G/S-Fc, scTRAIL$_3$-FAVSGAA-25 G/S-Fc, scTRAIL$_3$-FAVSGAA-"W"-Fc, scTRAIL$_3$-FAVSGAA-Fc, Fc-scTRAIL$_3$-FAVSGAA and Fc-scTRAIL$_3$-FLVGGGPQRVA were analyzed for their bioactivity in a cell viability assay using Colo205 cells sensitized with 250 ng/ml of the proteasome inhibitor bortezomib (BZB) or without sensitization (mean±S.D., n=3).

Figure 42:
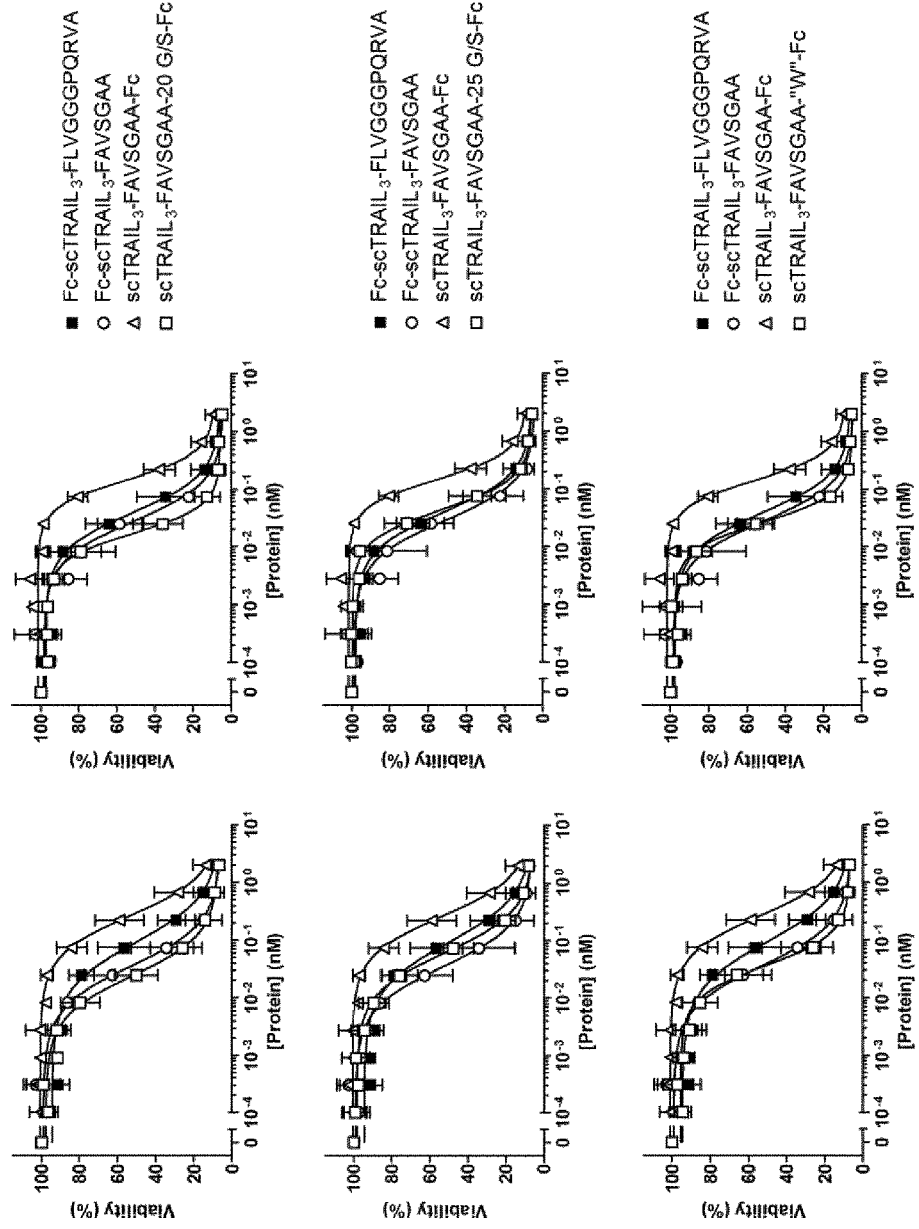

FIG. 42: Cell viability assay in HCT116 cells applying scTRAIL$_3$ Fc fusion proteins Preparations of scTRAIL$_3$-FAVSGAA-20 G/S-Fc, scTRAIL$_3$-FAVSGAA-25 G/S-Fc, scTRAIL$_3$-FAVSGAA-"W"-Fc, scTRAIL$_3$-FAVSGAA-Fc, Fc-scTRAIL$_3$-FAVSGAA and Fc-scTRAIL$_3$-FLVGGGPQRVA were analyzed for their bioactivity in a cell viability assay using HCT116 cells sensitized with 5 ng/ml of the proteasome inhibitor bortezomib (BZB) or without sensitization (mean±S.D., n=3).

Figure 43:
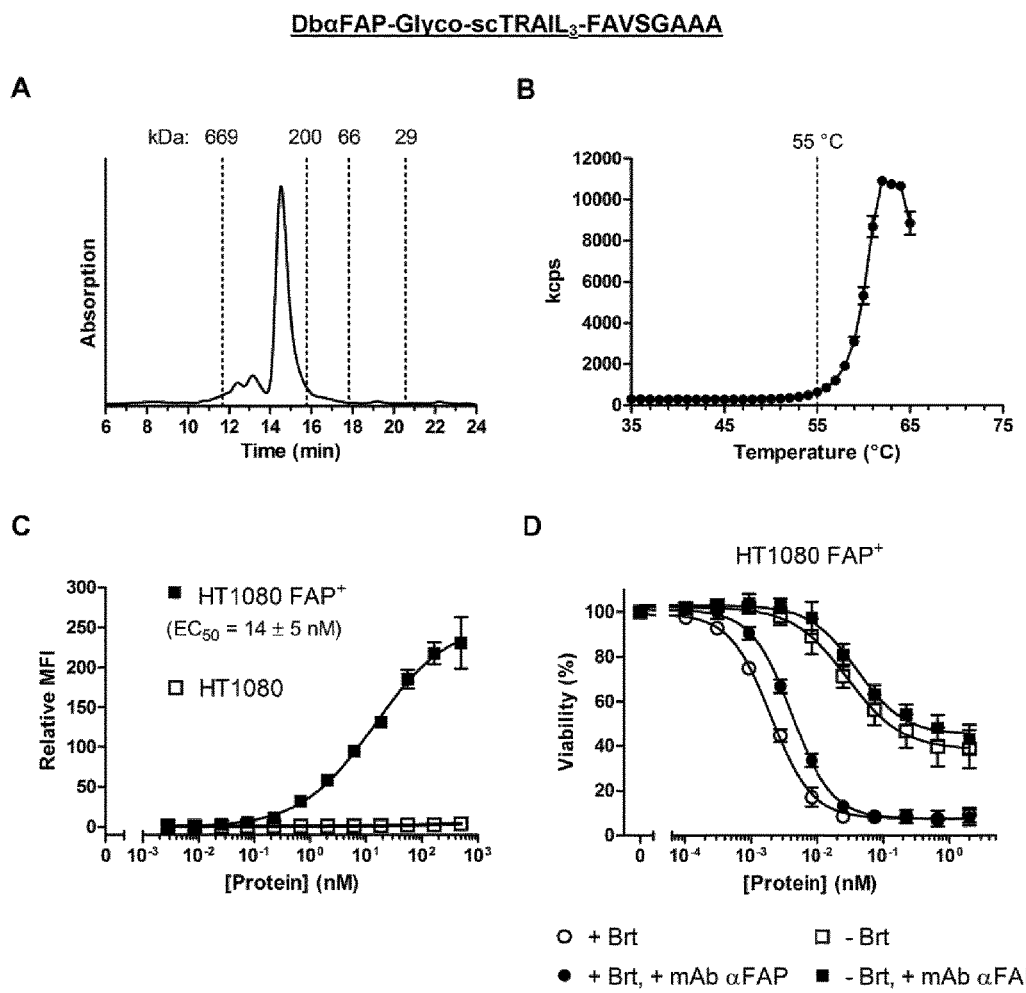

FIG. 43: Biochemical properties and target-dependent bioactivity of DbaFAP-Glyco-scTRAIL3-FAVSGAA (A) Size exclusion chromatogram of Db anti-FAP-Glyco-scTRAIL$_3$-FAVSGAA (SEQ ID NO: 255). (B) Melting point of Db anti-FAP-Glyco-scTRAIL$_3$-FAVSGAA as detected by dynamic light scattering. (C) Binding of Db anti-FAP-Glyco-scTRAIL$_3$-FAVSGAA to HT1080 tumor cells transfected with FAP in comparison to HT1080 wt (control) (mean±S.D., n=2). (D) Bioactivity of Db anti-FAP-Glyco-scTRAIL$_3$-FAVSGAA on HT1080 FAP cells in presence or absence of competing anti-FAP IgG antibody in vitro (Brt, bortezomib) (mean±S.D., n=4).

Figure 44:
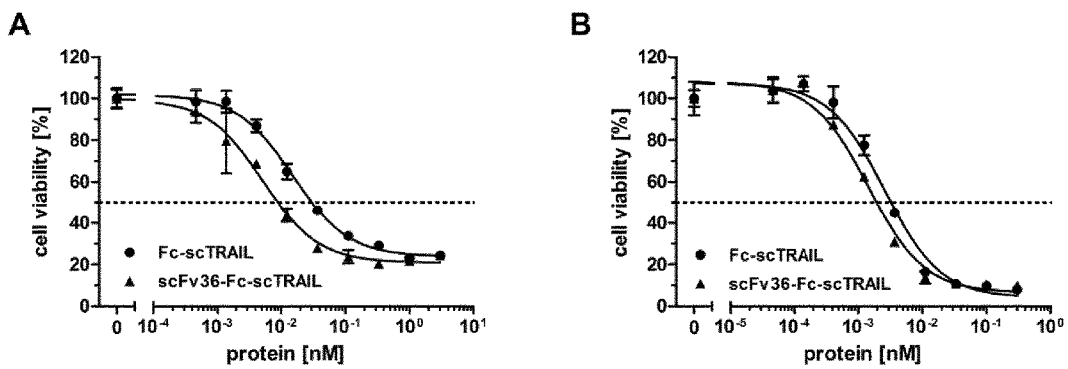

FIG. 44: Cell viability assay in HT1080 FAP+ cells applying Fc-scTRAIL and scFv36-Fc-scTRAIL$_3$ fusion proteins Preparation of Fc-scTRAIL$_3$-FLVGGGPQRVA and scFv36-Fc-scTRAIL$_3$-FLVGGGPQRVA were analyzed for their bioactivity in a cell viability assay using stably transfected HT1080 FAP cells in the absence (A) or presence (B) of bortezomib (13 nM final concentration) (mean±SD).

Figure 45:
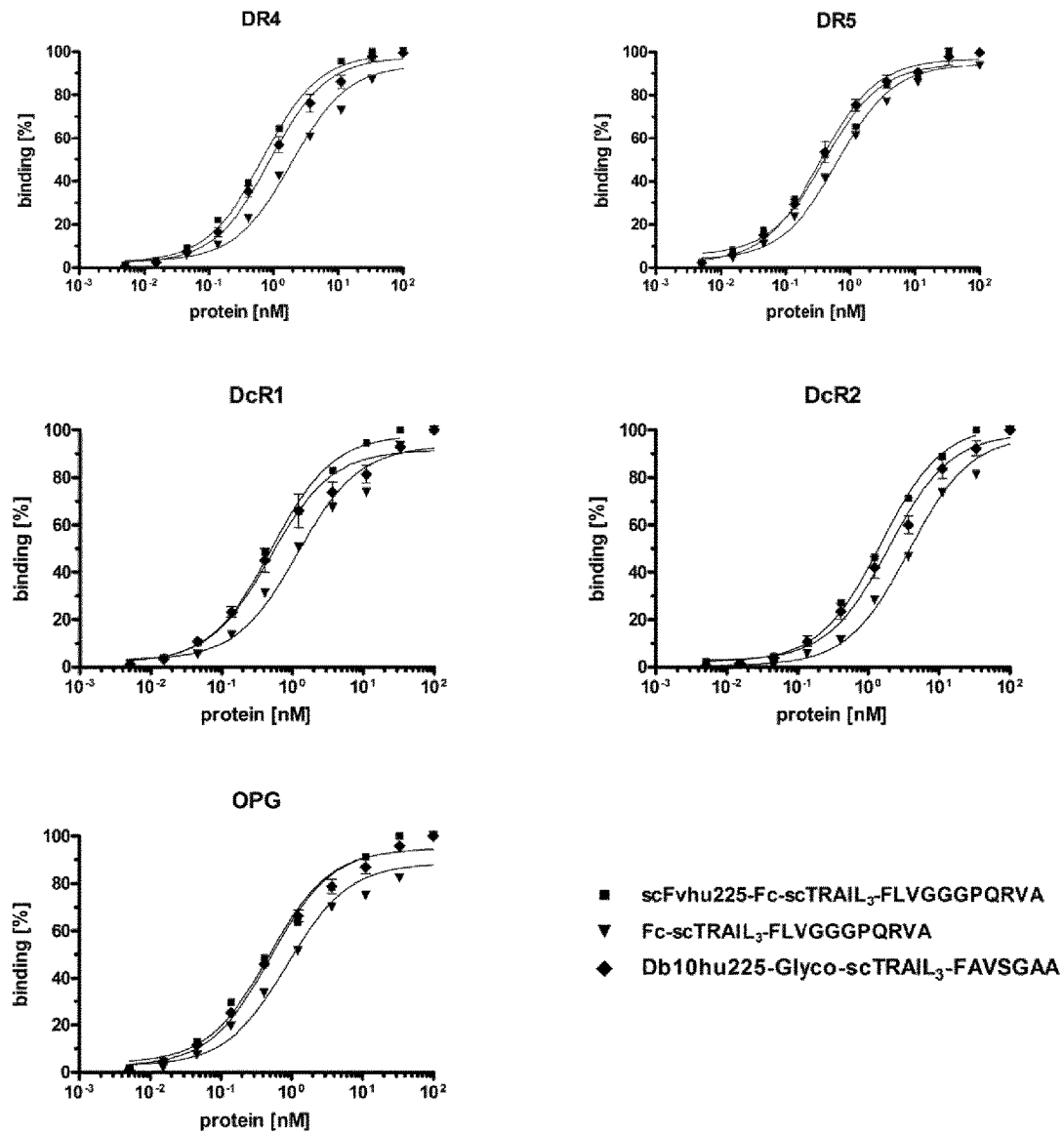

FIG. 45: Binding of scTRAIL$_3$ fusion proteins to human TRAIL receptors via ELISA Preparations of scFhu225-Fc-scTRAIL$_3$-FLVGGGPQRVA, Fc-scTRAIL$_3$-FLVGGGPQRVA, and Db10hu225-Glyco-scTRAIL$_3$-FAVSGAA were analyzed in ELISA for binding to human DR4-Fc (TRAIL-R1-Fc), DR5-Fc (TRAIL-R2-Fc), DcR1-Fc (TRAIL-R3-Fc), DcR2-Fc (TRAIL-R4-Fc), and OPG-Fc (mean±SD).

DETAILED DESCRIPTION OF THE INVENTION

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Several documents are cited throughout the text of this specification. Each of the documents cited herein (including all patents, patent applications, scientific publications, manufacturer's specifications, instructions etc.), whether supra or infra, is hereby incorporated by reference in its entirety. Nothing herein is to be construed as an admission that the invention is not entitled to antedate such disclosure by virtue of prior invention. Some of the documents cited herein are characterized as being "incorporated by reference". In the event of a conflict between the definitions or teachings of such incorporated references and definitions or teachings recited in the present specification, the text of the present specification takes precedence.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Definitions

In the following, some definitions of terms frequently used in this specification are provided. These terms will, in each instance of its use, in the remainder of the specification have the respectively defined meaning and preferred meanings.

As used in this specification and the appended claims, the singular forms "a", "an", and "the" include plural referents, unless the content clearly dictates otherwise.

The term "polypeptide" refers to any peptide-bond-linked polymer of amino acids. A polypeptide can be one chain or may be composed of more than one chain, which are held together by covalent bonds, e.g. disulphide bonds and/or non-covalent bonds. Modifications of the peptide bonds or of side chains residues are possible, provided the activity of the resulting chemical entity (e.g. component A linked to component B) is not totally lost. The term shall not be construed as limiting the length of the polypeptide.

In the context of the present invention, the term "peptide" refers to a short polymer of amino acids linked by peptide bonds. It has the same chemical (peptide) bonds as proteins but is commonly shorter in length. The shortest peptide is a dipeptide consisting of two amino acids joined by a peptide bond. There can also be tripeptides, tetrapeptides, pentapeptides etc. A peptide has an amino end and a carboxyl end, unless it is a cyclic peptide. Peptides usable in the present invention (including peptide derivatives, peptide variants, peptide fragments, peptide segments, peptide epitopes and peptide domains) can be further modified by chemical modification. This means such a chemically modified peptide may comprise other chemical groups than the 20 naturally occurring proteinogenic amino acids. Examples of such other chemical groups include without limitation glycosylated amino acids and phosphorylated amino acids. Chemical modifications of a peptide may provide advantageous properties as compared to the parent peptide, e.g. one or more of enhanced stability, increased biological half-life, or increased solubility.

The term "protein" as used in the context of the present specification refers to a molecule comprising one or more polypeptides that resume a secondary and tertiary structure and additionally refers to a protein that is made up of several polypeptides, i.e. several subunits, forming quaternary structures. The protein has sometimes non-peptide groups attached, which can be called prosthetic groups or cofactors.

The term "C-terminus" (also known as the carboxyl-terminus, carboxy-terminus, C-terminal tail, C-terminal end, or COOH-terminus) as referred to within the context of the present invention is the end of an amino acid chain (protein or polypeptide), terminated by a free carboxyl group (—COOH). When the protein is translated from messenger RNA, it is created from N-terminus to C-terminus The term "N-terminus" (also known as the amino-terminus, $NH_2$-terminus, N-terminal end or amine-terminus) refers to the start of a protein or polypeptide terminated by an amino acid with a free amine group (—$NH_2$). The convention for writing peptide sequences is to put the N-terminus on the left and write the sequence from N- to C-terminus.

The term "TNF homology domain of TNF-ligand family member proteins" (THD) as used in the present specification refers to a protein domain shared by all tumor necrosis factor (TNF, formerly known as TNFα or TNF alpha) ligand family members. Homology implies evolutionary lineage from a common ancestor. A homology domain is a conserved part of a given protein sequence and (tertiary) structure that can evolve, function, and exist independently of the rest of the protein chain. It is a structural feature shared by all members of a certain protein family. Each domain forms a compact three-dimensional structure and often can be independently stable, folded and critical for biological activity. The C-terminus of a THD within the meaning of the present invention is defined by the C-terminal consensus sequence: -S/T/V-F/Y/S-F-G-A/L/V/I-$X_1$ (SEQ ID NO: 1) and the N-terminus is defined by one of the two N-terminal consensus sequences: $X_2$-V/A/F-A-H-V/L/I/Y (SEQ ID NO: 2) or $X_3$-V/W/F/C-A/L-E/Y/Q/H-L (SEQ ID NO: 3), wherein $X_1$ is a non-polar/hydrophobic or polar/neutral amino acid, preferably selected from the group consisting of F, V, Q, A, I, L, and Y; $X_2$ is selected from the group consisting of P, K, V, I, and A; and $X_3$ is selected from the group consisting of D, S, M, and I. On the basis of a given TNF-ligand family member protein sequence and using above defined C-terminal and N-terminal homology sequences the skilled person can determine for the given TNF-ligand family member protein the THD. Among the members of the TNF family, the position and length of individual THDs vary considerably, but can be defined by the occurrence of conserved amino acid residues as identified by multiple sequence alignments using appropriate software tools (Bodmer et al., 2002). More importantly, crystal structures can reveal distinct interactions between amino acid residues involved in, for example, homotrimerization of TNF family ligands. Informations of such kind can be helpful to refine THDs for given members of the TNF superfamily as described in Bodmer et al., 2002. Furthermore, functional aspects like protein solubility or bioactivity, such as receptor binding and activation, of engineered protein variants can provide important hints regarding crucial amino acid residues or the minimal length of individual THDs. The term THDs comprises polypeptides based on naturally occurring TNF-ligand family member protein sequences as well as variants thereof, which retain the ability to bind specifically to the receptor of the respective TNF-ligand family member. Preferably such THD variants have an affinity of at least 50% of the wild type THD, more preferably at least 60%, 70%, 80%, 90% and most preferably at least 99%.

TNF-ligand family member proteins comprise a group of multifunctional cytokines that can cause, e.g. programmed cell death (apoptosis), differentiation, cell survival, and immune regulation. TNF is a monocyte-derived cytokine that has been implicated in tumor regression, septic shock, and cachexia which is recognized by its specific receptor. Nineteen proteins have been identified as part of the TNF-ligand family on the basis of sequence, functional, and structural similarities. All these cytokines seem to form homotrimeric (or heterotrimeric in the case of LT-alpha/beta) complexes that are recognized by their specific receptors. The following proteins are members of the TNF-ligand family: TNF-related apoptosis inducing ligand (TRAIL; TNFSF10), a cytokine that induces apoptosis; CD40L (TNFSF5=tumor necrosis factor superfamily member 5), a cytokine that seems to be important in B-cell development and activation; CD27L (TNFSF7), a cytokine that plays a role in T-cell activation which induces the proliferation of co-stimulated T cells and enhances the generation of cytolytic T cells; CD30L (TNFSF8), a cytokine that induces proliferation of T cells; FasL (TNFSF6), a cell surface protein involved in cell death; 4-1BBL (TNFSF9), an inducible T cell surface molecule that contributes to T-cell stimulation; OX40L (TNFSF4), a cell surface protein that co-stimulates T cell proliferation and cytokine production. Further members of the TNF-ligand family members comprise EDA; LTA (TNFSF1); LTB (TNFSF3); CD153 (TNFSF8); RANKL (TNFSF11); TWEAK (TNFSF12); APRIL (TNFSF13); BAFF (TNFSF13B); LIGHT (TNFSF14); VEGI (TNFSF15); GITRL (TNFSF18). More information about the sequences of TNF-ligand family members may be obtained for example from publicly accessible databases such as Genbank. TNF-ligand family members interact with their cognate receptors, e.g. TNF with TNFR1 and TNFR2, TRAIL with TRAILR1 (DR4), TRAILR2 (DR5), TRAILR3 (DcR1), TRAILR4 (DcR2) and OPG. The ligands mediate oligomerization and activation of their respective receptors. The interaction of members of the TNF receptor family with its ligands is characterized by binding of the receptors at the space between two of the three TNF-ligand family member protein monomers of the TNF-ligand family member protein homotrimer, the biological active form of TNF and other members of the TNF-ligand family.

The apoptosis-inducing cytokine TRAIL is expressed on many cells of the innate and adaptive immune system in a stimulus dependent manner. TRAIL exerts its function via high affinity binding of multiple receptors. Two of these receptors (DR4 and DR5) recruit adapter proteins via death domain interactions and initiate the formation of the death inducing signaling complex (DISC) leading in turn to the induction of apoptosis. Binding of homotrimeric TRAI1 to DR4 and DR5 induces oligomerization of the receptors and initiation of a caspase-mediated pathway. Besides the induction of apoptosis, TRAIL is also capable of weakly activating NFκB and MAP kinase pathways. TRAIL has shown activity against primary tumor explants derived from patient pancreatic and colorectal cancer. Anti-tumor activity of TRAIL may be enhanced when administered in combination with other chemotherapeutics. Thus, agonizing TRAIL-death receptors is a promising strategy for therapy of hyperproliferative disorders and autoimmune disorders.

The term "consensus sequence" as used within this specification refers to a calculated order of most frequent residues, either nucleotide or amino acid, found at each position in a sequence alignment between two or more sequences. It represents the results of a multiple sequence alignment in which related sequences are compared to each other and similar sequence motifs are calculated. Conserved sequence motifs are depicted as consensus sequences, which indicate identical amino acids, i.e. amino acids identical among the compared sequences, conserved amino acids, i.e. amino acids which vary among the compared amino acid sequence but wherein all amino acids belong to a certain functional or structural group of amino acids, e.g. polar or neutral, and variable amino acids, i.e. amino acids which show no apparent relatedness among the compared sequence.

The consensus sequence of the C-terminus and N-terminus of the THD is a sequence that is located within the TNF-ligand family member sequence, respectively, and is particularly conserved among TNF-ligand family members. These sequences delineate the part of the TNF-ligand family member participating in the trimerization. Accordingly, the two consensus sequences serve as C-terminal and N-terminal reference points within a given TNF-ligand family member, which may comprise additional N- or C-terminal amino acids that may not be present in other TNF-ligand family members. Thus, the use of consensus sequences allows to refer to the same region of different TNF-ligand family member without referring to a specific position as the N-terminal and C-terminal end of the fragment of the TNF-ligand family member present in the polypeptides of the invention. Human TRAIL, for example, comprises the following amino acid sequence spanning amino acid positions 121 to 125: VAAHI (SEQ ID NO: 25). Accordingly, the skilled person can determine the absolute amino acid position of the amino acids of the C-terminal and N-terminal consensus sequence by determining its absolute position within the full-length amino acid sequence of a given TNF-ligand family member. For example $X_2$ of the N-terminal consensus sequence corresponds to the amino acid at position 122 of human TRAIL, and is preferably valine. $X_2$ corresponds to position 145 in human FasL and is preferably lysine. It corresponds to amino acid position 88 in human TNF and is preferably proline. It is immediately apparent to the skilled person that the different lengths of N-terminal amino acids preceding the N-terminal consensus sequence in different TNF-ligand family members requires a definition of the C- and N-terminal reference point that is independent of the absolute position of the THD within the respective TNF-ligand family member.

The term "dimerization domain" as used herein refers to a protein or polypeptide, a fragment or part of a protein or polypeptide which mediates a close proximity between two identical or different protein or polypeptide molecules (monomers) of the invention and thus, enables protein-protein interaction which allows dimerization of two structurally similar or different monomers joined by non-covalent or covalent bonds. The dimerization leads to the formation of a macromolecular complex formed by two, covalently or non-covalently bound, macromolecules such as proteins.

In the context of the present invention the term "half-life-extension domain" refers to a binding moiety which prolongs the serum/plasma half-life of a pharmaceutically active moiety, i.e. a pharmaceutically active moiety exhibits a prolonged serum/plasma half-life when being part of the half-life-extension domain. The binding moiety may be but is not limited to a polypeptide or protein.

The terms "target specific binding domain" or "ligand" are used interchangeably in the context of the present invention and refer to a binding moiety comprising a structural unit which facilitates or improves specific binding of the polypeptide of the second aspect of the present invention to its target. This domain may be a natural ligand, a carbohydrate, a protein or a peptide, for example isolated by display technologies from ligand libraries (Sergeeva 2006). The binding of such a target specific binding domain is considered specific to a given target if it binds with the highest affinity to the respective target and only with lower affinity, e.g. at least 10-fold lower, preferably at least 100-fold lower affinity to other targets even to targets with a related amino acid sequence.

The term "target" or "target molecule" as used in the present invention refers to a natural existing cellular or molecular structure towards which other molecules have a certain binding affinity or to which other molecules specifically bind. "Specific binding" means that a binding moiety (e.g. an antibody) binds stronger to a target, such as an epitope, for which it is specific compared to the binding to another target if it binds to the first target with a dissociation constant ($K_d$) which is lower than the dissociation constant for the second target. Targets can be recognized by their ligands which bind with a certain affinity to their targets and thus, the ligand binding to its respective target results in a biological effect. Preferably, the binding is both specific and occurs with a high affinity, preferably with $K_d$ of less than $10^{-7}$, $10^{-8}$, $10^{-9}$, $10^{-10}$ M or less. Such affinity is preferably measured at 37° C. Suitable assays include surface plasmon resonance measurements (e.g. Biacore), quartz crystal microbalance measurements (e.g. Attana), and competition assays.

The terms "$V_L$ region" and "$V_H$ region" refers to $V_L$ and $V_H$ regions of an antibody; i.e. the N-terminal variable region of the light chain of an immunoglobulin and the N-terminal variable region of the heavy chain of an immunoglobulin, respectively. The individual $V_L$ and $V_H$ regions are each composed of three hypervariable regions (complementary determining region (CDR)1, CDR2 and CDR3) and four framework regions (framework (FR) region 1, FR2, FR3, FR4). Identifying the respective subregions within a given sequence is routine in the art and may for example be accomplished by IgBlast of the NCBI. The variable regions of the heavy and the light chain form together the binding region of an antibody. In immunoglobulins, the $V_L$ and the $V_H$ regions are located on different polypeptide chains, but they can be located on the same chain in recombinant antibody derivatives. Interactions of a $V_L$ and a $V_H$ region allows the polypeptide of the present invention to interact with its respective target antigen.

The term "antigen" according to the present invention refers to any structure recognized by molecules of the immune response, e.g. antibodies, T cell receptors (TCRs) and the like. An antigen may be foreign or toxic to the body or may be a cellular protein that is associated with a particular disease. Antigens are recognized by highly variable antigen receptors (B-cell receptor or T-cell receptor) of the adaptive immune system and may elicit a humoral or cellular immune response. Antigens that elicit such a response are also referred to as immunogen. A fraction of the proteins inside cells, irrespective of whether they are foreign or cellular, are processed into smaller peptides and presented to by the major histocompatibility complex (MHC). A cellular immune response is elicited, if the small peptide fragment is bound by a T-cell receptor. Cell surface antigens can be selected from the group of cytokine receptors, integrins, cell adhesion molecules, cell type-specific cell surface antigen, tissue-specific cell surface antigen, cell surface-expressed tumor-associated antigen, cluster of differentiation antigens, or carbohydrates.

"Antibodies" as used in the context of the present invention are glycoproteins belonging to the immunoglobulin superfamily; the terms antibody and immunoglobulin are often used interchangeably. An antibody refers to a protein molecule produced by plasma cells and is used by the immune system to identify and neutralize foreign objects such as bacteria and viruses. The antibody recognizes a unique part of the foreign target, its antigen.

The term "antibody fragment" as used herein, refers to one or more fragments of an antibody that retain the ability to specifically bind to an antigen. Examples of binding fragments encompassed within the term "antibody fragment" include a fragment antigen binding (Fab) fragment, a Fab' fragment, a F(ab')$_2$ fragment, a heavy chain antibody, a single-domain antibody (sdAb), a single-chain fragment variable (scFv), a fragment variable (Fv), a VH domain, a VL domain, a single domain antibody, a nanobody, an IgNAR (immunoglobulin new antigen receptor), a di-scFv, a bispecific T-cell engager (BITEs), a dual affinity re-targeting (DART) molecule, a triple body, a diabody, a single-chain diabody, an alternative scaffold protein, and a fusion protein thereof.

The term "diabody" as used within this specification refers to a fusion protein or a bivalent antibody which can bind different antigens. A diabody is composed of two single protein chains which comprise fragments of an antibody, namely variable fragments. Diabodies comprise a heavy chain variable domain ($V_H$) connected to a light-chain variable domain ($V_L$) on the same polypeptide chain ($V_H$-$V_L$, or $V_L$-$V_H$). By using a short peptide connecting the two variable domains, the domains are forced to pair with the complementary domain of another chain and thus, create two antigen-binding sites. Diabodies can target the same (monospecific) or different antigens (bispecific).

A "single domain antibody", refers to antibody fragments consisting of a single, monomeric variable domain of an antibody. Simply, they only comprise the monomeric heavy chain variable regions of heavy chain antibodies produced by camelids or cartilaginous fish. Due to their different origins they are also referred to VHH or VNAR (variable new antigen receptor)-fragments. Alternatively, single-domain antibodies can be obtained by monomerization of variable domains of conventional mouse or human antibodies by the use of genetic engineering. They show a molecular mass of approximately 12-15 kDa and thus, are the smallest antibody fragments capable of antigen recognition. Further examples include nanobodies or nanoantibodies.

The term "antibody mimetic" as used within the context of the present specification refers to compounds which can specifically bind antigens, similar to an antibody, but are not structurally related to antibodies. Usually, antibody mimetics are artificial peptides or proteins with a molar mass of about 3 to 20 kDa which comprise one, two or more exposed domains specifically binding to an antigen. Examples include inter alia the LACI-D1 (lipoprotein-associated coagulation inhibitor); affilins, e.g. human-γ B crystalline or human ubiquitin; cystatin; Sac7D from *Sulfolobus acidocaldarius*; lipocalin and anticalins derived from lipocalins; DARPins (designed ankyrin repeat domains); SH3 domain of Fyn; Kunits domain of protease inhibitors; monobodies, e.g. the $10^{th}$ type III domain of fibronectin; adnectins:

knottins (cysteine knot miniproteins); atrimers; evibodies, e.g. CTLA4-based binders, affibodies, e.g. three-helix bundle from Z-domain of protein A from *Staphylococcus aureus*; Trans-bodies, e.g. human transferrin; tetranectins, e.g. monomeric or trimeric human C-type lectin domain; microbodies, e.g. trypsin-inhibitor-II; affilins; armadillo repeat proteins. Nucleic acids and small molecules are sometimes considered antibody mimetics as well (aptamers), but not artificial antibodies, antibody fragments and fusion proteins composed from these. Common advantages over antibodies are better solubility, tissue penetration, stability towards heat and enzymes, and comparatively low production costs.

As used herein, the term "variant" is to be understood as a peptide or protein which differs in comparison to the peptide or protein from which it is derived by one or more changes in its length or sequence. The polypeptide from which a protein variant is derived is also known as the parent or parental polypeptide. The term "variant" comprises "fragments" or "derivatives" of the parent molecule. Typically, "fragments" are smaller in length or size than the parent molecule, whilst "derivatives" exhibit one or more differences in their sequence in comparison to the parent molecule. Also encompassed are posttranslational modifications of the parent proteins (e.g. glycosylation, biotinylation, phosphorylation, ubiquitinylation, palmitoylation, or proteolysis). Typically, a variant is constructed artificially, preferably by gene-technological means whilst the parent polypeptide or polynucleotide is a wild-type protein or polynucleotide. However, also naturally occurring variants are to be understood to be encompassed by the term "variant" as used herein. Further, the variants usable in the present invention may also be derived from homologs, orthologs, or paralogs of the parent molecule or from artificially constructed variant, provided that the variant exhibits at least one biological activity of the parent molecule, i.e. is functionally active.

As used in this specification the term "nucleic acid" comprises polymeric or oligomeric macromolecules, or large biological molecules, essential for all known forms of life. Nucleic acids, which include DNA (deoxyribonucleic acid) and RNA (ribonucleic acid), are made from monomers known as nucleotides. Most naturally occurring DNA molecules consist of two complementary biopolymer strands coiled around each other to form a double helix. The DNA strand is also known as polynucleotides consisting of nucleotides. Each nucleotide is composed of a nitrogen-containing nucleobase as well as a monosaccharide sugar called deoxyribose or ribose and a phosphate group. Naturally occurring nucleobases comprise guanine (G), adenine (A), thymine (T), uracil (U) or cytosine (C). The nucleotides are joined to one another in a chain by covalent bonds between the sugar of one nucleotide and the phosphate of the next, resulting in an alternating sugar-phosphate backbone. If the sugar is desoxyribose, the polymer is DNA. If the sugar is ribose, the polymer is RNA. Typically, a polynucleotide is formed through phosphodiester bonds between the individual nucleotide monomers. In the context of the present invention the term "nucleic acid" includes but is not limited to ribonucleic acid (RNA), deoxyribonucleic acid (DNA), and mixtures thereof such as e.g. RNA-DNA hybrids (within one strand), as well as cDNA, genomic DNA, recombinant DNA, cRNA and mRNA. A nucleic acid may consist of an entire gene, or a portion thereof, the nucleic acid may also be a miRNA, siRNA, or a piRNA.

As used in this specification the term "vector", also referred to as an expression construct, is usually a plasmid or virus designed for protein expression in cells. The vector is used to introduce a specific gene into a target cell, and can use the cell's mechanism for protein synthesis to produce the protein encoded by the gene. The expression vector is engineered to contain regulatory sequences that act as enhancer and promoter regions and lead to efficient transcription of the gene carried on the expression vector. The goal of a well-designed expression vector is the production of significant amount of stable messenger RNA, and therefore proteins. Examples of suitable vectors include but are not limited to plasmids, cosmids, phages, viruses or artificial chromosomes. An example for a commonly used expression vector is pGEX-4T2.

The term "pharmaceutical composition" as used in the present application refers to a substance and/or a combination of substances being used for the identification, prevention or treatment of a tissue status or disease. The pharmaceutical composition is formulated to be suitable for administration to a patient in order to prevent and/or treat disease. Further a pharmaceutical composition refers to the combination of an active agent with a carrier, inert or active, making the composition suitable for therapeutic use. Pharmaceutical compositions can be formulated for oral, parenteral, topical, inhalative, rectal, sublingual, transdermal, subcutaneous or vaginal application routes according to their chemical and physical properties. Pharmaceutical compositions comprise solid, semisolid, liquid, transdermal therapeutic systems (TTS). Solid compositions are selected from the group consisting of tablets, coated tablets, powder, granulate, pellets, capsules, effervescent tablets or transdermal therapeutic systems. Also comprised are liquid compositions, selected from the group consisting of solutions, syrups, infusions, extracts, solutions for intravenous application, solutions for infusion or solutions of the carrier systems of the present invention. Semisolid compositions that can be used in the context of the invention comprise emulsion, suspension, creams, lotions, gels, globules, buccal tablets and suppositories.

The term "active agent" refers to the substance in a pharmaceutical composition or formulation that is biologically active, i.e. that provides pharmaceutical value. A pharmaceutical composition may comprise one or more active agents which may act in conjunction with or independently of each other. The active agent can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as but not limited to those derived from sodium, potassium, ammonium, calcium, ferric hydroxides, isopropylamine, triethylamine, 2-ethylamino ethanol, histidine, procaine, and the like.

The term "disease" and "disorder" are used interchangeably herein, referring to an abnormal condition, especially an abnormal medical condition such as an illness or injury, wherein a cell, a tissue, an organ, or an individual is not able to efficiently fulfil its function anymore. Typically, but not necessarily, a disease is associated with specific symptoms or signs indicating the presence of such disease. The presence of such symptoms or signs may thus, be indicative for a cell, a tissue, an organ, or an individual suffering from a disease. An alteration of these symptoms or signs may be indicative for the progression of such a disease. A progression of a disease is typically characterised by an increase or decrease of such symptoms or signs which may indicate a "worsening" or "bettering" of the disease. The "worsening" of a disease is characterised by a decreasing ability of a cell, tissue, organ or individual/patient to fulfil its function efficiently, whereas the "bettering" of a disease is typically characterised by an increase in the ability of a cell, tissue, an organ or an individual/patient to fulfil its function efficiently.

The term "hyperproliferative disorder" as used in the present application refers to disorders wherein the cell division of the cells is increased in relation to normal tissue. Such disorders are characterized by an abnormal proliferation (production) i.e. overproduction of cells. Hyperproliferative disorders comprise tumor diseases. Tumor diseases may comprise benign or malignant tumors wherein malignant tumor diseases are referred to as cancer. The term hyperproliferative disorder comprises cancers as well as pre-cancerous disorders. Cancer comprises proliferative disorders of mesenchymal origin, i.e. connective tissue (sarcomas) and of epithelial tissues (carcinomas). Common examples of sarcomas are osteosarcoma, chondrosarcoma, liposarcoma, leiomyosarcoma, angiosarcoma and fibrosarcoma and sarcomas of the gastrointestinal tract (GIST). Examples for carcinomas are carcinomas of the skin, testis, liver, gastrointestinal tract such as esophagus, stomach, pancreas, and colon, nasopharynx, bladder, cervix, ovarian, urethra, bladder; prostate and other genitourinary carcinomas, lung, kidney, endocrine tissues such as thyroid and pituitary gland, teratocarcinomas, carcinomas of the brain. Malignancies of the hematologic system are classified as lymphoma or leukemia. Inflammation orchestrates the microenvironment around tumors, contributing to proliferation, survival and migration of cancer cells, thus potentially promoting malignant disease.

Inflammation is in principle a protective immunovascular response that involves immune cells, blood vessels, and a plethora of molecular mediators. The purpose of inflammation is to eliminate the initial cause of cell injury, clear out necrotic cells and tissues damaged from the original insult and the inflammatory process, and to initiate tissue repair. The term "inflammatory disorder" as used in the context of the present invention refers to a situation wherein a physiological inflammatory response turns into a potentially harmful effect for the body. Inflammatory disorders causing damage to normal tissues comprise but are not limited to autoimmune disorders and neurodegenerative diseases.

Embodiments

In the following passages different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous. In the work leading to the present invention, it was surprisingly shown that the polypeptides of the invention display improved stability and half-life and further can be used for the generation of antibody fusion proteins. Based on these results the present invention in a first aspect relates to a polypeptide comprising:

(i) component A comprising, consisting essentially or consisting of:

at least three THDs, wherein the C-terminus of the first and second THD, respectively, which is in each case defined by the C-terminal consensus sequence (SEQ ID NO: 1)
$-S/T/V-F/Y/S-F-G-A/L/V/I-X_1$, is linked to the N-terminus of the second and third THD, respectively, which is in each case defined by the N-terminal consensus sequence (SEQ ID NO: 2)
$X_2$-V/A/F-A-H-V/L/I/Y
or (SEQ ID NO: 3)
$X_3$-V/W/F/C-A/L-E/Y/Q/H-L, through a peptide $X_a$, which is in each case independently selected and has a length of 3 to 8 amino acids, wherein $X_1$ is a non-polar/hydrophobic or polar/neutral amino acid, preferably selected from the group consisting of F, V, Q, A, I, L, and Y;

wherein $X_2$ is selected from the group consisting of P, K, V, I, and A;

wherein $X_3$ is selected from the group consisting of D, S, M, and I;

(ii) component B comprising a dimerization domain consisting of an antibody $V_L$ and $V_H$ region linked directly to each other with a peptide that has a length of between 7 and 11 amino acids.

Component A of the polypeptides of the present invention, preferably has a thermal stability of at least 48° C., more preferably of at least 49° C., more preferably of at least 50° C., more preferably of at least 51° C., more preferably of at least 52° C., more preferably of at least 53° C., more preferably of at least 54° C., more preferably of at least 55° C., more preferably of at least 56° C. and most preferably of at least 57° C. Preferably, the polypeptide of the first aspect comprising component A has at least the above indicated thermal stabilities. The skilled person is well aware how to measure thermal stabilities of polypeptides. Exemplary methods are taught herein below.

Accordingly, it is preferred that component A comprises, essentially consists or consists of the following arrangement of polypeptide elements from N- to C-terminus, wherein "THD1" is an abbreviation of the "first THD", "THD2 is an abbreviation for the "second THD" etc.: THD1-$X_a$-THD2-$X_a$-THD3.

As outlined above the C-terminal and N-terminal consensus sequences serve the purpose of defining the C- and N-terminal end of the region of the THD of TNF-family members that is necessarily included in the fragment of the respective TNF-ligand family member. The basis for this is the observation of the present inventors that the inclusion of a THD defined by these C- and N-terminal endpoints in the context of a connecting sequence $X_a$ of the indicated length leads to a single chain TNF-ligand polypeptide which provides the above noted advantages. In the following the determination of a THD and its sequence on the basis of the C-terminal and N-terminal consensus sequences is illustrated exemplary for the preferred human TNF-ligand family member TRAIL. The sequence of human TRAIL is indicated in SEQ ID NO: 5. It comprises the amino acid sequence "VAAHI" spanning amino acid positions 122 to 125. This sequence conforms to the N-terminal consensus sequence $X_2$-V/A/F-A-H-V/L/I/Y, when $X_2$ is V (the other consensus positions are highlighted by bold print). V is located at amino acid position 122 of human TRAIL. Thus, the N-terminal end of a THD derived from human TRAIL is at amino acid position 122. Similarly, human TRAIL comprises the sequence S-F-F-G-A-F (SEQ ID NO: 6) spanning amino acid positions 273 to 278. This sequence conforms to the C-terminal consensus sequence -S/T/V-F/Y/S-F-G-A/L/V/I-$X_1$, when $X_1$ is F (the other consensus positions are highlighted by bold print). Thus, the C-terminal end of a THD derived from human TRAIL is at amino acid position 278. Taken together, the THD of human TRAIL spans amino acid positions 122 to 278. A similar analysis for human TNF (see SEQ ID NO: 11) indicates that the THD of human TNF spans amino acid positions 88 to 228. It is noted that the actual N- and C-terminal sequence of THD1, THD2, THD3, etc comprised in component A does not need to be identical to the wild-type amino sequence of the respective TNF-ligand family member from which the THD is derived. It is sufficient if the amino acids intervening the N- and C-terminal consensus sequence or a variant thereof are included and a N- and C-terminal sequence that conforms to the C-terminal consensus sequence and to the respective N-terminal consensus sequence used for the determination of the N-terminal end. This is illustrated exemplary for human TRAIL: The N-terminal sequence of a THD based on human TRAIL is $X_2$-V/A/F-A-H-V/L/I/Y, wherein $X_2$ has one of the meanings indicated above, this sequence is followed by amino acids 126 to 272 of SEQ ID NO: 1 and the C-terminal sequence is S/T/V-F/Y/S-F-G-A/L/V/I-$X_1$, wherein $X_1$ has one of the meanings indicated above.

Taken together the C-terminal end of the first THD, the N-terminal and C-terminal end of the second THD and the N-terminal end of the third THD are defined. It is apparent to the skilled person that the definition of the C-terminal end and N-terminal end of the THDs comprised in component A is required in as far as these two ends are connected via peptides $X_a$. It is preferred, however, that also the first THD comprises the N-terminal consensus sequence and that the respective last THD, preferably the third THD comprises the C-terminal consensus sequence.

In a preferred embodiment of the first aspect of the present invention, component A comprises at least three identical THDs.

Preferably, the TNF-ligand family members from which the THDs are derived are selected from the group consisting of TNF, CD95L (FasL), LT alpha, LT beta, CD40L, TWEAK, LIGHT, CD27L, BAFF, TRAIL. Preferred are the human TNF ligand family members human TNF, human CD95L (FasL), human LTα, human LTβ, human CD40L, human TWEAK, human LIGHT, human CD27L, human BAFF, human TRAIL. More preferably, component A comprises at least three THDs of TRAIL, even more preferred of human TRAIL.

In another preferred embodiment the sequence of the TNF-ligand family member from which the THD is derived is selected from the group consisting of SEQ ID NO: 5 (TRAIL), SEQ ID NO: 7 (FasL), SEQ ID NO: 8 (LIGHT), SEQ ID NO: 9 (Ltα), SEQ ID NO: 10 (Ltβ), SEQ ID NO: 11 (TNF), SEQ ID NO: 12 (CD40L), SEQ ID NO: 13 (TWEAK), SEQ ID NO: 14 (CD27L), SEQ ID NO: 15 (BAFF).

As outlined above component A comprises at least three TNF homology domains of TNF-ligand family member proteins (THD), wherein the C-terminus of the first and second THD, respectively, and optionally of the third and further THDs is in each case defined by the C-terminal consensus sequence

-S/T/V-F/Y/S-F-G-A/L/V/I-$X_1$ (SEQ ID NO: 1)

wherein $X_1$ is a non-polar/hydrophob or polar/neutral amino acid, preferably selected from the group consisting of F, V, Q, A, I, L, and Y;

Preferably, the C-terminal amino acid sequence of the first and second THD, respectively, and optionally the third and all further THDs is selected from the group consisting of the sequences S-F-F-G-A-F (SEQ ID NO: 6), T-F-F-G-L-Y (SEQ ID NO: 16), S-Y-F-G-A-F (SEQ ID NO: 17), V-F-F-G-A-F (SEQ ID NO: 18), T-F-F-G-A-V (SEQ ID NO: 19), V-Y-F-G-I-I (SEQ ID NO: 20), T-S-F-G-L-L (SEQ ID NO: 21), T-Y-F-G-L-F (SEQ ID NO: 22), T-F-F-G-V-Q (SEQ ID NO: 23), and T-F-F-G-A-L (SEQ ID NO: 24). Preferably, the C-terminal amino acid sequence of the first and second THD is S-F-F-G-A-F (SEQ ID NO: 6).

It is preferred that the C-terminal amino acid sequence and N-terminal sequence, respectively, of the THD is closely related to the amino acid sequence of the TNF-ligand family member from which the THD is derived. Thus, the C-terminal amino acid sequence of a THD derived from human TRAIL is preferably S-F-F-G-A-F (SEQ ID NO: 6) or a closely related sequence. For THDs derived from human TRAIL $X_1$ is preferably F. Similarly, for THDs derived from human FasL the C-terminal amino acid sequence is preferably T-F-F-G-L-Y (SEQ ID NO: 16) or a closely related sequence. For THDs derived from human FasL $X_1$ is preferably Y. For THDs derived from human LIGHT the C-terminal amino acid sequence is preferably S-Y-F-G-A-F (SEQ ID NO: 17) or a closely related sequence. For THDs derived from human LIGHT $X_1$ is preferably F. For THDs derived from human Ltα the C-terminal amino acid sequence is preferably V-F-F-G-A-F (SEQ ID NO: 18) or a closely related sequence. For THDs derived from human LTβ $X_1$ is preferably F. For THDs derived from human LTβ the C-terminal amino acid sequence is preferably T-F-F-G-A-V (SEQ ID NO: 19) or a closely related sequence. For THDs derived from human LTβ $X_1$ is preferably V. For THDs derived from human TNF the C-terminal amino acid sequence is preferably V-Y-F-G-I-I (SEQ ID NO: 20) or a closely related sequence. For THDs derived from human TNF $X_1$ is preferably I. For THDs derived from human CD40L the C-terminal amino acid sequence is preferably T-S-F-G-L-L (SEQ ID NO: 21) or a closely related sequence. For THDs derived from human CD40L $X_1$ is preferably L. For THDs derived from human TWEAK the C-terminal amino acid sequence is preferably T-Y-F-G-L-F (SEQ ID NO: 22) or a closely related sequence. For THDs derived from human TWEAK $X_1$ is preferably F. For THDs derived from human CD27L the C-terminal amino acid sequence is preferably T-F-F-G-V-G (SEQ ID NO: 23) or a closely related sequence. For THDs derived from human CD27L $X_1$ is preferably G. For THDs derived from human BAFF the C-terminal amino acid sequence is preferably T-F-F-G-A-L (SEQ ID NO: 24) or a closely related sequence. For THDs derived from human BAFF $X_1$ is preferably L.

In the context of defining the N-terminal and C-terminal amino acid sequences the phrase "closely related" refers to variants which comprise an amino acid alteration in one or two, preferably one of the six and five amino acids, respectively, which still fit(s) the C-terminal and N-terminal consensus sequence, respectively.

The C-terminus of the first and second THD, respectively, or optionally of the third and further THDs as defined above and is linked to the N-terminus of the second and third THD, respectively which is defined by the N-terminal consensus sequence $$X_2\text{-}V/A/F\text{-}A\text{-}H\text{-}V/L/I/Y \quad \text{(SEQ ID NO: 2)}$$

wherein X₂ is selected from the group consisting of P, K, V, I, and A.

Preferably, the N-terminus of the second and third THD, respectively is selected from the group consisting of the sequences V-A-A-H-I (SEQ ID NO: 25). K-V-A-H-L (SEQ ID NO: 26), P-A-A-H-L (SEQ ID NO: 27), P-V-A-H-V (SEQ ID NO: 28), I-A-A-H-V (SEQ ID NO: 29), and I-A-A-H-Y (SEQ ID NO: 30). Preferably, the N-terminus of the second and third THD is V-A-A-H-I-T (SEQ ID NO: 25).

It is preferred that the N-terminal amino acid sequence actually comprised in the THD is closely related to the amino acid sequence of the TNF-ligand family member from which the THD is derived. Accordingly, the N-terminal amino acid sequence of a THD derived from human TRAIL is preferably V-A-A-H-I (SEQ ID NO: 25) or a closely related sequence. For THDs derived from human TRAIL X₂ is preferably V, A, or I, most preferably V. The N-terminal amino acid sequence of a THD derived from human FasL is preferably K-V-A-H-L (SEQ ID NO: 26) or a closely related sequence. For THDs derived from human FasL X₂ is preferably K. The N-terminal amino acid sequence of a THD derived from human LIGTH, LTα or LTβ is preferably P-A-A-H-L (SEQ ID NO: 27) or a closely related sequence. For THDs derived from human LIGHT, LTα or LTβ. X₂ is preferably P. The N-terminal amino acid sequence of a THD derived from human TNF preferably P-V-A-H-V (SEQ ID NO: 28) or a closely related sequence. For THDs derived from human TNF X₂ is preferably P. The N-terminal amino acid sequence of a THD derived from human CD40L preferably I-A-A-H-V (SEQ ID NO: 29) or a closely related sequence. For THDs derived from human CD40L X₂ is preferably I. The N-terminal amino acid sequence of a THD derived from human TWEAK preferably I-A-A-H-Y (SEQ ID NO: 30) or a closely related sequence. For THDs derived from human TWEAK X₂ is preferably I.

As outlined above component A comprises the C-terminus of the first and second THD, respectively, which is defined above and is linked to the N-terminus of the second and third THD which is defined by the N-terminal consensus sequence $$X_3\text{-}V/W/F/C\text{-}A/L\text{-}E/Y/Q/H\text{-}L \quad \text{(SEQ ID NO: 3)}$$

wherein X₃ is selected from the group consisting of D, S, M, and I. This N-terminal consensus sequence is preferably present, if one or more THDs are derived from CD27L or BAFF.

Preferably the N-terminus of the second and third THD, respectively is selected from the group consisting of the sequences D-V-A-E-L (SEQ ID NO: 31), D-W-A-E-L (SEQ ID NO: 32), D-F-A-E-L (SEQ ID NO: 33), D-C-A-E-L, (SEQ ID NO: 34), D-V-L-E-L (SEQ ID NO: 35), D-V-A-Y-L (SEQ ID NO: 36), D-V-L-Y-L (SEQ ID NO: 37), D-V-A-Q-L (SEQ ID NO: 38), D-V-L-Q-L (SEQ ID NO: 39), D-V-A-H-L (SEQ ID NO: 40), D-V-L-H-L (SEQ ID NO: 41), D-W-L-E-L (SEQ ID NO: 42), D-W-A-Y-L (SEQ ID NO: 43), D-W-L-Y-L (SEQ ID NO: 44), D-W-A-Q-L (SEQ ID NO: 45), D-W-L-Q-L (SEQ ID NO: 46), D-W-A-H-L (SEQ ID NO: 47), D-W-L-H-L (SEQ ID NO: 48), D-F-L-E-L (SEQ ID NO: 49), D-F-A-Y-L (SEQ ID NO: 50), D-F-L-Y-L (SEQ ID NO: 51), D-F-A-Q-L (SEQ ID NO: 52), D-F-L-Q-L (SEQ ID NO: 53), D-F-A-H-L (SEQ ID NO: 54), D-F-L-H-L (SEQ ID NO: 55), D-C-L-E-L (SEQ ID NO: 56), D-C-A-Y-L (SEQ ID NO: 57), D-C-L-Y-L (SEQ ID NO: 58), D-C-A-Q-L (SEQ ID NO: 59), D-C-L-Q-L (SEQ ID NO: 60), D-C-A-H-L (SEQ ID NO: 61), and D-C-L-H-L (SEQ ID NO: 62). Preferably, the N-terminus of the second and third THD, respectively is selected from the group consisting of the sequences S-V-A-E-L (SEQ ID NO: 63), S-W-A-E-L (SEQ ID NO: 64), S-F-A-E-L (SEQ ID NO: 65), S-C-A-E-L, (SEQ ID NO: 66), S-V-L-E-L (SEQ ID NO: 67), S-V-A-Y-L (SEQ ID NO: 68), S-V-L-Y-L (SEQ ID NO: 69), S-V-A-Q-L (SEQ ID NO: 70), S-V-L-Q-L (SEQ ID NO: 71), S-V-A-H-L (SEQ ID NO: 72), S-V-L-H-L (SEQ ID NO: 73), S-W-L-E-L (SEQ ID NO: 74), S-W-A-Y-L (SEQ ID NO: 75), S-W-L-Y-L (SEQ ID NO: 76), S-W-A-Q-L (SEQ ID NO: 77), S-W-L-Q-L (SEQ ID NO: 78), S-W-A-H-L (SEQ ID NO: 79), S-W-L-H-L (SEQ ID NO: 80), S-F-L-E-L (SEQ ID NO: 81), S-F-A-Y-L (SEQ ID NO: 82), S-F-L-Y-L (SEQ ID NO: 83), S-F-A-Q-L (SEQ ID NO: 84), S-F-L-Q-L (SEQ ID NO: 85), S-F-A-H-L (SEQ ID NO: 86), S-F-L-H-L (SEQ ID NO: 87), S-C-L-E-L (SEQ ID NO: 88), S-C-A-Y-L (SEQ ID NO: 89), S-C-L-Y-L (SEQ ID NO: 90), S-C-A-Q-L (SEQ ID NO: 91), S-C-L-Q-L (SEQ ID NO: 92), S-C-A-H-L (SEQ ID NO: 93), and S-C-L-H-L (SEQ ID NO: 94). Preferably, the N-terminus of the second and third THD, respectively is selected from the group consisting of the sequences M-V-A-E-L (SEQ ID NO: 95), M-W-A-E-L (SEQ ID NO: 96), M-F-A-E-L (SEQ ID NO: 97), M-C-A-E-L, (SEQ ID NO: 98), M-V-L-E-L (SEQ ID NO: 99), M-V-A-Y-L (SEQ ID NO: 100), M-V-L-Y-L (SEQ ID NO: 101), M-V-A-Q-L (SEQ ID NO: 102), M-V-L-Q-L (SEQ ID NO: 103), M-V-A-H-L (SEQ ID NO: 104), M-V-L-H-L (SEQ ID NO: 105), M-W-L-E-L (SEQ ID NO: 106), M-W-A-Y-L (SEQ ID NO: 107), M-W-L-Y-L (SEQ ID NO: 108), M-W-A-Q-L (SEQ ID NO: 109), M-W-L-Q-L (SEQ ID NO: 110), M-W-A-H-L (SEQ ID NO: 111), M-W-L-H-L (SEQ ID NO: 112), M-F-L-E-L (SEQ ID NO: 113), M-F-A-Y-L (SEQ ID NO: 114), M-F-L-Y-L (SEQ ID NO: 115), M-F-A-Q-L (SEQ ID NO: 116), M-F-L-Q-L (SEQ ID NO: 117), M-F-A-H-L (SEQ ID NO: 118), M-F-L-H-L (SEQ ID NO: 119), M-C-L-E-L (SEQ ID NO: 120), M-C-A-Y-L (SEQ ID NO: 121), M-C-L-Y-L (SEQ ID NO: 122), M-C-A-Q-L (SEQ ID NO: 123), M-C-L-Q-L (SEQ ID NO: 124), M-C-A-H-L (SEQ ID NO: 125), M-C-L-H-L (SEQ ID NO: 126). Preferably the N-terminus of the second and third THD, respectively is selected from the group consisting of the sequences I-V-A-E-L (SEQ ID NO: 127), I-W-A-E-L (SEQ ID NO: 128), I-F-A-E-L (SEQ ID NO: 129), I-C-A-E-L, (SEQ ID NO: 130), I-V-L-E-L (SEQ ID NO: 131), I-V-A-Y-L (SEQ ID NO: 132), I-V-L-Y-L (SEQ ID NO: 133), I-V-A-Q-L (SEQ ID NO: 134), I-V-L-Q-L (SEQ ID NO: 135), I-V-A-H-L (SEQ ID NO: 136), I-V-L-H-L (SEQ ID NO: 137), I-W-L-E-L (SEQ ID NO: 138), I-W-A-Y-L (SEQ ID NO: 139), I-W-L-Y-L (SEQ ID NO: 140), I-W-A-Q-L (SEQ ID NO: 131), I-W-L-Q-L (SEQ ID NO: 142), I-W-A-H-L (SEQ ID NO: 143), I-W-L-H-L (SEQ ID NO: 144), I-F-L-E-L (SEQ ID NO: 145), I-F-A-Y-L (SEQ ID NO: 146), I-F-L-Y-L (SEQ ID NO: 147), I-F-A-Q-L (SEQ ID NO: 148), I-F-L-Q-L (SEQ ID NO: 149), I-F-A-H-L (SEQ ID NO: 150), I-F-L-H-L (SEQ ID NO: 151), I-C-L-E-L (SEQ ID NO: 152), I-C-A-Y-L (SEQ ID NO: 153), I-C-L-Y-L (SEQ ID NO: 154), I-C-A-Q-L (SEQ ID NO: 155), I-C-L-Q-L (SEQ ID NO: 156), I-C-A-H-L (SEQ ID NO: 157), and I-C-L-H-L (SEQ ID NO: 158).

The N-terminal amino acid sequence of a THD derived from human CD27L is preferably D-V-A-E-L (SEQ ID NO: 31) or a closely related sequence. For THDs derived from human CD27L $X_3$ is preferably D. The N-terminal amino acid sequence of a THD derived from human BAFF is preferably D-C-L-Q-L (SEQ ID NO: 60) or a closely related sequence. For THDs derived from human BAFF $X_3$ is preferably D.

Preferably, component A comprises the C-terminal sequences of the first and second THD selected from the group consisting of S-F-F-G-A-F (SEQ ID NO: 6), T-F-F-G-L-Y (SEQ ID NO: 16), S-Y-F-G-A-F (SEQ ID NO: 17), V-F-F-G-A-F (SEQ ID NO: 18), T-F-F-G-A-V (SEQ ID NO: 19), V-Y-F-G-I-I (SEQ ID NO: 20), T-S-F-G-L-L (SEQ ID NO: 21), T-Y-F-G-L-F (SEQ ID NO: 22), T-F-F-G-V-Q (SEQ ID NO: 23), T-F-F-G-A-L (SEQ ID NO: 24) or a closely related sequence thereof and the N-terminal sequences of the second and third THD selected from the group V-A-A-H-I-T (SEQ ID NO: 25), K-V-A-H (SEQ ID NO: 26), P-A-A-H-L (SEQ ID NO: 27), P-V-A-H-V (SEQ ID NO: 28), I-A-A-H-V (SEQ ID NO: 29), I-A-A-H-Y (SEQ ID NO: 30), D-V-A-E-L (SEQ ID NO: 31) and D-C-L-Q-L (SEQ ID NO: 60) or a closely related sequences thereof.

It is preferred that the C-terminal amino acid sequence of a THD derived from human TRAIL is preferably S-F-F-G-A-F (SEQ ID NO: 6) or a closely related sequence and the N-terminal amino acid sequence is preferably V-A-A-H-I (SEQ ID NO: 25) or a closely related sequence. For THDs derived from human TRAIL $X_1$ is preferably F and $X_2$ is preferably V, A, or I, most preferably V.

Similarly, for THDs derived from human FasL the C-terminal amino acid sequence is preferably T-F-F-G-L-Y (SEQ ID NO: 16) or a closely related sequence and the N-terminal amino acid sequence is preferably K-V-A-H-L (SEQ ID NO: 26) or a closely related sequence. For THDs derived from human FasL $X_1$ is preferably Y and $X_2$ is preferably K.

For THDs derived from human LIGHT the C-terminal amino acid sequence is preferably S-Y-F-G-A-F (SEQ ID NO: 17) or a closely related sequence and the N-terminal amino acid sequence is preferably P-A-A-H-L (SEQ ID NO: 27) or a closely related sequence. For THDs derived from human LIGHT $X_1$ is preferably F and $X_2$ is preferably P.

For THDs derived from human LTα the C-terminal amino acid sequence is preferably V-F-F-G-A-F (SEQ ID NO: 18) or a closely related sequence and the N-terminal amino acid sequence is preferably P-A-A-H-L (SEQ ID NO: 27) or a closely related sequence. For THDs derived from human LTα $X_1$ is preferably F and $X_2$ is preferably P.

For THDs derived from human LTβ the C-terminal amino acid sequence is preferably T-F-F-G-A-V (SEQ ID NO: 19) or a closely related sequence and the N-terminal amino acid sequence is preferably P-A-A-H-L (SEQ ID NO: 27) or a closely related sequence. For THDs derived from human LTβ $X_1$ is preferably V and $X_2$ is preferably P.

For THDs derived from human TNF the C-terminal amino acid sequence is preferably V-Y-F-G-I-I (SEQ ID NO: 20) or a closely related sequence and the N-terminal amino acid sequence is preferably P-V-A-H-V (SEQ ID NO: 28) or a closely related sequence. For THDs derived from human TNF $X_1$ is preferably I and $X_2$ is preferably P.

For THDs derived from human CD40L the C-terminal amino acid sequence is preferably T-S-F-G-L-L (SEQ ID NO: 21) or a closely related sequence and the N-terminal amino acid sequence is preferably I-A-A-H-V (SEQ ID NO: 29) or a closely related sequence. For THDs derived from human CD40L $X_1$ is preferably L and $X_2$ is preferably I.

For THDs derived from human TWEAK the C-terminal amino acid sequence is preferably T-Y-F-G-L-F (SEQ ID NO: 22) or a closely related sequence and the N-terminal amino acid sequence is preferably I-A-A-H-Y (SEQ ID NO: 30) or a closely related sequence. For THDs derived from human TWEAK $X_1$ is preferably F and $X_2$ is preferably I.

For THDs derived from human CD27L the C-terminal amino acid sequence is preferably T-F-F-G-V-G (SEQ ID NO: 23) or a closely related sequence and the N-terminal amino acid sequence of a THD derived from human CD27L is preferably D-V-A-E-L (SEQ ID NO: 31) or a closely related sequence. For THDs derived from human CD27L $X_1$ is preferably G and $X_3$ is preferably D.

For THDs derived from human BAFF the C-terminal amino acid sequence is preferably T-F-F-G-A-L (SEQ ID NO: 24) or a closely related sequence and the N-terminal amino acid sequence is preferably D-C-L-Q-L (SEQ ID NO: 60) or a closely related sequence. For THDs derived from human BAFF $X_1$ is preferably L and $X_3$ is preferably D.

Preferred are combinations of the C-terminal sequence of the first and second THD and N-terminal sequences of the second and third THD as follows: T-F-F-G-L-Y (SEQ ID NO: 16) and K-V-A-H (SEQ ID NO: 26), S-Y-F-G-A-F (SEQ ID NO: 17) and P-A-A-H-L (SEQ ID NO: 26), V-F-F-G-A-F (SEQ ID NO: 18) and P-A-A-H-L (SEQ ID NO: 27), T-F-F-G-A-V (SEQ ID NO: 19) and P-A-A-H-L (SEQ ID NO: 27), V-Y-F-G-I-I (SEQ ID NO: 20) and P-V-A-H-V (SEQ ID NO: 27), T-S-F-G-L-L (SEQ ID NO: 21) and I-A-A-H-V (SEQ ID NO: 29), T-Y-F-G-L-F (SEQ ID NO: 22) and I-A-A-H-Y (SEQ ID NO: 29), T-F-F-G-V-Q (SEQ ID NO: 23) and D-V-A-E-L (SEQ ID NO: 31), T-F-F-G-A-L (SEQ ID NO: 24) and D-C-L-Q-L (SEQ ID NO: 60).

Most preferred is the combination S-F-F-G-A-F (SEQ ID NO: 6) and V-A-A-H-I (SEQ ID NO: 25).

It is understood that in each of the preceding cases each of the respective THDs also comprise the amino acid sequence of the respective TNF-ligand family member or variant thereof intervening the respective N-terminal and C-terminal sequence.

The at least three THDs are connected to each other by at least two intervening peptides $X_a$, wherein the first THD (THD1) is connected with one peptide $X_a$ to the second THD (THD2), which is connected with one peptide $X_a$ to the third THD (THD3) and so forth; if more than three THDs are comprised. The peptide $X_a$ may in each case be different or all peptides $X_a$ may be identical. It is preferred that the peptides $X_a$ are identical. The peptide $X_a$ preferably comprises amino acid sequences N-terminal to the N-terminal consensus sequence of the respective THD or C-terminal of the C-terminal consensus sequence. In each case these sequences may comprise mutations. Preferably, such peptides have an amino acid length in the range of 3 to 8 amino acids. The peptides can have a length of 3, 4, 5, 6, 7, or 8 amino acids, particularly preferred lengths are 4 or 5, most preferably 4 amino acids.

As outlined above component A comprises the C-terminus of the first and second THD, respectively, which is defined by a consensus sequence as described above and is linked to the N-terminus of the second and third THD, respectively, defined by a consensus sequence as described above, through a peptide $X_a$, which is in each case independently selected and has a length of 3 to 8 amino acids.

Preferably, the peptide $X_a$ consists of

wherein $X_e$ is selected from the group consisting of L, L-V, L-V-G, L-V-G-G (SEQ ID NO: 159), L-V-G-G-I (SEQ ID NO: 160), L-V-S, L-V-S-G (SEQ ID NO: 161), A, A-V, A-V-S, A-V-G, A-V-G-G (SEQ ID NO: 162), A-V-S-G (SEQ ID NO: 163), I-V, I-V-S, I-V-G, I-V-G-G (SEQ ID NO: 164), I-V-S-G (SEQ ID NO: 165), K, K-L, M, M-V, A, A-L, M-V-G, M-V-Q, G, G-V, G-V-H, W, W-V, W-V-R, W-V-R-P ((SEQ ID NO: 167), K-L-L, I, A-V, Q, Q-V, and Q-V-H; $X_f$ is absent or selected from the group consisting of G, S, G-G, S-G, G-S, S-S, G-G-G, G-G-S, G-S-G, S-G-G, G-S-S, S-G-S and S-S-S; and $X_g$ is absent or selected from the group consisting of R, Q-R, P-Q-R, G-P-Q-R (SEQ ID NO: 166), L-R, N, V-N, K, L-K, L, G-L, K, D-K, Q, P-Q, A, R-A, W, G-W, Q, and T-Q.

Preferably,
(i) $X_e$ is selected from L, L-V, L-V-G, L-V-G-G (SEQ ID NO: 159), L-V-S, L-V-S-G (SEQ ID NO: 161), A, A-V, A-V-S, A-V-G, A-V-G-G, A-V-S-G (SEQ ID NO: 163), I-V, I-V-S, I-V-G, I-V-G-G, (SEQ ID NO: 164) and I-V-S-G (SEQ ID NO: 165); $X_f$ is absent or selected from G, S, G-G, S-G, G-S, and S-S; and $X_g$ is absent or selected from R, Q-R, P-Q-R, and G-P-Q-R (SEQ ID NO: 166);
(ii) $X_e$ is selected from K, and K-L; $X_f$ is absent or selected from G, S, G-G, S-G, G-S, and S-S; and $X_g$ is absent or selected from R, and L-R,
(iii) $X_e$ is selected from M, M-V; $X_f$ is absent or selected from G, S, G-G, S-G, G-S, and S-S; and $X_g$ is absent or selected from N and V-N;
(iv) $X_e$ is selected from A, and A-L; $X_f$ is absent or selected from G, S, G-G, S-G, G-S, and S-S; and $X_g$ is absent or selected from K and L-K;
(v) $X_e$ is selected from M, M-V, and M-V-G; $X_f$ is absent or selected from G, S, G-G, S-G, G-S, and S-S; and $X_g$ is absent or selected from L, and G-L;
(vi) $X_e$ is selected from A, and A-L; $X_f$ is absent or selected from G, S, G-G, S-G, G-S, and S-S; and $X_g$ is absent or selected from K, and D-K;
(vii) $X_e$ is selected from K, and K-L; $X_f$ is absent or selected from G, S, G-G, S-G, G-S, and S-S; and $X_g$ is absent or selected from Q, and P-Q;
(viii) $X_e$ is selected from Q, Q-V, and Q-V-H; $X_f$ is absent or selected from G, S, G-G, S-G, G-S, and S-S; and $X_g$ is absent or selected from A, and R-A;
(ix) $X_e$ is selected from W, W-V, W-V-R, and W-V-R-P; $X_f$ is absent or selected from G, S, G-G, S-G, G-S, and S-S; and $X_g$ is absent or selected from W, and G-W; or
(x) $X_e$ is selected from K, K-L, and K-L-L; $X_f$ is absent or selected from G, S, G-G, S-G, G-S, and S-S; and $X_g$ is absent or selected from Q, and T-Q.

More preferably, the at least three THDs of component A are connected by the peptide $X_a$ which is selected from the group consisting of I-V-S-G (SEQ ID NO: 165), A-V-S-G (SEQ ID NO: 163), I-V-G-G (SEQ ID NO: 164), A-V-G-G (SEQ ID NO: 162), L-V-S-G (SEQ ID NO: 161), L-V-G-G (SEQ ID NO: 159), L-V-G-G-R (SEQ ID NO: 168), L-V-G-G-G (SEQ ID NO: 169), L-V-G-G-P (SEQ ID NO: 170), L-V-G-G-A (SEQ ID NO: 171), L-V-G-G-P-Q (SEQ ID NO: 172), L-V-G-G-P-Q-R (SEQ ID NO: 173), L-V-G-G-G-P-Q-R (SEQ ID NO: 174), and L-V-G-G-G-G-P-Q (SEQ ID NO: 175), more preferably I-V-S-G (SEQ ID NO: 165), A-V-S-G (SEQ ID: 163), L-V-S-G (SEQ ID NO: 161) or L-V-G-G (SEQ ID NO: 159), even more preferably L-V-G-G (SEQ ID NO: 159) or A-V-S-G (SEQ ID: 163) and most preferably A-V-S-G (SEQ ID: 163). These amino acid sequences are preferred for $X_a$, if the THDs are derived from TRAIL, in particular human TRAIL.

In one embodiment the arginine at position 121 of TRAIL, preferably of huTRAIL, if comprised in $X_a$, is preferably replaced with glycine. This replacement will not decrease thermal stability. The replacement with lysine is less preferred.

In one embodiment the glycine at position 281 of TRAIL, preferably of huTRAIL, if comprised in $X_a$, can be replaced with serine. This replacement decreases aggregate formation.

Preferably, the amino acid sequence of the junction between two THDs, i.e. the C-terminal sequence-$X_a$-N-terminal sequence", preferably at the junction of the first and second and the second and third or subsequent THD domains of component A is selected from the group consisting of ($X_a$ is in each case underlined):

```
                                        (SEQ ID NO: 176)
S-F-F-G-A-F-L-V-G-G-G-P-Q-R-V-A-A-H-I;

(SEQ ID NO: 177)
S-F-F-G-A-F-L-V-G-G-P-Q-R-V-A-A-H-I;

(SEQ ID NO: 178)
S-F-F-G-A-F-L-V-S-G-I-A-A-H-I;

(SEQ ID NO: 179)
S-F-F-G-A-F-A-V-G-G-I-A-A-H-I;

(SEQ ID NO: 180)
S-F-F-G-A-F-A-V-G-G-I-A-A-H-I;

(SEQ ID NO: 181)
S-F-F-G-A-F-I-V-G-G-I-A-A-H-I;

(SEQ ID NO: 182)
S-F-F-G-A-F-A-V-S-G-I-A-A-H-I
and (SEQ ID NO: 183)
S-F-F-G-A-F-I-V-S-G-I-A-A-H-I.
```

These amino acid sequences are preferred for C-terminal sequence-$X_a$-N-terminal sequence junctions of two THDs, if the THDs are derived from TRAIL, in particular human TRAIL.

It is most preferred that the amino acid sequence of the C-terminal sequence-$X_a$-N-terminal sequence that are at the junction of the first and second, and second and third or subsequent THD domains of component A is selected from the group consisting of ($X_a$ is in each case underlined): S-F-F-G-A-L-V-G-G-V-A-A-H-I (SEQ ID NO: 184); S-F-F-G-A-F-L-V-G-G-R-V-A-A-H-I (SEQ ID NO: 185); S-F-F-G-A-F-L-V-G-G-I-A-A-H-I (SEQ ID NO: 186); S-F-F-G-A-F-L-V-G-G-A-A-A-H-I (SEQ ID NO: 187) or S-F-F-G-A-F-A-V-S-G-A-A-A-H-I (SEQ ID NO: 188). These amino acid sequences are preferred for C-terminal sequence-$X_a$-N-terminal sequence junctions of two THDs, if the THDs are derived from TRAIL, in particular human TRAIL.

In another preferred embodiment the at least three THDs of component A are identical which is indicated by subscript indices of the respective TNF-ligand family member THD, i.e. $scTRAIL_3$. This symbolizes three linked TRAIL THD molecules.

In another preferred embodiment the polypeptide of the first aspect of the present invention comprises a component B comprising a dimerization domain consisting of an antibody $V_L$ and $V_H$ region linked directly to each other with a peptide that has a length of between 7 and 11 amino acids.

Preferably, the $V_L$ and $V_H$ region of an antibody specifically bind to a target molecule on the cell surface. Preferably, the target molecule is selected from the group consisting of tyrosine-kinase-receptors (EGFR, HER2, HER3, HER4), VEGFRs, heteromeric integrin α- or β-receptor family, tumor stroma markers like fibroblast activation protein (FAP) endoglyx-1, or endosialin, galectin, EpCAM, CEA, CD44 and tumor specific variants thereof and other tumor selective cell surface markers, CD2, CD5, CD7, CD19, CD20, CD21, CD22, CD24, CD25, CD30, CD33, CD38, CD40, CD52, CD56, CD71, CD72, CD73, CD105, CD117, CD123, CD133, c-Met, PDGFR, IGF1-R, HMW-MAA, TAG-72, GD2, GD3, GM2, folate receptor, Lgr5, Ley, Muc-1, Muc-2, PSMA, PSCA and uPAR. More preferably, the target molecule is FAP, EGFR, HER2 or HER3.

Preferably the $V_L$ region comprises, essentially consists or consists of the amino acid sequence according to SEQ ID NO: 4 and/or the $V_H$ region comprises, essentially consists or consists of the amino acid sequence according to SEQ ID NO: 237, if the target antigen is EGFR. Preferably the $V_L$ region comprises, essentially consists or consists of the amino acid sequence according to SEQ ID NO: 238 and/or the $V_H$ region comprises, essentially consists or consists of the amino acid sequence according to SEQ ID NO: 239, if the target antigen is HER-2. Preferably the $V_L$ region comprises, essentially consists or consists of the amino acid sequence according to SEQ ID NO: 240 and/or the $V_H$ region comprises, essentially consists or consists of the amino acid sequence according to SEQ ID NO: 241, if the target antigen is HER-3.

Preferably, the $V_H$ and $V_L$ region are directly linked to each other by a peptide of 7, 8, 9, 10 or 11 amino acids in length. This peptide is preferably a flexible amino acid stretch. Particularly preferred is that the $V_H$ and $V_L$ region are directly linked to each other by a peptide of 5, 8 or 10 amino acids in length which is selected from the group consisting of G-G-G-G-S (SEQ ID NO: 189), G-G-G-G-S-G-G-G: (SEQ ID NO: 190) or G-G-G-G-S-G-G-G-G-S (SEQ ID NO: 199).

In another preferred embodiment component A is linked to component B by a peptide $X_b$. The peptide $X_b$ preferably has a length of between 5 to 35 amino acids, more preferably between 10 to 30, more preferably 12 to 25, i.e. 5, 6, 7, 8, 9, 10, 11, 12, 13, 14, 15 16, 17, 18, 19, 20, 21, 22, 23, 24, 25, 26, 27, 28, 29, 30, 31, 32, 33, 34 or 35, preferably 16 amino acids. It is preferred that the peptide $X_b$ is selected from glycine and/or serine rich peptides. A peptide is considered glycine and/or serine rich, if at least 70% of the amino acids are selected from glycine and/or serine, preferably more than 75%, more than 80%, more than 90%. Other amino acids that may be present comprise are preferably those that do not result in structural rigidity, e.g. proline, thus preferably small amino acids are comprised in addition to serine and/or glycine. Preferred examples of such small amino acids are alanine or threonine. Preferred examples of peptides are selected from (GGS)$_n$, (GGSGG)$_m$, (SEQ ID NO: 257), wherein n is an integer between 1 to 12, preferably between 3 to 7 and m is an integer between 1 to 7, preferably between 3 to 5. Further preferred peptides are selected from the group consisting of SEQ ID NO 192 (GGSGGASSGG), SEQ ID NO: 193 (GGSGGGSSGG), SEQ ID NO 194 (AAAGNGTSNGTSEFG) SEQ ID NO: 258 (GSGNGTSNGTSGSSGG) and SEQ ID NO: 259 (GSGNGTSNGTSGSSRT). It is further preferred that $X_b$ comprises at least on glycosylation motif. Glycosylation motifs comprise for instance nitrogen atoms in asparagine chains. Even more preferably, $X_b$ has a length of 16 amino acids and has two glycosylation motifs. (SEQ ID NO: 194, A-A-A-G-N-G-T-S-N-G-T-S-E-F-G-G). The glycosylation motif is preferably inserted in one of the above outlined preferred peptides. Preferably, at or close to the middle of the peptide.

It is preferred that peptide $X_b$ may be selected independently of any peptide selected for linking the at least three THD of component A.

Preferably, the structure of the polypeptide according to the first aspect of the present invention comprises, essentially consists or consists of (from N- to C-terminus, A: component A; B: component B; $X_a$: peptide linking the at least three THDs of component A; $X_b$: linking component A to component B; it is noted that below structures do not exclude the possibility that additional peptides are attached N- and/or C-terminally)

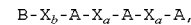

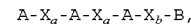

or may be

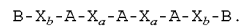

As outlined above the polypeptide of the first aspect may comprise more than three components A, e.g. 4, 5, 6, 7, 8, or 9, more preferably 6 or 9. These may all be arranged consecutively and component B is then position N- and/or C terminally or one or more component B may be interspersed between component A. Preferred structures of the polypeptide according to the first aspect of the present invention comprises, essentially consists or consists of (from N- to C-terminus):

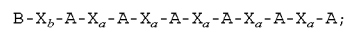

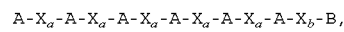

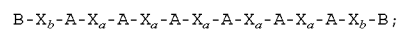

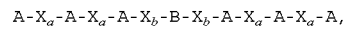

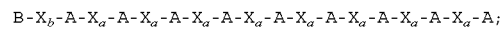

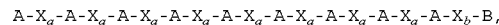

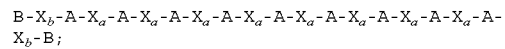

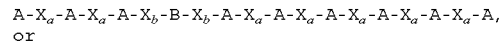

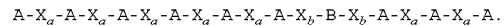

In another preferred embodiment the polypeptide comprising component A linked to component B is selected from the group consisting of Db-scTRAIL$_3$-FAVSGAA (SEQ ID NO: 195), dsDb3M6-scTRAIL$_3$-FLVGGGPQRVA (SEQ ID NO: 196), Db10-scTRAIL$_3$-FAVSGGA (SEQ ID NO: 197), Db-glyco-scTRAIl$_3$-FAVSGAA (SEQ ID NO: 198), Db-glyco-scTRAIL$_3$-FAVSGIA (SEQ ID NO: 199). More preferably, the polypeptide comprising component A linked to component B is selected from the group consisting of Db8-glyco-scTRAIL$_3$-FAVSGGA (SEQ ID NO: 200), Db10-glyco-scTRAIL$_3$-FAVSGGA (SEQ ID NO: 201).

Another optional element which may or may not be present in a polypeptide according to the first aspect of the present invention is a tag allowing for example the detection and or purification of a polypeptide of the first aspect of the present invention. Examples for such tags are His-tag, FLAG-tag, HA-tag, STREP-tag, myc-tag or GST (see Arnau et al., 2006). Preferably, such tag is positioned outside the region comprising the at least three THDs of component A and component B. It is also possible to position a protease cleavage site (e.g. a Thrombin cleavage site) adjacent to the tag, in this context it is preferred that the tags are positioned directly at the C-terminus or N-terminus of the tag allowing to remove the tag after purification. Preferably, the tag is N-terminally to be cleaved after detection or purification.

In a second aspect the present invention relates to a polypeptide comprising component C comprising: at least three THDs, wherein the C-terminus of the first and second THD, respectively, which is in each case defined by the consensus sequence

-S/T/V-F/Y/S-F-G-A/L/V/I-X$_1$, (SEQ ID NO: 1)

is linked to the N-terminus of the second and third THD, respectively, which is in each case defined by the consensus sequence

X$_2$-V/A/F-A-H-V/L/I/Y (SEQ ID NO: 2)

or

X$_3$-V/W/F/C-A/L-E/Y/Q/H-L, (SEQ ID NO: 3)

through a peptide X$_c$, which is in each case independently selected and has a length of 3 to 5 amino acids,
wherein X$_1$ is a non-polar/hydrophob or polar/neutral amino acid, preferably selected from the group consisting of F, V, Q, A, I, L, and Y;
wherein X$_2$ is selected from the group consisting of P, K, V, I, and A; and
wherein X$_3$ is selected from the group consisting of D, S, M, and I.

In a preferred embodiment component C comprises at least three TNF homology domains of TNF-ligand family member proteins (THD), wherein the C-terminus of the first and second THD, respectively, in each case defined by the consensus sequence

-S/T/V-F/Y/S-F-G-A/L/V/I-X$_1$ (SEQ ID NO: 1)

wherein X$_1$ is a non-polar/hydrophob or polar/neutral amino acid, preferably selected from the group consisting of F, V, Q, A, I, L, and Y. Component C is identical to component A described above regarding the first aspect of the invention but for the fact that the peptide X$_c$ connecting the THDs in component C has a length of between 3 to 5 amino acids rather than between 3 to 8 amino acids as peptide X$_a$. This also applies to all preferred and particular preferred embodiments of component A outlined in detail above.

Component C of the polypeptide of the present invention, preferably has a thermal stability of at least 48° C., more preferably of at least 49° C., more preferably of at least 50° C., more preferably of at least 51° C., more preferably of at least 52° C., more preferably of at least 53° C., more preferably of at least 54° C., more preferably of at least 55° C., more preferably of at least 56° C., more preferably of at least 57° C., more preferably of at least 58° C., more preferably of at least 59° C. and most preferably at least 60° C. Preferably, the polypeptide of the second aspect comprising component C has at least the above indicated thermal stabilities. The skilled person is well aware how to measure thermal stabilities of polypeptides. Exemplary methods are taught herein below.

As outlined above component C comprises the C-terminus of the first and second THD, respectively, which is defined by a consensus sequence as described above and is connected to the N-terminus of the second and third THD, respectively, defined by a consensus sequence as described above through a peptide X$_c$, which is in each case independently selected and has a length of 3 to 5 amino acids, preferably 4 amino acids. Preferably, the peptide X, consists of X$_e$-X$_f$-X$_g$ wherein X$_e$ is selected from the group consisting of L, L-V, L-V-G, L-V-G-G, L-V-S, L-V-S-G, A, A-V, A-V-S, A-V-G, A-V-G-G, A-V-S-G, I-V, I-V-S, I-V-G, I-V-G-G, I-V-S-G, K, K-L, M, M-V, A, A-L, M-V-G, M-V-Q, G, G-V, G-V-H, W, W-V, W-V-R, W-V-R-P, K-L-L, I, A-V, Q, Q-V, and Q-V-H;
X$_f$ is absent or selected from the group consisting of G, S, G-G, S-G, G-S, S-S, G-G-G, G-G-S, G-S-G, S-G-G, G-S-S, S-G-S and S-S-S; and
X$_g$ is absent or selected from the group consisting of R, Q-R, P-Q-R, G-P-Q-R, L-R, N, V-N, K, L-K, L, G-L, K, D-K, Q, P-Q, A, R-A, W, G-W, Q, and T-Q.

Preferably,
(i) X$_e$ is selected from L, L-V, L-V-G, L-V-G-G, L-V-S, L-V-S-G, A, A-V, A-V-S, A-V-G, A-V-G-G, A-V-S-G, I-V, I-V-S, I-V-G, I-V-G-G, and I-V-S-G; X$_f$ is absent or selected from G, S, G-G, S-G, G-S, and S-S; and X$_g$ is absent or selected from R, Q-R, P-Q-R, and G-P-Q-R;
(ii) X$_e$ is selected from K, and K-L; X$_f$ is absent or selected from G, S, G-G, S-G, G-S, and S-S; and X$_g$ is absent or selected from R, and L-R,
(iii) X$_e$ is selected from M, M-V; X$_f$ is absent or selected from G, S, G-G, S-G, G-S, and S-S; and X$_g$ is absent or selected from N and V-N;
(iv) X$_e$ is selected from A, and A-L; X$_f$ is absent or selected from G, S, G-G, S-G, G-S, and S-S; and X$_g$ is absent or selected from K and L-K;
(v) X$_e$ is selected from M, M-V, and M-V-G; X$_f$ is absent or selected from G, S, G-G, S-G, G-S, and S-S; and X$_g$ is absent or selected from L, and G-L;
(vi) X$_e$ is selected from A, and A-L; X$_f$ is absent or selected from G, S, G-G, S-G, G-S, and S-S; and X$_g$ is absent or selected from K, and D-K;
(vii) X$_e$ is selected from K, and K-L; X$_f$ is absent or selected from G, S, G-G, S-G, G-S, and S-S; and X$_g$ is absent or selected from Q, and P-Q;
(viii) X$_e$ is selected from Q, Q-V, and Q-V-H; X$_f$ is absent or selected from G, S, G-G, S-G, G-S, and S-S; and X$_g$ is absent or selected from A, and R-A;
(ix) X$_e$ is selected from W, W-V, W-V-R, and W-V-R-P; X$_f$ is absent or selected from G, S, G-G, S-G, G-S, and S-S; and X$_g$ is absent or selected from W, and G-W; or
(x) X$_e$ is selected from K, K-L, and K-L-L; X$_f$ is absent or selected from G, S, G-G, S-G, G-S, and S-S; and X$_g$ is absent or selected from Q, and T-Q.

More preferably, the at least three THD domains of component C are linked by the peptide X$_c$ which is selected from the group consisting of L-V-G, I-V-S-G, A-V-S-G, A-V-S-G-A, I-V-G-G, A-V-G-G, A-V-G-G-A, L-V-S-G, L-V-G-G, L-V-G-G-R, L-V-G-G-G, L-V-G-G-P, L-V-G-G-A.

More preferably, the at least three THDs of component A are connected by the peptide $X_a$ which is selected from the group consisting of I-V-S-G (SEQ ID NO: 165), A-V-S-G (SEQ ID NO: 163), I-V-G-G (SEQ ID NO: 164), A-V-G-G (SEQ ID NO: 162), L-V-S-G (SEQ ID NO: 161), L-V-G-G (SEQ ID NO: 159), L-V-G-G-R (SEQ ID NO: 168), L-V-G-G-G (SEQ ID NO: 169), L-V-G-G-P (SEQ ID NO: 170), L-V-G-G-A (SEQ ID NO: 171), L-V-G-G-P-Q (SEQ ID NO: 172), L-V-G-G-P-Q-R (SEQ ID NO: 173), L-V-G-G-G-P-Q-R (SEQ ID NO: 174), and L-V-G-G-G-G-P-Q (SEQ ID NO: 175), more preferably I-V-S-G (SEQ ID NO: 165), A-V-S-G (SEQ ID: 163), L-V-S-G (SEQ ID NO: 161) or L-V-G-G (SEQ ID NO: 159), even more preferably L-V-G-G (SEQ ID NO: 159) or A-V-S-G (SEQ ID: 163) and most preferably A-V-S-G (SEQ ID: 163). These amino acid sequences are preferred for $X_a$, if the THDs are derived from TRAIL, in particular human TRAIL.

In one embodiment the arginine at position 121 of TRAIL, preferably of huTRAIL, if comprised in $X_a$, is preferably replaced with glycine. This replacement will not decrease thermal stability. The replacement with lysine is less preferred.

In one embodiment the glycine at position 281 of TRAIL, preferably of huTRAIL, if comprised in $X_a$, can be replaced with serine. This replacement decreases aggregate formation.

Preferably, the amino acid sequence of the C-terminal sequence-$X_e$-N-terminal sequence that are at the junction of the first and second, and second and third or subsequent THD domains of component A is selected from the group consisting of ($X_c$ is in each case underlined): S-F-F-G-A-F-L-V-S-G-I-A-A-H-I (SEQ ID NO: 178); S-F-F-G-A-F-A-V-G-G-A-A-A-H-I (SEQ ID NO: 179); S-F-F-G-A-F-A-V-G-G-I-A-A-H-I (SEQ ID NO: 180); S-F-F-G-A-F-I-V-G-G-I-A-A-H-I (SEQ ID NO: 181); S-F-F-G-A-F-A-V-S-G-I-A-A-H-I (SEQ ID NO: 182) and S-F-F-G-A-F-I-V-S-G-I-A-A-H-I (SEQ ID NO: 183). These amino acid sequences are preferred for C-terminal sequence-$X_c$-N-terminal sequence that are the THD junction, if the THDs are derived from TRAIL, in particular human TRAIL.

It is most preferred that, the amino acid sequence of the C-terminal sequence-$X_c$-N-terminal sequence that are at the junction of the first and second, and second and third or subsequent THD domains of component A is selected from the group consisting of ($X_c$ is in each case underlined): S-F-F-G-A-L-V-G-G-V-A-A-H-I (SEQ ID NO: 184); S-F-F-G-A-F-L-V-G-G-R-V-A-A-H-I (SEQ ID NO: 185); S-F-F-G-A-F-L-V-G-G-I-A-A-H-I (SEQ ID NO: 186); S-F-F-G-A-F-L-V-G-G-A-A-A-H-I (SEQ ID NO: 187) or S-F-F-G-A-F-A-V-S-G-A-A-A-H-I (SEQ ID NO: 188). These amino acid sequences are preferred for C-terminal sequence-X-N-terminal sequence that are the THD junction, if the THDs are derived from TRAIL, in particular human TRAIL.

In another preferred embodiment the polypeptide of the second aspect of the present invention comprises a component D which is selected from the group consisting of a dimerization or multimerization domain, a half-life extension domain, a target specific binding domain or combinations thereof. Preferred components D possess both a dimerization or multimerization domain and a target specific binding domain.

It is preferred that the dimerization or multimerization or the target specific binding domains are proteins or parts thereof coupled to the polypeptide of the second aspect of the present invention. Dimerization domains are dimerization domains from an antibody, e.g. an Fc region, a CH3 domain of IgG, IgA, or IgD, a CH2 domain of IgE or IgM, a CH4 domain of IgE or IgM, and the CH1 and CL domain. A preferred dimerization domain from an antibody, is the CH2 domain of IgE (EHD2), variants or fragments thereof. Other dimerization or multimerization domains include barnase-barstar, C4bp, CD59, peptides derived from collagen, GST, the α and β subunits of inactive human chorionic gonadotropin, maltose-binding protein (MBP), p53 and fragments thereof, phosphatase, streptavidin, surfactant protein D, tenascin, tetranectin, dock-and-lock (DNL) motifs, and uteroglobin.

They are preferably combined with a target specific binding domain which may be an antibody or a target specific binding fragment thereof, an antibody light chain or a target specific binding fragment thereof, an antibody heavy chain or a target specific binding fragment thereof, a single-chain fragment variable (scFv), a diabody, a single-chain diabody a single domain antibody or an antibody mimetic.

If component D comprises, essentially consists or consists an antibody heavy chain or a target specific binding fragment thereof, it is preferred that a further polypeptide according to the second aspect of the invention is provided in which component D comprises, essentially consists or consists of the antibody light chain or a target specific binding fragment thereof. Preferably, both the antibody heavy and light chain or the target specific binding fragments thereof, bind to the same target.

In another preferred embodiment component D comprises, essentially consists or consists of a dimerization and one or more target-specific binding domains (ts-domain). Preferably, this ts-domain is a scFv, diabody, IgG, heavy or light chain or target specific binding fragment thereof. Preferred examples are antibody Fc fragments, variants or fragments thereof, e.g. an EHD2, combined with an antibody or target specific binding fragment thereof, single-chain fragment variable (scFv), a diabody, a single-chain diabody, a single domain antibody or an antibody mimetic. Particular preferred components D are selected from the group consisting of EHD2 (SEQ ID NO: 202), scFvhu225-EHD2 (SEQ ID NO: 203), scFv4D5-EHD2 (SEQ ID NO: 204), and scFv3M6-EHD2 (SEQ ID NO: 206). The combination of dimerization domain and one or more target specific binding domain, specifically binding to a particular cell type, leads to constructs inducing rapid apoptosis of that cell type.

In another preferred embodiment component D comprises, essentially consists or consists of a target specific binding domain which is preferably an antibody fragment or an antibody mimetic. The antibody fragment is preferably selected from the group consisting of a fragment antigen binding (Fab) fragment, a Fab' fragment, a heavy chain antibody, a single-domain antibody (sdAb), a single-chain variable fragment (scFv), a $V_H$ domain, a $V_L$ domain, a single domain antibody, a nanobody, an IgNAR (immunoglobulin new antigen receptor), a di-scFv, a bispecific T-cell engager (BITEs), a dual affinity re-targeting (DART) molecule, single-chain diabody, an alternative scaffold protein. Antibody-mimetics are selected from the group consisting of LACI-D1 (lipoprotein-associated coagulation inhibitor); affilins, e.g. human-γ B crystalline or human ubiquitin; cystatin; Sac7D from *Sulfolobus acidocaldarius*; lipocalin and anticalins derived from lipocalins; DARPins (designed ankyrin repeat domains); a domain of a membrane receptor; SH3 domain of Fyn; Kunits domain of protease inhibitors; monobodies, e.g. the $10^{th}$ type III domain of fibronectin;

adnectins: knottins (cysteine knot miniproteins); fynomers; atrimers; evibodies, e.g. CTLA4-based binders, affibodies, e.g. three-helix bundle from Z-domain of protein A from *Staphylococcus aureus*; Trans-bodies, e.g. human transferrin; tetranectins, e.g. monomeric human C-type lectin domain; microbodies, e.g. trypsin-inhibitor-II; affilins and armadillo repeat proteins. Most preferably the target specific binding domain is a Fab-fragment or a single-chain variable fragment (scFv).

It is further preferred that the target-specific binding domain is a complete antibody, a heavy chain of an antibody or a light chain of an antibody or a target specific binding fragment thereof, a diabody, a single chain antibody or an antibody mimetic. More preferably, the target specific binding domain is a diabody. Such a fusion protein or a bivalent antibody can bind different antigens and is composed of two single protein chains which comprise parts of an antibody, namely single-chain variable (scFv) fragments. Fragments comprise a heavy-chain variable domain ($V_H$) connected to a light-chain variable domain ($V_L$) on the same polypeptide chain ($V_H$-$V_L$). Preferably the $V_L$ and $V_H$ region of an antibody specifically bind to a target molecule on the cell surface.

Target molecules that are preferably targeted with the target specific binding domain are a receptor molecule or a membrane molecule specific to tumor cells. Preferably, the target molecule is selected from the group consisting of tyrosine-kinase-receptors (EGFR, HER2, HER3, HER4), VEGFRs, heteromeric integrin α- or β-receptor family, tumor stroma markers like fibroblast activation protein (FAP) endoglyx-1, or endosialin, galectin, EpCAM, CEA, CD44 and tumor specific variants thereof and other tumor selective cell surface markers, CD2, CD5, CD7, CD19, CD20, CD21, CD22, CD24, CD25, CD30, CD33, CD38, CD40, CD52, CD56, CD71, CD72, CD73, CD105, CD117, CD123, CD133, c-Met, PDGFR, IGF1-R, HMW-MAA, TAG-72, GD2, GD3, GM2, folate receptor, Lgr5, Ley, Muc-1, Muc-2, PSMA, PSCA and uPAR. More preferably, the target molecule is FAP, EGFR, HER2 or HER3.

Preferably, the diabody consists of an antibody $V_L$ and $V_H$ region linked directly to each other with a peptide that has a length of between 0 and 15, 4 to 13, preferably 7 to 11, most preferably 8 to 10 amino acids. Preferably, the diabody consists of a $V_L$ and $V_H$ domain linked directly to each other with a peptide of between 5, 6, 7, 8, 9, 10, 11, 12, 13, 14 or 15 amino acids. Preferably, the $V_H$ and $V_L$ region are directly linked to each other by a peptide of 7, 8, 9, 10 or 11 amino acids in length. Surprisingly such long peptides still provided stable diabodies in the context of component C. This peptide is preferably a flexible amino acid stretch. More preferably, the $V_H$ and $V_L$ region are directly linked to each other by a peptide of 4 to 15 glycinde and/or serine residues or 5, 8 or 10 amino acids in length, preferably by one of the sequences selected from the group consisting of SEQ ID NO: 260 (GGGGS), SEQ ID NO: 207 (8 aa: GGGGSGGG) and SEQ ID NO: 208 (10 aa: GGGGSGGGGS).

Preferably the $V_L$ region comprises, essentially consists or consists of the amino acid sequence according to SEQ ID NO: 4 and/or the $V_H$ region comprises, essentially consists or consists of the amino acid sequence according to SEQ ID NO: 237, if the target antigen is EGFR. Preferably the $V_L$ region comprises, essentially consists or consists of the amino acid sequence according to SEQ ID NO: 238 and/or the $V_H$ region comprises, essentially consists or consists of the amino acid sequence according to SEQ ID NO: 239, if the target antigen is HER-2. Preferably the $V_L$ region comprises, essentially consists or consists of the amino acid sequence according to SEQ ID NO: 240 and/or the $V_H$ region comprises, essentially consists or consists of the amino acid sequence according to SEQ ID NO: 241, if the target antigen is HER-3.

Even more preferably, the polypeptide comprising component C linked to component D is selected from the group consisting of Db-scTRAIL$_3$-FAVSGAA (SEQ ID NO: 195), dsDb3M6-scTRAIL3-FLVGGGPQRVA (SEQ ID NO: 196), Db10-scTRAIL$_3$-FAVSGGA (SEQ ID NO: 197), Db-glyco-scTRAIL$_3$-FAVSGAA (SEQ ID NO: 198), Db-glyco-scTRAIL$_3$-FAVSGIA (SEQ ID NO: 199).

Preferably, the target specific binding domain is an antibody or fragment. Preferably, the fragment is selected from the group consisting of a complete antibody, a fragment antigen binding (Fab) fragment, a Fab' fragment, a F(ab')$_2$ fragment, a heavy chain antibody, a single-domain antibody (sdAb), a single-chain variable fragment (scFv), or a part thereof, a di-scFv, a bispecific T-cell engager (BITEs), a dual affinity re-targeting (DART) molecule, a triple body, an alternative scaffold protein, and a fusion protein thereof, and combinations thereof. More preferably, the target specific binding domain comprises a Fc region and a single chain variable fragment (scFv). Even more preferably, the target specific binding domain linked to component C comprises Fc region parts. Even more preferably, the polypeptide comprising component C and component D is selected from the group consisting of scFvhu225-Fc-scTRAIL$_3$-FLVGGGPQRVA (SEQ ID NO: 209), Fc-scTRAIL$_3$-FLVGGGPQRVA (SEQ ID NO: 210) or scFv4D5-Fc-scTRAIL$_3$-FLVGGGPQRVA (SEQ ID NO: 211).

It is particularly preferred that the target specific binding domain is a single chain variable fragment and the dimerization or multimerization domain is either a Fc fragment or EHD2.

In another preferred embodiment component C is linked to component D by a peptide $X_d$. The peptide $X_d$ preferably has a length of between 5 to 35 amino acids, preferably 10 to 30 amino acids, more preferably 15 to 25, most preferably 18 to 22 amino acids, i.e. 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 and 35 amino acids, preferably 19, 20 or 21 amino acids, most preferably 20 amino acids. It is preferred that the peptide $X_d$ is a glycine and/or serine rich peptides. A peptide is considered glycine and/or serine rich, if at least 70% of the amino acids are selected from glycine and/or serine, preferably more than 75%, more than 80%, more than 90%. Other amino acids that may be present comprise are preferably those that do not result in structural rigidity, e.g. proline, thus preferably small amino acids are comprised in addition to serine and/or glycine. Preferred examples of such small amino acids are alanine or threonine. Preferred examples of peptides are selected from $(GGS)_n$, $(GGSGG)_m$, (SEQ ID NO: 257), wherein n is an integer between 1 to 12, preferably between 3 to 7 and m is an integer between 1 to 7, preferably between 3 to 5. Further preferred peptides are selected from the group consisting of SEQ ID NO 192 GGSGGASSGG), SEQ ID NO: 193 (GGSGGGSSGG) SEQ ID NO: 194 (AAGNGTSNGTSEFGG) SEQ ID NO: 258 (GSGNGTSNGTSGSSGG) and SEQ ID NO: 259 (GS-GNGTSNGTSGSSRT). It is further preferred that $X_d$ comprises at least on glycosylation motif. Glycosylation motifs comprise for instance nitrogen atoms in asparagine chain. Even more preferably, $X_d$ has a length of 16 amino acids and has two glycosylation motifs (SEQ ID NO: 194, A-A-A-G-N-G-T-S-N-G-T-S-E-F-G-G). The glycosylation motif is preferably inserted in one of the above outlined preferred peptides. Preferably, at or close to the middle of the peptide.

Peptide $X_d$ preferably has a length of between 18 to 22, if the dimerization is either a Fc fragment or EHD2, preferably a Fc fragment. Preferably, the structure of the polypeptide according to the second aspect of the present invention linked to a component D comprises (from N- to C-terminus, D: component D; $X_c$: peptide linking the at least three THDs of component C; $X_d$: linking component C to component D)

$THD-X_c-THD-X_c-THD-X_d-D$, $D-X_d-THD-X_c-THD-X_c-THD$, or $D-X_d-THD-X_c-THD-X_c-THD-X_d-D$,

As outlined above the polypeptide of the second aspect may comprise more than three components C, e.g. 4, 5, 6, 7, 8, or 9, more preferably 6 or 9. Such constructs show an even larger heat stability than those only comprising 3 components C. The components C may all be arranged consecutively and component D is then position N- and/or C terminally or one or more component D may be interspersed between component C. Preferred structures of the polypeptide according to the first aspect of the present invention comprises, essentially consists or consists of (from N- to C-terminus):

$D-X_d-C-X_c-C-X_c-C-X_c-C-X_c-C-X_c-C$;

$C-X_c-C-X_c-C-X_c-C-X_c-C-X_c-C-X_dD$, $D-X_d-C-X_c-C-X_c-C-X_c-C-X_c-C-X_c-C-X_d-D$;

$C-X_c-C-X_c-C-X_d-D-X_b-C-X_c-C-X_c-C$, $D-X_d-C-X_c-C-X_c-C-X_c-C-X_c-C-X_c-C-X_c-C-X_c-C$;

$C-X_c-C-X_c-C-X_c-C-X_c-C-X_c-C-X_c-C-X_c-C-X_d-D$, $D-X_d-C-X_c-C-X_c-C-X_c-C-X_c-C-X_c-C-X_c-C-X_c-C-X_d-D$;

$C-X_c-C-X_c-C-X_d-D-X_b-C-X_c-C-X_c-C-X_c-C-X_c-C$, or $C-X_c-C-X_c-C-X_c-C-X_c-C-X_c-C-X_d-D-X_b-C-X_c-C-X_c-C$.

Another optional element which may or may not be present in a polypeptide according to the first aspect of the present invention is a tag allowing for example the detection and or purification of a polypeptide of the first aspect of the present invention. Examples for such tags are His-tag, FLAG-tag, HA-tag, STREP-tag, myc-tag or GST. Preferably, such tag is positioned outside the region comprising the at least three THDs of component C and component D. It is also possible to position a protease cleavage site (e.g. a Thrombin cleavage site) adjacent to the tag, e.g. directly C-terminally of an N-terminal tag allowing to remove the tag after purification. In this context it is preferred that the tags are positioned directly at the C-terminus or N-terminus of the polypeptide allowing to remove the tag after purification. Preferably, the tag is N-terminally to be cleaved after detection or purification.

The polypeptide of the first and second aspect of the present invention relate also to polypeptide complexes of the polypeptides of the first and second aspect of the present invention, e.g. homodimeric, and/or homotrimeric complexes of component A of the polypeptide of the first aspect of the present invention and the polypeptide according to the second aspect of the present invention. Thus, the polypeptides of the first and second aspect of the present invention are capable of forming multimers, such as dimers, trimers, tetramers etc. It is preferred that component A of the polypeptide of the first aspect of the present invention and the polypeptide of the second aspect of the present invention form trimers. It is preferred that component B of the first aspect and component D of the second aspect of the present invention are capable of forming multimers such as dimers, trimers, tetramers etc. In a particularly preferred embodiment component B of the first aspect and component D of the second aspect of the present invention are selected such that multimerization, such as dimerization of the polypeptide of the first aspect of the present invention and the polypeptide of the second aspect of the present invention comprising component C linked to component D, is possible. More preferably, the polypeptide of the first aspect of the present invention and the polypeptide of the second aspect of the present invention comprising component C linked to component D exhibit a multimeric form, such as a dimeric, trimeric, tetrameric etc. form, most preferably a dimeric form. Accordingly, in a particular preferred embodiment the polypeptide of the first aspect of the present invention and the polypeptide of the second aspect of the present invention comprising component C linked to component D is dimeric.

In a third aspect the present invention provides a nucleic acid encoding the polypeptides according to the first and second aspect of the present invention. The nucleic acid may be RNA or DNA or a hybrid thereof. Preferably, the nucleic acid also comprises sequences allowing for the expression of the polypeptide according the first and second aspect of the present invention in a suitable expression system. The nucleic acid can be codon optimized for the respective expression system.

In a fourth aspect the present invention provides a vector comprising the nucleic acid of the third aspect of the present invention. It is preferred that the genes of interest encoded by the introduced polynucleotide are expressed within the cell upon introduction of the vector or vectors. Preferably, the vector provides for transcription and expression of the polypeptide encoded by the nucleic acid in a suitable host cell system. Preferably, the expression vector is selected from the group consisting of a bacterial, yeast, baculovirus, plant and mammalian expression vector, more preferably the expression vector is a bacterial expression vector or a cell-free expression vector.

In a fifth aspect the present invention provides a pharmaceutical composition comprising the polypeptide of the first or the second aspect of the present invention, or the nucleic acid of the third aspect, or the vector of the fourth aspect and pharmaceutical acceptable carriers and/or suitable excipients. The pharmaceutical composition is selected from the group consisting of solid, liquid, semi-solid or transdermal therapeutic systems. It is envisioned that the pharmaceutical compositions of the invention comprise one or more polypeptides of the first and/or second aspect of the invention.

The present inventors have noted that the apoptosis inducing activity of the polypeptides of the first and/or second aspect of the present invention can be further enhanced by including in the pharmaceutical composition one or more proteasome inhibitor. Proteasome inhibitors are drugs that block the action of proteasomes, cellular complexes that break down proteins. Preferred proteasome inhibitors are selected from the group comprising bortezomib, lactacystin, disulfiram, epigallocatechin-3-gallate, salinosporamide A, carfilzomib, epoxomicin, ixazomib, ONX 0912, CEP-18770, and MLN9708, preferably bortezomib.

It is also envisioned that the pharmaceutical composition comprises a combination of one polypeptide of the present invention in combination with a chemotherapeutic agent, e.g. gemcitabine, capecitabine, doxorubicin, methotrexate, 5-fluorouracil, azathioprine, cytarabin, fludarabin, tegafur, 6-thioguanine, cisplatin, carboplatin, paclitaxel, docetaxel, vinorelbin, vinchristin, etoposid, teniposid, irinotecan, rituximab, panitumumab, bortezumib, vorinostat, ganitumumab, cetixumab, or sorafenib.

The pharmaceutical composition may also comprise both one or more proteasome inhibitors and one or more chemotherapeutic agents.

In a sixth aspect the present invention relates to a polypeptide of the first or the second aspect, a nucleic acid of the third aspect or a vector of the fourth aspect for use as a medicament.

In a seventh aspect the present invention relates to a polypeptide of the first or the second aspect, a nucleic acid of the third aspect or a vector of the fourth aspect or the pharmaceutical composition of the fifth aspect for use in the diagnosis, prophylaxis or treatment of hyperproliferative disorders and inflammatory disorders.

Preferred hyperproliferative diseases are selected from the group consisting of precancerosis; dysplasia; metaplasia; and cancer.

Particular preferred cancers to be treated by the polypeptides of the present invention are carcinomas of the gastrointestinal tract, liver, kidney, bladder, prostate, endometrium, ovary, testes, skin, invasive oral cancers, small cell and non-small cell lung carcinomas, hormone-dependent breast cancers, hormone-independent breast cancers, transitional and squamous cell cancers, neurological malignancies including neuroblastoma, gliomas, astrocytomas, osteosarcomas, soft tissue sarcomas, hemangioamas, endocrinological tumors, hematologic neoplasias including leukemias, lymphomas, and other myeloproliferative and lymphoproliferative diseases, carcinomas in situ, hyperplastic lesions, adenomas, fibromas, histiocytosis, chronic inflammatory proliferative diseases, vascular proliferative diseases and virus-induced proliferative diseases, skin diseases characterized by hyperproliferation of keratinocytes and/or T cells. Particular preferred diseases treatable with the compounds of the present invention are solid tumors, in particular lung, breast, pancreas, colorectal, ovarian, prostatic and gastric cancers and adenocarcinomas.

The precancerosis treatable with the polypeptides of the present invention are preferably selected from the group consisting of precancerosis of the skin, in particular actinic keratosis, cutaneaous horn, actinic cheilitis, tar keratosis, arsenic keratosis, x-ray keratosis, Bowen's disease, bowenoid papulosis, lentigo maligna, lichen sclerosus, and lichen rubber mucosae; precancerosis of the digestive tract, in particular erythroplakia, leukoplakia, Barrett's esophagus, Plummer-Vinson syndrome, crural ulcer, gastropathia hypertrophica gigantea, borderline carcinoma, neoplastic intestinal polyp, rectal polyp, porcelain gallbladder; gynaecological precancerosis, in particular carcinoma ductale in situ (CDIS), cervical intraepithelial neoplasia (CIN), leukoplakia, endometrial hyperplasia (grade III), vulvar dystrophy, vulvar intraepithelial neoplasia (VIN), hydatidiform mole; urologic precancerosis, in particular bladder papillomatosis, Queyrat's erythroplasia, testicular intraepithelial neoplasia (TIN), leukoplakia; carcinoma in situ (CIS); precancerosis caused by chronic inflammation, in particular pyoderma, osteomyelitis, acne conglobata, lupus vulgaris, and fistula.

Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exist chronic irritation or inflammation. Dysplastic disorders which can be treated with the compounds of the present invention include, but are not limited to, anhidrotic ectodermal dysplasia, anterofacial dysplasia, asphyxiating thoracic dysplasia, atriodigital dysplasia, bronchopulmonary dysplasia, cerebral dysplasia, cervical dysplasia, chondroectodermal dysplasia, cleidocranial dysplasia, congenital ectodermal dysplasia, craniodiaphysial dysplasia, craniocarpotarsal dysplasia, craniometaphysial dysplasia, dentin dysplasia, diaphysial dysplasia, ectodermal dysplasia, enamel dysplasia, encephalo-ophthalmic dysplasia, dysplasia epiphysialis heminelia, dysplasia epiphysialis multiplex, dysplasia epiphysalis punctata, epithelial dysplasia, faciodigitogenital dysplasia, familial fibrous dysplasia of jaws, familial white folded dysplasia, fibromuscular dysplasia, fibrous dysplasia of bone, florid osseous dysplasia, hereditary renal-retinal dysplasia hidrotic ectodermal dysplasia, hypohidrotic ectodermal dysplasia, lymphopenic thymic dysplasia, mammary dysplasia, mandibulofacial dysplasia, metaphysical dysplasia, Mondini dysplasia, monostotic fibrous dysplasia, mucoepithelial dysplasia, multiple epiphysial dysplasia, oculoauriculovertebral dysplasia, oculodentodigital dysplasia, oculovertebral dysplasia, odontogenic dysplasia, ophthalmomandibulomelic dysplasia, periapical cemental dysplasia, polyostotic fibrous dysplasia, pseudoachondroplastic spondyloepiphysial dysplasia, retinal dysplasia, septo-optic dysplasia, spondyloepiphysial dysplasia, and ventriculoradial dysplasia.

Metaplasia is a form of controlled cell growth in which one type of adult or fully differentiated cell substitutes for another type of adult cell. Metaplastic disorders, which are treatable are preferably selected from the group consisting of agnogenic myeloid metaplasia, apocrine metaplasia, atypical metaplasia, autoparenchymatous metaplasia, connective tissue metaplasia, epithelial metaplasia, intestinal metaplasia, metaplastic anemia, metaplastic ossification, metaplastic polyps, myeloid metaplasia, primary myeloid metaplasia, secondary myeloid metaplasia, squamous metaplasia, squamous metaplasia of amnion, symptomatic myeloid metaplasia and regenerative metaplasia.

Many skin diseases are characterized by hyperproliferation of keratinocytes and/or T cells. Examples of such diseases which are treatable with the compounds of the present invention comprise without limitations psoriasis in particular psoriasis vulgaris, psoriasis capitis, psoriasis guttata, psoriasis inversa; neurodermatitis; ichtyosises; alopecia areata; alopecia totalis; alopecia subtotalis; alopecia universalis; alopecia diffusa; atopic dermatitis; lupus erythematodes of the skin; dermatomyositis of the skin; atopic eczema; morphea; scleroderma; alopecia areata Ophiasis type; androgenic alopecia; allergic contact dermatitis; irritative contact dermatitis; contact dermatitis; pemphigus vulgaris; pemphigus foliaceus; pemphigus vegetans; scarring mucous membrane pemphigoid; bullous pemphigoid; mucous membrane pemphigoid; dermatitis; dermatitis herpetiformis Duhring; urticaria; necrobiosis lipoidica; erythema nodosum; prurigo simplex; prurigo nodularis; prurigo acuta; linear IgA dermatosis; polymorphic light dermatosis; erythema solaris; exanthema of the skin; drug exanthema;

purpura chronica progressiva; dihydrotic eczema; eczema; fixed drug exanthema; photoallergic skin reaction; and periorale dermatitis.

Inflammatory disorders that can be treated with the polypeptides of the invention include but are not limited to Acute disseminated encephalomyelitis (ADEM), Addison's disease, Agammaglobulinemia, Alopecia areata, Amyotrophic lateral sclerosis (Also Lou Gehrig's disease; Motor Neuron Disease), Ankylosing Spondylitis, Antiphospholipid syndrome, Antisynthetase syndrome, Atopic allergy, Atopic dermatitis, Autoimmune aplastic anemia, Autoimmune cardiomyopathy, Autoimmune enteropathy, Autoimmune hemolytic anemia, Autoimmune hepatitis, Autoimmune inner ear disease, Autoimmune lymphoproliferative syndrome, Autoimmune pancreatitis, Autoimmune peripheral neuropathy, Autoimmune polyendocrine syndrome, Autoimmune progesterone dermatitis, Autoimmune thrombocytopenic purpura, Autoimmune urticarial, Autoimmune uveitis, Balo disease/Balo concentric sclerosis, Behçet's disease, Berger's disease, Bickerstaff s encephalitis, Blau syndrome, Bullous pemphigoid, Cancer, Castleman's disease, Celiac disease, Chagas disease, Chronic inflammatory demyelinating polyneuropathy, Chronic inflammatory demyelinating polyneuropathy, Chronic obstructive pulmonary disease, Chronic recurrent multifocal osteomyelitis, Churg-Strauss syndrome, Cicatricial pemphigoid, Cogan syndrome, Cold agglutinin disease, Complement component 2 deficiency, Contact dermatitis, Cranial arteritis, CREST syndrome, Crohn's disease, Cushing's Syndrome, Cutaneous leukocytoclastic angiitis, Dego's disease, Dercum's disease, Dermatitis herpetiformis, Dermatomyositis, Diabetes mellitus type 1, Diffuse cutaneous systemic sclerosis, Discoid lupus erythematosus, Dressler's syndrome, Drug-induced lupus, Eczema, Endometriosis, Enthesitis-related arthritis, Eosinophilic fasciitis, Eosinophilic gastroenteritis, Eosinophilic pneumonia, Epidermolysis bullosa acquisita, Erythema nodosum, Erythroblastosis fetalis, Essential mixed cryoglobulinemia, Evan's syndrome, Fibrodysplasia ossificans progressive, Fibrosing alveolitis (or Idiopathic pulmonary fibrosis), Gastritis, Gastrointestinal pemphigoid, Glomerulonephritis, Goodpasture's syndrome, Graves' disease, Guillain-Barre syndrome (GBS), Hashimoto's encephalopathy, Hashimoto's thyroiditis, Henoch-Schonlein purpura, Herpes gestationis aka Gestational Pemphigoid, Hidradenitis suppurativa, Hughes-Stovin syndrome, Hypogammaglobulinemia, Idiopathic inflammatory demyelinating diseases, Idiopathic pulmonary fibrosis, Idiopathic thrombocytopenic purpura (See Autoimmune thrombocytopenic purpura), IgA nephropathy, Inclusion body myositis, Interstitial cystitis, Juvenile idiopathic arthritis aka Juvenile rheumatoid arthritis, Kawasaki's disease, Lambert-Eaton myasthenic syndrome, Leukocytoclastic vasculitis, Lichen planus, Lichen sclerosus, Linear IgA disease (LAD), Lupoid hepatitis aka Autoimmune hepatitis, Lupus erythematosus, Majeed syndrome, Microscopic colitis, Microscopic polyangiitis, Miller-Fisher syndrome, Mixed connective tissue disease, Morphea, Mucha-Habermann disease aka Pityriasis lichenoides et varioliformis acuta, Multiple sclerosis, Myasthenia gravis, Myositis, Meniere's disease, Narcolepsy, Neuromyelitis optica (also Devic's disease), Neuromyotonia, Occular cicatricial pemphigoid, Opsoclonus, yoclonus syndrome, Ord's thyroiditis, Palindromic rheumatism, PANDAS (pediatric autoimmune neuropsychiatric disorders associated with streptococcus), Paraneoplastic cerebellar degeneration, Paroxysmal nocturnal hemoglobinuria (PNH), Parry Romberg syndrome, Pars planitis, Parsonage-Turner syndrome, Pemphigus vulgaris, Perivenous encephalomyelitis, Pernicious anaemia, POEMS syndrome, Polyarteritis nodosa, Polymyalgia rheumatic, Polymyositis, Primary biliary cirrhosis, Primary sclerosing cholangitis, Progressive inflammatory neuropathy, Psoriasis, Psoriatic arthritis, Pure red cell aplasia, Pyoderma gangrenosum, Rasmussen's encephalitis, Raynaud phenomenon, Reiter's syndrome, Relapsing polychondritis, Restless leg syndrome, Retroperitoneal fibrosis, Rheumatic fever, Rheumatoid arthritis, Sarcoidosis, Schizophrenia, Schmidt syndrome another form of APS, Schnitzler syndrome, Scleritis, Scleroderma, Serum Sickness, Sjögren's syndrome, Spondyloarthropathy, Stiff person syndrome, Still's disease see Juvenile Rheumatoid Arthritis, Subacute bacterial endocarditis (SBE), Susac's syndrome, Sweet's syndrome, Sydenham chorea, Sympathetic ophthalmia, Systemic lupus erythematosus see Lupus erythematosus, Takayasu's arteritis, Temporal arteritis (also known as "giant cell arteritis"), Thrombocytopenia, Tolosa-Hunt syndrome, Transverse myelitis, Ulcerative colitis (one of two types of idiopathic inflammatory bowel disease "IBD"), undifferentiated connective tissue disease different from Mixed connective tissue disease, undifferentiated spondyloarthropathy, Urticarial vasculitis, Vasculitis, Vitiligo, and Wegener's granulomatosis. Hypersensitvity includes but is not limited to allergy, such as asthma, anaphylaxis or atopy; cytotoxic-antibody-dependent diseases such as autoimmune hemolytic anemia, thrombocytopenia, rheumatic heart disease, erythroblastosis fetal, Goodpasture's syndrome, membranous nephropathy, Graves' disease, myasthenia gravis; immune complex diseases such as serum sickness, arthus reaction, rheumatoid arthritis, post streptococcal glomerulo nephritis, lupus nephritis systemic lupus erythematosus, extrinsic allergic alveolitis (hypersensitivity pneumonitis), cell-mediated immune response such as contact dermatitis, Mantoux test, chronic transplant rejection, and multiple sclerosis.

EXAMPLES

Example 1: New Derivatives of Single-Chain TRAIL Produced in Soluble Form

A single-chain TRAIL molecule (scTRAIL) is composed of three TRAIL subunits connected by two peptides. A state-of-the-art scTRAIL molecule in which the individual subunits start with aa 95 connected by 8 amino acids ((GGGS)$_2$) (SEQ ID NO:261) is described as 95L8. To distinguish the molecules described in the following invention from state-of-the-art molecules, we use a nomenclature describing the characteristic amino acid sequence between the conserved C-terminal residue Phe278 and the N-terminal residue Ala123 of the TNF homology domain of scTRAIL. These amino acids were defined as reference points within the TRAIL molecule only and can be followed by additional N- and/or C-terminal TRAIL sequences. The index "3" was added to the name of the molecule in case that three identical TRAIL subunits are joined. This nomenclature is used throughout the text to define the residues within the C- and N-terminal consensus sequence as well as the connecting amino acid sequence, which are also designated $X_a$ and $X_c$, respectively, for the polypeptides of the invention. For example, the C-terminal consensus sequence of TRAIL linked by an intervening peptide to the N-terminal consensus sequence of TRAIL in the polypeptide according to SEQ ID NO: 212 has the following sequence (bold amino acid sequences are used for naming the construct):

| SFFGAF | LVGGGGSVRERGPQR | VAAHI |
|---|---|---|
| (SEQ ID NO: 6) | (SEQ ID NO: 262) | (SEQ ID NO: 25) |
| C-terminal Consensus | intervening peptide | N-terminal consensus |

Accordingly, the scTRAIL construct is named: scTRAIL₃-FLVGGGGSVRERGPQRVA. Since the length of the intervening peptide does not fit the definition of X_a and X_c, respectively, this polypeptide is an exemplary prior art polypeptide but not a polypeptide according to the invention.

A scTRAIL variant comprising TRAIL subunits starting with residue 95 and ending with residue 281 (95L8), i.e. having the following composition: subunit-1 (aa 95-281 of TRAIL of SEQ ID NO: 5)-(GGGS)₂-subunit 2 (aa 95-281 of TRAIL of SEQ ID NO: 5)-(GGGS)₂-subunit 3 (aa 95-281 of TRAIL of SEQ ID NO: 5), was used as a starting point with the aim of generating a panel of new scTRAIL molecules with improved properties as outlined above. The new scTRAIL variants are characterized by shortened N-termini of the THD and unique configurations of the peptides connecting the THDs. In a first set, four new scTRAIL molecules with individual subunits starting from amino acid residue 114 and 120, respectively, were generated. Two different Gly/Ser polypeptides with a length of 4 (GGGS) (SEQ ID NO:263) or 8 residues (GGGS)₂ (SEQ ID NO:261) were used in these molecules, leading to the variants scTRAIL₃-FLVGGGGSVRERGPQRVA (SEQ ID NO: 212), scTRAIL₃-FLVGGGGSGGGSVRERGPQRVA (SEQ ID NO: 213), scTRAIL₃-FLVGGGGSQRVA (SEQ ID NO: 214), and scTRAIL₃-FLVGGGGSGGGSQRVA (SEQ ID NO: 215), (see FIG. 1A, Table 1). Additionally, scTRAIL molecules starting from Gly118 were generated, whereby those molecules only comprised wild-type TRAIL sequences scTRAIL₃-FLVGGPQRVA (SEQ ID NO: 216), or comprised a single glycine substitution scTRAIL₃-FLVGGGPQRVA (SEQ ID NO: 217), or two glycine substitutions scTRAIL₃-FLVGGGGPQRVA (SEQ ID NO: 218), (see Table 1). Furthermore, we reduced the sequence length of THD and the intervening amino acid sequences, yielding the molecules scTRAIL₃-FLVGGQRVA (SEQ ID NO: 219), scTRAIL₃-FLVGGRVA (SEQ ID NO: 220), and scTRAIL₃-FLVGGVA (SEQ ID NO: 2=21), respectively (see FIG. 1B). The scTRAIL₃ expression constructs were cloned using the previously described pIRESpuro-scTRAIL plasmid vector (Schneider et al., 2010, Siegemund et al., 2012). In a first step, individual DNA modules coding for each of the three scTRAIL₃ subunits were PCR-amplified by oligonucleotides comprising the described sequence modifications. Complementary regions at the ends of the DNA modules were used to assemble the entire scTRAIL₃ DNA construct in a multilevel PCR process prior to cloning into pIRESpuro-scTRAIL via EcoRI/NotI. All TRAIL molecules contained an additional N-terminal FLAG tag for purification and detection. The scTRAIL variants were expressed in HEK293 cells and purified by anti-FLAG affinity chromatography from the cell culture supernatant as published (Siegemund et al., 2014). All these scTRAIL variants could be purified in soluble form from cell culture supernatants of transfected HEK293 cells. In contrast, a scTRAIL molecule with Val122 mutated to glycine, i.e. scTRAIL₃-FLVGGGA (SEQ ID NO: 222), as well as molecules with Leu279 mutated in addition to glycine, e.g. scTRAIL₃-FLGGGA (SEQ ID NO: 223), were found to yield insoluble proteins (see FIG. 2A, Table 2).

Structural modeling of scTRAIL suggested that the C-terminal residues Leu279 and Val280 are involved in a hydrophobic interaction with the N-terminal Val122, which seems to be crucial for the structural integrity and solubility of the whole molecule. This was supported by the finding that mutation of Leu279 and/or Val122 to glycine resulted in insoluble protein. Therefore, we decided to introduce C-terminal and N-terminal mutations to substitute the pivotal positions 279 and 122 by other hydrophobic or small neutral amino acid residues (see FIG. 1E) in order to improve stability and proper folding of these scTRAIL variants (see Table 2 and 3, FIG. 2B). Three of these six variants were proved to be soluble and bioactive, namely scTRAIL₃-FLVGGIA (SEQ ID NO: 224), scTRAIL₃-FLVGGAA (SEQ ID NO: 225), and scTRAIL₃-FAVGGAA (SEQ ID NO: 226). In a second round of optimization, the sequence positions 279, 281 and 122 were varied with distinct combinations of isoleucine, alanine or serine residues (see FIG. 1F). The molecules scTRAIL₃-FAVSGAA (SEQ ID NO: 227), scTRAIL₃-FAVGGIA (SEQ ID NO: 228), scTRAIL₃-FIVGGIA (SEQ ID NO: 229), scTRAIL₃-FLVSGIA (SEQ ID NO: 230), scTRAIL₃-FIVSGIA (SEQ ID NO: 231), and scTRAIL₃-FAVSGIA (SEQ ID NO: 232), whereby the TRAIL monomers are connected by a single glycine (G), could be expressed in a soluble, active form.

Example 2: Improved Thermal Stability of Novel scTRAIL Molecules

The thermal stability of all soluble scTRAIL molecules were determined by dynamic light scattering using a zetasizer nano (Malvern) and a protein concentration of 100 µg/ml in PBS. Starting with 35° C., temperature was increased at 1° C. intervals with 2 min incubation for each temperature step. The melting point was defined as the temperature where a drastic increase in kcps values was observed (see FIG. 3). A melting point of 46° C. was determined for soluble, homotrimeric TRAIL. Similar values were observed for variants with N-terminal start of the subunits at position 95 or 114, combined with peptides longer than 4 aa residues, such as scTRAIL-95L8 and scTRAIL₃-FLVGGGGSGGGSVRERGPQRVA. All other variants exhibited an increased thermal stability with the best variant scTRAIL₃-FLVGGVA (SEQ ID NO: 233), possessing a melting point of 57° C. (see Table 3, FIG. 3). These findings indicated that a reduced length of the TRAIL monomers and shorter intervening peptide sequence correlate with higher melting temperatures and therefore with better protein stability, presumably due to a reduced conformational flexibility of the molecule. Favorable versions of scTRAIL carrying N- as well as C-terminal substitutions of amino acids, e.g. scTRAIL₃-FAVSGAA, showed a 7° C. increase of the melting temperature, compared with the parental version scTRAIL-95L8, e.g., scTRAIL₃-FLVGGGGSQRVA. In general, all scTRAIL molecules comprising shortened N-terminal sequences starting at amino acid position 118 of human TRAIL or even shorter variants, when combined with short intervening peptide sequences (0-2 amino acids), were shown to have a higher protein stability compared to the published scTRAIL molecules, e.g. scTRAIL-95L8 and commercially available sTRAIL.

Example 3: Mutation of Gly281 to Serine Improves Solubility and Reduces Aggregation Propensity To analyze expression levels of the newly designed molecules, equal cell numbers of stably transfected HEK293 pools were seeded, cultivated for three days in serum free medium and supernatants and cell pellet samples were tested by Western blot with an anti-FLAG antibody for secretion of soluble (Table 2) and total protein expression, respectively. Derivatives bearing a Gly281Ser mutation e.g. scTRAIL$_3$-FAVSGAA, scTRAIL$_3$-FIVSGIA, and scTRAIL$_3$-FAVSGIA showed improved expression compared to scTRAIL-95L8. This finding was unexpected since Gly281 is a surface-exposed amino acid residue not involved in any secondary structures (Hymowitz et al., 1999; Hymowitz et al., 2000). Our data suggest that this modification has a positive influence on the solubility of scTRAIL proteins. Furthermore, we checked the properties of the purified scTRAIL molecules by SDS-PAGE and size exclusion chromatography (SEC). Reducing SDS-PAGE followed by Coomassie staining revealed that the majority of each protein is present as a single band, corresponding to the respective calculated molecular masses. We found that new scTRAIL proteins show mostly a monomeric composition as analyzed by SEC (see FIG. 4). Nonetheless, minor amounts of low-order multimers, putatively dimers, were detected in the samples. We quantified the ratio of these multimers relative to the total amount of protein by integration of SEC peaks. Preparations of newly developed scTRAIL variants comprising substitutions at positions 281, 121 and 122, e.g. scTRAIL$_3$-FLVSGIA, scTRAIL$_3$-FIVSGIA and scTRAIL$_3$-FAVSGIA, were found to have remarkably low percentages of multimers of 5% of the total protein or less. A common characteristic of all these scTRAIL variants is the presence of the sequence motif "G281S-R121G-V122I".

Example 4: The New scTRAIL Molecules Show Unaltered TRAIL Receptor Binding Activity To evaluate functionality of the various TRAIL variants, specific binding to TRAILR-positive Colo205 cells was quantified by immunofluorescence flow cytometry. Cells (300.000 cells/well) were incubated with serial dilutions of scTRAIL variants starting at 30 µg/ml and bound molecules were detected with anti-FLAG and anti-mouse-FITC antibodies. Analyzed scTRAIL variants showed specific binding, with EC$_{50}$ values in the low nanomolar range. As an example, cell binding of three variants is shown in FIG. 5A, with slightly superior binding of the variants scTRAIL$_3$-FAVGGAA and scTRAIL$_3$-FLVGGAA compared to the variant scTRAIL$_3$-FLVGGVA. In addition, different scTRAIL variants for specific binding to DR5 were analyzed by ELISA (see FIG. 5B). All tested scTRAIL molecules were shown to bind to DR5-Fc fusion with EC50 values in the low nanomolar range, in accordance with the flow cytometry data.

Example 5: The New scTRAIL Molecules Efficiently Induce Apoptosis In Vitro

The apoptosis-inducing activity of the new scTRAIL variants was tested in a cytotoxicity assay using Colo205 colon carcinoma cells sensitized with 250 ng/ml bortezomib. All soluble scTRAIL$_3$ molecules were shown to be bioactive (see FIG. 6) with EC$_{50}$ values in the sub-nanomolar range. scTRAIL variants with low tendency to form dimers or higher order aggregates are preferable components for directed engineering of dimeric scTRAIL molecules. The relation between the molecular composition and the specific bioactivity was analyzed in detail for scTRAIL$_3$-FLVGGVA. To this, equimolar concentrations of SEC-separated dimers and monomers were analyzed for their apoptotic activity on the cancer cell lines Colo205, NCI-H460 and HT1080 (see FIG. 7). Spontaneously formed dimers of scTRAIL$_3$-FLVGGVA were found to be more bioactive than the monomers on all tested cell lines. Depending on the cell line-specific intrinsic characteristics of the DR4- and DR5-triggered apoptosis, monomers of scTRAIL$_3$-FLVGGVA were either nearly inactive (Colo205) or were 50-fold (HT1080), respectively 13-fold (NCI-H460) less bioactive than the dimers. This result supports our rationale that an effective TRAIL-based protein therapeutic must comprise two trivalent TRAIL units, achieved in the scTRAIL$_3$ format which allows directed dimerization via genetic fusion to specific dimerization motifs and/or targeting antibody derivatives with intrinsic dimerization, such as diabodies. The latter format, diabody-scTRAIL, in addition ensures targeting of TRAIL to restrict activity, e.g. apoptosis induction, to a target positive cell, e.g. a tumor cell.

Example 6: Db-scTRAIL$_3$ Fusion Proteins Comprising Derivatives of scTRAIL

A previously described Db-scTRAIL (TRAIL module aa 95-281, linked by two peptides of 8 aa each (Db-scTRAIL-95L8, Siegemund et al., 2012)) showed typically a heterogeneous molecular composition in the size exclusion chromatography (see FIG. 8A). Analyzing individual SEC fractions by SDS-PAGE and subsequent anti-FLAG Western blotting we found that the peak with the higher retention time comprises, in addition to full length protein, a truncated species (see FIG. 8B) with a molecular mass between 35 and 40 kDa. Further, Db-scTRAIL-95L8 by chemical crosslinking using BS$_3$ was analyzed. The dimeric constitution of the molecule could be confirmed as seen by the presence of a major crosslinking product with a molecular mass of 190 kDa. In addition we observed a side product (~130 kDa), which corresponded to a dimeric Db-scTRAIL with a truncation in one of its two polypeptide chains. This assumption could be confirmed by molecular crosslinking and Western blotting of SEC-separated fractions of the protein, in which fractions representing the smaller form showed an additional crosslinking product with the respective size of 130 kDa. The partially truncated forms of Db-scTRAIL were shown to be less bioactive than the full-length protein on various cell lines (see FIG. 9) supporting our hypothesis that a new molecular design is necessary to bypass structural and functional deficiencies of these TRAIL fusion proteins. The newly designed Db-scTRAIL fusion proteins comprise the optimized scTRAIL$_3$ derivatives described in Examples 1-5 (as well as modifications of peptides within the diabody and those connecting diabody to the scTRAIL variants). The molecules scTRAIL$_3$-FAVSGAA and scTRAIL$_3$-FAVSGIA as preferred derivatives for the generation of advanced Db-scTRAIL$_3$ fusion proteins were selected. ScTRAIL$_3$-FAVSGAA showed best expression properties among all scTRAIL$_3$ derivatives combined with a high thermal stability. The second variant scTRAIL$_3$-FAVSGIA was selected because of its lower aggregation tendency compared with other scTRAIL$_3$ derivatives. To yield advanced diabody fusion proteins comprising preferred scTRAIL$_3$ derivatives, we replaced state-of-the-art scTRAIL sequences from the existing vector construct pCR3-Db-scTRAIL (Siegemund et al., 2012) by the new constructs using EcoRI/XbaI cloning, followed by stable HEK293 cell line generation. Recombinant products from cell culture supernatants were purified using anti-FLAG affinity chromatography and subjected to biochemical and functional analyses. In a first optimization approach, analyses of the new molecule Db-scTRAIL$_3$-FAVSGAA revealed by Coomassie staining a single band with a molecular mass of 86 kDa upon reducing SDS-PAGE. In SEC analysis of Db-scTRAIL$_3$-FAVSGAA we observed a smaller hydrodynamic radius and a strong reduction of truncated species compared to Db-scTRAIL-95L8 (see FIG. 10, lower left). For potential further improvement, in a next step, introduction of glycosylation sites were investigated. A modified peptide for connecting the diabody with the scTRAIL moiety was defined by the amino acid residues AAAGNGTSNGTSEFGG (SEQ ID NO:194). This peptide comprises two N-glycosylation sites which were shown to be glycosylated upon recombinant expression of this newly designed molecule, Db-Glyco-scTRAIL$_3$-FAVSGAA. Surprisingly, Db-Glyco-scTRAIL$_3$-FAVSGAA showed less aggregation than the corresponding Db-scTRAIL$_3$-FAVSGAA, while the presence of truncated species remained at a low level, comparable to Db-scTRAIL$_3$-FAVSGAA (see FIG. 11, upper). As a consequence, the use of scTRAIL derivatives in combination with a new glycosylated peptide between the C-terminal scFv (diabody) domain and the N-terminus of scTRAIL led to molecules which are less prone to fragmentation and aggregation. Nevertheless, a minor proportion of aggregates and truncated forms were still detectable (see FIG. 11, upper, FIG. 12A).

In order to further optimize the molecular integrity and stability of Db-scTRAIL$_3$, variants with modified peptides connecting V$_H$ and V$_L$, such that the intrinsic feature of spontaneous diabody formation is not limited were developed (see FIG. 12B). Therefore, Db-Glyco-scTRAIL$_3$-FAVSGAA served as a model to analyze the impact of diabody connecting peptide lengths of 5 (GGGGS (SEQ ID NO:260), state-of-the-art control) vs. 8 (GGGGSGGG) (SEQ ID NO:207) and 10 amino acid residues (GGGGSGGGGS) (SEQ ID NO:208), respectively. Unexpectedly, we found that expression of fusion proteins with the longest variant of the diabody connecting peptide Db10-Glyco-scTRAIL$_3$-FAVSGAA resulted in the lowest percentage of fragmented species, while dimerization, i.e. generation of a functionally intact diabody, was fully maintained (see FIG. 12B, right). To prove the additional advantage of introduction of N-terminal glycosylation sites into the peptide between diabody and scTRAIL$_3$ also for this advanced diabody-scTRAIL$_3$ fusion protein format Db10-Glyco-scTRAIL$_3$-FAVSGAA, we designed and produced an unglycosylated variant Db10-scTRAIL$_3$-FAVSGAA for reasons of comparison. The former, glycosylated variant showed higher protein quality as revealed from SEC (see FIG. 11, lower). A second selected scTRAIL derivative, scTRAIL$_3$-FAVSGIA, was used in the fusion protein Db-Glyco-scTRAIL$_3$-FAVSGIA. The protein quality of this derivative was found to be comparable to the variant Db10-Glyco-scTRAIL$_3$-FAVSGAA (see FIG. 12B, C).

Example 7: Novel Db-scTRAIL$_3$ Molecules Show Improved Thermal Stability

As for the scTRAIL derivatives, the thermal stability of all new Db-scTRAIL$_3$ molecules (see FIG. 13) was determined. It was found that Db-scTRAIL fusion proteins comprising the new scTRAIL$_3$ derivatives scTRAIL$_3$-FAVSGAA and scTRAIL$_3$-FAVSGIA are characterized by a higher thermal stability than the previous state of the art molecules Db-scTRAIL-95L8 or Db-Glyco-scTRAIL-95L8, serving as reference. As an example, a melting point of 55° C. for the molecule Db-scTRAIL$_3$-FAVSGAA was measured, whereas 50° C. was determined for Db-scTRAIL-95L8. Similar protein stability was observed irrespectively of the presence of the glycosylated peptide, leading to the conclusion that the modified scTRAIL$_3$ module largely contributes to the increase in thermal stability. Surprisingly, the use of an elongated diabody connecting peptide, as exemplified in the molecules Db10-scTRAIL$_3$-FAVSGAA and Db10-Glyco-scTRAIL$_3$-FAVSGAA, did not result in a decreased protein stability, compared to Db-Glyco-scTRAIL$_3$-FAVSGAA comprising the standard connecting peptide of 5 amino acids in length.

Example 8: Receptor and Target Antigen Binding of Novel Anti-EGFR Db-scTRAIL$_3$ Fusion Proteins The receptor affinity of the advanced anti-EGFR Db-scTRAIL$_3$ molecules was evaluated by flow cytometry using the fibrosarcoma cell line HT 1080 (see FIG. 14). Similar to data obtained for the scTRAIL derivatives, the developed diabodies displayed EC$_{50}$ values in the nanomolar range. For bifunctional fusion proteins, such as diabody-scTRAIL$_3$, the underlying binding mechanisms are more complex due to specific and simultaneous interaction with two different types of receptors, EGFR and TRAILR. Binding to respective target cells of the new Db-scTRAIL$_3$ variants was comparable to the references, Db-scTRAIL-95L8 and Db-Glyco-scTRAIL-95L8, with no significant difference in EC$_{50}$. Thus, the functionality of the scTRAIL derivatives with respect to specific binding to cognate receptors is maintained in the new diabody fusion protein structure and the modifications of the connecting peptides, e.g. introduction of glycosylation sites and extended diabody, as well as in scTRAIL N- as well as C-terminal mutations, did not impact high affinity binding to the respective targets on the cell surface.

Example 9: Improved Bioactivity of Novel Anti-EGFR Db-scTRAIL$_3$ Fusion Proteins The apoptosis-inducing activity of the new Db-scTRAIL$_3$ molecules Db-Glyco-scTRAIL$_3$-FAVSGAA, Db-Glyco-scTRAIL$_3$-FAVSGIA, Db8-Glyco-scTRAIL$_3$-FAVSGAA and Db10-Glyco-scTRAIL$_3$-FAVSGAA was tested in cell death assays on Colo205, HCT116 (both colon carcinoma) and HT1080 (fibrosarcoma) cells. Therefore, 20,000 cells/well were seeded in 96-well plates. On the following day, cells were treated with the indicated concentrations of the apoptosis sensitizer Bortezomib in combination with titrations of the TRAIL proteins in triplicates for 16 h. Cell death was assayed by crystal violet staining. All of the new Db-scTRAIL$_3$ molecules were shown to be highly bioactive (see FIGS. 15, 16, 17, Table 4), with superior cell death induction on several tumor cell lines, e.g. HCT116 and HT1080. Due to the unique biology of each cancer cell line, apparent differences in TRAIL sensitivity of different tumor cells were expected for new Db-scTRAIL$_3$ molecules, too. Irrespective of these differences in TRAIL sensitivity of tumor cells and targeting dependence of apoptosis induction, the new Db-scTRAIL$_3$ molecules developed here display improved functional activity compared to the control Db-scTRAIL-95L8. The data presented in FIG. 9 shows that a higher percentage of full-length protein, as evident in preparations of the advanced Db-scTRAIL$_3$ molecules, directly correlates with the higher bioactivity observed in vitro. The contribution of targeting to bioactivity could be demonstrated for all molecules by blocking studies in which EGFR binding of the diabody-scTRAIL$_3$ competed with EGFR specific antibody Cetuximab, added in excess to the test system (FIGS. 15, 16, 17, Table 4). It was shown that the advantages of structural improvement of the apoptosis-inducing ligand scTRAIL, resulting in e.g. higher protein stability and high specific bioactivity, are transferable to the construction of target-specific scTRAIL molecules in the diabody-scTRAIL fusion protein format. Additional inventive steps of protein design were introduced including glycoengineering and length variation of connecting peptide sequences between distinct domains of the fusion proteins to yield considerable improvements with regard to production efficacy, product quality (molecular integrity, protein stability) and functional activity (PK and apoptosis inducing activity) of the new generation of target-specific Db-scTRAIL$_3$ molecules.

Example 10: Targeted Dimeric scTRAIL$_3$ Fusion Proteins Containing scTRAIL$_3$FLVGGGPQRVA To further validate the concept of targeted dimeric scTRAIL fusion proteins, four different formats were generated, including, besides Db-scTRAIL$_3$ (SEQ ID NO: 234), a disulfide-stabilized version thereof (dsDb-scTRAIL$_3$) (SEQ ID NO: 235), an EHD2 fusion protein (scFv-EHD2-scTRAIL$_3$) (SEQ ID NO: 236), and an Fc construct (scFv-Fc-scTRAIL$_3$). All four different formats were developed with target specificities for EGFR, HER2 and HER3, thereby containing the same scTRAIL$_3$ variant (scTRAIL$_3$-FLVGGGPQRVA). Furthermore, corresponding non-targeted constructs were generated (scTRAIL$_3$, EHD2-scTRAIL$_3$, Fc-scTRAIL$_3$). All fusion proteins were produced with stably transfected HEK293 cells and purified from the supernatant via anti-FLAG affinity chromatography. SDS-PAGE analysis and size exclusion chromatography confirmed purity and integrity of all proteins (see FIGS. 18 and 19). Only minor amounts of low-order multimers were detected by SEC, demonstrating that targeted dimeric scTRAIL$_3$ molecules can be generated via fusion to diabodies, EHD2, or Fc parts. Exemplarily, the thermal stability of the Db-scTRAIL$_3$-FLVGGGPQRVA construct targeting EGFR was analyzed by dynamic light scattering (see FIG. 20). The measured melting point of 54° C. corresponds to those of the other novel fusion proteins and is thus higher compared to the previously described molecules Db-scTRAIL-95L8 or Db-Glyco-scTRAIL-95L8 (see FIG. 13).

Example 11: Receptor and Antigen Binding of Targeted Dimeric scTRAIL$_3$-FLVGGGPQRVA Fusion Proteins The new scTRAIL$_3$-FLVGGGPQRVA fusion proteins were evaluated concerning their ability to bind to their corresponding target antigen and TRAIL-R2 by ELISA as well as by IF flow cytometry using intact Colo 205 cells. Antigen binding was analyzed in ELISA using Fc fusion proteins of EGFR, HER2 and HER3. All proteins showed specific, concentration-dependent binding to the corresponding antigen and all formats targeting the same antigen showed binding with similar $EC_{50}$ values (see FIG. 21, Table 5). The $EC_{50}$ values of the EGFR-targeting fusion proteins thereby correspond to those of the above mentioned constructs. Further ELISA studies revealed similar binding of all proteins to TRAIL-R2-Fc, independent of their format or antigen specificity (see FIG. 22, Table 5). The ELISA results were confirmed by flow cytometry studies with antigen- and TRAIL receptor-expressing Colo205 cells (see FIG. 23, Table 5). These data show that all proteins possess full functionality concerning binding to their antigen and TRAIL-R2, independent of their format or target specificity.

Example 12: Bioactivity of Novel Targeted Dimeric scTRAIL$_3$-FLVGGGPQRVA Fusion Proteins Cell death induction of the novel targeted dimeric scTRAIL$_3$-FLVGGGPQRVA fusion proteins was analyzed using Colo205 and HCT-116 cells. One day before treatment, 50,000 Colo205 cells/well or 15,000 HCT-116 cells/well were seeded in 96-well plates. After pretreatment of the cells with the sensitizer Bortezomib (250 ng/ml, 650 nM) or medium as control for 30 min, cells were incubated with serial dilutions of the fusion proteins for 16 h. Cell death was analyzed by crystal violet staining. To evaluate the effect of targeting, Cetuximab (200-fold molar excess) was added simultaneously to pretreatment with either Bortezomib or medium for EGFR-targeting and non-targeted constructs. All formats of EGFR-targeting fusion proteins showed strong induction of cell death on Colo205 (see FIG. 24A) and HCT-116 cells (FIG. 26), which could be further enhanced in the presence of Bortezomib. By addition of Cetuximab, the effects of EGFR-targeting fusion proteins could be reduced to the level of the non-targeted constructs (see FIG. 24, Table 6). Furthermore, the HER2- and HER3-targeting proteins showed potent cell death induction on Colo205 as well as HCT-116 cells in the absence and presence of Bortezomib (see FIG. 25, 26). This confirms the suitability of our new fusion proteins of different formats and targeting specificities for effective induction of cell death in various cancer cell lines.

Example 13: Pharmacokinetics of Novel Dimeric scTRAIL$_3$-FLVGGGPQRVA Fusion Proteins Targeting EGFR One advantage of generating different formats of scTRAIL$_3$-FLVGGGPQRVA fusion proteins is the possibility to modify the pharmacokinetic properties. To evaluate the PK profiles, 25 µg protein were injected intravenously into the tail of female CD1 mice. After 3 min, 30 min, 1 h, 2 h, 6 h, 1 d, 3 d and 7 d serum samples were taken. Protein concentrations in the serum were quantified by ELISA and normalized to the 3 min value. The terminal half-lives of the fusion proteins were increased from about 2 h for the diabody constructs to 6.5 h for the EHD2 fusion protein and to greater 17 h in case of scFv-Fc-scTRAIL$_3$ (see FIG. 27, Table 7). Thus, the different formats offer a possibility to improve the pharmacokinetic properties, which is an important issue concerning therapeutic application of proteins.

Example 14: Genetic Fusion of scTRAIL$_3$-FAVSGAA to the C-Terminus of an IgG Kappa Light Chain or Heavy Chain Yielding an IgG-scTRAIL$_3$ Fusion Protein In order to combine several advantageous principles in one molecule, i.e. dimeric configuration of scTRAIL$_3$, tumor associated antigen targeting by an IgG antibody and improvement of the pharmacokinetic profile by interaction of the IgG Fc moiety with FcRn, we fused scTRAIL$_3$-FAVSGAA to the C-terminus of either IgG kappa light chain or heavy chain separated by a 15 amino acid residues long peptide with two N-glycosylation sites. In the example shown, an EGFR-specific human IgG1 with mutated Fc domain affecting ADCC and CDC function was used as a scaffold for IgG-scTRAIL, but non-mutated Fc domain is equally suited. Expression cassettes for IgG heavy and light chains, with or without fusion to scTRAIL$_3$, were cloned into a double gene vector based on the GS System pEE vectors (Lonza), followed by transient transfection of HEK293 cells and production in serum free OptiMEM I medium supplemented with 50 μM ZnCl$_2$. Facilitated by N-terminal FLAG tags fused to the heavy chain, we were able to affinity-purify IgG and IgG-scTRAIL$_3$ fusion proteins. Reducing SDS-PAGE followed by Coomassie staining revealed the occurrence of gene products corresponding to heavy chain (51 kDa) (SEQ ID NO: 242), kappa light chain (24 kDa) (SEQ ID NO: 243, light chain-scTRAIL$_3$-FAVS-GAA (80 kDa) (SEQ ID NO: 244) and heavy chain-scTRAIL$_3$-FAVSGAA (107 kDa) (SEQ ID NO: 205) (FIG. 28).

Example 15: Induction of Caspase-8 and -3/7 Activity by scTRAIL$_3$-FLVGGGPQRVA Fusion Proteins Since it has been shown previously that targeting and dimeric assembly of scTRAIL greatly improves apoptosis induction, three scTRAIL$_3$-FLVGGGPQRVA constructs were analyzed to investigate these effects on the level of caspase-8 and -3/7 activity. Colo205 cells (15,000/well) were cultivated for 24 h at 37° C., 5% CO$_2$. After preincubation with bortezomib (650 nM final concentration) or medium for 30 min, cells were treated with scTRAIL$_3$-FLVGGGPQRVA constructs for different time periods. Levels of active caspase-8 and -3/7 were detected using Caspase-Glo® 8 Assay and Caspase-Glo® 3/7 Assay (Promega) according to the manufacturer's instructions. Bortezomib alone only marginally induced activation of caspase-8 and -3/7 at the analyzed concentration and treatment intervals (FIG. 29 A, B). At a concentration of 100 pM scTRAIL, incubation of the cells with scTRAIL$_3$-FLVGGGPQRVA resulted in activation of caspase-8 and -3/7 detectable upon 20 h incubation. Compared to that the dimeric Fc-scTRAIL$_3$-FLVGGGPQRVA (SEQ ID NO: 210) showed faster activation kinetics with a marked caspase activity already after 8 h. The dimeric EGFR-targeting fusion protein scFvhu225-Fc-scTRAIL$_3$-FLVGGGPQRVA (SEQ ID NO: 209) showed an even further accelerated activation reaching high activity already after 2 h and inducing considerable higher levels of active caspases compared to Fc-scTRAIL$_3$-FLVGGGPQRVA (SEQ ID NO: 210) and scTRAIL$_3$-FLVGGGPQRVA. Using a concentration of 1 nM scTRAIL, all constructs showed faster activation kinetics for initiator and executioner caspases. At this dose, both Fc fusion proteins displayed similar activation profiles reaching comparable levels of active caspase-8 and -3/7, however slightly delayed for the non-targeted molecule. Despite a faster induction of caspase activity at this higher concentration, scTRAIL$_3$-FLVGGGPQRVA was not able to induce activity levels as high as those measured for the dimeric constructs. In the absence of bortezomib, treatment with a concentration of 1 nM scTRAIL units induced caspase-8 and -3/7 activity with a similar kinetic as compared to that measured in the presence of bortezomib. However, slightly lower maximum activity levels were reached, especially for the executioner caspases. Thus, dimeric assembly of scTRAIL, e.g. via fusion to an Fc part, increases the activity of those molecules, which can be further enhanced by fusion to a targeting moiety, e.g. a scFv.

Example 16: In Vivo Anti-Tumor Activity of scTRAIL$_3$-FLVGGGPQRVA Fusion Proteins To prove the anti-tumor activity of dimeric EGFR-targeting scTRAIL$_3$-FLVGGGPQRVA fusion proteins in vivo, a Colo205 xenograft model was used. In a first experiment, 3×10$^6$ Colo205 cells were injected subcutaneously into the left and right flank of female NMRI nu/nu mice (10 weeks old). Treatment was started when tumors reached a volume of ~100 mm$^3$. Mice received six treatments with 5 μg bortezomib (i.p.) and 0.5 nmol protein in 150 μl PBS or PBS as control (i.v.). After three treatments every other day, treatment intervals were gradually increased by one day. All analyzed formats showed similar anti-tumor effects inducing complete tumor regression (FIG. 30A). This proves the suitability of all formats for in vivo therapy. A second experiment was performed using the same xenograft model. When tumors reached a size of ~100 mm$^3$, mice received combinatorial injections of 5 μg bortezomib (i.p.) and 0.3 nmol or 0.1 nmol protein in 150 μl PBS (i.v.). Control mice were treated with bortezomib (i.p.) and PBS (i.v.). Mice received treatments twice a week (every fourth and third day, respectively) for three weeks. Similar to treatment with 0.5 nmol, a dose of 0.3 nmol scFvhu225-Fc-scTRAIL$_3$-FLVGGGPQRVA (SEQ ID NO: 209) induced complete tumor regression (FIG. 30B). Even for a dose as low as 0.1 nmol, anti-tumor effects were observed demonstrating the high therapeutic activity of these molecules in combination with bortezomib.

Example 17: EGFR-Specific Binding is Maintained in Anti-EGFR IgG-scTRAIL-FAVSGAA Fusion Proteins IgG fusion proteins comprising scTRAIL$_3$-FAVSGAA (SEQ ID NO: 227) at the C-terminus of either light chain (anti-EGFR IgG LC-scTRAIL$_3$-FAVSGAA), heavy chain (anti-EGFR IgG HC-scTRAIL$_3$-FAVSGAA) or both (anti-EGFR IgG LC/HC-scTRAIL$_3$-FAVSGAA) of a human EGFR-specific IgG1 antibody were expressed in soluble form from transiently transfected HEK293 cells and affinity-purified by anti-FLAG chromatography. The size exclusion chromatography analysis of the anti-EGFR IgG-scTRAIL$_3$ fusion proteins and the scaffold anti-EGFR IgG revealed a correct molecular assembly of the proteins (FIG. 31A). Exemplified here for anti-EGFR IgG HC-scTRAIL$_3$-FAVSGAA, a melting point of 56° C. was determined by dynamic light scattering (FIG. 31B). Thus, anti-EGFR IgG HC-scTRAIL$_3$-FAVSGAA is characterized by the same thermal stability such as Db10-Glyco-scTRAIL$_3$-FAVSGAA, providing additional evidence that increased thermal stability of the scTRAIL$_3$ molecules is maintained in the context of fusion to an IgG.

The binding of anti-EGFR IgG-scTRAIL$_3$-FAVSGAA variants and the reference molecule anti-EGFR IgG was tested by flow cytometry on the EGFR-positive colon carcinoma cell lines Colo205 and HCT116, or via ELISA on purified EGFR-Fc. The IgG used here was derived from cetuximab by humanization of mouse V$_H$ and V$_L$, followed by their insertion into a human IgG1 framework. As depicted in FIG. 32A and Table 8, anti-EGFR IgG shows a binding behavior almost equal to the parental antibody cetuximab on Colo205 and HCT116 cells. Upon genetic fusion of anti-EGFR IgG with scTRAIL$_3$-FAVSGAA in the configurations described at the beginning, the resulting proteins maintained binding to the tested cell lines, albeit the EC$_{50}$ values of the fusion proteins were throughout higher than for anti-EGFR IgG (FIG. 32B, C, Table 9). Interestingly, among the dimeric scTRAIL$_3$ fusion proteins, the configuration with fusion of scTRAIL$_3$ to the IgG heavy chain seems to interfere less with EGFR binding than the light chain fusion, proven by lower EC$_{50}$ values detected for anti-EGFR IgG HC-scTRAIL$_3$-FAVSGAA (Table 9).

Example 18: Anti-EGFR IgG-scTRAIL$_3$-FAVSGAA Fusion Proteins Show EGFR-Dependent Increase of scTRAIL$_3$ Bioactivity on Tumor Cell Lines Bioactivities of the IgG-scTRAIL$_3$ fusion proteins were compared in presence or absence of a molar excess of cetuximab in order to demonstrate EGFR-dependent enhancement of cell death induction in the tumor cell lines HCT116, Colo205 (colon carcinoma) and HT1080 (fibrosarcoma) (FIGS. 33-35, Table 10). Additionally, bioactivities were tested in presence of the apoptosis sensitizer bortezomib. The dimeric fusion proteins anti-EGFR IgG LC-scTRAIL$_3$-FAVSGAA and anti-EGFR IgG HC-scTRAIL$_3$-FAVSGAA were bioactive with EC$_{50}$ values in the low picomolar range, resembling roughly the bioactivity of Db10-Glyco-scTRAIL$_3$-FAVSGAA. Importantly, competition of EGFR binding by excessive amounts of cetuximab resulted in reduced bioactivities on all cell lines tested, providing evidence for increased tumor cell killing as a consequence of tumor antigen targeting. The tetrameric form anti-EGFR IgG LC/HC-scTRAIL$_3$-FAVSGAA was characterized by higher bioactivities than the dimeric formats throughout on all tested cell lines, suggesting a correlation between number of scTRAIL moieties within one molecule and bioactivity. Depending on the characteristics of each cell line, further enhanced cell killing was shown upon co-treatment with bortezomib for all anti-EGFR IgG-scTRAIL$_3$-FAVSGAA variants.

Example 19: Anti-EGFR IgG HC-scTRAIL$_3$-FAVSGAA Shows Enhanced Serum Half-Life To shed light on the pharmacokinetics of the new IgG-scTRAIL$_3$ fusion proteins, we analyzed the serum half-life of anti-EGFR IgG HC-scTRAIL$_3$-FAVSGAA in CD1 mice and observed a terminal serum half-life $t_{1/2}\beta$ of 16.09±2.62 h and an AUC of 488.83±82.32% h (FIG. 36). As a reference, Db-scTRAIL$_3$-FLVGGGPQRVA was measured with a terminal serum half-life $t_{1/2}\beta$ of 2.57±0.17 h and an AUC of 235.23±48.04% h, suggesting FcRn-mediated elongation of the serum half-life of IgG-scTRAIL$_3$-FAVSGAA molecules and therefore a high potential for sustained antitumor activity.

Example 20: In Vivo Study of Db10-Glyco-scTRAIL$_3$-FAVSGAA

The antitumor bioactivity of Db10-Glyco-scTRAIL$_3$-FAVSGAA was investigated using the established mouse xenograft model of the human colon carcinoma cell line Colo205. Db-scTRAIL$_3$ fusion was applied intravenously when tumors reached a volume of ~100 mm$^3$. Three different doses of 0.1 nmol, 0.3 nmol and 1 nmol protein were applied in a daily regimen for 8 days in combination with intraperitoneal injection of clinical grade bortezomib. Whereas treatment with 0.1 nmol did not induce measurable antitumor effects, a transient, partial inhibition of tumor growth was observed for the 0.3 nmol group, which was, however, statistically not significant (FIG. 37A). In contrast, a strong and rapid reduction of tumor volumes with macroscopically undetectable tumors in 9/12 cases at day 20 was observed for the 1 nmol dose. A re-growth of tumors was observed for a subpopulation around day 25 (subgroup I) and for a second subpopulation around day 42 (subgroup II). Both subgroups received a second, identical treatment cycle starting at day 28 (subgroup I) or day 43 (subgroup II) (FIG. 37A). An antitumor response was again observed for both groups. At the end of the observation period (d109), 4/12 tumors stayed in complete macroscopic remission and 3 other tumors were in a stable, not actively growing state with volumes below 100 mm$^3$.

Serum concentrations of Db10-Glyco-scTRAIL$_3$-FAVSGAA were determined by ELISA 0.05 h, 4 h, and 24 h after the first injection, as well as 4 h and 24 after the last injection of the first cycle, showing that similar serum concentrations were reached after the first and last injection (FIG. 37B). Additionally, the pharmacokinetics of Db10-Glyco-scTRAIL$_3$-FAVSGAA were studied in immunocompetent CD-1 mice, revealing a terminal half-life of 3.6±0.1 h and an AUC of 8.8±1.4 (µg/ml)*h (FIG. 37C).

The safety of the applied doses of Db10-Glyco-scTRAIL-FAVSGAA was monitored by measuring serum activities of alanine aminotransferase (ALT) and α-amylase (FIG. 37D, E). Serum samples were taken from all groups 4 hours and 24 hours after the first injection as well as 24 h after the last injection of the first treatment cycle and compared to untreated animals. In both assays, no statistically significant increase of ALT and α-amylase levels were observed for all treatment groups compared to the untreated animals, except for the α-amylase value of the 1 nmol group at day 9 (24 h after last injection, 199 U/L vs. 161 U/L, p<0.05).

Example 21: Fusion Proteins of scTRAIL$_3$-FAVSGAA with Fc

In order to demonstrate the suitability of scTRAIL$_3$-FAVSGAA (SEQ ID NO: 227) in a dimeric protein format comprising the Fc moiety of human IgG1 for dimerization and elongation of serum half-life, we generated fusion proteins with C-terminal (Fc-scTRAIL$_3$-FAVSGAA; SEQ ID NO: 246) or N-terminal configuration (scTRAIL$_3$-FAVSGAA-Fc; SEQ ID NO: 245) of the scTRAIL$_3$ moiety (see Table 14 for additional details on the structure of the constructs used in this example). In addition, a tetrameric assembly of scTRAIL$_3$-FAVSGAA (scTRAIL$_3$-FAVSGAA-Fc-scTRAIL$_3$-FAVSGAA; SEQ ID NO: 247) was investigated to prove that higher numbers of scTRAIL units in one molecule correlate directly with higher bioactivity. In this first series of molecules, scTRAIL$_3$-FAVSGAA and Fc were connected via a 16 aa residues linker with two N-glycosylation sites (GSGNGTSNGTSGSSGG (SEQ ID NO:258). Linkers of that kind were used in one polypeptide chain in case of the tetrameric protein scTRAIL$_3$-FAVSGAA-Fc-scTRAIL$_3$-FAVSGAA (GSGNGTSNGTSGSSRT (SEQ ID NO:259) and GSGNGTSNGTSGSSGG (SEQ ID NO:258)). The resulting proteins Fc-scTRAIL$_3$-FAVSGAA, scTRAIL$_3$-FAVSGAA-Fc and scTRAIL$_3$-FAVSGAA-Fc-scTRAIL$_3$-FAVSGAA were expressed in transiently or stably transfected HEK293 cells in a soluble form and purified by anti-FLAG affinity chromatography. As shown by SEC, all proteins were present in a correctly dimerized form (FIG. 38A). ELISA studies on TRAIL R1-Fc and TRAIL R2-Fc revealed better binding properties for Fc-scTRAIL$_3$-FAVSGAA, but also scTRAIL$_3$-FAVSGAA-Fc and scTRAIL$_3$-FAVSGAA-Fc-scTRAIL$_3$-FAVSGAA and the monomeric control protein scTRAIL$_3$-FLVGGGPQRVA bound concentration-dependent to the TRAIL receptors (FIG. 38B). Higher bioactivities compared with monomeric scTRAIL$_3$-FLVGGGPQRVA were observed for Fc-scTRAIL$_3$-FAVS- GAA and scTRAIL$_3$-FAVSGAA-Fc in in vitro bioactivity assays on Colo205 cells, putatively due to dimeric configuration of scTRAIL (FIG. 38C, Table 11). The tetrameric assembly scTRAIL$_3$-FAVSGAA-Fc-scTRAIL$_3$-FAVSGAA showed the highest bioactivity of all tested scTRAIL$_3$ Fc fusion proteins. The sensitization with bortezomib resulted in additionally enhanced bioactivities for all tested proteins.

In a subsequent study, we investigated the optimal length and composition of the peptide linker connecting scTRAIL$_3$-FAVSGAA with Fc. Therefore, scTRAIL$_3$-FAVSGAA was fused C-terminally with Fc using glycine/serine linkers of 5, 10, 15, 20 and 25 aa residues length, yielding the proteins scTRAIL$_3$-FAVSGAA-5 G/S-Fc (SEQ ID NO: 249), scTRAIL$_3$-FAVSGAA-10 G/S-Fc (SEQ ID NO: 250), scTRAIL$_3$-FAVSGAA-15 G/S-Fc (SEQ ID NO: 251), scTRAIL$_3$-FAVSGAA-20 G/S-Fc (SEQ ID NO: 252) and scTRAIL$_3$-FAVSGAA-25 G/S-Fc (SEQ ID NO: 253). In addition, scTRAIL$_3$-FAVSGAA and Fc were fused without linker (scTRAIL$_3$-FAVSGAA-0-Fc; SEQ ID NO: 248) or with an alpha-helical linker comprising 33 aa residues (scTRAIL$_3$-FAVSGAA-"W"-Fc; SEQ ID NO: 254).

All of these scTRAIL$_3$-FAVSGAA-Fc fusion proteins could be expressed in a soluble form from transiently or stably transfected HEK293 cells, as proven by TRAIL ELISA (FIG. 39A). Affinity-purified full length proteins were obtained from six variants and analyzed by SEC for molecular composition (FIG. 39B). The variants scTRAIL$_3$-FAVSGAA-0-Fc, scTRAIL$_3$-FAVSGAA-5 G/S-Fc, scTRAIL$_3$-FAVSGAA-10 G/S-Fc, scTRAIL$_3$-FAVSGAA-15 G/S-Fc, scTRAIL$_3$-FAVSGAA-20 G/S-Fc, scTRAIL$_3$-FAVSGAA-25 G/S-Fc and scTRAIL$_3$-FAVSGAA-"W"-Fc were present in a correct dimeric constitution. Dynamic light scattering analysis revealed a melting point of 60° C. for scTRAIL$_3$-FAVSGAA-20 G/S-Fc (FIG. 39C). The melting points of the other fusion proteins scTRAIL$_3$-FAVSGAA-25 G/S-Fc, scTRAIL$_3$-FAVSGAA-"W"-Fc and scTRAIL$_3$-FAVSGAA-Fc were in the range of 54-55° C., indicating that the higher thermal stability of scTRAIL$_3$-FAVSGAA (54° C.) contributed to a higher overall protein stability also in the scTRAIL Fc fusion protein format.

Regarding binding to TRAIL R1-Fc and TRAIL R2-Fc in ELISA, the proteins scTRAIL$_3$-FAVSGAA-20 G/S-Fc, scTRAIL$_3$-FAVSGAA-25 G/S-Fc and scTRAIL$_3$-FAVSGAA-"W"-Fc bound, depending of the specific receptor, with EC$_{50}$ values in the nanomolar or sub-nanomolar range without major differences among each other (FIG. 40A). Lowest EC$_{50}$ values were detected for molecules with N-terminal fusion of Fc to scTRAIL$_3$. In contrast, scTRAIL$_3$-FAVSGAA-Fc showed less effective binding than the other proteins. All proteins bound with comparable properties to Colo205 or HCT116 tumor cells in flow cytometry, whereupon molecules with flexible glycine/serine linkers showed stronger binding signals than the variant scTRAIL$_3$-FAVSGAA-"W"-Fc comprising a mostly rigid alpha-helical peptide linker (FIG. 40B). The bioactivity of scTRAIL$_3$-FAVSGAA-20 G/S-Fc, scTRAIL$_3$-FAVSGAA-25 G/S-Fc and scTRAIL$_3$-FAVSGAA-"W"-Fc was evaluated in vitro by comparison with the reference molecules scTRAIL$_3$-FLVGGGPQRVA, Fc-scTRAIL$_3$-FAVSGAA, scTRAIL$_3$-FAVSGAA-Fc on Colo205 and HCT116 cells (Table 13, FIGS. 41, 42). On Colo205 cells, scTRAIL$_3$-FAVSGAA-20 G/S-Fc, scTRAIL$_3$-FAVSGAA-"W"-Fc and scTRAIL$_3$-FLVGGGPQRVA showed the best bioactivities with almost equal EC$_{50}$ values of ~20 pM (w/o bortezomib) and ~5 pM (with bortezomib), respectively. In contrast, on HCT116 cells, the molecule scTRAIL$_3$-FAVSGAA-20 G/S-Fc showed the best bioactivity among the analyzed scTRAIL$_3$ fusion proteins with Fc.

Example 22: Db-scTRAIL Fusion Proteins Targeting FAP

Targeting of tumor stroma markers like fibroblast activation protein (FAP) is considered as a promising approach to enhance the specificity and anti-tumor activity of TRAIL based protein therapeutics, e.g. because of the lower genetic variability of activated tumor fibroblasts. We accomplished FAP targeting in the Db-scTRAIL and scFv-Fc-scTRAIL format by use of humanized antigen binding domains derived from scFv36 (Baum et al., 2007).

In the molecule Db anti-FAP-Glyco-scTRAIL$_3$-FAVSGAA (SEQ ID NO: 255), the FAP-specific V$_H$ and V$_L$ domains were genetically connected with a peptide linker according to SEQ ID NO: 260 (GGGGS), facilitating diabody formation and hence a dimeric configuration of scTRAIL$_3$-FAVSGAA, which is fused via a 16 aa residues peptide linker comprising two N-glycosylation sites (AAAGNGTSNGTSEFGG, SEQ ID NO: 194). Db anti-FAP-Glyco-scTRAIL$_3$-FAVSGAA was expressed as soluble protein from stably transfected HEK293 cells and showed mostly monomolecular, dimerized constitution in SEC upon anti-FLAG affinity purification (FIG. 43A). A melting point of 55° C. was determined for the protein by dynamic light scattering, which resembles data obtained from EGFR-specific Db-scTRAIL or IgG-scTRAIL molecules comprising stability-enhanced scTRAIL$_3$-FAVSGAA (FIG. 43B). Db anti-FAP-Glyco-scTRAIL$_3$-FAVSGAA bound concentration dependent with an EC$_{50}$ of 14±5 nM to HT1080 fibrosarcoma cells overexpressing the FAP antigen in flow cytometry, whereas no binding was detected on HT1080 wild-type cells (FIG. 43C). Most importantly, functional FAP targeting was revealed in an in vitro bioactivity assay on HT1080 FAP$^+$ cells, using competition with a molar excess of an anti-FAP IgG (FIG. 43D). In this setting, an EC$_{50}$ value of 40±1 pM was determined for Db anti-FAP-Glyco-scTRAIL$_3$-FAVSGAA under competing conditions, whereas incubation without αFAP IgG resulted in higher cytotoxicity (EC$_{50}$=29 pM). Simultaneous sensitization with bortezomib resulted in generally higher bioactivities, reflected by EC$_{50}$ values of 4.1 pM and 2.0 pM for competing and non-competing conditions, respectively.

Example 23: scFv-Fc-scTRAIL$_3$ Fusion Protein Targeting FAP

A single-chain fragment variable (scFv) targeting fibroblast activation protein (FAP) was fused to the N-terminus (polypeptide linker: AAAGGSGG (SEQ ID NO:275)) and the scTRAIL$_3$-FLVGGGPQRVA to the C-terminus (polypeptide linker: GGSGGGSSGG (SEQ ID NO:193)) of the Fc-part and produced in stably transfected HEK293 cells. Stably transfected HT1080 FAP$^+$ cells (20,000/well) were cultivated for 24 h at 37° C., 5% CO$_2$. After preincubation with bortezomib (13 nM final concentration) or medium for 30 min, cells were treated with titration of the Fc-scTRAIL$_3$-FLVGGGPQRVA (SEQ ID NO: 210) or the FAP-targeting fusion protein scFv36-Fc-scTRAIL$_3$-FLVGGGPQRVA for 16 hours. Viability was measured by staining cells with crystal violet. For the dimeric FAP-targeting fusion protein scFv36-Fc-scTRAIL$_3$-FLVGGGPQRVA, EC$_{50}$ values of 5.2 pM and 1.4 pM were determined in the absence or presence of bortezomib, respectively (FIG. 44). In contrast, Fc-sc- TRAIL$_3$-FLVGGGPQRVA (SEQ ID NO: 210) showed reduced bioactivity on HT1080 FAP$^+$ cells with EC$_{50}$ values of 15.2 pM (without bortezomib) and 2.6 pM (in combination with bortezomib).

Example 24: Binding of scTRAIL$_3$ Fusion Proteins to Human TRAIL Receptors

The binding properties of the scTRAIL$_3$-fusion proteins to all five human TRAIL receptors were analyzed via ELISA. The extracellular domain (ECD) of the human death receptors (DR) 4 (TRAIL-R1) and 5 (TRAIL-R2), or of the human decoy receptors (DcR) 1 (TRAIL-R3) and 2 (TRAIL-R4) as well as human osteoprotegerin (OPG) was fused to the N-terminus of the Fc-part and was expressed in transiently transfected HEK293 cells. ELISA-plates were coated with ECD-Fc or OPG-Fc fusion proteins (3 µg/ml). After blocking with MPBS (2% milk in PBS), titrations of scFvhu225-Fc-scTRAIL$_3$-FLVGGGPQRVA (SEQ ID NO: 209), Fc-scTRAIL$_3$-FLVGGGPQRVA (SEQ ID NO: 210), and Db10hu225-Glyco-scTRAIL$_3$-FAVSGAA were incubated for 1 h at room temperature. Bound scTRAIL$_3$-fusion proteins were detected via HRP-conjugated anti-Flag antibody. ELISA studies revealed concentration-dependent binding and EC$_{50}$ values in the nanomolar or sub-nanomolar range (FIG. 45).

Tables

TABLE 1

| Name | Subunit (aa) | Subunit C-Term.* | Peptide | Subunit N-Terminus** | Mutations |
|---|---|---|---|---|---|
|  | 114-281 | ..FLVG | — | VRERGPARVAAH.. | — |
| scTRAIL-95L8 | 95-281 | ..FLVG | GGGSGGGS | TSEETISTVQEKQQ NISPLVRERGPQRV AAH. | — |
| scTRAIL$_3$-FLVGGGSGGGSV RERGPQRVA | 114-281 | ..FLVG | GGGSGGGS | VRERGPQRVAAH.. | — |
| scTRAIL$_3$-FLVGGGSVRERG PQRVA | 114-281 | ..FLVG | GGGS | VRERGPQRVAAH.. | — |
| scTRAIL$_3$-FLVGGGPQRVA | 118-281 | ..FLVG | GG | GPQRVAAH.. | — |
| scTRAIL$_3$-FLVGGPQRVA | 118-281 | ..FLVG | G | GPQRVAAH.. | — |
| scTRAIL$_3$-FLVGPQRVA | 118-281 | ..FLVG | — | GPQRVAAH.. | — |
| scTRAIL$_3$-FLVGGGSGGGSQRVA | 120-281 | ..FLVG | GGGSGGGS | QRVAAH.. | — |
| scTRAIL$_3$-FLVGGGSQRVA | 120-281 | ..FLVG | GGGS | QRVAAH.. | — |
| scTRAIL$_3$-FLVGQRVA | 120-281 | ..FLVG | G | QRVAAH.. | — |
| scTRAIL$_3$-FLVGRVA | 121-281 | ..FLVG | G | RVAAH.. | — |
| scTRAIL$_3$-FLVGVA | 122-281 | ..FLVG | G | VAAH.. | — |
| scTRAIL$_3$-FLVGAA | 122-281 | ..FLVG | G | AAAH.. | V122A |
| scTRAIL$_3$-FLVGIA | 122-281 | ..FLVG | G | IAAH.. | V122I |
| scTRAIL$_3$-FLVGGA | 122-281 | ..FLVG | G | GAAH.. | V122G |
| scTRAIL$_3$-FLVGLA | 122-281 | ..FLVG | G | LAAH.. | V122L |
| scTRAIL$_3$-FLVGMA | 122-281 | ..FLVG | G | MAAH.. | V122M |
| scTRAIL$_3$-FLGGGA | 122-281 | ..FLGG | G | GAAH.. | V280G/V122G |
| scTRAIL$_3$-FLGGA | 122-281 | ..FLGG | — | GAAH.. | V280G/V122G |
| scTRAIL$_3$-FGVGGA | 122-281 | ..FGVG | G | GAAH.. | L279G/V122G |
| scTRAIL$_3$-FAVGAA | 122-281 | ..FAVG | G | AAAH.. | L279A/V122A |
| scTRAIL$_3$-FAVGIA | 122-281 | ..FAVG | G | IAAH.. | L279A/V122I |
| scTRAIL$_3$-FIVGIA | 122-281 | ..FIVG | G | IAAH.. | L279I/V122I |

TABLE 1-continued

| Name | Subunit (aa) | Subunit C-Term.* Peptide | Subunit N-Terminus** | Mutations |
|---|---|---|---|---|
| scTRAIL₃-FAVSGAA | 122-281 | ..FAVS G | AAAH.. | L279A/G281S/V122A |
| scTRAIL₃-FLVSGIA | 122-281 | ..FLVS G | IAAH.. | G281S/V122I |
| scTRAIL₃-FIVSGIA | 122-281 | ..FIVS G | IAAH.. | L279I/G281S/V122I |
| scTRAIL₃-FAVSGIA | 122-281 | ..FAVS G | IAAH.. | L279A/G281S/V122I |

*The C-terminal amino acid of scTRAIL, preferably human scTRAIL that is included according to above outlined nomenclature of the constructs is highlighted in bold. It corresponds to -X₁ of the C-terminal consensus sequence according to SEQ ID NO: 1).
**The N-terminal amino acids of scTRAIL, preferably human scTRAIL that are included according to above outlined nomenclature of the constructs are highlighted in bold. They correspond to X₂-V/A/F- of the N-terminal consensus sequence according to SEQ ID NO: 2.

TABLE 2

Solubility of scTRAIL molecules

| Name | Solubility |
|---|---|
| sTRAIL | yes |
| scTRAIL-95L8 | yes |
| scTRAIL₃-FLVGGGGSGGGSVRERGPQRVA | yes |
| scTRAIL₃-FLVGGGGSVRERGPQRVA | yes |
| scTRAIL₃-FLVGGGGPQRVA | yes |
| scTRAIL₃-FLVGGGPQRVA | yes |
| scTRAIL₃-FLVGGPQRVA | yes |
| scTRAIL₃-FLVGGGGSGGGSQRVA | yes |
| scTRAIL₃-FLVGGGGSQRVA | yes |
| scTRAIL₃-FLVGGQRVA | yes |
| scTRAIL₃-FLVGGRVA | yes |
| scTRAIL₃-FLVGGVA | yes |
| scTRAIL₃-FLVGGAA | yes |
| scTRAIL₃-FLVGGIA | yes |
| scTRAIL₃-FLVGGGA | no |
| scTRAIL₃-FLVGGLA | no |
| scTRAIL₃-FLVGGMA | no |
| scTRAIL₃-FLGGGA | no |
| scTRAIL₃-FLGGGA | no |
| scTRAIL₃-FGVGGGA | no |
| scTRAIL₃-FAVGGAA | yes |
| scTRAIL₃-FAVGGIA | yes |
| scTRAIL₃-FIVGGIA | yes |
| scTRAIL₃-FAVSGAA | yes |
| scTRAIL₃-FLVSGIA | yes |
| scTRAIL₃-FIVSGIA | yes |
| scTRAIL₃-FAVSGIA | yes |

TABLE 3

Thermal stability of scTRAIL molecules

| Name | Tm (° C.) |
|---|---|
| sTRAIL | 46 |
| scTRAIL-95L8 | 47 |
| scTRAIL₃-FLVGGGGSGGGSVRERGPQRVA | 46 |
| scTRAIL₃-FLVGGGGSVRERGPQRVA | 47 |
| scTRAIL₃-FLVGGGGPQRVA | 52 |
| scTRAIL₃-FLVGGGPQRVA | 52 |
| scTRAIL₃-FLVGGPQRVA | 53 |
| scTRAIL₃-FLVGGGGSGGGSQRVA | 49 |
| scTRAIL₃-FLVGGGGSQRVA | 50 |
| scTRAIL₃-FLVGGQRVA | nd |
| scTRAIL₃-FLVGGRVA | 54 |
| scTRAIL₃-FLVGGVA | 57 |
| scTRAIL₃-FLVGGAA | 53.5 |
| scTRAIL₃-FLVGGIA | 54 |
| scTRAIL₃-FLVGGGA | nd |
| scTRAIL₃-FLVGGLA | nd |
| scTRAIL₃-FLVGGMA | nd |
| scTRAIL₃-FLGGGGA | nd |
| scTRAIL₃-FLGGGA | nd |
| scTRAIL₃-FGVGGGA | nd |

TABLE 3-continued

Thermal stability of scTRAIL molecules

| Name | Tm (° C.) |
|---|---|
| scTRAIL$_3$-FAVGGAA | 53 |
| scTRAIL$_3$-FAVGGIA | 53 |
| scTRAIL$_3$-FIVGGIA | 52 |
| scTRAIL$_3$-FAVSGAA | 54 |
| scTRAIL$_3$-FLVSGIA | 51.5 |
| scTRAIL$_3$-FIVSGIA | 51 |
| scTRAIL$_3$-FAVSGIA | 50.5 |

TABLE 4

EC$_{50}$ values of cell death induction of various Db-scTRAIL molecules on tumor cells in the presence of Bortezomib+/−antibody Cetuximab (Cet) competing for EGFR binding.

| EC$_{50}$, Mean ± SE (pM) | Colo205 | HT1080 | HCT116 |
|---|---|---|---|
| Db-scTRAIL-95L8 | 24 ± 4 | 3 ± 0.7 | 127 ± 2 |
| Db-scTRAIL-95L8 + Cet. | 48 ± 5 | 15 ± 4 | 381 ± 16 |
| Db-Glyco-scTRAIL$_3$-FAVSGAA | 33 ± 6 | 1 ± 0.6 | 66 ± 10 |
| Db-Glyco-scTRAIL$_3$-FAVSGAA + Cet. | 74 ± 15 | 10 ± 4 | 450 ± 2 |
| Db-Glyco-scTRAIL$_3$-FAVSGIA | 19 ± 3 | 0.6 ± 0.2 | 43 ± 2 |
| Db-Glyco-scTRAIL$_3$-FAVSGIA + Cet. | 32 ± 5 | 5 ± 1 | 161 ± 3 |
| Db8-Glyco-scTRAIL$_3$-FAVSGAA | 26 ± 2 | 0.9 ± 0.2 | 51 ± 8 |
| Db8-Glyco-scTRAIL$_3$-FAVSGAA + Cet. | 61 ± 7 | 7 ± 2 | 300 ± 10 |
| Db10-Glyco-scTRAIL$_3$-FAVSGAA | 13 ± 2 | 0.7 ± 0.2 | 39 ± 4 |
| Db10-Glyco-scTRAIL$_3$-FAVSGAA + Cet. | 66 ± 17 | 8 ± 2 | 298 ± 3 |

TABLE 5

EC$_{50}$ values [nM] of binding to target antigens (EGFR, HER2, HER3*), TRAIL-R2 and to Colo205 cells measured by ELISA and flow cytometry, respectively.

| Construct | Antigen binding ELISA | TRAIL-R2 binding ELISA | FACS Colo205 |
|---|---|---|---|
| Dbhu225-scTRAIL$_3$-FLVGGGPQRVA | 0.77 | 0.79 | 0.87 |
| dsDbhu225-scTRAIL$_3$-FLVGGGPQRVA | 0.98 | 1.29 | 0.86 |
| scFvhu225-EHD2-scTRAIL$_3$-FLVGGGPQRVA | 1.25 | 1.82 | 0.58 |
| scFvhu225-Fc-scTRAIL$_3$-FLVGGGPQRVA | 0.86 | 1.52 | 1.33 |
| Db4D5-scTRAIL$_3$-FLVGGGPQRVA | 8.33 | 1.55 | 18.08 |
| dsDb4D5-scTRAIL$_3$-FLVGGGPQRVA | 4.53 | 1.48 | 23.21 |
| scFv4D5-EHD2-scTRAIL$_3$-FLVGGGPQRVA | 4.98 | 2.21 | 14.34 |
| scFv4D5-Fc-scTRAIL$_3$-FLVGGGPQRVA | 4.13 | 0.73 | 27.96 |
| Db3M6-scTRAIL$_3$-FLVGGGPQRVA | 5.88 | 2.81 | 10.44 |
| dsDb3M6-scTRAIL$_3$-FLVGGGPQRVA | 8.54 | 2.83 | 32.49 |
| scFv3M6-EHD2-scTRAIL$_3$-FLVGGGPQRVA | 11.63 | 2.65 | 19.93 |
| scFv3M6-Fc-scTRAIL$_3$-FLVGGGPQRVA | — | — | 13.11 |
| scTRAIL$_3$-FLVGGGPQRVA | — | 1.74 | 5.67 |
| EHD2-scTRAIL$_3$-FLVGGGPQRVA | — | 1.94 | >100 |
| Fc-scTRAIL$_3$-FLVGGGPQRVA | — | 2.42 | >100 |

*target antigens and DR5 for ELISA are Fc fusion proteins

TABLE 6

EC$_{50}$ values [pM] of cell death induction on Colo205 and HCT-116 cells in the absence and presence of Bortezomib(250 ng/ml, 650 nM) in the absence and presence of Cetuximab (200-fold molar excess).

| Construct | Colo205 without/with bortezomib | Colo205 in presence of Cetuximab without/with bortezomib | HCT-116 without/with bortezomib |
|---|---|---|---|
| Dbhu225-scTRAIL$_3$-FLVGGGPQRVA | 41.0/3.8 | 101.6/13.8 | 35.2/1.2 |
| dsDbhu225-scTRAIL$_3$-FLVGGGPQRVA | 21.2/2.5 | 42.3/7.2 | 25.2/0.8 |
| scFvhu225-EHD2-scTRAIL$_3$-FLVGGGPQRVA | 11.9/1.8 | 69.3/6.7 | 11.1/0.6 |
| scFvhu225-Fc-scTRAIL$_3$-FLVGGGPQRVA | 12.5/2.3 | 66.2/5.7 | 11.9/0.5 |

TABLE 7

Initial and terminal half-lives [h] and areas under the curve [% h] of EGFR-targeting scTRAIL$_3$-FLVGGGPQRVA fusion proteins. Data are represented as mean ± S.D. (n = 3).

| Construct | $t_{1/2}\alpha$ [h] | $t_{1/2}\beta$ [h] | AUC [% h] |
|---|---|---|---|
| Dbhu225-scTRAIL$_3$-FLVGGGPQRVA | 1.09 ± 0.22 | 2.42 ± 0.09 | 215.98 ± 52.04 |
| dsDbhu225-scTRAIL$_3$-FLVGGGPQRVA | 1.28 ± 0.15 | 2.32 ± 0.12 | 291.96 ± 20.87 |
| scFvhu225-EHD2-scTRAIL$_3$-FLVGGGPQRVA | 1.49 ± 0.11 | 6.55 ± 0.20 | 401.94 ± 51.37 |
| scFvhu225-Fc-scTRAIL$_3$-FLVGGGPQRVA | 2.05 ± 0.23 | 17.37 ± 3.14 | 543.20 ± 39.90 |

TABLE 8

EC$_{50}$ values of binding of cetuximab and derived humanized anti-EGFR IgG to EGFR$^+$ cell lines.

| Molecule | Colo205 EC$_{50}$ of binding (pM) | HCT116 EC$_{50}$ of binding (pM) |
|---|---|---|
| cetuximab | 19 ± 8 | 9 ± 3 |
| anti-EGFR IgG | 28 ± 6 | 8 ± 3 |

TABLE 9

EC$_{50}$ values of binding of anti-EGFR IgG-scTRAIL$_3$-FAVSGAA fusion proteins to EGFR$^+$ cell lines (flow cytometry) or EGFR-Fc (ELISA).

| Molecule | Colo205 EC$_{50}$ of binding (pM) | HCT116 EC$_{50}$ of binding (pM) | EGFR-Fc EC$_{50}$ of binding (pM) |
|---|---|---|---|
| anti-EGFR IgG | 60 ± 41 | 70 ± 21 | 156 ± 19 |
| anti-EGFR IgG LC-scTRAIL$_3$-FAVSGAA | 148 ± 83 | 181 ± 79 | 460 ± 27 |
| anti-EGFR IgG HC-scTRAIL$_3$-FAVSGAA | 81 ± 59 | 118 ± 33 | 343 ± 72 |
| anti-EGFR IgG LC/HC-scTRAIL$_3$-FAVSGAA | 146 ± 28 | 91 ± 72 | 315 ± 87 |

TABLE 10

EC$_{50}$ values of bioactivity of anti-EGFR IgG-scTRAIL$_3$-FAVSGAA fusion proteins on EGFR$^+$ cell lines in presence or without bortezomib (BZB). An excess of cetuximab was used for competition, where indicated.

| Molecule | HT1080 (pM) −BZB | HT1080 (pM) +BZB | Colo205 (pM) −BZB | Colo205 (pM) +BZB | HCT116 (pM) −BZB | HCT116 (pM) +BZB |
|---|---|---|---|---|---|---|
| Db10-Glyco-scTRAIL$_3$-FAVSGAA | 1.8 ±0.3 | 0.23 ±0.17 | 35 ±9 | 8.1 ±0.8 | 7.7 ±1.7 | 2.1 ±1.4 |
| anti-EGFR IgG LC-scTRAIL$_3$-FAVSGAA | 1.4 ±0.2 | 0.4 ±0.1 | 41 ±14 | 10 ±4 | 8.5 ±1.8 | 5.2 ±0.8 |
| anti-EGFR IgG LC-scTRAIL$_3$-FAVSGAA + cetuximab | 52 ±8 | 4.2 ±1.9 | 304 ±168 | 25 ±11 | 75 ±33 | 19 ±4 |
| anti-EGFR IgG HC-scTRAIL$_3$-FAVSGAA | 1.3 ±0.1 | 0.2 ±0.17 | 32 ±17 | 5.9 ±2.9 | 4.8 ±0.5 | 1.3 ±0.6 |
| anti-EGFR IgG HC-scTRAIL$_3$-FAVSGAA + cetuximab | 34 ±8 | 6.3 ±0.5 | 74 ±38 | 17 ±1 | 47 ±25 | 3.9 ±0.6 |
| anti-EGFR IgG LC/HC-scTRAIL$_3$-FAVSGAA | 0.3 ±0.01 | 0.036 | 6.9 ±2.5 | 1.1 ±0.2 | 0.6 ±0.2 | 0.3 ±0.1 |
| anti-EGFR IgG LC/HC-scTRAIL$_3$-FAVSGAA + cetuximab | 5.9 ±0.4 | 0.13 | 10 ±5 | 1.8 ±0.7 | 6.7 ±0.6 | 1.5 ±0.04 |

TABLE 11

EC$_{50}$ values of bioactivity of scTRAIL$_3$-FAVSGAA Fc fusion proteins comprising glycosylated peptide linkers between scTRAIL$_3$-FAVSGAA and Fc on Colo205 in presence or without bortezomib (BZB). Monomeric scTRAIL$_3$-FLVGGGGPQRVA served as a reference (mean ± S.D., n = 3).

| Molecule | Colo205 (EC$_{50}$ in pM) −BZB | Colo205 (EC$_{50}$ in pM) +BZB |
|---|---|---|
| scTRAIL$_3$-FLVGGGGPQRVA | — | 670 ± 96 |
| Fc-scTRAIL$_3$-FAVSGAA | 220 ± 50 | 35 ± 7 |
| scTRAIL$_3$-FAVSGAA-Fc | 218 ± 9 | 31 ± 9 |
| scTRAIL$_3$-FAVSGAA-Fc-scTRAIL$_3$-FAVSGAA | 62 ± 13 | 21 ± 7 |

TABLE 12

EC$_{50}$ values of binding (ELISA) of scTRAIL$_3$-FAVSGAA Fc fusion proteins comprising glycine/serine or glycosylated peptide linkers to TRAIL R1-Fc and TRAIL R2-Fc. Fc-scTRAIL$_3$-FLVGGGPQRVA served as a reference (mean ± S.D., n = 3).

| Molecule | TRAIL R1-Fc (EC$_{50}$ in nM) | TRAIL R2-Fc (EC$_{50}$ in nM) |
|---|---|---|
| scTRAIL$_3$-FAVSGAA-20 G/S-Fc | 4.45 ± 0.93 | 0.43 ± 0.26 |
| scTRAIL$_3$-FAVSGAA-25 G/S-Fc | 3.24 ± 0.58 | 0.42 ± 0.23 |
| scTRAIL$_3$-FAVSGAA-"W"-Fc | 3.91 ± 0.84 | 0.54 ± 0.34 |
| scTRAIL$_3$-FAVSGAA-Fc | 6.36 ± 1.29 | 0.69 ± 0.37 |
| Fc-scTRAIL$_3$-FAVSGAA | 2.15 ± 1.01 | 0.34 ± 0.15 |
| Fc-scTRAIL$_3$-FLVGGGPQRVA | 1.63 ± 1.07 | 0.34 ± 0.23 |

TABLE 13

EC$_{50}$ values of bioactivities of scTRAIL$_3$-FAVSGAA or scTRAIL$_3$-FLVGGGPQRVA fusion proteins with Fc on Colo205 and HCT116 tumor cell lines in presence or without bortezomib (BZB) (mean ± S.D., n = 3).

| Molecule | Colo205 (EC$_{50}$ in pM) −BZB | Colo205 (EC$_{50}$ in pM) +BZB | HCT116 (EC$_{50}$ in pM) −BZB | HCT116 (EC$_{50}$ in pM) +BZB |
|---|---|---|---|---|
| Fc-scTRAIL$_3$-FLVGGGPQRVA | 17.2 ± 8.0 | 3.8 ± 0.8 | 92.1 ± 38.0 | 38.7 ± 17.6 |
| Fc-scTRAIL$_3$-FAVSGAA | 45.6 ± 6.6 | 15.7 ± 8.9 | 35.6 ± 18.2 | 27.4 ± 10.2 |
| scTRAIL$_3$-FAVSGAA-Fc | 288 ± 97 | 24.9 ± 17.8 | 261 ± 84 | 145 ± 25 |
| scTRAIL$_3$-FAVSGAA-20 G/S-Fc | 20.7 ± 1.0 | 5.3 ± 1.3 | 23.8 ± 7.7 | 16.9 ± 3.4 |
| scTRAIL$_3$-FAVSGAA-25 G/S-Fc | 56.7 ± 24.8 | 12.5 ± 3.3 | 61.3 ± 16.1 | 42.9 ± 8.9 |
| scTRAIL$_3$-FAVSGAA-"W"-Fc | 20.1 ± 4.0 | 4.7 ± 2.1 | 35.4 ± 7.5 | 26.4 ± 5.4 |

TABLE 14

Structure of constructs tested in Examples 17 to 24.

| Molecule | Sequence (connecting linker) | Length (aa) |
|---|---|---|
| scTRAIL₃-FAVSGAA-Fc | scTRAIL₃-FAVSGAA---GSGNGTSNGTSGSSGG---Fc | 16 |
| Fc-scTRAIL₃-FAVSGAA | Fc---GSGNGTSNGTSGSSGG---scTRAIL₃-FAVSGAA | 16 |
| scTRAIL₃-FAVSGAA-Fc-scTRAIL₃-FAVSGAA | scTRAIL₃-FAVSGAA---GSGNGTSNGTSGSSRT---Fc---GSGNGTSNGTSGSSGG---scTRAIL₃-FAVSGAA | 2 × 16 |
| scTRAIL₃-0-FAVSGAA-Fc | scTRAIL₃-FAVSGAA---Fc | — |
| scTRAIL₃-5 G/S-FAVSGAA-Fc | scTRAIL₃-FAVSGAA---GGSGG---Fc | 5 |
| scTRAIL₃-10 G/S-FAVSGAA-Fc | scTRAIL₃-FAVSGAA---GGSGGGGSGG---Fc | 10 |
| scTRAIL₃-15 G/S-FAVSGAA-Fc | scTRAIL₃-FAVSGAA---GGSGGGGSGGGGSGG---Fc | 15 |
| scTRAIL₃-20 G/S-FAVSGAA-Fc | scTRAIL₃-FAVSGAA---GGSGGGGSGGGGSGGGGSGG---Fc | 20 |
| scTRAIL₃-25 G/S-FAVSGAA-Fc | scTRAIL₃-FAVSGAA---GGSGGGGSGGGGSGGGGSGGGGSGG---Fc | 25 |
| scTRAIL₃-"W"-FAVSGAA-Fc | scTRAIL₃-FAVSGAA---GGSGEAAAKEAAAKEAAAKEAAAKEAAAKGSGG---Fc | 33 |
| DbαFAP-Glyco-scTRAIL₃-FAVSGAA | DbαFAP---AAAGNGTSNGTSEFGG---scTRAIL₃-FAVSGAA | 16 |

REFERENCES

1. Arnau J, Lauritzen C, Petersen G E, Pedersen J. Current strategies for the use of affinity tags and tag removal for the purification of recombinant proteins. Protein Expr Purif. 2006 July; 48(1):1-13.
2. Baum, P., Miller, D., Rüger, R., and Kontermann, R. E. (2007). Single-chain Fv immunoliposomes for the targeting of fibroblast activation protein-expressing tumor stromal cells. J. Drug Target. 15, 399-406.
3. Bodmer J L, Schneider P, Tschopp J. The molecular architecture of the TNF superfamily. Trends Biochem Sci. 2002 January; 27(1):19-26.
4. Chen W, Qiu L, Hou J, Zhang X, Ke X, Wang Z et al. (2012a). Phase Ib study of recombinant circularly permuted TRAIL (CPT) in relapsed or refractory multiple myeloma patients. 54th ASH annual meeting abstr 1857.
5. Chen W, Hou J, Zhao Y, Qiu L, Ke X, Wang Z et al. (2012b). Circularly permuted TRAIL (CPT) combined with thalidomide for the treatment of relapsed or refractory multiple myeloma: an open-label, multicenter phase II clinical trial. 54th ASH annual meeting abstr 2958.
6. de Bruyn M, Bremer E, Helfrich W. Antibody-based fusion proteins to target death receptors in cancer. Cancer Lett. 2013 May 28; 332(2):175-83.
7. Gao D, Narasimhan D L, Macdonald J, Brim R, Ko M C, Landry D W, Woods J H, Sunahara R K, Zhan C G. Thermostable variants of cocaine esterase for long-time protection against cocaine toxicity. Mol Pharmacol. 2009 February; 75(2):318-23.
8. Herbst R S, Kurzrock R, Hong D S, Valdivieso M, Hsu C P, Goyal L, Juan G, Hwang Y C, Wong S, Hill J S, Friberg G, LoRusso P M. A first-in-human study of conatumumab in adult patients with advanced solid tumors. Clin Cancer Res. 2010a December 1; 16(23):5883-91.
9. Herbst R S, Eckhardt S G, Kurzrock R, Ebbinghaus S, O'Dwyer P J, Gordon M S, Novotny W, Goldwasser M A, Tohnya T M, Lum B L, Ashkenazi A, Jubb A M, Mendelson D S. Phase I dose-escalation study of recombinant human Apo2L/TRAIL, a dual proapoptotic receptor agonist, in patients with advanced cancer. J Clin Oncol. 2010b June 10; 28(17):2839-46.
10. Holland P M, Death receptor agonist therapies for cancer, which is the right TRAIL?, Cytokine and Growth Factor Revies, 2014, 25: 185-193
11. Hymowitz S G, Christinger H W, Fuh G, Ultsch M, O'Connell M, Kelley R F, Ashkenazi A, de Vos A M. Triggering cell death: the crystal structure of Apo2L/TRAIL in a complex with death receptor 5. Mol Cell. 1999 October; 4(4):563-71.
12. Hymowitz S G, O'Connell M P, Ultsch M H, Hurst A, Totpal K, Ashkenazi A, de Vos A M, Kelley R F. A unique zinc-binding site revealed by a high-resolution X-ray structure of homotrimeric Apo2L/TRAIL. Biochemistry. 2000 Feb. 1; 39(4):633-40.
13. Micheau O, Shirley S, Dufour F. Death receptors as targets in cancer. Br J Pharmacol. 2013 August; 169(8): 1723-44.
14. Plummer R, Attard G, Pacey S, Li L, Razak A, Perrett R, Barrett M, Judson I, Kaye S, Fox N L, Halpern W, Corey A, Calvert H, de Bono J. Phase 1 and pharmacokinetic study of lexatumumab in patients with advanced cancers. Clin Cancer Res. 2007 Oct. 15; 13(20):6187-94.
15. Schneider B, Münkel S, Krippner-Heidenreich A, Grunwald I, Wels W S, Wajant H, Pfizenmaier K, Gerspach J. Potent antitumoral activity of TRAIL through generation of tumor-targeted single-chain fusion proteins. Cell Death Dis. 2010 Aug. 26; 1:e68.
16. Seifert O, Plappert A, Fellermeier S, Siegemund M, Pfizenmaier K, Kontermann R E. Tetravalent antibody-scTRAIL fusion proteins with improved properties. Mol Cancer Ther. 2014 January; 13(1):101-11.
17. Sergeeva A, Kolonin M G, Molldrem J J, Pasqualini R, Arap W. Display technologies: application for the discovery of drug and gene delivery agents. Adv Drug Deliv Rev. 2006 Dec. 30; 58(15):1622-54.
18. Siegemund M, Pollak N, Seifert O, Wahl K, Hanak K, Vogel A, Nussler A K, Göttsch D, Münkel S, Bantel H, Kontermann R E, Pfizenmaier K. Superior antitumoral activity of dimerized targeted single-chain TRAIL fusion proteins under retention of tumor selectivity. Cell Death Dis. 2012 Apr. 12; 3:e295.
19. Tolcher A W, Mita M, Meropol N J, von Mehren M, Patnaik A, Padavic K, Hill M, Mays T, McCoy T, Fox N L, Halpern W, Corey A, Cohen R B. Phase I pharmacokinetic and biologic correlative study of mapatumumab, a fully human monoclonal antibody with agonist activity to tumor necrosis factor-related apoptosis-inducing ligand receptor-1. J Clin Oncol. 2007 Apr. 10; 25(11):1390-5. Erratum in: J Clin Oncol. 2007 Oct. 10; 25(29):4701.
20. Trarbach T, Moehler M, Heinemann V, Köhne C H, Przyborek M, Schulz C, Sneller V, Gallant G, Kanzler S. Phase II trial of mapatumumab, a fully human agonistic monoclonal antibody that targets and activates the tumour necrosis factor apoptosis-inducing ligand receptor-1 (TRAIL-R1), in patients with refractory colorectal cancer. Br J Cancer. 2010 Feb. 2; 102(3):506-12.

The invention claimed is:

1. A polypeptide comprising:
   (i) component A comprising:
      at least three tumor necrosis factor (TNF) homology domains of TNF-ligand family member proteins (THD), wherein the C-terminus of the first and second THD, respectively, which is in each case defined by the C-terminal consensus sequence $$\text{-S/T/V-F/Y/S-F-G-A/L/V/I-X}_1, \quad (\text{SEQ ID NO: 1})$$

is linked to the N-terminus of the second and third THD, respectively, which is in each case defined by the N-terminal consensus sequence $$X_2\text{-V/A/F-A-H-V/L/I/Y} \quad (\text{SEQ ID NO: 2})$$
      or
      $$X_3\text{-V/W/F/C-A/L-E/Y/Q/H-L} \quad (\text{SEQ ID NO: 3})$$

through a peptide $X_a$, which is in each case independently selected and has a length of 3 to 8 amino acids,
      wherein $X_1$ is a non-polar/hydrophobic or polar/neutral amino acid;
      wherein $X_2$ is selected from the group consisting of P, K, V, I, and A;
      wherein $X_3$ is selected from the group consisting of D, S, M, and I;
   (ii) component B comprising
      a dimerization domain consisting of an antibody VL and VH region linked directly to each other with a peptide that has a length of between 7 and 11 amino acids.

2. The polypeptide according to claim 1, wherein the $V_L$ and $V_H$ region of an antibody specifically bind to a target molecule on the cell surface.

3. The polypeptide according to claim 1, wherein component A is linked to component B by a peptide $X_b$.

4. The polypeptide according to claim 1 wherein the peptide $X_a$ consists of $$X_e\text{-}X_f\text{-}X_g,$$

wherein
$X_e$ is selected from the group consisting of L, L-V, L-V-G, L-V-G-G (SEQ ID NO: 159), L-V-S, L-V-S-G (SEQ ID NO: 161), A, A-V, A-V-S, A-V-G, A-V-G-G (SEQ ID NO: 162), A-V-S-G (SEQ ID NO: 163), I-V, I-V-S, I-V-G, I-V-G-G (SEQ ID NO: 164), I—V-S-G (SEQ ID NO: 165), K, K-L, M, M-V, A, A-L, M-V-G, M-V-Q, G, G-V, G-V-H, W, W-V, W-V-R, W-V-R-P (SEQ ID NO: 167), K-L-L, I, A-V, Q, Q-V, and Q-V-H;
$X_f$ is absent or selected from the group consisting of G, S, G-G, S-G, G-S, S-S, G-G-G, G-G-S, G-S-G, S-G-G, G-S-S, S-G-S and S-S-S; and
$X_g$ is absent or selected from the group consisting of R, Q-R, P-Q-R, G-P-Q-R (SEQ ID NO: 166), L-R, N, V-N, K, L-K, L, G-L, K, D-K, Q, P-Q, A, R-A, W, G-W, Q, and T-Q.

5. A polypeptide according to claim 1, wherein the at least three THDs are identical.

6. The polypeptide according to claim 1, wherein the sequence of the TNF-ligand family member is selected from the group consisting of SEQ ID NO: 5, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15.

7. The polypeptide according to claim 1, wherein the non-polar/hydrophobic or polar/neutral amino acid of $X_1$ is selected from the group consisting of F, V, Q, A, I, L, and Y.

8. The polypeptide of claim 2, wherein the target molecule is selected from the group consisting of tyrosine-kinase-receptors (EGFR, HER2, HER3, HER4), VEGFRs, heteromeric integrin α- or β-receptor family, tumor stroma markers, preferably fibroblast activation protein (FAP), galectin, EpCAM, CEA, CD44 and tumor specific variants thereof and other tumor selective cell surface markers, CD2, CDS, CD7, CD19, CD20, CD21, CD22, CD24, CD25, CD30, CD33, CD38, CD40, CD52, CD56, CD71, CD72, CD73, CD105, CD117, CD123, CD133, c-Met, PDGFR, IGF1-R, HMW-MAA, TAG-72, GD2, GD3, GM2, folate receptor, Lgr5, Ley, Muc-1, Muc-2, PSMA, PSCA and uPAR.

9. The polypeptide according to claim 3, wherein the peptide $X_b$
   (i) has a length of 5 to 20 amino acids;
   (ii) comprises at least one glycosylation motif; or
   (iii) is selected from the group consisting of SEQ ID NO: 159, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174 and SEQ ID NO: 175.

10. The polypeptide according to claim 4, wherein
   (i) $X_e$ is selected from L, L-V, L-V-G, L-V-G-G (SEQ ID NO: 159), L-V-S, L-V-S-G (SEQ ID NO: 161), A, A-V, A-V-S, A-V-G, A-V-G-G (SEQ ID NO: 162), A-V-S-G (SEQ ID NO: 163), I—V, I—V—S, I—V-G, I-V-G-G (SEQ ID NO: 164), and I—V-S-G (SEQ ID NO: 165); $X_f$ is absent or selected from G, S, G-G, S-G, G-S, and S-S; and $X_g$ is absent or selected from R, Q-R, P-Q-R, and G-P-Q-R (SEQ ID NO: 166);
   (ii) $X_e$ is selected from K, and K-L; $X_f$ is absent or selected from G, S, G-G, S-G, G-S, and S-S; and $X_g$ is absent or selected from R, and L-R;
   (iii) $X_e$ is selected from M, M-V; $X_f$ is absent or selected from G, S, G-G, S-G, G-S, and S-S; and $X_g$ is absent or selected from N and V-N;
   (iv) $X_e$ is selected from A, and A-L; $X_f$ is absent or selected from G, S, G-G, S-G, G-S, and S-S; and $X_g$ is absent or selected from K and L-K;
   (v) $X_e$ is selected from M, M-V, and M-V-G; $X_f$ is absent or selected from G, S, G-G, S-G, G-S, and S-S; and $X_g$ is absent or selected from L, and G-L;
   (vi) $X_e$ is selected from A, and A-L; $X_f$ is absent or selected from G, S, G-G, S-G, G-S, and S-S; and $X_g$ is absent or selected from K, and D-K;
   (vii) $X_e$ is selected from K, and K-L; $X_f$ is absent or selected from G, S, G-G, S-G, G-S, and S-S; and $X_g$ is absent or selected from Q, and P-Q;
   (viii) $X_e$ is selected from Q, Q-V, and Q-V-H; $X_f$ is absent or selected from G, S, G-G, S-G, G-S, and S-S; and $X_g$ is absent or selected from A, and R-A;
   (ix) $X_e$ is selected from W, W—V, W—V—R, and W—V-R-P (SEQ ID NO: 167); $X_f$ is absent or selected from G, S, G-G, S-G, G-S, and S-S; and $X_g$ is absent or selected from W, and G-W; or
   (x) $X_e$ is selected from K, K-L, and K-L-L; $X_f$ is absent or selected from G, S, G-G, S-G, G-S, and S-S; and $X_g$ is absent or selected from Q, and T-Q; or
   the peptide $X_a$ is selected from the group consisting of I—V-S-G (SEQ ID NO: 165), A-V-S-G (SEQ ID NO:

163), I-V-G-G (SEQ ID NO: 164), A-V-G-G (SEQ ID NO: 162), L-V-S-G (SEQ ID NO: 161), L-V-G-G (SEQ ID NO: 159), L-V-G-G-R (SEQ ID NO: 168), L-V-G-G-G (SEQ ID NO: 169), L-V-G-G-P (SEQ ID NO: 170) or $X_a$ is selected from the group consisting of L-V-G-G-P-Q-R (SEQ ID NO: 173), L-V-G-G-G-P-Q-R (SEQ ID NO: 174), and L-V-G-G-G-P-Q-R (SEQ ID NO: 75).

11. The polypeptide of claim 6, wherein the polypeptide comprises or consists of the amino acid sequence selected from the group according to SEQ ID NO: 5, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15.

12. A polypeptide comprising:
component C comprising:
at least three TNF homology domains of TNF-ligand family member proteins (THD), wherein the C-terminus of the first and second THD, respectively, which is in each case defined by the C-terminal consensus sequence $$\text{-S/T/V-F/Y/S-F-G-A/L/V/I-}X_1, \quad \text{(SEQ ID NO: 1)}$$

is linked to the N-terminus of the second and third THD, respectively, which is in each case defined by the N-terminal consensus sequence $$X_2\text{-V/A/F-A-H-V/L/I/Y} \quad \text{(SEQ ID NO: 2)}$$
or
$$X_3\text{-V/W/F/C-A/L-E/Y/Q/H-L,} \quad \text{(SEQ ID NO: 3)}$$

through a peptide $X_c$, which is in each case independently selected and has a length of 3 to 5 amino acids,
wherein $X_1$ is a non-polar/hydrophobic or polar/neutral amino acid;
wherein $X_2$ is selected from the group consisting of P, K, V, I, and A; and
wherein $X_3$ is selected from the group consisting of D, S, M, and I.

13. A pharmaceutical composition comprising as an active agent the polypeptide according to claim 1.

14. The pharmaceutical composition according to claim 13 further comprising one or more proteasome inhibitor.

15. A nucleic acid encoding the polypeptide according to claim 1.

16. A vector comprising the nucleic acid according to claim 15.

17. The polypeptide according to claim 12, wherein the peptide $X_c$ consists of $$X_e\text{-}X_f\text{-}X_g$$

wherein
$X_e$ is selected from the group consisting of L, L-V, L-V-G, L-V-G-G (SEQ ID NO: 159), L-V-S, L-V-S-G (SEQ ID NO: 161), A, A-V, A-V-S, A-V-G, A-V-G-G (SEQ ID NO: 162), A-V-S-G (SEQ ID NO: 163), I-V, I-V-S, I-V-G, I-V-G-G (SEQ ID NO: 164), I—V-S-G (SEQ ID NO: 165), K, K-L, M, M-V, A, A-L, M-V-G, M-V-Q, G, G-V, G-V-H W, W-V, W-V-R, W-V-R-P (SEQ ID NO: 167), K-L-L, I, A-V, Q, Q-V, and Q-V-H;

$X_f$ is absent or selected from the group consisting of G, S, G-G, S-G, G-S, S-S, G-G-G, G-G-S, G-S-G, S-G-G, G-S-S, S-G-S and S-S-S; and $X_g$ is absent or selected from the group consisting of R, Q-R, P-Q-R, G-P-Q-R (SEQ ID NO: 166), L-R, N, V-N, K, L-K, L, G-L, K, D-K, Q, P-Q, A, R-A, W, G-W, Q, and T-Q.

18. The polypeptide according to claim 17 further comprising a component D which is selected from the group consisting of a dimerization or multimerization domain, a half-life-extension domain, a target-specific binding domain or combinations thereof.

19. The polypeptide according to claim 18, wherein the target-specific binding domain is an antibody or fragment thereof; a diabody; a single chain antibody or an antibody mimetic; affilins; human-γ B crystalline or human ubiquitin; cystatin; Sac7D from *Sulfolobus acidocaldarius*; lipocalin and anticalins derived from lipocalins; DARPins (designed ankyrin repeat domains); a domain of a membrane receptor; SH3 domain of Fyn; Kunits domain of protease inhibitors; monobodies; the 10$^{th}$ type III domain of fibronectin; adnectins; knottins (cysteine knot miniproteins); fynomers; atrimers; evibodies; CTLA4-based binders; affibodies; three-helix bundle from Z-domain of protein A from *Staphylococcus aurus*; Trans-bodies; human transferrin; tetranectins; monomeric or trimeric human C-type lectin domain; microbodies; trypsin-inhibitor-II; or armadillo repeat proteins.

20. The polypeptide according to claim 17, wherein the at least three THDs are linked to component D by a peptide $X_d$.

21. The polypeptide according to claim 17, wherein the non-polar/hydrophobic or polar/neutral amino acid of $X_1$ is selected from the group consisting of F, V, Q, A, I, L, and Y.

22. The polypeptide according to claim 20, wherein the peptide $X_d$,
(i) has a length of 5 to 15 amino acids;
(ii) comprises at least one glycosylation motif; or
(iii) is selected from the group consisting of SEQ ID NO: 192, SEQ ID NO: 193 and SEQ ID NO: 194.

23. The polypeptide according to claim 12, wherein
(i) $X_e$ is selected from L, L-V, L-V-G, L-V-G-G (SEQ ID NO: 159), L-V-S, L-V-S-G (SEQ ID NO: 161), A, A-V, A-V-S, A-V-G, A-V-G-G (SEQ ID NO: 162), A-V-S-G (SEQ ID NO: 163), I-V, I-V-S, I-V-G, I-V-G-G (SEQ ID NO: 164), and I-V-S-G (SEQ ID NO: 165); $X_f$ is absent or selected from G, S, G-G, S-G, G-S, and S-S; and $X_g$ is absent or selected from R, Q-R, P-Q-R, and G-P-Q-R (SEQ ID NO: 166);
(ii) $X_e$ is selected from K, and K-L; $X_f$ is absent or selected from G, S, G-G, S-G, G-S, and S-S; and $X_g$ is absent or selected from R, and L-R;
(iii) $X_e$ is selected from M, M-V; $X_f$ is absent or selected from G, S, G-G, S-G, G-S, and S-S; and $X_g$ is absent or selected from N and V-N;
(iv) $X_e$ is selected from A, and A-L; $X_f$ is absent or selected from G, S, G-G, S-G, G-S, and S-S; and $X_g$ is absent or selected from K and L-K;
(v) $X_e$ is selected from M, M-V, and M-V-G; $X_f$ is absent or selected from G, S, G-G, S-G, G-S, and S-S; and $X_g$ is absent or selected from L, and G-L;
(vi) $X_e$ is selected from A, and A-L; $X_f$ is absent or selected from G, S, G-G, S-G, G-S, and S-S; and $X_g$ is absent or selected from K, and D-K;
(vii) $X_e$ is selected from K, and K-L; $X_f$ is absent or selected from G, S, G-G, S-G, G-S, and S-S; and $X_g$ is absent or selected from Q, and P-Q;

(viii) $X_e$ is selected from Q, Q-V, and Q-V-H; $X_f$ is absent or selected from G, S, G-G, S-G, G-S, and S-S; and $X_g$ is absent or selected from A, and R-A;

(ix) $X_e$ is selected from W, W-V, W-V-R, and W-V-R-P (SEQ ID NO: 167); $X_f$ is absent or selected from G, S, G-G, S-G, G-S, and S-S; and $X_g$ is absent or selected from W, and G-W; or (x) $X_e$ is selected from K, K-L, and K-L-L; $X_f$ is absent or selected from G, S, G-G, S-G, G-S, and S-S; and $X_g$ is absent or selected from Q, and T-Q; or the peptide $X_c$ is selected from the group consisting of I-V-S-G (SEQ ID NO: 165), A-V-S-G (SEQ ID NO: 163), I-V-G-G (SEQ ID NO: 164), A-V-G-G (SEQ ID NO: 162), L-V-S-G (SEQ ID NO: 161), L-V-G-G (SEQ ID NO: 159), L-V-G-G-R (SEQ ID NO: 168), L-V-G-G-G (SEQ ID NO: 169), L-V-G-G-P (SEQ ID NO: 170) or $X_a$ is selected from the group consisting of L-V-G-G-P-Q-R (SEQ ID NO: 173), L-V-G-G-G-P-Q-R (SEQ ID NO: 174), and L-V-G-G-G-G-P-Q-R (SEQ ID NO: 75).

* * * * *

```
                         SEQUENCE LISTING

<160> NUMBER OF SEQ ID NOS: 275

<210> SEQ ID NO 1
<211> LENGTH: 6
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: can be S, T, or V
<220> FEATURE:
<221> NAME/KEY: MISC_FEATURE
<222> LOCATION: (2)..(2)
<223> OTHER INFORMATION: can be F, Y, or S
<220> FEATURE:
<221> NAME/KEY: MISC_FEATURE
<222> LOCATION: (5)..(5)
<223> OTHER INFORMATION: can be A, L, V or I
<220> FEATURE:
<221> NAME/KEY: MISC_FEATURE
<222> LOCATION: (6)..(6)
<223> OTHER INFORMATION: is a polar or non-polar amino acid

<400> SEQUENCE: 1

Xaa Xaa Phe Gly Xaa Xaa
1               5

<210> SEQ ID NO 2
<211> LENGTH: 5
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: can be P, K, V, I, or A
<220> FEATURE:
<221> NAME/KEY: MISC_FEATURE
<222> LOCATION: (2)..(2)
<223> OTHER INFORMATION: can be V, A, or F
<220> FEATURE:
<221> NAME/KEY: MISC_FEATURE
<222> LOCATION: (5)..(5)
<223> OTHER INFORMATION: can be V, L, I, Y
<220> FEATURE:
<221> NAME/KEY: MISC_FEATURE
<222> LOCATION: (5)..(5)
<223> OTHER INFORMATION: can be V, L, I, or Y

<400> SEQUENCE: 2

Xaa Xaa Ala His Xaa
1               5
```

-continued

<210> SEQ ID NO 3
<211> LENGTH: 5
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: can be D, S, M, or I
<220> FEATURE:
<221> NAME/KEY: MISC_FEATURE
<222> LOCATION: (2)..(2)
<223> OTHER INFORMATION: can be V, W, F or C
<220> FEATURE:
<221> NAME/KEY: MISC_FEATURE
<222> LOCATION: (3)..(3)
<223> OTHER INFORMATION: can be A or L
<220> FEATURE:
<221> NAME/KEY: MISC_FEATURE
<222> LOCATION: (4)..(4)
<223> OTHER INFORMATION: can be E, Y, Q, or H

<400> SEQUENCE: 3

Xaa Xaa Xaa Xaa Leu
1               5

<210> SEQ ID NO 4
<211> LENGTH: 108
<212> TYPE: PRT
<213> ORGANISM: Homo sapiens

<400> SEQUENCE: 4

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Ser Ile Gly Thr Asn
            20                  25                  30

Ile His Trp Tyr Gln Gln Lys Pro Gly Lys Ala Pro Lys Leu Leu Ile
        35                  40                  45

Lys Tyr Ala Ser Glu Ser Ile Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Asn Asn Asn Trp Pro Thr
                85                  90                  95

Thr Phe Gly Ala Gly Thr Lys Leu Glu Ile Lys Arg
            100                 105

<210> SEQ ID NO 5
<211> LENGTH: 281
<212> TYPE: PRT
<213> ORGANISM: Homo sapiens

<400> SEQUENCE: 5

Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Met Gln Asp Lys
        35                  40                  45

Tyr Ser Lys Ser Gly Ile Ala Cys Phe Leu Lys Glu Asp Asp Ser Tyr
    50                  55                  60

Trp Asp Pro Asn Asp Glu Glu Ser Met Asn Ser Pro Cys Trp Gln Val
65                  70                  75                  80

```
Lys Trp Gln Leu Arg Gln Leu Val Arg Lys Met Ile Leu Arg Thr Ser
                85                  90                  95

Glu Glu Thr Ile Ser Thr Val Gln Glu Lys Gln Gln Asn Ile Ser Pro
            100                 105                 110

Leu Val Arg Glu Arg Gly Pro Gln Arg Val Ala Ala His Ile Thr Gly
        115                 120                 125

Thr Arg Gly Arg Ser Asn Thr Leu Ser Ser Pro Asn Ser Lys Asn Glu
130                 135                 140

Lys Ala Leu Gly Arg Lys Ile Asn Ser Trp Glu Ser Ser Arg Ser Gly
145                 150                 155                 160

His Ser Phe Leu Ser Asn Leu His Leu Arg Asn Gly Glu Leu Val Ile
                165                 170                 175

His Glu Lys Gly Phe Tyr Tyr Ile Tyr Ser Gln Thr Tyr Phe Arg Phe
            180                 185                 190

Gln Glu Glu Ile Lys Glu Asn Thr Lys Asn Asp Lys Gln Met Val Gln
        195                 200                 205

Tyr Ile Tyr Lys Tyr Thr Ser Tyr Pro Asp Pro Ile Leu Leu Met Lys
210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
                245                 250                 255

Phe Val Ser Val Thr Asn Glu His Leu Ile Asp Met Asp His Glu Ala
            260                 265                 270

Ser Phe Phe Gly Ala Phe Leu Val Gly
        275                 280

<210> SEQ ID NO 6
<211> LENGTH: 6
<212> TYPE: PRT
<213> ORGANISM: Homo sapiens

<400> SEQUENCE: 6

Ser Phe Phe Gly Ala Phe
1               5

<210> SEQ ID NO 7
<211> LENGTH: 281
<212> TYPE: PRT
<213> ORGANISM: Homo sapiens

<400> SEQUENCE: 7

Met Gln Gln Pro Phe Asn Tyr Pro Tyr Pro Gln Ile Tyr Trp Val Asp
1               5                   10                  15

Ser Ser Ala Ser Ser Pro Trp Ala Pro Pro Gly Thr Val Leu Pro Cys
            20                  25                  30

Pro Thr Ser Val Pro Arg Arg Pro Gly Gln Arg Arg Pro Pro Pro Pro
        35                  40                  45

Pro Pro Pro Pro Pro Leu Pro Pro Pro Pro Pro Pro Pro Pro Leu Pro
50                  55                  60

Pro Leu Pro Leu Pro Pro Leu Lys Lys Arg Gly Asn His Ser Thr Gly
65                  70                  75                  80

Leu Cys Leu Leu Val Met Phe Phe Met Val Leu Val Ala Leu Val Gly
                85                  90                  95

Leu Gly Leu Gly Met Phe Gln Leu Phe His Leu Gln Lys Glu Leu Ala
            100                 105                 110
```

```
Glu Leu Arg Glu Ser Thr Ser Gln Met His Thr Ala Ser Ser Leu Glu
            115                 120                 125

Lys Gln Ile Gly His Pro Ser Pro Pro Glu Lys Lys Glu Leu Arg
    130                 135                 140

Lys Val Ala His Leu Thr Gly Lys Ser Asn Ser Arg Ser Met Pro Leu
145                 150                 155                 160

Glu Trp Glu Asp Thr Tyr Gly Ile Val Leu Leu Ser Gly Val Lys Tyr
                165                 170                 175

Lys Lys Gly Gly Leu Val Ile Asn Glu Thr Gly Leu Tyr Phe Val Tyr
            180                 185                 190

Ser Lys Val Tyr Phe Arg Gly Gln Ser Cys Asn Asn Leu Pro Leu Ser
            195                 200                 205

His Lys Val Tyr Met Arg Asn Ser Lys Tyr Pro Gln Asp Leu Val Met
    210                 215                 220

Met Glu Gly Lys Met Met Ser Tyr Cys Thr Thr Gly Gln Met Trp Ala
225                 230                 235                 240

Arg Ser Ser Tyr Leu Gly Ala Val Phe Asn Leu Thr Ser Ala Asp His
                245                 250                 255

Leu Tyr Val Asn Val Ser Glu Leu Ser Leu Val Asn Phe Glu Glu Ser
            260                 265                 270

Gln Thr Phe Phe Gly Leu Tyr Lys Leu
            275                 280

<210> SEQ ID NO 8
<211> LENGTH: 240
<212> TYPE: PRT
<213> ORGANISM: Homo sapiens

<400> SEQUENCE: 8

Met Glu Glu Ser Val Val Arg Pro Ser Val Phe Val Val Asp Gly Gln
1               5                   10                  15

Thr Asp Ile Pro Phe Thr Arg Leu Gly Arg Ser His Arg Arg Gln Ser
            20                  25                  30

Cys Ser Val Ala Arg Val Gly Leu Gly Leu Leu Leu Leu Leu Met Gly
        35                  40                  45

Ala Gly Leu Ala Val Gln Gly Trp Phe Leu Leu Gln Leu His Trp Arg
    50                  55                  60

Leu Gly Glu Met Val Thr Arg Leu Pro Asp Gly Pro Ala Gly Ser Trp
65                  70                  75                  80

Glu Gln Leu Ile Gln Glu Arg Arg Ser His Glu Val Asn Pro Ala Ala
                85                  90                  95

His Leu Thr Gly Ala Asn Ser Ser Leu Thr Gly Ser Gly Gly Pro Leu
            100                 105                 110

Leu Trp Glu Thr Gln Leu Gly Leu Ala Phe Leu Arg Gly Leu Ser Tyr
            115                 120                 125

His Asp Gly Ala Leu Val Val Thr Lys Ala Gly Tyr Tyr Tyr Ile Tyr
    130                 135                 140

Ser Lys Val Gln Leu Gly Gly Val Gly Cys Pro Leu Gly Leu Ala Ser
145                 150                 155                 160

Thr Ile Thr His Gly Leu Tyr Lys Arg Thr Pro Arg Tyr Pro Glu Glu
                165                 170                 175

Leu Glu Leu Leu Val Ser Gln Gln Ser Pro Cys Gly Arg Ala Thr Ser
            180                 185                 190

Ser Ser Arg Val Trp Trp Asp Ser Ser Phe Leu Gly Gly Val Val His
```

```
                195                 200                 205
Leu Glu Ala Gly Glu Lys Val Val Arg Val Leu Asp Glu Arg Leu
            210                 215                 220
Val Arg Leu Arg Asp Gly Thr Arg Ser Tyr Phe Gly Ala Phe Met Val
225                 230                 235                 240
```

<210> SEQ ID NO 9
<211> LENGTH: 205
<212> TYPE: PRT
<213> ORGANISM: Homo sapiens

<400> SEQUENCE: 9

```
Met Thr Pro Pro Glu Arg Leu Phe Leu Pro Arg Val Arg Gly Thr Thr
1               5                   10                  15
Leu His Leu Leu Leu Leu Gly Leu Leu Leu Val Leu Leu Pro Gly Ala
                20                  25                  30
Gln Gly Leu Pro Gly Val Gly Leu Thr Pro Ser Ala Ala Gln Thr Ala
            35                  40                  45
Arg Gln His Pro Lys Met His Leu Ala His Ser Thr Leu Lys Pro Ala
        50                  55                  60
Ala His Leu Ile Gly Asp Pro Ser Lys Gln Asn Ser Leu Leu Trp Arg
65                  70                  75                  80
Ala Asn Thr Asp Arg Ala Phe Leu Gln Asp Gly Phe Ser Leu Ser Asn
                85                  90                  95
Asn Ser Leu Leu Val Pro Thr Ser Gly Ile Tyr Phe Val Tyr Ser Gln
            100                 105                 110
Val Val Phe Ser Gly Lys Ala Tyr Ser Pro Lys Ala Thr Ser Ser Pro
        115                 120                 125
Leu Tyr Leu Ala His Glu Val Gln Leu Phe Ser Ser Gln Tyr Pro Phe
130                 135                 140
His Val Pro Leu Leu Ser Ser Gln Lys Met Val Tyr Pro Gly Leu Gln
145                 150                 155                 160
Glu Pro Trp Leu His Ser Met Tyr His Gly Ala Ala Phe Gln Leu Thr
                165                 170                 175
Gln Gly Asp Gln Leu Ser Thr His Thr Asp Gly Ile Pro His Leu Val
            180                 185                 190
Leu Ser Pro Ser Thr Val Phe Phe Gly Ala Phe Ala Leu
        195                 200                 205
```

<210> SEQ ID NO 10
<211> LENGTH: 244
<212> TYPE: PRT
<213> ORGANISM: Homo sapiens

<400> SEQUENCE: 10

```
Met Gly Ala Leu Gly Leu Glu Gly Arg Gly Gly Arg Leu Gln Gly Arg
1               5                   10                  15
Gly Ser Leu Leu Leu Ala Val Ala Gly Ala Thr Ser Leu Val Thr Leu
                20                  25                  30
Leu Leu Ala Val Pro Ile Thr Val Leu Ala Val Leu Ala Leu Val Pro
            35                  40                  45
Gln Asp Gln Gly Gly Leu Val Thr Glu Thr Ala Asp Pro Gly Ala Gln
        50                  55                  60
Ala Gln Gln Gly Leu Gly Phe Gln Lys Leu Pro Glu Glu Glu Pro Glu
65                  70                  75                  80
Thr Asp Leu Ser Pro Gly Leu Pro Ala Ala His Leu Ile Gly Ala Pro
```

```
                85                  90                  95
Leu Lys Gly Gln Gly Leu Gly Trp Glu Thr Thr Lys Glu Gln Ala Phe
                100                 105                 110
Leu Thr Ser Gly Thr Gln Phe Ser Asp Ala Glu Gly Leu Ala Leu Pro
                115                 120                 125
Gln Asp Gly Leu Tyr Tyr Leu Tyr Cys Leu Val Gly Tyr Arg Gly Arg
            130                 135                 140
Ala Pro Pro Gly Gly Gly Asp Pro Gln Gly Arg Ser Val Thr Leu Arg
145                 150                 155                 160
Ser Ser Leu Tyr Arg Ala Gly Gly Ala Tyr Gly Pro Gly Thr Pro Glu
                165                 170                 175
Leu Leu Leu Glu Gly Ala Glu Thr Val Thr Pro Val Leu Asp Pro Ala
                180                 185                 190
Arg Arg Gln Gly Tyr Gly Pro Leu Trp Tyr Thr Ser Val Gly Phe Gly
            195                 200                 205
Gly Leu Val Gln Leu Arg Arg Gly Glu Arg Val Tyr Val Asn Ile Ser
        210                 215                 220
His Pro Asp Met Val Asp Phe Ala Arg Gly Lys Thr Phe Phe Gly Ala
225                 230                 235                 240
Val Met Val Gly

<210> SEQ ID NO 11
<211> LENGTH: 233
<212> TYPE: PRT
<213> ORGANISM: Homo sapiens

<400> SEQUENCE: 11

Met Ser Thr Glu Ser Met Ile Arg Asp Val Glu Leu Ala Glu Glu Ala
1               5                   10                  15
Leu Pro Lys Lys Thr Gly Gly Pro Gln Gly Ser Arg Arg Cys Leu Phe
                20                  25                  30
Leu Ser Leu Phe Ser Phe Leu Ile Val Ala Gly Ala Thr Thr Leu Phe
            35                  40                  45
Cys Leu Leu His Phe Gly Val Ile Gly Pro Gln Arg Glu Glu Phe Pro
        50                  55                  60
Arg Asp Leu Ser Leu Ile Ser Pro Leu Ala Gln Ala Val Arg Ser Ser
65                  70                  75                  80
Ser Arg Thr Pro Ser Asp Lys Pro Val Ala His Val Val Ala Asn Pro
                85                  90                  95
Gln Ala Glu Gly Gln Leu Gln Trp Leu Asn Arg Arg Ala Asn Ala Leu
                100                 105                 110
Leu Ala Asn Gly Val Glu Leu Arg Asp Asn Gln Leu Val Val Pro Ser
            115                 120                 125
Glu Gly Leu Tyr Leu Ile Tyr Ser Gln Val Leu Phe Lys Gly Gln Gly
        130                 135                 140
Cys Pro Ser Thr His Val Leu Leu Thr His Thr Ile Ser Arg Ile Ala
145                 150                 155                 160
Val Ser Tyr Gln Thr Lys Val Asn Leu Leu Ser Ala Ile Lys Ser Pro
                165                 170                 175
Cys Gln Arg Glu Thr Pro Glu Gly Ala Glu Ala Lys Pro Trp Tyr Glu
                180                 185                 190
Pro Ile Tyr Leu Gly Gly Val Phe Gln Leu Glu Lys Gly Asp Arg Leu
            195                 200                 205
Ser Ala Glu Ile Asn Arg Pro Asp Tyr Leu Asp Phe Ala Glu Ser Gly
```

Gln Val Tyr Phe Gly Ile Ile Ala Leu
225                 230

<210> SEQ ID NO 12
<211> LENGTH: 261
<212> TYPE: PRT
<213> ORGANISM: Homo sapiens

<400> SEQUENCE: 12

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Glu Asn Ser Phe Glu
            100                 105                 110

Met Gln Lys Gly Asp Gln Asn Pro Gln Ile Ala Ala His Val Ile Ser
        115                 120                 125

Glu Ala Ser Ser Lys Thr Thr Ser Val Leu Gln Trp Ala Glu Lys Gly
130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
            180                 185                 190

Leu Cys Leu Lys Ser Pro Gly Arg Phe Glu Arg Ile Leu Leu Arg Ala
        195                 200                 205

Ala Asn Thr His Ser Ser Ala Lys Pro Cys Gly Gln Gln Ser Ile His
    210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
            260

<210> SEQ ID NO 13
<211> LENGTH: 249
<212> TYPE: PRT
<213> ORGANISM: Homo sapiens

<400> SEQUENCE: 13

Met Ala Ala Arg Arg Ser Gln Arg Arg Arg Gly Arg Arg Gly Glu Pro
1               5                   10                  15

Gly Thr Ala Leu Leu Val Pro Leu Ala Leu Gly Leu Gly Leu Ala Leu
            20                  25                  30

Ala Cys Leu Gly Leu Leu Leu Ala Val Val Ser Leu Gly Ser Arg Ala

-continued

```
                    35                  40                  45
Ser Leu Ser Ala Gln Glu Pro Ala Gln Glu Leu Val Ala Glu
 50                  55                  60

Asp Gln Asp Pro Ser Glu Leu Asn Pro Gln Thr Glu Ser Gln Asp
 65                  70                  75                  80

Pro Ala Pro Phe Leu Asn Arg Leu Val Arg Pro Arg Ser Ala Pro
                     85                  90                  95

Lys Gly Arg Lys Thr Arg Ala Arg Ala Ile Ala Ala His Tyr Glu
                100                 105                 110

Val His Pro Arg Pro Gly Gln Asp Gly Ala Gln Ala Gly Val Asp Gly
             115                 120                 125

Thr Val Ser Gly Trp Glu Glu Ala Arg Ile Asn Ser Ser Pro Leu
130                 135                 140

Arg Tyr Asn Arg Gln Ile Gly Glu Phe Ile Val Thr Arg Ala Gly Leu
145                 150                 155                 160

Tyr Tyr Leu Tyr Cys Gln Val His Phe Asp Glu Gly Lys Ala Val Tyr
                    165                 170                 175

Leu Lys Leu Asp Leu Leu Val Asp Gly Val Leu Ala Leu Arg Cys Leu
                180                 185                 190

Glu Glu Phe Ser Ala Thr Ala Ala Ser Ser Leu Gly Pro Gln Leu Arg
                195                 200                 205

Leu Cys Gln Val Ser Gly Leu Leu Ala Leu Arg Pro Gly Ser Ser Leu
210                 215                 220

Arg Ile Arg Thr Leu Pro Trp Ala His Leu Lys Ala Ala Pro Phe Leu
225                 230                 235                 240

Thr Tyr Phe Gly Leu Phe Gln Val His
                    245

<210> SEQ ID NO 14
<211> LENGTH: 193
<212> TYPE: PRT
<213> ORGANISM: Homo sapiens

<400> SEQUENCE: 14

Met Pro Glu Glu Gly Ser Gly Cys Ser Val Arg Arg Arg Pro Tyr Gly
 1               5                  10                  15

Cys Val Leu Arg Ala Ala Leu Val Pro Leu Val Ala Gly Leu Val Ile
                20                  25                  30

Cys Leu Val Val Cys Ile Gln Arg Phe Ala Gln Ala Gln Gln Gln Leu
                 35                  40                  45

Pro Leu Glu Ser Leu Gly Trp Asp Val Ala Glu Leu Gln Leu Asn His
 50                  55                  60

Thr Gly Pro Gln Gln Asp Pro Arg Leu Tyr Trp Gln Gly Gly Pro Ala
 65                  70                  75                  80

Leu Gly Arg Ser Phe Leu His Gly Pro Glu Leu Asp Lys Gly Gln Leu
                     85                  90                  95

Arg Ile His Arg Asp Gly Ile Tyr Met Val His Ile Gln Val Thr Leu
                100                 105                 110

Ala Ile Cys Ser Ser Thr Thr Ala Ser Arg His His Pro Thr Thr Leu
                115                 120                 125

Ala Val Gly Ile Cys Ser Pro Ala Ser Arg Ser Ile Ser Leu Leu Arg
                130                 135                 140

Leu Ser Phe His Gln Gly Cys Thr Ile Ala Ser Gln Arg Leu Thr Pro
145                 150                 155                 160
```

Leu Ala Arg Gly Asp Thr Leu Cys Thr Asn Leu Thr Gly Thr Leu Leu
                165                 170                 175

Pro Ser Arg Asn Thr Asp Glu Thr Phe Phe Gly Val Gln Trp Val Arg
            180                 185                 190

Pro

<210> SEQ ID NO 15
<211> LENGTH: 285
<212> TYPE: PRT
<213> ORGANISM: Homo sapiens

<400> SEQUENCE: 15

Met Asp Asp Ser Thr Glu Arg Glu Gln Ser Arg Leu Thr Ser Cys Leu
1               5                   10                  15

Lys Lys Arg Glu Glu Met Lys Leu Lys Glu Cys Val Ser Ile Leu Pro
            20                  25                  30

Arg Lys Glu Ser Pro Ser Val Arg Ser Ser Lys Asp Gly Lys Leu Leu
        35                  40                  45

Ala Ala Thr Leu Leu Leu Ala Leu Leu Ser Cys Cys Leu Thr Val Val
    50                  55                  60

Ser Phe Tyr Gln Val Ala Ala Leu Gln Gly Asp Leu Ala Ser Leu Arg
65                  70                  75                  80

Ala Glu Leu Gln Gly His His Ala Glu Lys Leu Pro Ala Gly Ala Gly
                85                  90                  95

Ala Pro Lys Ala Gly Leu Glu Glu Ala Pro Ala Val Thr Ala Gly Leu
            100                 105                 110

Lys Ile Phe Glu Pro Pro Ala Pro Gly Glu Gly Asn Ser Ser Gln Asn
        115                 120                 125

Ser Arg Asn Lys Arg Ala Val Gln Gly Pro Glu Glu Thr Val Thr Gln
    130                 135                 140

Asp Cys Leu Gln Leu Ile Ala Asp Ser Glu Thr Pro Thr Ile Gln Lys
145                 150                 155                 160

Gly Ser Tyr Thr Phe Val Pro Trp Leu Leu Ser Phe Lys Arg Gly Ser
                165                 170                 175

Ala Leu Glu Glu Lys Glu Asn Lys Ile Leu Val Lys Glu Thr Gly Tyr
            180                 185                 190

Phe Phe Ile Tyr Gly Gln Val Leu Tyr Thr Asp Lys Thr Tyr Ala Met
        195                 200                 205

Gly His Leu Ile Gln Arg Lys Lys Val His Val Phe Gly Asp Glu Leu
    210                 215                 220

Ser Leu Val Thr Leu Phe Arg Cys Ile Gln Asn Met Pro Glu Thr Leu
225                 230                 235                 240

Pro Asn Asn Ser Cys Tyr Ser Ala Gly Ile Ala Lys Leu Glu Glu Gly
                245                 250                 255

Asp Glu Leu Gln Leu Ala Ile Pro Arg Glu Asn Ala Gln Ile Ser Leu
            260                 265                 270

Asp Gly Asp Val Thr Phe Phe Gly Ala Leu Lys Leu Leu
        275                 280                 285

<210> SEQ ID NO 16
<211> LENGTH: 6
<212> TYPE: PRT
<213> ORGANISM: Homo sapiens

<400> SEQUENCE: 16

Thr Phe Phe Gly Leu Tyr

```
<210> SEQ ID NO 17
<211> LENGTH: 6
<212> TYPE: PRT
<213> ORGANISM: Homo sapiens

<400> SEQUENCE: 17

Ser Tyr Phe Gly Ala Phe
1               5

<210> SEQ ID NO 18
<211> LENGTH: 6
<212> TYPE: PRT
<213> ORGANISM: Homo sapiens

<400> SEQUENCE: 18

Val Phe Phe Gly Ala Phe
1               5

<210> SEQ ID NO 19
<211> LENGTH: 6
<212> TYPE: PRT
<213> ORGANISM: Homo sapiens

<400> SEQUENCE: 19

Thr Phe Phe Gly Ala Phe
1               5

<210> SEQ ID NO 20
<211> LENGTH: 6
<212> TYPE: PRT
<213> ORGANISM: Homo sapiens

<400> SEQUENCE: 20

Val Tyr Phe Gly Ile Ile
1               5

<210> SEQ ID NO 21
<211> LENGTH: 6
<212> TYPE: PRT
<213> ORGANISM: Homo sapiens

<400> SEQUENCE: 21

Thr Ser Phe Gly Leu Leu
1               5

<210> SEQ ID NO 22
<211> LENGTH: 6
<212> TYPE: PRT
<213> ORGANISM: Homo sapiens

<400> SEQUENCE: 22

Thr Tyr Phe Gly Leu Phe
1               5

<210> SEQ ID NO 23
<211> LENGTH: 6
<212> TYPE: PRT
<213> ORGANISM: Homo sapiens

<400> SEQUENCE: 23

Thr Phe Phe Gly Val Gln
1               5
```

```
<210> SEQ ID NO 24
<211> LENGTH: 6
<212> TYPE: PRT
<213> ORGANISM: Homo sapiens

<400> SEQUENCE: 24

Thr Phe Phe Gly Ala Leu
1               5

<210> SEQ ID NO 25
<211> LENGTH: 5
<212> TYPE: PRT
<213> ORGANISM: Homo sapiens

<400> SEQUENCE: 25

Val Ala Ala His Ile
1               5

<210> SEQ ID NO 26
<211> LENGTH: 5
<212> TYPE: PRT
<213> ORGANISM: Homo sapiens

<400> SEQUENCE: 26

Lys Val Ala His Leu
1               5

<210> SEQ ID NO 27
<211> LENGTH: 5
<212> TYPE: PRT
<213> ORGANISM: Homo sapiens

<400> SEQUENCE: 27

Pro Ala Ala His Leu
1               5

<210> SEQ ID NO 28
<211> LENGTH: 5
<212> TYPE: PRT
<213> ORGANISM: Homo sapiens

<400> SEQUENCE: 28

Pro Val Ala His Val
1               5

<210> SEQ ID NO 29
<211> LENGTH: 5
<212> TYPE: PRT
<213> ORGANISM: Homo sapiens

<400> SEQUENCE: 29

Ile Ala Ala His Val
1               5

<210> SEQ ID NO 30
<211> LENGTH: 5
<212> TYPE: PRT
<213> ORGANISM: Homo sapiens

<400> SEQUENCE: 30

Ile Ala Ala His Tyr
1               5

<210> SEQ ID NO 31
```

```
<211> LENGTH: 5
<212> TYPE: PRT
<213> ORGANISM: Homo sapiens

<400> SEQUENCE: 31

Asp Val Ala Glu Leu
1               5

<210> SEQ ID NO 32
<211> LENGTH: 5
<212> TYPE: PRT
<213> ORGANISM: Homo sapiens

<400> SEQUENCE: 32

Asp Trp Ala Glu Leu
1               5

<210> SEQ ID NO 33
<211> LENGTH: 5
<212> TYPE: PRT
<213> ORGANISM: Homo sapiens

<400> SEQUENCE: 33

Asp Phe Ala Glu Leu
1               5

<210> SEQ ID NO 34
<211> LENGTH: 5
<212> TYPE: PRT
<213> ORGANISM: Homo sapiens

<400> SEQUENCE: 34

Asp Cys Ala Glu Leu
1               5

<210> SEQ ID NO 35
<211> LENGTH: 5
<212> TYPE: PRT
<213> ORGANISM: Homo sapiens

<400> SEQUENCE: 35

Asp Val Leu Glu Leu
1               5

<210> SEQ ID NO 36
<211> LENGTH: 5
<212> TYPE: PRT
<213> ORGANISM: Homo sapiens

<400> SEQUENCE: 36

Asp Val Ala Tyr Leu
1               5

<210> SEQ ID NO 37
<211> LENGTH: 5
<212> TYPE: PRT
<213> ORGANISM: Homo sapiens

<400> SEQUENCE: 37

Asp Val Leu Tyr Leu
1               5

<210> SEQ ID NO 38
<211> LENGTH: 5
<212> TYPE: PRT
```

```
<213> ORGANISM: Homo sapiens

<400> SEQUENCE: 38

Asp Val Ala Gln Leu
1               5

<210> SEQ ID NO 39
<211> LENGTH: 5
<212> TYPE: PRT
<213> ORGANISM: Homo sapiens

<400> SEQUENCE: 39

Asp Val Leu Gln Leu
1               5

<210> SEQ ID NO 40
<211> LENGTH: 5
<212> TYPE: PRT
<213> ORGANISM: Homo sapiens

<400> SEQUENCE: 40

Asp Val Ala His Leu
1               5

<210> SEQ ID NO 41
<211> LENGTH: 5
<212> TYPE: PRT
<213> ORGANISM: Homo sapiens

<400> SEQUENCE: 41

Asp Val Leu His Leu
1               5

<210> SEQ ID NO 42
<211> LENGTH: 5
<212> TYPE: PRT
<213> ORGANISM: Homo sapiens

<400> SEQUENCE: 42

Asp Trp Leu Glu Leu
1               5

<210> SEQ ID NO 43
<211> LENGTH: 5
<212> TYPE: PRT
<213> ORGANISM: Homo sapiens

<400> SEQUENCE: 43

Asp Trp Ala Tyr Leu
1               5

<210> SEQ ID NO 44
<211> LENGTH: 5
<212> TYPE: PRT
<213> ORGANISM: Homo sapiens

<400> SEQUENCE: 44

Asp Trp Leu Tyr Leu
1               5

<210> SEQ ID NO 45
<211> LENGTH: 5
<212> TYPE: PRT
<213> ORGANISM: Homo sapiens
```

```
<400> SEQUENCE: 45

Asp Trp Ala Gln Leu
1               5

<210> SEQ ID NO 46
<211> LENGTH: 5
<212> TYPE: PRT
<213> ORGANISM: Homo sapiens

<400> SEQUENCE: 46

Asp Trp Leu Gln Leu
1               5

<210> SEQ ID NO 47
<211> LENGTH: 5
<212> TYPE: PRT
<213> ORGANISM: Homo sapiens

<400> SEQUENCE: 47

Asp Trp Ala His Leu
1               5

<210> SEQ ID NO 48
<211> LENGTH: 5
<212> TYPE: PRT
<213> ORGANISM: Homo sapiens

<400> SEQUENCE: 48

Asp Trp Leu His Leu
1               5

<210> SEQ ID NO 49
<211> LENGTH: 5
<212> TYPE: PRT
<213> ORGANISM: Homo sapiens

<400> SEQUENCE: 49

Asp Phe Leu Glu Leu
1               5

<210> SEQ ID NO 50
<211> LENGTH: 5
<212> TYPE: PRT
<213> ORGANISM: Homo sapiens

<400> SEQUENCE: 50

Asp Phe Ala Tyr Leu
1               5

<210> SEQ ID NO 51
<211> LENGTH: 5
<212> TYPE: PRT
<213> ORGANISM: Homo sapiens

<400> SEQUENCE: 51

Asp Phe Leu Tyr Leu
1               5

<210> SEQ ID NO 52
<211> LENGTH: 5
<212> TYPE: PRT
<213> ORGANISM: Homo sapiens

<400> SEQUENCE: 52
```

Asp Phe Ala Gln Leu
1               5

<210> SEQ ID NO 53
<211> LENGTH: 5
<212> TYPE: PRT
<213> ORGANISM: Homo sapiens

<400> SEQUENCE: 53

Asp Phe Leu Gln Leu
1               5

<210> SEQ ID NO 54
<211> LENGTH: 5
<212> TYPE: PRT
<213> ORGANISM: Homo sapiens

<400> SEQUENCE: 54

Asp Phe Ala His Leu
1               5

<210> SEQ ID NO 55
<211> LENGTH: 5
<212> TYPE: PRT
<213> ORGANISM: Homo sapiens

<400> SEQUENCE: 55

Asp Phe Leu His Leu
1               5

<210> SEQ ID NO 56
<211> LENGTH: 5
<212> TYPE: PRT
<213> ORGANISM: Homo sapiens

<400> SEQUENCE: 56

Asp Cys Leu Glu Leu
1               5

<210> SEQ ID NO 57
<211> LENGTH: 5
<212> TYPE: PRT
<213> ORGANISM: Homo sapiens

<400> SEQUENCE: 57

Asp Cys Ala Tyr Leu
1               5

<210> SEQ ID NO 58
<211> LENGTH: 5
<212> TYPE: PRT
<213> ORGANISM: Homo sapiens

<400> SEQUENCE: 58

Asp Cys Leu Tyr Leu
1               5

<210> SEQ ID NO 59
<211> LENGTH: 5
<212> TYPE: PRT
<213> ORGANISM: Homo sapiens

<400> SEQUENCE: 59

Asp Cys Ala Gln Leu
1               5

```
<210> SEQ ID NO 60
<211> LENGTH: 5
<212> TYPE: PRT
<213> ORGANISM: Homo sapiens

<400> SEQUENCE: 60

Asp Cys Leu Gln Leu
1               5

<210> SEQ ID NO 61
<211> LENGTH: 5
<212> TYPE: PRT
<213> ORGANISM: Homo sapiens

<400> SEQUENCE: 61

Asp Cys Ala His Leu
1               5

<210> SEQ ID NO 62
<211> LENGTH: 5
<212> TYPE: PRT
<213> ORGANISM: Homo sapiens

<400> SEQUENCE: 62

Asp Cys Leu His Leu
1               5

<210> SEQ ID NO 63
<211> LENGTH: 5
<212> TYPE: PRT
<213> ORGANISM: Homo sapiens

<400> SEQUENCE: 63

Ser Val Ala Glu Leu
1               5

<210> SEQ ID NO 64
<211> LENGTH: 5
<212> TYPE: PRT
<213> ORGANISM: Homo sapiens

<400> SEQUENCE: 64

Ser Trp Ala Glu Leu
1               5

<210> SEQ ID NO 65
<211> LENGTH: 5
<212> TYPE: PRT
<213> ORGANISM: Homo sapiens

<400> SEQUENCE: 65

Ser Phe Ala Glu Leu
1               5

<210> SEQ ID NO 66
<211> LENGTH: 5
<212> TYPE: PRT
<213> ORGANISM: Homo sapiens

<400> SEQUENCE: 66

Ser Cys Ala Glu Leu
1               5
```

```
<210> SEQ ID NO 67
<211> LENGTH: 5
<212> TYPE: PRT
<213> ORGANISM: Homo sapiens

<400> SEQUENCE: 67

Ser Val Leu Glu Leu
1               5

<210> SEQ ID NO 68
<211> LENGTH: 5
<212> TYPE: PRT
<213> ORGANISM: Homo sapiens

<400> SEQUENCE: 68

Ser Val Ala Tyr Leu
1               5

<210> SEQ ID NO 69
<211> LENGTH: 5
<212> TYPE: PRT
<213> ORGANISM: Homo sapiens

<400> SEQUENCE: 69

Ser Val Leu Tyr Leu
1               5

<210> SEQ ID NO 70
<211> LENGTH: 5
<212> TYPE: PRT
<213> ORGANISM: Homo sapiens

<400> SEQUENCE: 70

Ser Val Ala Gln Leu
1               5

<210> SEQ ID NO 71
<211> LENGTH: 5
<212> TYPE: PRT
<213> ORGANISM: Homo sapiens

<400> SEQUENCE: 71

Ser Val Leu Gln Leu
1               5

<210> SEQ ID NO 72
<211> LENGTH: 5
<212> TYPE: PRT
<213> ORGANISM: Homo sapiens

<400> SEQUENCE: 72

Ser Val Ala His Leu
1               5

<210> SEQ ID NO 73
<211> LENGTH: 5
<212> TYPE: PRT
<213> ORGANISM: Homo sapiens

<400> SEQUENCE: 73

Ser Val Leu His Leu
1               5

<210> SEQ ID NO 74
<211> LENGTH: 5
```

```
<212> TYPE: PRT
<213> ORGANISM: Homo sapiens

<400> SEQUENCE: 74

Ser Trp Leu Glu Leu
1               5

<210> SEQ ID NO 75
<211> LENGTH: 5
<212> TYPE: PRT
<213> ORGANISM: Homo sapiens

<400> SEQUENCE: 75

Ser Trp Ala Tyr Leu
1               5

<210> SEQ ID NO 76
<211> LENGTH: 5
<212> TYPE: PRT
<213> ORGANISM: Homo sapiens

<400> SEQUENCE: 76

Ser Trp Leu Tyr Leu
1               5

<210> SEQ ID NO 77
<211> LENGTH: 5
<212> TYPE: PRT
<213> ORGANISM: Homo sapiens

<400> SEQUENCE: 77

Ser Trp Ala Gln Leu
1               5

<210> SEQ ID NO 78
<211> LENGTH: 5
<212> TYPE: PRT
<213> ORGANISM: Homo sapiens

<400> SEQUENCE: 78

Ser Trp Leu Gln Leu
1               5

<210> SEQ ID NO 79
<211> LENGTH: 5
<212> TYPE: PRT
<213> ORGANISM: Homo sapiens

<400> SEQUENCE: 79

Ser Trp Ala His Leu
1               5

<210> SEQ ID NO 80
<211> LENGTH: 5
<212> TYPE: PRT
<213> ORGANISM: Homo sapiens

<400> SEQUENCE: 80

Ser Trp Leu His Leu
1               5

<210> SEQ ID NO 81
<211> LENGTH: 5
<212> TYPE: PRT
<213> ORGANISM: Homo sapiens
```

<400> SEQUENCE: 81

Ser Phe Leu Glu Leu
1               5

<210> SEQ ID NO 82
<211> LENGTH: 5
<212> TYPE: PRT
<213> ORGANISM: Homo sapiens

<400> SEQUENCE: 82

Ser Phe Ala Tyr Leu
1               5

<210> SEQ ID NO 83
<211> LENGTH: 5
<212> TYPE: PRT
<213> ORGANISM: Homo sapiens

<400> SEQUENCE: 83

Ser Phe Leu Tyr Leu
1               5

<210> SEQ ID NO 84
<211> LENGTH: 5
<212> TYPE: PRT
<213> ORGANISM: Homo sapiens

<400> SEQUENCE: 84

Ser Phe Ala Gln Leu
1               5

<210> SEQ ID NO 85
<211> LENGTH: 5
<212> TYPE: PRT
<213> ORGANISM: Homo sapiens

<400> SEQUENCE: 85

Ser Phe Leu Gln Leu
1               5

<210> SEQ ID NO 86
<211> LENGTH: 5
<212> TYPE: PRT
<213> ORGANISM: Homo sapiens

<400> SEQUENCE: 86

Ser Phe Ala His Leu
1               5

<210> SEQ ID NO 87
<211> LENGTH: 5
<212> TYPE: PRT
<213> ORGANISM: Homo sapiens

<400> SEQUENCE: 87

Ser Phe Leu His Leu
1               5

<210> SEQ ID NO 88
<211> LENGTH: 5
<212> TYPE: PRT
<213> ORGANISM: Homo sapiens

<400> SEQUENCE: 88

```
Ser Cys Leu Glu Leu
1               5

<210> SEQ ID NO 89
<211> LENGTH: 5
<212> TYPE: PRT
<213> ORGANISM: Homo sapiens

<400> SEQUENCE: 89

Ser Cys Ala Tyr Leu
1               5

<210> SEQ ID NO 90
<211> LENGTH: 5
<212> TYPE: PRT
<213> ORGANISM: Homo sapiens

<400> SEQUENCE: 90

Ser Cys Leu Tyr Leu
1               5

<210> SEQ ID NO 91
<211> LENGTH: 5
<212> TYPE: PRT
<213> ORGANISM: Homo sapiens

<400> SEQUENCE: 91

Ser Cys Ala Gln Leu
1               5

<210> SEQ ID NO 92
<211> LENGTH: 5
<212> TYPE: PRT
<213> ORGANISM: Homo sapiens

<400> SEQUENCE: 92

Ser Cys Leu Gln Leu
1               5

<210> SEQ ID NO 93
<211> LENGTH: 5
<212> TYPE: PRT
<213> ORGANISM: Homo sapiens

<400> SEQUENCE: 93

Ser Cys Ala His Leu
1               5

<210> SEQ ID NO 94
<211> LENGTH: 5
<212> TYPE: PRT
<213> ORGANISM: Homo sapiens

<400> SEQUENCE: 94

Ser Cys Leu His Leu
1               5

<210> SEQ ID NO 95
<211> LENGTH: 5
<212> TYPE: PRT
<213> ORGANISM: Homo sapiens

<400> SEQUENCE: 95

Met Val Ala Glu Leu
```

<210> SEQ ID NO 96
<211> LENGTH: 5
<212> TYPE: PRT
<213> ORGANISM: Homo sapiens

<400> SEQUENCE: 96

Met Trp Ala Glu Leu
1               5

<210> SEQ ID NO 97
<211> LENGTH: 5
<212> TYPE: PRT
<213> ORGANISM: Homo sapiens

<400> SEQUENCE: 97

Met Phe Ala Glu Leu
1               5

<210> SEQ ID NO 98
<211> LENGTH: 5
<212> TYPE: PRT
<213> ORGANISM: Homo sapiens

<400> SEQUENCE: 98

Met Cys Ala Glu Leu
1               5

<210> SEQ ID NO 99
<211> LENGTH: 5
<212> TYPE: PRT
<213> ORGANISM: Homo sapiens

<400> SEQUENCE: 99

Met Val Leu Glu Leu
1               5

<210> SEQ ID NO 100
<211> LENGTH: 5
<212> TYPE: PRT
<213> ORGANISM: Homo sapiens

<400> SEQUENCE: 100

Met Val Ala Tyr Leu
1               5

<210> SEQ ID NO 101
<211> LENGTH: 5
<212> TYPE: PRT
<213> ORGANISM: Homo sapiens

<400> SEQUENCE: 101

Met Val Leu Tyr Leu
1               5

<210> SEQ ID NO 102
<211> LENGTH: 5
<212> TYPE: PRT
<213> ORGANISM: Homo sapiens

<400> SEQUENCE: 102

Met Val Ala Gln Leu
1               5

```
<210> SEQ ID NO 103
<211> LENGTH: 5
<212> TYPE: PRT
<213> ORGANISM: Homo sapiens

<400> SEQUENCE: 103

Met Val Leu Gln Leu
1               5

<210> SEQ ID NO 104
<211> LENGTH: 5
<212> TYPE: PRT
<213> ORGANISM: Homo sapiens

<400> SEQUENCE: 104

Met Val Ala His Leu
1               5

<210> SEQ ID NO 105
<211> LENGTH: 5
<212> TYPE: PRT
<213> ORGANISM: Homo sapiens

<400> SEQUENCE: 105

Met Val Leu His Leu
1               5

<210> SEQ ID NO 106
<211> LENGTH: 5
<212> TYPE: PRT
<213> ORGANISM: Homo sapiens

<400> SEQUENCE: 106

Met Trp Leu Glu Leu
1               5

<210> SEQ ID NO 107
<211> LENGTH: 5
<212> TYPE: PRT
<213> ORGANISM: Homo sapiens

<400> SEQUENCE: 107

Met Trp Ala Tyr Leu
1               5

<210> SEQ ID NO 108
<211> LENGTH: 5
<212> TYPE: PRT
<213> ORGANISM: Homo sapiens

<400> SEQUENCE: 108

Met Trp Leu Tyr Leu
1               5

<210> SEQ ID NO 109
<211> LENGTH: 5
<212> TYPE: PRT
<213> ORGANISM: Homo sapiens

<400> SEQUENCE: 109

Met Trp Ala Gln Leu
1               5

<210> SEQ ID NO 110
```

```
<211> LENGTH: 5
<212> TYPE: PRT
<213> ORGANISM: Homo sapiens

<400> SEQUENCE: 110

Met Trp Leu Gln Leu
1               5

<210> SEQ ID NO 111
<211> LENGTH: 5
<212> TYPE: PRT
<213> ORGANISM: Homo sapiens

<400> SEQUENCE: 111

Met Trp Ala His Leu
1               5

<210> SEQ ID NO 112
<211> LENGTH: 5
<212> TYPE: PRT
<213> ORGANISM: Homo sapiens

<400> SEQUENCE: 112

Met Trp Leu His Leu
1               5

<210> SEQ ID NO 113
<211> LENGTH: 5
<212> TYPE: PRT
<213> ORGANISM: Homo sapiens

<400> SEQUENCE: 113

Met Phe Leu Glu Leu
1               5

<210> SEQ ID NO 114
<211> LENGTH: 5
<212> TYPE: PRT
<213> ORGANISM: Homo sapiens

<400> SEQUENCE: 114

Met Phe Ala Tyr Leu
1               5

<210> SEQ ID NO 115
<211> LENGTH: 5
<212> TYPE: PRT
<213> ORGANISM: Homo sapiens

<400> SEQUENCE: 115

Met Phe Leu Tyr Leu
1               5

<210> SEQ ID NO 116
<211> LENGTH: 5
<212> TYPE: PRT
<213> ORGANISM: Homo sapiens

<400> SEQUENCE: 116

Met Phe Ala Gln Leu
1               5

<210> SEQ ID NO 117
<211> LENGTH: 5
<212> TYPE: PRT
```

<213> ORGANISM: Homo sapiens

<400> SEQUENCE: 117

Met Phe Leu Gln Leu
1               5

<210> SEQ ID NO 118
<211> LENGTH: 5
<212> TYPE: PRT
<213> ORGANISM: Homo sapiens

<400> SEQUENCE: 118

Met Phe Ala His Leu
1               5

<210> SEQ ID NO 119
<211> LENGTH: 5
<212> TYPE: PRT
<213> ORGANISM: Homo sapiens

<400> SEQUENCE: 119

Met Phe Leu His Leu
1               5

<210> SEQ ID NO 120
<211> LENGTH: 5
<212> TYPE: PRT
<213> ORGANISM: Homo sapiens

<400> SEQUENCE: 120

Met Cys Leu Glu Leu
1               5

<210> SEQ ID NO 121
<211> LENGTH: 5
<212> TYPE: PRT
<213> ORGANISM: Homo sapiens

<400> SEQUENCE: 121

Met Cys Ala Tyr Leu
1               5

<210> SEQ ID NO 122
<211> LENGTH: 5
<212> TYPE: PRT
<213> ORGANISM: Homo sapiens

<400> SEQUENCE: 122

Met Cys Leu Tyr Leu
1               5

<210> SEQ ID NO 123
<211> LENGTH: 5
<212> TYPE: PRT
<213> ORGANISM: Homo sapiens

<400> SEQUENCE: 123

Met Cys Ala Gln Leu
1               5

<210> SEQ ID NO 124
<211> LENGTH: 5
<212> TYPE: PRT
<213> ORGANISM: Homo sapiens

```
<400> SEQUENCE: 124

Met Cys Leu Gln Leu
1               5

<210> SEQ ID NO 125
<211> LENGTH: 5
<212> TYPE: PRT
<213> ORGANISM: Homo sapiens

<400> SEQUENCE: 125

Met Cys Ala His Leu
1               5

<210> SEQ ID NO 126
<211> LENGTH: 5
<212> TYPE: PRT
<213> ORGANISM: Homo sapiens

<400> SEQUENCE: 126

Met Cys Leu His Leu
1               5

<210> SEQ ID NO 127
<211> LENGTH: 5
<212> TYPE: PRT
<213> ORGANISM: Homo sapiens

<400> SEQUENCE: 127

Ile Val Ala Glu Leu
1               5

<210> SEQ ID NO 128
<211> LENGTH: 5
<212> TYPE: PRT
<213> ORGANISM: Homo sapiens

<400> SEQUENCE: 128

Ile Trp Ala Glu Leu
1               5

<210> SEQ ID NO 129
<211> LENGTH: 5
<212> TYPE: PRT
<213> ORGANISM: Homo sapiens

<400> SEQUENCE: 129

Ile Phe Ala Glu Leu
1               5

<210> SEQ ID NO 130
<211> LENGTH: 5
<212> TYPE: PRT
<213> ORGANISM: Homo sapiens

<400> SEQUENCE: 130

Ile Cys Ala Glu Leu
1               5

<210> SEQ ID NO 131
<211> LENGTH: 5
<212> TYPE: PRT
<213> ORGANISM: Homo sapiens

<400> SEQUENCE: 131
```

```
Ile Val Leu Glu Leu
1               5

<210> SEQ ID NO 132
<211> LENGTH: 5
<212> TYPE: PRT
<213> ORGANISM: Homo sapiens

<400> SEQUENCE: 132

Ile Val Ala Tyr Leu
1               5

<210> SEQ ID NO 133
<211> LENGTH: 5
<212> TYPE: PRT
<213> ORGANISM: Homo sapiens

<400> SEQUENCE: 133

Ile Val Leu Tyr Leu
1               5

<210> SEQ ID NO 134
<211> LENGTH: 5
<212> TYPE: PRT
<213> ORGANISM: Homo sapiens

<400> SEQUENCE: 134

Ile Val Ala Gln Leu
1               5

<210> SEQ ID NO 135
<211> LENGTH: 5
<212> TYPE: PRT
<213> ORGANISM: Homo sapiens

<400> SEQUENCE: 135

Ile Val Leu Gln Leu
1               5

<210> SEQ ID NO 136
<211> LENGTH: 5
<212> TYPE: PRT
<213> ORGANISM: Homo sapiens

<400> SEQUENCE: 136

Ile Val Ala His Leu
1               5

<210> SEQ ID NO 137
<211> LENGTH: 5
<212> TYPE: PRT
<213> ORGANISM: Homo sapiens

<400> SEQUENCE: 137

Ile Val Leu His Leu
1               5

<210> SEQ ID NO 138
<211> LENGTH: 5
<212> TYPE: PRT
<213> ORGANISM: Homo sapiens

<400> SEQUENCE: 138

Ile Trp Leu Glu Leu
1               5
```

```
<210> SEQ ID NO 139
<211> LENGTH: 5
<212> TYPE: PRT
<213> ORGANISM: Homo sapiens

<400> SEQUENCE: 139

Ile Trp Ala Tyr Leu
1               5

<210> SEQ ID NO 140
<211> LENGTH: 5
<212> TYPE: PRT
<213> ORGANISM: Homo sapiens

<400> SEQUENCE: 140

Ile Trp Leu Tyr Leu
1               5

<210> SEQ ID NO 141
<211> LENGTH: 5
<212> TYPE: PRT
<213> ORGANISM: Homo sapiens

<400> SEQUENCE: 141

Ile Trp Ala Gln Leu
1               5

<210> SEQ ID NO 142
<211> LENGTH: 5
<212> TYPE: PRT
<213> ORGANISM: Homo sapiens

<400> SEQUENCE: 142

Ile Trp Leu Gln Leu
1               5

<210> SEQ ID NO 143
<211> LENGTH: 5
<212> TYPE: PRT
<213> ORGANISM: Homo sapiens

<400> SEQUENCE: 143

Ile Trp Ala His Leu
1               5

<210> SEQ ID NO 144
<211> LENGTH: 5
<212> TYPE: PRT
<213> ORGANISM: Homo sapiens

<400> SEQUENCE: 144

Ile Trp Leu His Leu
1               5

<210> SEQ ID NO 145
<211> LENGTH: 5
<212> TYPE: PRT
<213> ORGANISM: Homo sapiens

<400> SEQUENCE: 145

Ile Phe Leu Glu Leu
1               5
```

```
<210> SEQ ID NO 146
<211> LENGTH: 5
<212> TYPE: PRT
<213> ORGANISM: Homo sapiens

<400> SEQUENCE: 146

Ile Phe Ala Tyr Leu
1               5

<210> SEQ ID NO 147
<211> LENGTH: 5
<212> TYPE: PRT
<213> ORGANISM: Homo sapiens

<400> SEQUENCE: 147

Ile Phe Leu Tyr Leu
1               5

<210> SEQ ID NO 148
<211> LENGTH: 5
<212> TYPE: PRT
<213> ORGANISM: Homo sapiens

<400> SEQUENCE: 148

Ile Phe Ala Gln Leu
1               5

<210> SEQ ID NO 149
<211> LENGTH: 5
<212> TYPE: PRT
<213> ORGANISM: Homo sapiens

<400> SEQUENCE: 149

Ile Phe Leu Gln Leu
1               5

<210> SEQ ID NO 150
<211> LENGTH: 5
<212> TYPE: PRT
<213> ORGANISM: Homo sapiens

<400> SEQUENCE: 150

Ile Phe Ala His Leu
1               5

<210> SEQ ID NO 151
<211> LENGTH: 5
<212> TYPE: PRT
<213> ORGANISM: Homo sapiens

<400> SEQUENCE: 151

Ile Phe Leu His Leu
1               5

<210> SEQ ID NO 152
<211> LENGTH: 5
<212> TYPE: PRT
<213> ORGANISM: Homo sapiens

<400> SEQUENCE: 152

Ile Cys Leu Glu Leu
1               5

<210> SEQ ID NO 153
<211> LENGTH: 5
```

```
<212> TYPE: PRT
<213> ORGANISM: Homo sapiens

<400> SEQUENCE: 153

Ile Cys Ala Tyr Leu
1               5

<210> SEQ ID NO 154
<211> LENGTH: 5
<212> TYPE: PRT
<213> ORGANISM: Homo sapiens

<400> SEQUENCE: 154

Ile Cys Leu Tyr Leu
1               5

<210> SEQ ID NO 155
<211> LENGTH: 5
<212> TYPE: PRT
<213> ORGANISM: Homo sapiens

<400> SEQUENCE: 155

Ile Cys Ala Gln Leu
1               5

<210> SEQ ID NO 156
<211> LENGTH: 5
<212> TYPE: PRT
<213> ORGANISM: Homo sapiens

<400> SEQUENCE: 156

Ile Cys Leu Gln Leu
1               5

<210> SEQ ID NO 157
<211> LENGTH: 5
<212> TYPE: PRT
<213> ORGANISM: Homo sapiens

<400> SEQUENCE: 157

Ile Cys Ala His Leu
1               5

<210> SEQ ID NO 158
<211> LENGTH: 5
<212> TYPE: PRT
<213> ORGANISM: Homo sapiens

<400> SEQUENCE: 158

Ile Cys Leu His Leu
1               5

<210> SEQ ID NO 159
<211> LENGTH: 4
<212> TYPE: PRT
<213> ORGANISM: Homo sapiens

<400> SEQUENCE: 159

Leu Val Gly Gly
1

<210> SEQ ID NO 160
<211> LENGTH: 5
<212> TYPE: PRT
<213> ORGANISM: Homo sapiens
```

<400> SEQUENCE: 160

Leu Val Gly Gly Ile
1               5

<210> SEQ ID NO 161
<211> LENGTH: 4
<212> TYPE: PRT
<213> ORGANISM: Homo sapiens

<400> SEQUENCE: 161

Leu Val Ser Gly
1

<210> SEQ ID NO 162
<211> LENGTH: 4
<212> TYPE: PRT
<213> ORGANISM: Homo sapiens

<400> SEQUENCE: 162

Ala Val Gly Gly
1

<210> SEQ ID NO 163
<211> LENGTH: 4
<212> TYPE: PRT
<213> ORGANISM: Homo sapiens

<400> SEQUENCE: 163

Ala Val Ser Gly
1

<210> SEQ ID NO 164
<211> LENGTH: 4
<212> TYPE: PRT
<213> ORGANISM: Homo sapiens

<400> SEQUENCE: 164

Ile Val Gly Gly
1

<210> SEQ ID NO 165
<211> LENGTH: 4
<212> TYPE: PRT
<213> ORGANISM: Homo sapiens

<400> SEQUENCE: 165

Ile Val Ser Gly
1

<210> SEQ ID NO 166
<211> LENGTH: 4
<212> TYPE: PRT
<213> ORGANISM: Homo sapiens

<400> SEQUENCE: 166

Gly Pro Gln Arg
1

<210> SEQ ID NO 167
<211> LENGTH: 4
<212> TYPE: PRT
<213> ORGANISM: Homo sapiens

<400> SEQUENCE: 167

Trp Val Arg Pro
1

<210> SEQ ID NO 168
<211> LENGTH: 5
<212> TYPE: PRT
<213> ORGANISM: Homo sapiens

<400> SEQUENCE: 168

Leu Val Val Gly Arg
1               5

<210> SEQ ID NO 169
<211> LENGTH: 5
<212> TYPE: PRT
<213> ORGANISM: Homo sapiens

<400> SEQUENCE: 169

Leu Val Gly Gly Gly
1               5

<210> SEQ ID NO 170
<211> LENGTH: 5
<212> TYPE: PRT
<213> ORGANISM: Homo sapiens

<400> SEQUENCE: 170

Leu Val Gly Gly Pro
1               5

<210> SEQ ID NO 171
<211> LENGTH: 5
<212> TYPE: PRT
<213> ORGANISM: Homo sapiens

<400> SEQUENCE: 171

Leu Val Gly Gly Ala
1               5

<210> SEQ ID NO 172
<211> LENGTH: 6
<212> TYPE: PRT
<213> ORGANISM: Homo sapiens

<400> SEQUENCE: 172

Leu Val Gly Gly Pro Gln
1               5

<210> SEQ ID NO 173
<211> LENGTH: 7
<212> TYPE: PRT
<213> ORGANISM: Homo sapiens

<400> SEQUENCE: 173

Leu Val Gly Gly Pro Gln Arg
1               5

<210> SEQ ID NO 174
<211> LENGTH: 8
<212> TYPE: PRT
<213> ORGANISM: Homo sapiens

<400> SEQUENCE: 174

Leu Val Gly Gly Gly Pro Gln Arg

```
1               5

<210> SEQ ID NO 175
<211> LENGTH: 8
<212> TYPE: PRT
<213> ORGANISM: Homo sapiens

<400> SEQUENCE: 175

Leu Val Gly Gly Gly Pro Gln
1               5

<210> SEQ ID NO 176
<211> LENGTH: 19
<212> TYPE: PRT
<213> ORGANISM: Homo sapiens

<400> SEQUENCE: 176

Ser Phe Phe Gly Ala Phe Leu Val Gly Gly Pro Gln Arg Val Ala
1               5                   10                  15

Ala His Ile

<210> SEQ ID NO 177
<211> LENGTH: 18
<212> TYPE: PRT
<213> ORGANISM: Homo sapiens

<400> SEQUENCE: 177

Ser Phe Phe Gly Ala Phe Leu Val Gly Gly Pro Gln Arg Val Ala Ala
1               5                   10                  15

His Ile

<210> SEQ ID NO 178
<211> LENGTH: 15
<212> TYPE: PRT
<213> ORGANISM: Homo sapiens

<400> SEQUENCE: 178

Ser Phe Phe Gly Ala Phe Leu Val Ser Gly Ile Ala Ala His Ile
1               5                   10                  15

<210> SEQ ID NO 179
<211> LENGTH: 15
<212> TYPE: PRT
<213> ORGANISM: Homo sapiens

<400> SEQUENCE: 179

Ser Phe Phe Gly Ala Phe Ala Val Gly Gly Ala Ala Ala His Ile
1               5                   10                  15

<210> SEQ ID NO 180
<211> LENGTH: 16
<212> TYPE: PRT
<213> ORGANISM: Homo sapiens

<400> SEQUENCE: 180

Ser Phe Phe Gly Ala Phe Ala Val Gly Gly Ile Ala Ala Ala His Ile
1               5                   10                  15

<210> SEQ ID NO 181
<211> LENGTH: 15
<212> TYPE: PRT
<213> ORGANISM: Homo sapiens

<400> SEQUENCE: 181
```

-continued

Ser Phe Phe Gly Ala Phe Ile Val Gly Gly Ile Ala Ala His Ile
1               5                   10                  15

<210> SEQ ID NO 182
<211> LENGTH: 15
<212> TYPE: PRT
<213> ORGANISM: Homo sapiens

<400> SEQUENCE: 182

Ser Phe Phe Gly Ala Phe Ala Val Ser Gly Ile Ala Ala His Ile
1               5                   10                  15

<210> SEQ ID NO 183
<211> LENGTH: 15
<212> TYPE: PRT
<213> ORGANISM: Homo sapiens

<400> SEQUENCE: 183

Ser Phe Phe Gly Ala Phe Ile Val Ser Gly Ile Ala Ala His Ile
1               5                   10                  15

<210> SEQ ID NO 184
<211> LENGTH: 14
<212> TYPE: PRT
<213> ORGANISM: Homo sapiens

<400> SEQUENCE: 184

Ser Phe Phe Gly Ala Leu Val Gly Gly Val Ala Ala His Ile
1               5                   10

<210> SEQ ID NO 185
<211> LENGTH: 16
<212> TYPE: PRT
<213> ORGANISM: Homo sapiens

<400> SEQUENCE: 185

Ser Phe Phe Gly Ala Phe Leu Val Gly Gly Arg Val Ala Ala His Ile
1               5                   10                  15

<210> SEQ ID NO 186
<211> LENGTH: 15
<212> TYPE: PRT
<213> ORGANISM: Homo sapiens

<400> SEQUENCE: 186

Ser Phe Phe Gly Ala Phe Leu Val Gly Gly Ile Ala Ala His Ile
1               5                   10                  15

<210> SEQ ID NO 187
<211> LENGTH: 15
<212> TYPE: PRT
<213> ORGANISM: Homo sapiens

<400> SEQUENCE: 187

Ser Phe Phe Gly Ala Phe Leu Val Gly Gly Ala Ala Ala His Ile
1               5                   10                  15

<210> SEQ ID NO 188
<211> LENGTH: 15
<212> TYPE: PRT
<213> ORGANISM: Homo sapiens

<400> SEQUENCE: 188

Ser Phe Phe Gly Ala Phe Ala Val Ser Gly Ala Ala Ala His Ile

-continued

```
1               5                   10                  15
```

<210> SEQ ID NO 189
<211> LENGTH: 5
<212> TYPE: PRT
<213> ORGANISM: Homo sapiens

<400> SEQUENCE: 189

```
Gly Gly Gly Gly Ser
1               5
```

<210> SEQ ID NO 190
<211> LENGTH: 8
<212> TYPE: PRT
<213> ORGANISM: Homo sapiens

<400> SEQUENCE: 190

```
Gly Gly Gly Gly Ser Gly Gly Gly
1               5
```

<210> SEQ ID NO 191
<211> LENGTH: 10
<212> TYPE: PRT
<213> ORGANISM: Homo sapiens

<400> SEQUENCE: 191

```
Gly Gly Gly Gly Ser Gly Gly Gly Gly Ser
1               5                   10
```

<210> SEQ ID NO 192
<211> LENGTH: 10
<212> TYPE: PRT
<213> ORGANISM: Homo sapiens

<400> SEQUENCE: 192

```
Gly Gly Ser Gly Gly Ala Ser Ser Gly Gly
1               5                   10
```

<210> SEQ ID NO 193
<211> LENGTH: 10
<212> TYPE: PRT
<213> ORGANISM: Homo sapiens

<400> SEQUENCE: 193

```
Gly Gly Ser Gly Gly Gly Ser Ser Gly Gly
1               5                   10
```

<210> SEQ ID NO 194
<211> LENGTH: 16
<212> TYPE: PRT
<213> ORGANISM: Homo sapiens

<400> SEQUENCE: 194

```
Ala Ala Ala Gly Asn Gly Thr Ser Asn Gly Thr Ser Glu Phe Gly Gly
1               5                   10                  15
```

<210> SEQ ID NO 195
<211> LENGTH: 763
<212> TYPE: PRT
<213> ORGANISM: Homo sapiens

<400> SEQUENCE: 195

```
Met Asp Trp Thr Trp Arg Val Phe Cys Leu Leu Ala Val Ala Pro Gly
1               5                   10                  15
```

```
Ala His Ser Leu Glu Ala Ser Asp Tyr Lys Asp Asp Asp Lys Gly
            20                  25                  30

Ala Glu Val Gln Leu Val Glu Ser Gly Gly Gly Leu Val Gln Pro Gly
        35                  40                  45

Gly Ser Leu Arg Leu Ser Cys Ala Ala Ser Gly Phe Ser Leu Thr Asn
    50                  55                  60

Tyr Gly Val His Trp Val Arg Gln Ala Pro Gly Lys Gly Leu Glu Trp
65                  70                  75                  80

Leu Gly Val Ile Trp Ser Gly Gly Asn Thr Asp Tyr Asn Thr Pro Phe
                85                  90                  95

Thr Ser Arg Phe Thr Ile Ser Arg Asp Asn Ser Lys Asn Thr Leu Tyr
            100                 105                 110

Leu Gln Met Asn Ser Leu Arg Ala Glu Asp Thr Ala Val Tyr Tyr Cys
        115                 120                 125

Ala Arg Ala Leu Thr Tyr Tyr Asp Tyr Glu Phe Ala Tyr Trp Gly Gln
    130                 135                 140

Gly Thr Thr Val Thr Val Ser Ser Gly Gly Gly Ser Asp Ile Gln
145                 150                 155                 160

Leu Thr Gln Ser Pro Ser Phe Leu Ser Ala Ser Val Gly Asp Arg Val
            165                 170                 175

Thr Ile Thr Cys Arg Ala Ser Gln Ser Ile Gly Thr Asn Ile His Trp
        180                 185                 190

Tyr Gln Gln Lys Pro Gly Lys Ala Pro Lys Leu Leu Ile Lys Tyr Ala
    195                 200                 205

Ser Glu Ser Ile Ser Gly Val Pro Ser Arg Phe Ser Gly Ser Gly Ser
210                 215                 220

Gly Thr Glu Phe Thr Leu Thr Ile Ser Ser Leu Gln Pro Glu Asp Phe
225                 230                 235                 240

Ala Thr Tyr Tyr Cys Gln Gln Asn Asn Asn Trp Pro Thr Thr Phe Gly
            245                 250                 255

Ala Gly Thr Lys Leu Glu Ile Lys Arg Ala Ala Ala Gly Asn Gly Thr
        260                 265                 270

Ser Asn Gly Thr Ser Glu Phe Gly Gly Ile Ala Ala His Ile Thr Gly
    275                 280                 285

Thr Arg Gly Arg Ser Asn Thr Leu Ser Ser Pro Asn Ser Lys Asn Glu
290                 295                 300

Lys Ala Leu Gly Arg Lys Ile Asn Ser Trp Glu Ser Ser Arg Ser Gly
305                 310                 315                 320

His Ser Phe Leu Ser Asn Leu His Leu Arg Asn Gly Glu Leu Val Ile
            325                 330                 335

His Glu Lys Gly Phe Tyr Tyr Ile Tyr Ser Gln Thr Tyr Phe Arg Phe
        340                 345                 350

Gln Glu Glu Ile Lys Glu Asn Thr Lys Asn Asp Lys Gln Met Val Gln
    355                 360                 365

Tyr Ile Tyr Lys Tyr Thr Ser Tyr Pro Asp Pro Ile Leu Leu Met Lys
370                 375                 380

Ser Ala Arg Asn Ser Cys Trp Ser Lys Asp Ala Glu Tyr Gly Leu Tyr
385                 390                 395                 400

Ser Ile Tyr Gln Gly Gly Ile Phe Glu Leu Lys Glu Asn Asp Arg Ile
            405                 410                 415

Phe Val Ser Val Thr Asn Glu His Leu Ile Asp Met Asp His Glu Ala
        420                 425                 430

Ser Phe Phe Gly Ala Phe Ala Val Ser Gly Ile Ala Ala His Ile Thr
```

```
            435                 440                 445
Gly Thr Arg Gly Arg Ser Asn Thr Leu Ser Ser Pro Asn Ser Lys Asn
450                 455                 460
Glu Lys Ala Leu Gly Arg Lys Ile Asn Ser Trp Glu Ser Ser Arg Ser
465                 470                 475                 480
Gly His Ser Phe Leu Ser Asn Leu His Leu Arg Asn Gly Glu Leu Val
                485                 490                 495
Ile His Glu Lys Gly Phe Tyr Tyr Ile Tyr Ser Gln Thr Tyr Phe Arg
            500                 505                 510
Phe Gln Glu Glu Ile Lys Glu Asn Thr Lys Asn Asp Lys Gln Met Val
            515                 520                 525
Gln Tyr Ile Tyr Lys Tyr Thr Ser Tyr Pro Asp Pro Ile Leu Leu Met
530                 535                 540
Lys Ser Ala Arg Asn Ser Cys Trp Ser Lys Asp Ala Glu Tyr Gly Leu
545                 550                 555                 560
Tyr Ser Ile Tyr Gln Gly Gly Ile Phe Glu Leu Lys Glu Asn Asp Arg
                565                 570                 575
Ile Phe Val Ser Val Thr Asn Glu His Leu Ile Asp Met Asp His Glu
            580                 585                 590
Ala Ser Phe Phe Gly Ala Phe Ala Val Ser Gly Ile Ala Ala His Ile
            595                 600                 605
Thr Gly Thr Arg Gly Arg Ser Asn Thr Leu Ser Ser Pro Asn Ser Lys
            610                 615                 620
Asn Glu Lys Ala Leu Gly Arg Lys Ile Asn Ser Trp Glu Ser Ser Arg
625                 630                 635                 640
Ser Gly His Ser Phe Leu Ser Asn Leu His Leu Arg Asn Gly Glu Leu
                645                 650                 655
Val Ile His Glu Lys Gly Phe Tyr Tyr Ile Tyr Ser Gln Thr Tyr Phe
            660                 665                 670
Arg Phe Gln Glu Glu Ile Lys Glu Asn Thr Lys Asn Asp Lys Gln Met
            675                 680                 685
Val Gln Tyr Ile Tyr Lys Tyr Thr Ser Tyr Pro Asp Pro Ile Leu Leu
            690                 695                 700
Met Lys Ser Ala Arg Asn Ser Cys Trp Ser Lys Asp Ala Glu Tyr Gly
705                 710                 715                 720
Leu Tyr Ser Ile Tyr Gln Gly Gly Ile Phe Glu Leu Lys Glu Asn Asp
                725                 730                 735
Arg Ile Phe Val Ser Val Thr Asn Glu His Leu Ile Asp Met Asp His
            740                 745                 750
Glu Ala Ser Phe Phe Gly Ala Phe Ala Val Ser
            755                 760

<210> SEQ ID NO 196
<211> LENGTH: 752
<212> TYPE: PRT
<213> ORGANISM: Homo sapiens

<400> SEQUENCE: 196

Asp Tyr Lys Asp Asp Asp Lys Gly Gly Gly Gly Ser Gly Thr Glu
1               5                   10                  15
Val Gln Leu Leu Glu Ser Gly Gly Gly Leu Val Gln Pro Gly Gly Ser
                20                  25                  30
Leu Arg Leu Ser Cys Ala Ala Ser Gly Phe Thr Phe His Tyr Val
            35                  40                  45
```

Met Ala Trp Val Arg Gln Ala Pro Gly Lys Cys Leu Glu Trp Val Ser
    50              55                  60

Ser Ile Ser Ser Ser Gly Gly Trp Thr Leu Tyr Ala Asp Ser Val Lys
65              70                  75                  80

Gly Arg Phe Thr Ile Ser Arg Asp Asn Ser Lys Asn Thr Leu Tyr Leu
                85                  90                  95

Gln Met Asn Ser Leu Arg Ala Glu Asp Thr Ala Val Tyr Tyr Cys Thr
            100                 105                 110

Arg Gly Leu Lys Met Ala Thr Ile Phe Asp Tyr Trp Gly Gln Gly Thr
            115                 120                 125

Leu Val Thr Val Ser Ser Gly Gly Gly Ser Gln Ser Ala Leu Thr
            130                 135                 140

Gln Pro Ala Ser Val Ser Gly Ser Pro Gly Gln Ser Ile Thr Ile Ser
145                 150                 155                 160

Cys Thr Gly Thr Ser Ser Asp Val Gly Ser Tyr Asn Val Val Ser Trp
                165                 170                 175

Tyr Gln Gln His Pro Gly Lys Ala Pro Lys Leu Ile Ile Tyr Glu Val
            180                 185                 190

Ser Gln Arg Pro Ser Gly Val Ser Asn Arg Phe Ser Gly Ser Lys Ser
            195                 200                 205

Gly Asn Thr Ala Ser Leu Thr Ile Ser Gly Leu Gln Thr Glu Asp Glu
            210                 215                 220

Ala Asp Tyr Tyr Cys Ser Ser Tyr Ala Gly Ser Ile Phe Val Ile
225                 230                 235                 240

Phe Gly Cys Gly Thr Lys Val Thr Val Leu Ala Ala Ala Gly Gly Ser
                245                 250                 255

Gly Gly Gly Pro Gln Arg Val Ala Ala His Ile Thr Gly Thr Arg Gly
            260                 265                 270

Arg Ser Asn Thr Leu Ser Ser Pro Asn Ser Lys Asn Glu Lys Ala Leu
            275                 280                 285

Gly Arg Lys Ile Asn Ser Trp Glu Ser Ser Arg Ser Gly His Ser Phe
            290                 295                 300

Leu Ser Asn Leu His Leu Arg Asn Gly Glu Leu Val Ile His Glu Lys
305                 310                 315                 320

Gly Phe Tyr Tyr Ile Tyr Ser Gln Thr Tyr Phe Arg Phe Gln Glu Glu
                325                 330                 335

Ile Lys Glu Asn Thr Lys Asn Asp Lys Gln Met Val Gln Tyr Ile Tyr
            340                 345                 350

Lys Tyr Thr Ser Tyr Pro Asp Pro Ile Leu Leu Met Lys Ser Ala Arg
            355                 360                 365

Asn Ser Cys Trp Ser Lys Asp Ala Glu Tyr Gly Leu Tyr Ser Ile Tyr
            370                 375                 380

Gln Gly Gly Ile Phe Glu Leu Lys Glu Asn Asp Arg Ile Phe Val Ser
385                 390                 395                 400

Val Thr Asn Glu His Leu Ile Asp Met Asp His Glu Ala Ser Phe Phe
                405                 410                 415

Gly Ala Phe Leu Val Gly Gly Pro Gln Arg Val Ala Ala His Ile
            420                 425                 430

Thr Gly Thr Arg Gly Arg Ser Asn Thr Leu Ser Ser Pro Asn Ser Lys
            435                 440                 445

Asn Glu Lys Ala Leu Gly Arg Lys Ile Asn Ser Trp Glu Ser Ser Arg
450                 455                 460

Ser Gly His Ser Phe Leu Ser Asn Leu His Leu Arg Asn Gly Glu Leu

```
                465                 470                 475                 480
        Val Ile His Glu Lys Gly Phe Tyr Tyr Ile Tyr Ser Gln Thr Tyr Phe
                            485                 490                 495
        Arg Phe Gln Glu Glu Ile Lys Glu Asn Thr Lys Asn Asp Lys Gln Met
                        500                 505                 510
        Val Gln Tyr Ile Tyr Lys Tyr Thr Ser Tyr Pro Asp Pro Ile Leu Leu
                        515                 520                 525
        Met Lys Ser Ala Arg Asn Ser Cys Trp Ser Lys Asp Ala Glu Tyr Gly
                    530                 535                 540
        Leu Tyr Ser Ile Tyr Gln Gly Gly Ile Phe Glu Leu Lys Glu Asn Asp
        545                 550                 555                 560
        Arg Ile Phe Val Ser Val Thr Asn Glu His Leu Ile Asp Met Asp His
                        565                 570                 575
        Glu Ala Ser Phe Phe Gly Ala Phe Leu Val Gly Gly Pro Gln Arg
                    580                 585                 590
        Val Ala Ala His Ile Thr Gly Thr Arg Gly Arg Ser Asn Thr Leu Ser
                    595                 600                 605
        Ser Pro Asn Ser Lys Asn Glu Lys Ala Leu Gly Arg Lys Ile Asn Ser
                    610                 615                 620
        Trp Glu Ser Ser Arg Ser Gly His Ser Phe Leu Ser Asn Leu His Leu
        625                 630                 635                 640
        Arg Asn Gly Glu Leu Val Ile His Glu Lys Gly Phe Tyr Tyr Ile Tyr
                            645                 650                 655
        Ser Gln Thr Tyr Phe Arg Phe Gln Glu Glu Ile Lys Glu Asn Thr Lys
                        660                 665                 670
        Asn Asp Lys Gln Met Val Gln Tyr Ile Tyr Lys Tyr Thr Ser Tyr Pro
                    675                 680                 685
        Asp Pro Ile Leu Leu Met Lys Ser Ala Arg Asn Ser Cys Trp Ser Lys
                    690                 695                 700
        Asp Ala Glu Tyr Gly Leu Tyr Ser Ile Tyr Gln Gly Gly Ile Phe Glu
        705                 710                 715                 720
        Leu Lys Glu Asn Asp Arg Ile Phe Val Ser Val Thr Asn Glu His Leu
                        725                 730                 735
        Ile Asp Met Asp His Glu Ala Ser Phe Phe Gly Ala Phe Leu Val Gly
                        740                 745                 750

<210> SEQ ID NO 197
<211> LENGTH: 759
<212> TYPE: PRT
<213> ORGANISM: Homo sapiens

<400> SEQUENCE: 197

Met Asp Trp Thr Trp Arg Val Phe Cys Leu Leu Ala Val Ala Pro Gly
1               5                   10                  15

Ala His Ser Leu Glu Ala Ser Asp Tyr Lys Asp Asp Asp Lys Gly
            20                  25                  30

Ala Glu Val Gln Leu Val Glu Ser Gly Gly Gly Leu Val Gln Pro Gly
        35                  40                  45

Gly Ser Leu Arg Leu Ser Cys Ala Ala Ser Gly Phe Ser Leu Thr Asn
    50                  55                  60

Tyr Gly Val His Trp Val Arg Gln Ala Pro Gly Lys Gly Leu Glu Trp
65                  70                  75                  80

Leu Gly Val Ile Trp Ser Gly Gly Asn Thr Asp Tyr Asn Thr Pro Phe
                85                  90                  95
```

```
Thr Ser Arg Phe Thr Ile Ser Arg Asp Asn Ser Lys Asn Thr Leu Tyr
            100                 105                 110

Leu Gln Met Asn Ser Leu Arg Ala Glu Asp Thr Ala Val Tyr Tyr Cys
        115                 120                 125

Ala Arg Ala Leu Thr Tyr Tyr Asp Tyr Glu Phe Ala Tyr Trp Gly Gln
    130                 135                 140

Gly Thr Thr Val Thr Val Ser Ser Gly Gly Gly Gly Ser Gly Gly Gly
145                 150                 155                 160

Gly Ser Asp Ile Gln Leu Thr Gln Ser Pro Ser Phe Leu Ser Ala Ser
                165                 170                 175

Val Gly Asp Arg Val Thr Ile Thr Cys Arg Ala Ser Gln Ser Ile Gly
            180                 185                 190

Thr Asn Ile His Trp Tyr Gln Gln Lys Pro Gly Lys Ala Pro Lys Leu
        195                 200                 205

Leu Ile Lys Tyr Ala Ser Glu Ser Ile Ser Gly Val Pro Ser Arg Phe
    210                 215                 220

Ser Gly Ser Gly Ser Gly Thr Glu Phe Thr Leu Thr Ile Ser Ser Leu
225                 230                 235                 240

Gln Pro Glu Asp Phe Ala Thr Tyr Tyr Cys Gln Gln Asn Asn Asn Trp
                245                 250                 255

Pro Thr Thr Phe Gly Ala Gly Thr Lys Leu Glu Ile Lys Arg Ala Ala
            260                 265                 270

Ala Glu Phe Gly Gly Ala Ala Ala His Ile Thr Gly Thr Arg Gly Arg
        275                 280                 285

Ser Asn Thr Leu Ser Ser Pro Asn Ser Lys Asn Glu Lys Ala Leu Gly
    290                 295                 300

Arg Lys Ile Asn Ser Trp Glu Ser Ser Arg Ser Gly His Ser Phe Leu
305                 310                 315                 320

Ser Asn Leu His Leu Arg Asn Gly Glu Leu Val Ile His Glu Lys Gly
                325                 330                 335

Phe Tyr Tyr Ile Tyr Ser Gln Thr Tyr Phe Arg Phe Gln Glu Glu Ile
            340                 345                 350

Lys Glu Asn Thr Lys Asn Asp Lys Gln Met Val Gln Tyr Ile Tyr Lys
        355                 360                 365

Tyr Thr Ser Tyr Pro Asp Pro Ile Leu Leu Met Lys Ser Ala Arg Asn
    370                 375                 380

Ser Cys Trp Ser Lys Asp Ala Glu Tyr Gly Leu Tyr Ser Ile Tyr Gln
385                 390                 395                 400

Gly Gly Ile Phe Glu Leu Lys Glu Asn Asp Arg Ile Phe Val Ser Val
                405                 410                 415

Thr Asn Glu His Leu Ile Asp Met Asp His Glu Ala Ser Phe Phe Gly
            420                 425                 430

Ala Phe Ala Val Ser Gly Ala Ala Ala His Ile Thr Gly Thr Arg Gly
        435                 440                 445

Arg Ser Asn Thr Leu Ser Ser Pro Asn Ser Lys Asn Glu Lys Ala Leu
    450                 455                 460

Gly Arg Lys Ile Asn Ser Trp Glu Ser Ser Arg Ser Gly His Ser Phe
465                 470                 475                 480

Leu Ser Asn Leu His Leu Arg Asn Gly Glu Leu Val Ile His Glu Lys
                485                 490                 495

Gly Phe Tyr Tyr Ile Tyr Ser Gln Thr Tyr Phe Arg Phe Gln Glu Glu
            500                 505                 510

Ile Lys Glu Asn Thr Lys Asn Asp Lys Gln Met Val Gln Tyr Ile Tyr
```

```
                515                 520                 525
Lys Tyr Thr Ser Tyr Pro Asp Pro Ile Leu Leu Met Lys Ser Ala Arg
        530                 535                 540

Asn Ser Cys Trp Ser Lys Asp Ala Glu Tyr Gly Leu Tyr Ser Ile Tyr
545                 550                 555                 560

Gln Gly Gly Ile Phe Glu Leu Lys Glu Asn Asp Arg Ile Phe Val Ser
                565                 570                 575

Val Thr Asn Glu His Leu Ile Asp Met Asp His Glu Ala Ser Phe Phe
            580                 585                 590

Gly Ala Phe Ala Val Ser Gly Ala Ala His Ile Thr Gly Thr Arg
        595                 600                 605

Gly Arg Ser Asn Thr Leu Ser Ser Pro Asn Ser Lys Asn Glu Lys Ala
610                 615                 620

Leu Gly Arg Lys Ile Asn Ser Trp Glu Ser Ser Arg Ser Gly His Ser
625                 630                 635                 640

Phe Leu Ser Asn Leu His Leu Arg Asn Gly Glu Leu Val Ile His Glu
                645                 650                 655

Lys Gly Phe Tyr Tyr Ile Tyr Ser Gln Thr Tyr Phe Arg Phe Gln Glu
            660                 665                 670

Glu Ile Lys Glu Asn Thr Lys Asn Asp Lys Gln Met Val Gln Tyr Ile
        675                 680                 685

Tyr Lys Tyr Thr Ser Tyr Pro Asp Pro Ile Leu Leu Met Lys Ser Ala
    690                 695                 700

Arg Asn Ser Cys Trp Ser Lys Asp Ala Glu Tyr Gly Leu Tyr Ser Ile
705                 710                 715                 720

Tyr Gln Gly Gly Ile Phe Glu Leu Lys Glu Asn Asp Arg Ile Phe Val
                725                 730                 735

Ser Val Thr Asn Glu His Leu Ile Asp Met Asp His Glu Ala Ser Phe
            740                 745                 750

Phe Gly Ala Phe Ala Val Ser
        755

<210> SEQ ID NO 198
<211> LENGTH: 763
<212> TYPE: PRT
<213> ORGANISM: Homo sapiens

<400> SEQUENCE: 198

Met Asp Trp Thr Trp Arg Val Phe Cys Leu Leu Ala Val Ala Pro Gly
1               5                   10                  15

Ala His Ser Leu Glu Ala Ser Asp Tyr Lys Asp Asp Asp Lys Gly
            20                  25                  30

Ala Glu Val Gln Leu Val Glu Ser Gly Gly Leu Val Gln Pro Gly
        35                  40                  45

Gly Ser Leu Arg Leu Ser Cys Ala Ala Ser Gly Phe Ser Leu Thr Asn
    50                  55                  60

Tyr Gly Val His Trp Val Arg Gln Ala Pro Gly Lys Gly Leu Glu Trp
65                  70                  75                  80

Leu Gly Val Ile Trp Ser Gly Gly Asn Thr Asp Tyr Asn Thr Pro Phe
                85                  90                  95

Thr Ser Arg Phe Thr Ile Ser Arg Asp Asn Ser Lys Asn Thr Leu Tyr
            100                 105                 110

Leu Gln Met Asn Ser Leu Arg Ala Glu Asp Thr Ala Val Tyr Tyr Cys
        115                 120                 125
```

```
Ala Arg Ala Leu Thr Tyr Tyr Asp Tyr Glu Phe Ala Tyr Trp Gly Gln
130                 135                 140

Gly Thr Thr Val Thr Val Ser Ser Gly Gly Gly Ser Asp Ile Gln
145                 150                 155                 160

Leu Thr Gln Ser Pro Ser Phe Leu Ser Ala Ser Val Gly Asp Arg Val
            165                 170                 175

Thr Ile Thr Cys Arg Ala Ser Gln Ser Ile Gly Thr Asn Ile His Trp
                180                 185                 190

Tyr Gln Gln Lys Pro Gly Lys Ala Pro Lys Leu Leu Ile Lys Tyr Ala
        195                 200                 205

Ser Glu Ser Ile Ser Gly Val Pro Ser Arg Phe Ser Gly Ser Gly Ser
210                 215                 220

Gly Thr Glu Phe Thr Leu Thr Ile Ser Ser Leu Gln Pro Glu Asp Phe
225                 230                 235                 240

Ala Thr Tyr Tyr Cys Gln Gln Asn Asn Asn Trp Pro Thr Thr Phe Gly
                245                 250                 255

Ala Gly Thr Lys Leu Glu Ile Lys Arg Ala Ala Ala Gly Asn Gly Thr
            260                 265                 270

Ser Asn Gly Thr Ser Glu Phe Gly Ala Ala Ala His Ile Thr Gly
        275                 280                 285

Thr Arg Gly Arg Ser Asn Thr Leu Ser Ser Pro Asn Ser Lys Asn Glu
290                 295                 300

Lys Ala Leu Gly Arg Lys Ile Asn Ser Trp Glu Ser Ser Arg Ser Gly
305                 310                 315                 320

His Ser Phe Leu Ser Asn Leu His Leu Arg Asn Gly Glu Leu Val Ile
                325                 330                 335

His Glu Lys Gly Phe Tyr Tyr Ile Tyr Ser Gln Thr Tyr Phe Arg Phe
            340                 345                 350

Gln Glu Glu Ile Lys Glu Asn Thr Lys Asn Asp Lys Gln Met Val Gln
        355                 360                 365

Tyr Ile Tyr Lys Tyr Thr Ser Tyr Pro Asp Pro Ile Leu Leu Met Lys
370                 375                 380

Ser Ala Arg Asn Ser Cys Trp Ser Lys Asp Ala Glu Tyr Gly Leu Tyr
385                 390                 395                 400

Ser Ile Tyr Gln Gly Gly Ile Phe Glu Leu Lys Glu Asn Asp Arg Ile
                405                 410                 415

Phe Val Ser Val Thr Asn Glu His Leu Ile Asp Met Asp His Glu Ala
            420                 425                 430

Ser Phe Phe Gly Ala Phe Ala Val Ser Gly Ala Ala His Ile Thr
        435                 440                 445

Gly Thr Arg Gly Arg Ser Asn Thr Leu Ser Ser Pro Asn Ser Lys Asn
450                 455                 460

Glu Lys Ala Leu Gly Arg Lys Ile Asn Ser Trp Glu Ser Ser Arg Ser
465                 470                 475                 480

Gly His Ser Phe Leu Ser Asn Leu His Leu Arg Asn Gly Glu Leu Val
                485                 490                 495

Ile His Glu Lys Gly Phe Tyr Tyr Ile Tyr Ser Gln Thr Tyr Phe Arg
            500                 505                 510

Phe Gln Glu Glu Ile Lys Glu Asn Thr Lys Asn Asp Lys Gln Met Val
        515                 520                 525

Gln Tyr Ile Tyr Lys Tyr Thr Ser Tyr Pro Asp Pro Ile Leu Leu Met
530                 535                 540

Lys Ser Ala Arg Asn Ser Cys Trp Ser Lys Asp Ala Glu Tyr Gly Leu
```

```
                545                 550                 555                 560
        Tyr Ser Ile Tyr Gln Gly Gly Ile Phe Glu Leu Lys Glu Asn Asp Arg
                        565                 570                 575

Ile Phe Val Ser Val Thr Asn Glu His Leu Ile Asp Met Asp His Glu
                        580                 585                 590

Ala Ser Phe Phe Gly Ala Phe Ala Val Ser Gly Ala Ala His Ile
                        595                 600                 605

Thr Gly Thr Arg Gly Arg Ser Asn Thr Leu Ser Ser Pro Asn Ser Lys
                        610                 615                 620

Asn Glu Lys Ala Leu Gly Arg Lys Ile Asn Ser Trp Glu Ser Ser Arg
        625                 630                 635                 640

Ser Gly His Ser Phe Leu Ser Asn Leu His Leu Arg Asn Gly Glu Leu
                        645                 650                 655

Val Ile His Glu Lys Gly Phe Tyr Tyr Ile Tyr Ser Gln Thr Tyr Phe
                        660                 665                 670

Arg Phe Gln Glu Glu Ile Lys Glu Asn Thr Lys Asn Asp Lys Gln Met
                        675                 680                 685

Val Gln Tyr Ile Tyr Lys Tyr Thr Ser Tyr Pro Asp Pro Ile Leu Leu
                        690                 695                 700

Met Lys Ser Ala Arg Asn Ser Cys Trp Ser Lys Asp Ala Glu Tyr Gly
        705                 710                 715                 720

Leu Tyr Ser Ile Tyr Gln Gly Gly Ile Phe Glu Leu Lys Glu Asn Asp
                        725                 730                 735

Arg Ile Phe Val Ser Val Thr Asn Glu His Leu Ile Asp Met Asp His
                        740                 745                 750

Glu Ala Ser Phe Phe Gly Ala Phe Ala Val Ser
                        755                 760

<210> SEQ ID NO 199
<211> LENGTH: 763
<212> TYPE: PRT
<213> ORGANISM: Homo sapiens

<400> SEQUENCE: 199

Met Asp Trp Thr Trp Arg Val Phe Cys Leu Leu Ala Val Ala Pro Gly
        1               5                   10                  15

Ala His Ser Leu Glu Ala Ser Asp Tyr Lys Asp Asp Asp Lys Gly
                        20                  25                  30

Ala Glu Val Gln Leu Val Glu Ser Gly Gly Leu Val Gln Pro Gly
                        35                  40                  45

Gly Ser Leu Arg Leu Ser Cys Ala Ala Ser Gly Phe Ser Leu Thr Asn
                50                  55                  60

Tyr Gly Val His Trp Val Arg Gln Ala Pro Gly Lys Gly Leu Glu Trp
        65                  70                  75                  80

Leu Gly Val Ile Trp Ser Gly Gly Asn Thr Asp Tyr Asn Thr Pro Phe
                        85                  90                  95

Thr Ser Arg Phe Thr Ile Ser Arg Asp Asn Ser Lys Asn Thr Leu Tyr
                        100                 105                 110

Leu Gln Met Asn Ser Leu Arg Ala Glu Asp Thr Ala Val Tyr Tyr Cys
                        115                 120                 125

Ala Arg Ala Leu Thr Tyr Tyr Asp Tyr Glu Phe Ala Tyr Trp Gly Gln
                        130                 135                 140

Gly Thr Thr Val Thr Val Ser Ser Gly Gly Gly Gly Ser Asp Ile Gln
        145                 150                 155                 160
```

```
Leu Thr Gln Ser Pro Ser Phe Leu Ser Ala Ser Val Gly Asp Arg Val
                165                 170                 175
Thr Ile Thr Cys Arg Ala Ser Gln Ser Ile Gly Thr Asn Ile His Trp
            180                 185                 190
Tyr Gln Gln Lys Pro Gly Lys Ala Pro Lys Leu Leu Ile Lys Tyr Ala
        195                 200                 205
Ser Glu Ser Ile Ser Gly Val Pro Ser Arg Phe Ser Gly Ser Gly Ser
    210                 215                 220
Gly Thr Glu Phe Thr Leu Thr Ile Ser Ser Leu Gln Pro Glu Asp Phe
225                 230                 235                 240
Ala Thr Tyr Tyr Cys Gln Gln Asn Asn Asn Trp Pro Thr Thr Phe Gly
            245                 250                 255
Ala Gly Thr Lys Leu Glu Ile Lys Arg Ala Ala Gly Asn Gly Thr
        260                 265                 270
Ser Asn Gly Thr Ser Glu Phe Gly Gly Ile Ala Ala His Ile Thr Gly
    275                 280                 285
Thr Arg Gly Arg Ser Asn Thr Leu Ser Ser Pro Asn Ser Lys Asn Glu
    290                 295                 300
Lys Ala Leu Gly Arg Lys Ile Asn Ser Trp Glu Ser Ser Arg Ser Gly
305                 310                 315                 320
His Ser Phe Leu Ser Asn Leu His Leu Arg Asn Gly Glu Leu Val Ile
            325                 330                 335
His Glu Lys Gly Phe Tyr Tyr Ile Tyr Ser Gln Thr Tyr Phe Arg Phe
            340                 345                 350
Gln Glu Glu Ile Lys Glu Asn Thr Lys Asn Asp Lys Gln Met Val Gln
        355                 360                 365
Tyr Ile Tyr Lys Tyr Thr Ser Tyr Pro Asp Pro Ile Leu Leu Met Lys
370                 375                 380
Ser Ala Arg Asn Ser Cys Trp Ser Lys Asp Ala Glu Tyr Gly Leu Tyr
385                 390                 395                 400
Ser Ile Tyr Gln Gly Gly Ile Phe Glu Leu Lys Glu Asn Asp Arg Ile
            405                 410                 415
Phe Val Ser Val Thr Asn Glu His Leu Ile Asp Met Asp His Glu Ala
            420                 425                 430
Ser Phe Phe Gly Ala Phe Ala Val Ser Gly Ile Ala Ala His Ile Thr
        435                 440                 445
Gly Thr Arg Gly Arg Ser Asn Thr Leu Ser Ser Pro Asn Ser Lys Asn
        450                 455                 460
Glu Lys Ala Leu Gly Arg Lys Ile Asn Ser Trp Glu Ser Ser Arg Ser
465                 470                 475                 480
Gly His Ser Phe Leu Ser Asn Leu His Leu Arg Asn Gly Glu Leu Val
                485                 490                 495
Ile His Glu Lys Gly Phe Tyr Tyr Ile Tyr Ser Gln Thr Tyr Phe Arg
                500                 505                 510
Phe Gln Glu Glu Ile Lys Glu Asn Thr Lys Asn Asp Lys Gln Met Val
            515                 520                 525
Gln Tyr Ile Tyr Lys Tyr Thr Ser Tyr Pro Asp Pro Ile Leu Leu Met
        530                 535                 540
Lys Ser Ala Arg Asn Ser Cys Trp Ser Lys Asp Ala Glu Tyr Gly Leu
545                 550                 555                 560
Tyr Ser Ile Tyr Gln Gly Gly Ile Phe Glu Leu Lys Glu Asn Asp Arg
                565                 570                 575
Ile Phe Val Ser Val Thr Asn Glu His Leu Ile Asp Met Asp His Glu
```

-continued

```
                580                 585                 590
Ala Ser Phe Phe Gly Ala Phe Ala Val Ser Gly Ile Ala Ala His Ile
            595                 600                 605

Thr Gly Thr Arg Gly Arg Ser Asn Thr Leu Ser Ser Pro Asn Ser Lys
        610                 615                 620

Asn Glu Lys Ala Leu Gly Arg Lys Ile Asn Ser Trp Glu Ser Ser Arg
625                 630                 635                 640

Ser Gly His Ser Phe Leu Ser Asn Leu His Leu Arg Asn Gly Glu Leu
                645                 650                 655

Val Ile His Glu Lys Gly Phe Tyr Ile Tyr Ser Gln Thr Tyr Phe
            660                 665                 670

Arg Phe Gln Glu Glu Ile Lys Glu Asn Thr Lys Asn Asp Lys Gln Met
        675                 680                 685

Val Gln Tyr Ile Tyr Lys Tyr Thr Ser Tyr Pro Asp Pro Ile Leu Leu
        690                 695                 700

Met Lys Ser Ala Arg Asn Ser Cys Trp Ser Lys Asp Ala Glu Tyr Gly
705                 710                 715                 720

Leu Tyr Ser Ile Tyr Gln Gly Gly Ile Phe Glu Leu Lys Glu Asn Asp
                725                 730                 735

Arg Ile Phe Val Ser Val Thr Asn Glu His Leu Ile Asp Met Asp His
            740                 745                 750

Glu Ala Ser Phe Phe Gly Ala Phe Ala Val Ser
            755                 760
```

<210> SEQ ID NO 200
<211> LENGTH: 766
<212> TYPE: PRT
<213> ORGANISM: Homo sapiens

<400> SEQUENCE: 200

```
Met Asp Trp Thr Trp Arg Val Phe Cys Leu Leu Ala Val Ala Pro Gly
1               5                   10                  15

Ala His Ser Leu Glu Ala Ser Asp Tyr Lys Asp Asp Asp Asp Lys Gly
            20                  25                  30

Ala Glu Val Gln Leu Val Glu Ser Gly Gly Leu Val Gln Pro Gly
        35                  40                  45

Gly Ser Leu Arg Leu Ser Cys Ala Ala Ser Gly Phe Ser Leu Thr Asn
    50                  55                  60

Tyr Gly Val His Trp Val Arg Gln Ala Pro Gly Lys Gly Leu Glu Trp
65                  70                  75                  80

Leu Gly Val Ile Trp Ser Gly Gly Asn Thr Asp Tyr Asn Thr Pro Phe
                85                  90                  95

Thr Ser Arg Phe Thr Ile Ser Arg Asp Asn Ser Lys Asn Thr Leu Tyr
            100                 105                 110

Leu Gln Met Asn Ser Leu Arg Ala Glu Asp Thr Ala Val Tyr Tyr Cys
        115                 120                 125

Ala Arg Ala Leu Thr Tyr Tyr Asp Tyr Glu Phe Ala Tyr Trp Gly Gln
    130                 135                 140

Gly Thr Thr Val Thr Val Ser Ser Gly Gly Gly Gly Ser Gly Gly Gly
145                 150                 155                 160

Asp Ile Gln Leu Thr Gln Ser Pro Ser Phe Leu Ser Ala Ser Val Gly
                165                 170                 175

Asp Arg Val Thr Ile Thr Cys Arg Ala Ser Gln Ser Ile Gly Thr Asn
            180                 185                 190
```

```
Ile His Trp Tyr Gln Gln Lys Pro Gly Lys Ala Pro Lys Leu Leu Ile
            195                 200                 205
Lys Tyr Ala Ser Glu Ser Ile Ser Gly Val Pro Ser Arg Phe Ser Gly
        210                 215                 220
Ser Gly Ser Gly Thr Glu Phe Thr Leu Thr Ile Ser Ser Leu Gln Pro
225                 230                 235                 240
Glu Asp Phe Ala Thr Tyr Tyr Cys Gln Gln Asn Asn Asn Trp Pro Thr
                245                 250                 255
Thr Phe Gly Ala Gly Thr Lys Leu Glu Ile Lys Arg Ala Ala Ala Gly
                260                 265                 270
Asn Gly Thr Ser Asn Gly Thr Ser Glu Phe Gly Gly Ala Ala Ala His
            275                 280                 285
Ile Thr Gly Thr Arg Gly Arg Ser Asn Thr Leu Ser Ser Pro Asn Ser
        290                 295                 300
Lys Asn Glu Lys Ala Leu Gly Arg Lys Ile Asn Ser Trp Glu Ser Ser
305                 310                 315                 320
Arg Ser Gly His Ser Phe Leu Ser Asn Leu His Leu Arg Asn Gly Glu
                325                 330                 335
Leu Val Ile His Glu Lys Gly Phe Tyr Tyr Ile Tyr Ser Gln Thr Tyr
                340                 345                 350
Phe Arg Phe Gln Glu Glu Ile Lys Glu Asn Thr Lys Asn Asp Lys Gln
            355                 360                 365
Met Val Gln Tyr Ile Tyr Lys Tyr Thr Ser Tyr Pro Asp Pro Ile Leu
        370                 375                 380
Leu Met Lys Ser Ala Arg Asn Ser Cys Trp Ser Lys Asp Ala Glu Tyr
385                 390                 395                 400
Gly Leu Tyr Ser Ile Tyr Gln Gly Gly Ile Phe Glu Leu Lys Glu Asn
                405                 410                 415
Asp Arg Ile Phe Val Ser Val Thr Asn Glu His Leu Ile Asp Met Asp
            420                 425                 430
His Glu Ala Ser Phe Phe Gly Ala Phe Ala Val Ser Gly Ala Ala Ala
        435                 440                 445
His Ile Thr Gly Thr Arg Gly Arg Ser Asn Thr Leu Ser Ser Pro Asn
        450                 455                 460
Ser Lys Asn Glu Lys Ala Leu Gly Arg Lys Ile Asn Ser Trp Glu Ser
465                 470                 475                 480
Ser Arg Ser Gly His Ser Phe Leu Ser Asn Leu His Leu Arg Asn Gly
                485                 490                 495
Glu Leu Val Ile His Glu Lys Gly Phe Tyr Tyr Ile Tyr Ser Gln Thr
            500                 505                 510
Tyr Phe Arg Phe Gln Glu Glu Ile Lys Glu Asn Thr Lys Asn Asp Lys
        515                 520                 525
Gln Met Val Gln Tyr Ile Tyr Lys Tyr Thr Ser Tyr Pro Asp Pro Ile
    530                 535                 540
Leu Leu Met Lys Ser Ala Arg Asn Ser Cys Trp Ser Lys Asp Ala Glu
545                 550                 555                 560
Tyr Gly Leu Tyr Ser Ile Tyr Gln Gly Gly Ile Phe Glu Leu Lys Glu
                565                 570                 575
Asn Asp Arg Ile Phe Val Ser Val Thr Asn Glu His Leu Ile Asp Met
            580                 585                 590
Asp His Glu Ala Ser Phe Phe Gly Ala Phe Ala Val Ser Gly Ala Ala
        595                 600                 605
Ala His Ile Thr Gly Thr Arg Gly Arg Ser Asn Thr Leu Ser Ser Pro
```

```
                610                 615                 620
Asn Ser Lys Asn Glu Lys Ala Leu Gly Arg Lys Ile Asn Ser Trp Glu
625                 630                 635                 640

Ser Ser Arg Ser Gly His Ser Phe Leu Ser Asn Leu His Leu Arg Asn
                645                 650                 655

Gly Glu Leu Val Ile His Glu Lys Gly Phe Tyr Ile Tyr Ser Gln
                660                 665                 670

Thr Tyr Phe Arg Phe Gln Glu Glu Ile Lys Glu Asn Thr Lys Asn Asp
                675                 680                 685

Lys Gln Met Val Gln Tyr Ile Tyr Lys Tyr Thr Ser Tyr Pro Asp Pro
690                 695                 700

Ile Leu Leu Met Lys Ser Ala Arg Asn Ser Cys Trp Ser Lys Asp Ala
705                 710                 715                 720

Glu Tyr Gly Leu Tyr Ser Ile Tyr Gln Gly Gly Ile Phe Glu Leu Lys
                725                 730                 735

Glu Asn Asp Arg Ile Phe Val Ser Val Thr Asn Glu His Leu Ile Asp
                740                 745                 750

Met Asp His Glu Ala Ser Phe Phe Gly Ala Phe Ala Val Ser
                755                 760                 765

<210> SEQ ID NO 201
<211> LENGTH: 768
<212> TYPE: PRT
<213> ORGANISM: Homo sapiens

<400> SEQUENCE: 201

Met Asp Trp Thr Trp Arg Val Phe Cys Leu Leu Ala Val Ala Pro Gly
1               5                   10                  15

Ala His Ser Leu Glu Ala Ser Asp Tyr Lys Asp Asp Asp Asp Lys Gly
                20                  25                  30

Ala Glu Val Gln Leu Val Glu Ser Gly Gly Gly Leu Val Gln Pro Gly
            35                  40                  45

Gly Ser Leu Arg Leu Ser Cys Ala Ala Ser Gly Phe Ser Leu Thr Asn
50                  55                  60

Tyr Gly Val His Trp Val Arg Gln Ala Pro Gly Lys Gly Leu Glu Trp
65                  70                  75                  80

Leu Gly Val Ile Trp Ser Gly Gly Asn Thr Asp Tyr Asn Thr Pro Phe
                85                  90                  95

Thr Ser Arg Phe Thr Ile Ser Arg Asp Asn Ser Lys Asn Thr Leu Tyr
                100                 105                 110

Leu Gln Met Asn Ser Leu Arg Ala Glu Asp Thr Ala Val Tyr Tyr Cys
            115                 120                 125

Ala Arg Ala Leu Thr Tyr Tyr Asp Tyr Glu Phe Ala Tyr Trp Gly Gln
130                 135                 140

Gly Thr Thr Val Thr Val Ser Ser Gly Gly Gly Gly Ser Gly Gly Gly
145                 150                 155                 160

Gly Ser Asp Ile Gln Leu Thr Gln Ser Pro Ser Phe Leu Ser Ala Ser
                165                 170                 175

Val Gly Asp Arg Val Thr Ile Thr Cys Arg Ala Ser Gln Ser Ile Gly
            180                 185                 190

Thr Asn Ile His Trp Tyr Gln Gln Lys Pro Gly Lys Ala Pro Lys Leu
            195                 200                 205

Leu Ile Lys Tyr Ala Ser Glu Ser Ile Ser Gly Val Pro Ser Arg Phe
210                 215                 220
```

```
Ser Gly Ser Gly Ser Gly Thr Glu Phe Thr Leu Thr Ile Ser Ser Leu
225                 230                 235                 240

Gln Pro Glu Asp Phe Ala Thr Tyr Tyr Cys Gln Gln Asn Asn Asn Trp
            245                 250                 255

Pro Thr Thr Phe Gly Ala Gly Thr Lys Leu Glu Ile Lys Arg Ala Ala
            260                 265                 270

Ala Gly Asn Gly Thr Ser Asn Gly Thr Ser Glu Phe Gly Gly Ala Ala
        275                 280                 285

Ala His Ile Thr Gly Thr Arg Gly Arg Ser Asn Thr Leu Ser Ser Pro
    290                 295                 300

Asn Ser Lys Asn Glu Lys Ala Leu Gly Arg Lys Ile Asn Ser Trp Glu
305                 310                 315                 320

Ser Ser Arg Ser Gly His Ser Phe Leu Ser Asn Leu His Leu Arg Asn
            325                 330                 335

Gly Glu Leu Val Ile His Glu Lys Gly Phe Tyr Tyr Ile Tyr Ser Gln
            340                 345                 350

Thr Tyr Phe Arg Phe Gln Glu Glu Ile Lys Glu Asn Thr Lys Asn Asp
        355                 360                 365

Lys Gln Met Val Gln Tyr Ile Tyr Lys Tyr Thr Ser Tyr Pro Asp Pro
    370                 375                 380

Ile Leu Leu Met Lys Ser Ala Arg Asn Ser Cys Trp Ser Lys Asp Ala
385                 390                 395                 400

Glu Tyr Gly Leu Tyr Ser Ile Tyr Gln Gly Gly Ile Phe Glu Leu Lys
            405                 410                 415

Glu Asn Asp Arg Ile Phe Val Ser Val Thr Asn Glu His Leu Ile Asp
        420                 425                 430

Met Asp His Glu Ala Ser Phe Phe Gly Ala Phe Ala Val Ser Gly Ala
    435                 440                 445

Ala Ala His Ile Thr Gly Thr Arg Gly Arg Ser Asn Thr Leu Ser Ser
    450                 455                 460

Pro Asn Ser Lys Asn Glu Lys Ala Leu Gly Arg Lys Ile Asn Ser Trp
465                 470                 475                 480

Glu Ser Ser Arg Ser Gly His Ser Phe Leu Ser Asn Leu His Leu Arg
            485                 490                 495

Asn Gly Glu Leu Val Ile His Glu Lys Gly Phe Tyr Tyr Ile Tyr Ser
        500                 505                 510

Gln Thr Tyr Phe Arg Phe Gln Glu Glu Ile Lys Glu Asn Thr Lys Asn
    515                 520                 525

Asp Lys Gln Met Val Gln Tyr Ile Tyr Lys Tyr Thr Ser Tyr Pro Asp
530                 535                 540

Pro Ile Leu Leu Met Lys Ser Ala Arg Asn Ser Cys Trp Ser Lys Asp
545                 550                 555                 560

Ala Glu Tyr Gly Leu Tyr Ser Ile Tyr Gln Gly Gly Ile Phe Glu Leu
            565                 570                 575

Lys Glu Asn Asp Arg Ile Phe Val Ser Val Thr Asn Glu His Leu Ile
        580                 585                 590

Asp Met Asp His Glu Ala Ser Phe Phe Gly Ala Phe Ala Val Ser Gly
    595                 600                 605

Ala Ala Ala His Ile Thr Gly Thr Arg Gly Arg Ser Asn Thr Leu Ser
    610                 615                 620

Ser Pro Asn Ser Lys Asn Glu Lys Ala Leu Gly Arg Lys Ile Asn Ser
625                 630                 635                 640

Trp Glu Ser Ser Arg Ser Gly His Ser Phe Leu Ser Asn Leu His Leu
```

```
                        645                 650                 655
Arg Asn Gly Glu Leu Val Ile His Glu Lys Gly Phe Tyr Tyr Ile Tyr
            660                 665                 670

Ser Gln Thr Tyr Phe Arg Phe Gln Glu Ile Lys Glu Asn Thr Lys
            675                 680                 685

Asn Asp Lys Gln Met Val Gln Tyr Ile Tyr Lys Tyr Thr Ser Tyr Pro
690                 695                 700

Asp Pro Ile Leu Leu Met Lys Ser Ala Arg Asn Ser Cys Trp Ser Lys
705                 710                 715                 720

Asp Ala Glu Tyr Gly Leu Tyr Ser Ile Tyr Gln Gly Gly Ile Phe Glu
                725                 730                 735

Leu Lys Glu Asn Asp Arg Ile Phe Val Ser Val Thr Asn Glu His Leu
                740                 745                 750

Ile Asp Met Asp His Glu Ala Ser Phe Phe Gly Ala Phe Ala Val Ser
                755                 760                 765

<210> SEQ ID NO 202
<211> LENGTH: 106
<212> TYPE: PRT
<213> ORGANISM: Homo sapiens

<400> SEQUENCE: 202

Asp Phe Thr Pro Pro Thr Val Lys Ile Leu Gln Ser Ser Cys Asp Gly
1               5                   10                  15

Gly Gly His Phe Pro Pro Thr Ile Gln Leu Leu Cys Leu Val Ser Gly
            20                  25                  30

Tyr Thr Pro Gly Thr Ile Asn Ile Thr Trp Leu Glu Asp Gly Gln Val
        35                  40                  45

Met Asp Val Asp Leu Ser Thr Ala Ser Thr Thr Gln Glu Gly Glu Leu
    50                  55                  60

Ala Ser Thr Gln Ser Glu Leu Thr Leu Ser Gln Lys His Trp Leu Ser
65                  70                  75                  80

Asp Arg Thr Tyr Thr Cys Gln Val Thr Tyr Gln Gly His Thr Phe Glu
                85                  90                  95

Asp Ser Thr Lys Lys Cys Ala Asp Ser Asn
            100                 105

<210> SEQ ID NO 203
<211> LENGTH: 356
<212> TYPE: PRT
<213> ORGANISM: Artificial Sequence
<220> FEATURE:
<223> OTHER INFORMATION: scFvhu225-EHD2 fusion protein

<400> SEQUENCE: 203

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Asn Tyr
            20                  25                  30

Gly Val His Trp Val Arg Gln Ala Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95
```

```
Arg Ala Leu Thr Tyr Tyr Asp Tyr Glu Phe Ala Tyr Trp Gly Gln Gly
            100                 105                 110

Thr Thr Val Thr Val Ser Ser Gly Gly Gly Ser Gly Gly Gly
            115                 120                 125

Ser Gly Gly Gly Ser Asp Ile Gln Leu Thr Gln Ser Pro Ser Phe
130                 135                 140

Leu Ser Ala Ser Val Gly Asp Arg Val Thr Ile Thr Cys Arg Ala Ser
145                 150                 155                 160

Gln Ser Ile Gly Thr Asn Ile His Trp Tyr Gln Gln Lys Pro Gly Lys
                165                 170                 175

Ala Pro Lys Leu Leu Ile Lys Tyr Ala Ser Glu Ser Ile Ser Gly Val
            180                 185                 190

Pro Ser Arg Phe Ser Gly Ser Gly Ser Gly Thr Glu Phe Thr Leu Thr
            195                 200                 205

Ile Ser Ser Leu Gln Pro Glu Asp Phe Ala Thr Tyr Tyr Cys Gln Gln
            210                 215                 220

Asn Asn Asn Trp Pro Thr Thr Phe Gly Ala Gly Thr Lys Leu Glu Ile
225                 230                 235                 240

Lys Arg Ala Ala Ala Gly Gly Ser Gly Gly Asp Phe Thr Pro Pro Thr
                245                 250                 255

Val Lys Ile Leu Gln Ser Ser Cys Asp Gly Gly His Phe Pro Pro
            260                 265                 270

Thr Ile Gln Leu Leu Cys Leu Val Ser Gly Tyr Thr Pro Gly Thr Ile
            275                 280                 285

Asn Ile Thr Trp Leu Glu Asp Gly Gln Val Met Asp Val Asp Leu Ser
290                 295                 300

Thr Ala Ser Thr Thr Gln Glu Gly Glu Leu Ala Ser Thr Gln Ser Glu
305                 310                 315                 320

Leu Thr Leu Ser Gln Lys His Trp Leu Ser Asp Arg Thr Tyr Thr Cys
                325                 330                 335

Gln Val Thr Tyr Gln Gly His Thr Phe Glu Asp Ser Thr Lys Lys Cys
            340                 345                 350

Ala Asp Ser Asn
        355

<210> SEQ ID NO 204
<211> LENGTH: 357
<212> TYPE: PRT
<213> ORGANISM: Artificial Sequence
<220> FEATURE:
<223> OTHER INFORMATION: scFv4D5-EHD2

<400> SEQUENCE: 204

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95
```

```
Ser Arg Trp Gly Gly Asp Gly Phe Tyr Ala Met Asp Tyr Trp Gly Gln
            100                 105                 110

Gly Thr Leu Val Thr Val Ser Gly Gly Gly Gly Ser Gly Gly Gly
        115                 120                 125

Gly Ser Gly Gly Gly Gly Ser Asp Ile Gln Met Thr Gln Ser Pro Ser
        130                 135                 140

Ser Leu Ser Ala Ser Val Gly Asp Arg Val Thr Ile Thr Cys Arg Ala
145                 150                 155                 160

Ser Gln Asp Val Asn Thr Ala Val Ala Trp Tyr Gln Gln Lys Pro Gly
                165                 170                 175

Lys Ala Pro Lys Leu Leu Ile Tyr Ser Ala Ser Phe Leu Tyr Ser Gly
            180                 185                 190

Val Pro Ser Arg Phe Ser Gly Ser Arg Ser Gly Thr Asp Phe Thr Leu
        195                 200                 205

Thr Ile Ser Ser Leu Gln Pro Glu Asp Phe Ala Thr Tyr Tyr Cys Gln
210                 215                 220

Gln His Tyr Thr Thr Pro Pro Thr Phe Gly Gln Gly Thr Lys Val Glu
225                 230                 235                 240

Ile Lys Arg Ala Ala Ala Gly Gly Ser Gly Gly Asp Phe Thr Pro Pro
                245                 250                 255

Thr Val Lys Ile Leu Gln Ser Ser Cys Asp Gly Gly Gly His Phe Pro
            260                 265                 270

Pro Thr Ile Gln Leu Leu Cys Leu Val Ser Gly Tyr Thr Pro Gly Thr
        275                 280                 285

Ile Asn Ile Thr Trp Leu Glu Asp Gly Gln Val Met Asp Val Asp Leu
        290                 295                 300

Ser Thr Ala Ser Thr Thr Gln Glu Gly Glu Leu Ala Ser Thr Gln Ser
305                 310                 315                 320

Glu Leu Thr Leu Ser Gln Lys His Trp Leu Ser Asp Arg Thr Tyr Thr
                325                 330                 335

Cys Gln Val Thr Tyr Gln Gly His Thr Phe Glu Asp Ser Thr Lys Lys
            340                 345                 350

Cys Ala Asp Ser Asn
        355

<210> SEQ ID NO 205
<211> LENGTH: 977
<212> TYPE: PRT
<213> ORGANISM: Artificial Sequence
<220> FEATURE:
<223> OTHER INFORMATION: fusion protein hu225 IgG heavy
      chain-scTRAIL3-FAVSGAA

<400> SEQUENCE: 205

Met Glu Thr Asp Thr Leu Leu Leu Trp Val Leu Leu Leu Trp Val Pro
1               5                   10                  15

Gly Ser Thr Gly Ala Ser Asp Tyr Lys Asp Asp Asp Lys Gly Ala
            20                  25                  30

Glu Val Gln Leu Val Glu Ser Gly Gly Gly Leu Val Gln Pro Gly Gly
        35                  40                  45

Ser Leu Arg Leu Ser Cys Ala Ala Ser Gly Phe Ser Leu Thr Asn Tyr
        50                  55                  60

Gly Val His Trp Val Arg Gln Ala Pro Gly Lys Gly Leu Glu Trp Leu
65                  70                  75                  80

Gly Val Ile Trp Ser Gly Gly Asn Thr Asp Tyr Asn Thr Pro Phe Thr
```

```
                    85                  90                  95
Ser Arg Phe Thr Ile Ser Arg Asp Asn Ser Lys Asn Thr Leu Tyr Leu
                100                 105                 110

Gln Met Asn Ser Leu Arg Ala Glu Asp Thr Ala Val Tyr Tyr Cys Ala
                115                 120                 125

Arg Ala Leu Thr Tyr Tyr Asp Tyr Glu Phe Ala Tyr Trp Gly Gln Gly
                130                 135                 140

Thr Thr Val Thr Val Ser Ser Ala Ser Thr Lys Gly Pro Ser Val Phe
145                 150                 155                 160

Pro Leu Ala Pro Ser Ser Lys Ser Thr Ser Gly Gly Thr Ala Ala Leu
                165                 170                 175

Gly Cys Leu Val Lys Asp Tyr Phe Pro Glu Pro Val Thr Val Ser Trp
                180                 185                 190

Asn Ser Gly Ala Leu Thr Ser Gly Val His Thr Phe Pro Ala Val Leu
                195                 200                 205

Gln Ser Ser Gly Leu Tyr Ser Leu Ser Ser Val Val Thr Val Pro Ser
                210                 215                 220

Ser Ser Leu Gly Thr Gln Thr Tyr Ile Cys Asn Val Asn His Lys Pro
225                 230                 235                 240

Ser Asn Thr Lys Val Asp Lys Lys Val Glu Pro Lys Ser Cys Asp Lys
                245                 250                 255

Thr His Thr Cys Pro Pro Cys Pro Ala Pro Pro Val Ala Gly Pro Ser
                260                 265                 270

Val Phe Leu Phe Pro Pro Lys Pro Lys Asp Thr Leu Met Ile Ser Arg
                275                 280                 285

Thr Pro Glu Val Thr Cys Val Val Val Asp Val Ser His Glu Asp Pro
                290                 295                 300

Glu Val Lys Phe Asn Trp Tyr Val Asp Gly Val Glu Val His Asn Ala
305                 310                 315                 320

Lys Thr Lys Pro Arg Glu Glu Gln Tyr Asn Ser Thr Tyr Arg Val Val
                325                 330                 335

Ser Val Leu Thr Val Leu His Gln Asp Trp Leu Asn Gly Lys Glu Tyr
                340                 345                 350

Lys Cys Lys Val Ser Asn Lys Gly Leu Pro Ser Ser Ile Glu Lys Thr
                355                 360                 365

Ile Ser Lys Ala Lys Gly Gln Pro Arg Glu Pro Gln Val Tyr Thr Leu
                370                 375                 380

Pro Pro Ser Arg Asp Glu Leu Thr Lys Asn Gln Val Ser Leu Thr Cys
385                 390                 395                 400

Leu Val Lys Gly Phe Tyr Pro Ser Asp Ile Ala Val Glu Trp Glu Ser
                405                 410                 415

Asn Gly Gln Pro Glu Asn Asn Tyr Lys Thr Thr Pro Pro Val Leu Asp
                420                 425                 430

Ser Asp Gly Ser Phe Phe Leu Tyr Ser Lys Leu Thr Val Asp Lys Ser
                435                 440                 445

Arg Trp Gln Gln Gly Asn Val Phe Ser Cys Ser Val Met His Glu Ala
                450                 455                 460

Leu His Asn His Tyr Thr Gln Lys Ser Leu Ser Leu Ser Pro Gly Lys
465                 470                 475                 480

Ala Ala Gly Asn Gly Thr Ser Asn Gly Thr Ser Glu Phe Gly Gly Ala
                485                 490                 495

Ala Ala His Ile Thr Gly Thr Arg Gly Arg Ser Asn Thr Leu Ser Ser
                500                 505                 510
```

```
Pro Asn Ser Lys Asn Glu Lys Ala Leu Gly Arg Lys Ile Asn Ser Trp
        515                 520                 525

Glu Ser Ser Arg Ser Gly His Ser Phe Leu Ser Asn Leu His Leu Arg
        530                 535                 540

Asn Gly Glu Leu Val Ile His Glu Lys Gly Phe Tyr Tyr Ile Tyr Ser
545                 550                 555                 560

Gln Thr Tyr Phe Arg Phe Gln Glu Glu Ile Lys Glu Asn Thr Lys Asn
                565                 570                 575

Asp Lys Gln Met Val Gln Tyr Ile Tyr Lys Tyr Thr Ser Tyr Pro Asp
            580                 585                 590

Pro Ile Leu Leu Met Lys Ser Ala Arg Asn Ser Cys Trp Ser Lys Asp
        595                 600                 605

Ala Glu Tyr Gly Leu Tyr Ser Ile Tyr Gln Gly Gly Ile Phe Glu Leu
        610                 615                 620

Lys Glu Asn Asp Arg Ile Phe Val Ser Val Thr Asn Glu His Leu Ile
625                 630                 635                 640

Asp Met Asp His Glu Ala Ser Phe Phe Gly Ala Phe Ala Val Ser Gly
                645                 650                 655

Ala Ala Ala His Ile Thr Gly Thr Arg Gly Arg Ser Asn Thr Leu Ser
            660                 665                 670

Ser Pro Asn Ser Lys Asn Glu Lys Ala Leu Gly Arg Lys Ile Asn Ser
        675                 680                 685

Trp Glu Ser Ser Arg Ser Gly His Ser Phe Leu Ser Asn Leu His Leu
    690                 695                 700

Arg Asn Gly Glu Leu Val Ile His Glu Lys Gly Phe Tyr Tyr Ile Tyr
705                 710                 715                 720

Ser Gln Thr Tyr Phe Arg Phe Gln Glu Glu Ile Lys Glu Asn Thr Lys
                725                 730                 735

Asn Asp Lys Gln Met Val Gln Tyr Ile Tyr Lys Tyr Thr Ser Tyr Pro
            740                 745                 750

Asp Pro Ile Leu Leu Met Lys Ser Ala Arg Asn Ser Cys Trp Ser Lys
        755                 760                 765

Asp Ala Glu Tyr Gly Leu Tyr Ser Ile Tyr Gln Gly Gly Ile Phe Glu
        770                 775                 780

Leu Lys Glu Asn Asp Arg Ile Phe Val Ser Val Thr Asn Glu His Leu
785                 790                 795                 800

Ile Asp Met Asp His Glu Ala Ser Phe Phe Gly Ala Phe Ala Val Ser
                805                 810                 815

Gly Ala Ala Ala His Ile Thr Gly Thr Arg Gly Arg Ser Asn Thr Leu
            820                 825                 830

Ser Ser Pro Asn Ser Lys Asn Glu Lys Ala Leu Gly Arg Lys Ile Asn
        835                 840                 845

Ser Trp Glu Ser Ser Arg Ser Gly His Ser Phe Leu Ser Asn Leu His
    850                 855                 860

Leu Arg Asn Gly Glu Leu Val Ile His Glu Lys Gly Phe Tyr Tyr Ile
865                 870                 875                 880

Tyr Ser Gln Thr Tyr Phe Arg Phe Gln Glu Glu Ile Lys Glu Asn Thr
                885                 890                 895

Lys Asn Asp Lys Gln Met Val Gln Tyr Ile Tyr Lys Tyr Thr Ser Tyr
            900                 905                 910

Pro Asp Pro Ile Leu Leu Met Lys Ser Ala Arg Asn Ser Cys Trp Ser
        915                 920                 925
```

Lys Asp Ala Glu Tyr Gly Leu Tyr Ser Ile Tyr Gln Gly Gly Ile Phe
930                 935                 940

Glu Leu Lys Glu Asn Asp Arg Ile Phe Val Ser Val Thr Asn Glu His
945                 950                 955                 960

Leu Ile Asp Met Asp His Glu Ala Ser Phe Phe Gly Ala Phe Ala Val
                965                 970                 975

Ser

<210> SEQ ID NO 206
<211> LENGTH: 359
<212> TYPE: PRT
<213> ORGANISM: Artificial Sequence
<220> FEATURE:
<223> OTHER INFORMATION: scFv3M6-EHD2D

<400> SEQUENCE: 206

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

Val Met Ala Trp Val Arg Gln Ala Pro Gly Lys Gly Leu Glu Trp Val
        35                  40                  45

Ser Ser Ile Ser Ser Ser Gly Gly Trp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gly Leu Lys Met Ala Thr Ile Phe Asp Tyr Trp Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Gln Ser Ala Leu Thr Gln Pro Ala Ser Val
    130                 135                 140

Ser Gly Ser Pro Gly Gln Ser Ile Thr Ile Ser Cys Thr Gly Thr Ser
145                 150                 155                 160

Ser Asp Val Gly Ser Tyr Asn Val Val Ser Trp Tyr Gln Gln His Pro
                165                 170                 175

Gly Lys Ala Pro Lys Leu Ile Ile Tyr Glu Val Ser Gln Arg Pro Ser
            180                 185                 190

Gly Val Ser Asn Arg Phe Ser Gly Ser Lys Ser Gly Asn Thr Ala Ser
        195                 200                 205

Leu Thr Ile Ser Gly Leu Gln Thr Glu Asp Glu Ala Asp Tyr Tyr Cys
    210                 215                 220

Ser Ser Tyr Ala Gly Ser Ser Ile Phe Val Ile Phe Gly Gly Gly Thr
225                 230                 235                 240

Lys Val Thr Val Leu Ala Ala Ala Gly Ser Gly Gly Asp Phe Thr
                245                 250                 255

Pro Pro Thr Val Lys Ile Leu Gln Ser Ser Cys Asp Gly Gly His
            260                 265                 270

Phe Pro Pro Thr Ile Gln Leu Leu Cys Leu Val Ser Gly Tyr Thr Pro
        275                 280                 285

Gly Thr Ile Asn Ile Thr Trp Leu Glu Asp Gly Gln Val Met Asp Val
    290                 295                 300

Asp Leu Ser Thr Ala Ser Thr Thr Gln Glu Gly Glu Leu Ala Ser Thr

```
                    305                 310                 315                 320
        Gln Ser Glu Leu Thr Leu Ser Gln Lys His Trp Leu Ser Asp Arg Thr
                            325                 330                 335

Tyr Thr Cys Gln Val Thr Tyr Gln Gly His Thr Phe Glu Asp Ser Thr
                            340                 345                 350

Lys Lys Cys Ala Asp Ser Asn
                    355

<210> SEQ ID NO 207
<211> LENGTH: 8
<212> TYPE: PRT
<213> ORGANISM: Homo sapiens

<400> SEQUENCE: 207

Gly Gly Gly Gly Ser Gly Gly Gly
1               5

<210> SEQ ID NO 208
<211> LENGTH: 10
<212> TYPE: PRT
<213> ORGANISM: Homo sapiens

<400> SEQUENCE: 208

Gly Gly Gly Gly Ser Gly Gly Gly Gly Ser
1               5                   10

<210> SEQ ID NO 209
<211> LENGTH: 996
<212> TYPE: PRT
<213> ORGANISM: Homo sapiens

<400> SEQUENCE: 209

Asp Tyr Lys Asp Asp Asp Asp Lys Gly Gly Gly Gly Ser Gly Thr Glu
1               5                   10                  15

Val Gln Leu Val Glu Ser Gly Gly Gly Leu Val Gln Pro Gly Gly Ser
                20                  25                  30

Leu Arg Leu Ser Cys Ala Ala Ser Gly Phe Ser Leu Thr Asn Tyr Gly
            35                  40                  45

Val His Trp Val Arg Gln Ala Pro Gly Lys Gly Leu Glu Trp Leu Gly
        50                  55                  60

Val Ile Trp Ser Gly Gly Asn Thr Asp Tyr Asn Thr Pro Phe Thr Ser
65                  70                  75                  80

Arg Phe Thr Ile Ser Arg Asp Asn Ser Lys Asn Thr Leu Tyr Leu Gln
                85                  90                  95

Met Asn Ser Leu Arg Ala Glu Asp Thr Ala Val Tyr Tyr Cys Ala Arg
            100                 105                 110

Ala Leu Thr Tyr Tyr Asp Tyr Glu Phe Ala Tyr Trp Gly Gln Gly Thr
        115                 120                 125

Thr Val Thr Val Ser Ser Gly Gly Gly Ser Gly Gly Gly Gly Ser
        130                 135                 140

Gly Gly Gly Gly Ser Asp Ile Gln Leu Thr Gln Ser Pro Ser Phe Leu
145                 150                 155                 160

Ser Ala Ser Val Gly Asp Arg Val Thr Ile Thr Cys Arg Ala Ser Gln
                165                 170                 175

Ser Ile Gly Thr Asn Ile His Trp Tyr Gln Gln Lys Pro Gly Lys Ala
            180                 185                 190

Pro Lys Leu Leu Ile Lys Tyr Ala Ser Glu Ser Ile Ser Gly Val Pro
        195                 200                 205
```

```
Ser Arg Phe Ser Gly Ser Gly Ser Gly Thr Glu Phe Thr Leu Thr Ile
    210                 215                 220

Ser Ser Leu Gln Pro Glu Asp Phe Ala Thr Tyr Tyr Cys Gln Gln Asn
225                 230                 235                 240

Asn Asn Trp Pro Thr Thr Phe Gly Ala Gly Thr Lys Leu Glu Ile Lys
                245                 250                 255

Arg Ala Ala Ala Gly Ser Gly Gly Asp Lys Thr His Thr Cys Pro
                260                 265                 270

Pro Cys Pro Ala Pro Glu Leu Leu Gly Gly Pro Ser Val Phe Leu Phe
            275                 280                 285

Pro Pro Lys Pro Lys Asp Thr Leu Met Ile Ser Arg Thr Pro Glu Val
290                 295                 300

Thr Cys Val Val Val Asp Val Ser His Glu Asp Pro Glu Val Lys Phe
305                 310                 315                 320

Asn Trp Tyr Val Asp Gly Val Glu Val His Asn Ala Lys Thr Lys Pro
                325                 330                 335

Arg Glu Glu Gln Tyr Asn Ser Thr Tyr Arg Val Val Ser Val Leu Thr
                340                 345                 350

Val Leu His Gln Asp Trp Leu Asn Gly Lys Glu Tyr Lys Cys Lys Val
            355                 360                 365

Ser Asn Lys Ala Leu Pro Ala Pro Ile Glu Lys Thr Ile Ser Lys Ala
370                 375                 380

Lys Gly Gln Pro Arg Glu Pro Gln Val Tyr Thr Leu Pro Pro Ser Arg
385                 390                 395                 400

Asp Glu Leu Thr Lys Asn Gln Val Ser Leu Thr Cys Leu Val Lys Gly
                405                 410                 415

Phe Tyr Pro Ser Asp Ile Ala Val Glu Trp Glu Ser Asn Gly Gln Pro
                420                 425                 430

Glu Asn Asn Tyr Lys Thr Thr Pro Pro Val Leu Asp Ser Asp Gly Ser
            435                 440                 445

Phe Phe Leu Tyr Ser Lys Leu Thr Val Asp Lys Ser Arg Trp Gln Gln
450                 455                 460

Gly Asn Val Phe Ser Cys Ser Val Met His Glu Ala Leu His Asn His
465                 470                 475                 480

Tyr Thr Gln Lys Ser Leu Ser Leu Ser Pro Gly Gln Gly Gly Ser Gly
                485                 490                 495

Gly Gly Ser Ser Gly Gly Gly Pro Gln Arg Val Ala Ala His Ile Thr
            500                 505                 510

Gly Thr Arg Gly Arg Ser Asn Thr Leu Ser Ser Pro Asn Ser Lys Asn
            515                 520                 525

Glu Lys Ala Leu Gly Arg Lys Ile Asn Ser Trp Glu Ser Ser Arg Ser
530                 535                 540

Gly His Ser Phe Leu Ser Asn Leu His Leu Arg Asn Gly Glu Leu Val
545                 550                 555                 560

Ile His Glu Lys Gly Phe Tyr Tyr Ile Tyr Ser Gln Thr Tyr Phe Arg
                565                 570                 575

Phe Gln Glu Glu Ile Lys Glu Asn Thr Lys Asn Asp Lys Gln Met Val
            580                 585                 590

Gln Tyr Ile Tyr Lys Tyr Thr Ser Tyr Pro Asp Pro Ile Leu Leu Met
            595                 600                 605

Lys Ser Ala Arg Asn Ser Cys Trp Ser Lys Asp Ala Glu Tyr Gly Leu
610                 615                 620
```

-continued

Tyr Ser Ile Tyr Gln Gly Gly Ile Phe Glu Leu Lys Glu Asn Asp Arg
625                 630                 635                 640

Ile Phe Val Ser Val Thr Asn Glu His Leu Ile Asp Met Asp His Glu
            645                 650                 655

Ala Ser Phe Phe Gly Ala Phe Leu Val Gly Gly Pro Gln Arg Val
        660                 665                 670

Ala Ala His Ile Thr Gly Thr Arg Gly Arg Ser Asn Thr Leu Ser Ser
            675                 680                 685

Pro Asn Ser Lys Asn Glu Lys Ala Leu Gly Arg Lys Ile Asn Ser Trp
690                 695                 700

Glu Ser Ser Arg Ser Gly His Ser Phe Leu Ser Asn Leu His Leu Arg
705                 710                 715                 720

Asn Gly Glu Leu Val Ile His Glu Lys Gly Phe Tyr Tyr Ile Tyr Ser
                725                 730                 735

Gln Thr Tyr Phe Arg Phe Gln Glu Glu Ile Lys Glu Asn Thr Lys Asn
            740                 745                 750

Asp Lys Gln Met Val Gln Tyr Ile Tyr Lys Tyr Thr Ser Tyr Pro Asp
        755                 760                 765

Pro Ile Leu Leu Met Lys Ser Ala Arg Asn Ser Cys Trp Ser Lys Asp
770                 775                 780

Ala Glu Tyr Gly Leu Tyr Ser Ile Tyr Gln Gly Gly Ile Phe Glu Leu
785                 790                 795                 800

Lys Glu Asn Asp Arg Ile Phe Val Ser Val Thr Asn Glu His Leu Ile
                805                 810                 815

Asp Met Asp His Glu Ala Ser Phe Phe Gly Ala Phe Leu Val Gly Gly
            820                 825                 830

Gly Pro Gln Arg Val Ala Ala His Ile Thr Gly Thr Arg Gly Arg Ser
        835                 840                 845

Asn Thr Leu Ser Ser Pro Asn Ser Lys Asn Glu Lys Ala Leu Gly Arg
850                 855                 860

Lys Ile Asn Ser Trp Glu Ser Ser Arg Ser Gly His Ser Phe Leu Ser
865                 870                 875                 880

Asn Leu His Leu Arg Asn Gly Glu Leu Val Ile His Glu Lys Gly Phe
                885                 890                 895

Tyr Tyr Ile Tyr Ser Gln Thr Tyr Phe Arg Phe Gln Glu Glu Ile Lys
            900                 905                 910

Glu Asn Thr Lys Asn Asp Lys Gln Met Val Gln Tyr Ile Tyr Lys Tyr
        915                 920                 925

Thr Ser Tyr Pro Asp Pro Ile Leu Leu Met Lys Ser Ala Arg Asn Ser
930                 935                 940

Cys Trp Ser Lys Asp Ala Glu Tyr Gly Leu Tyr Ser Ile Tyr Gln Gly
945                 950                 955                 960

Gly Ile Phe Glu Leu Lys Glu Asn Asp Arg Ile Phe Val Ser Val Thr
                965                 970                 975

Asn Glu His Leu Ile Asp Met Asp His Glu Ala Ser Phe Phe Gly Ala
            980                 985                 990

Phe Leu Val Gly
        995

<210> SEQ ID NO 210
<211> LENGTH: 746
<212> TYPE: PRT
<213> ORGANISM: Homo sapiens

<400> SEQUENCE: 210

```
Asp Tyr Lys Asp Asp Asp Lys Gly Gly Gly Ser Gly Thr Asp
 1               5                  10                 15

Lys Thr His Thr Cys Pro Cys Pro Ala Pro Glu Leu Leu Gly Gly
             20                  25              30

Pro Ser Val Phe Leu Phe Pro Pro Lys Pro Lys Asp Thr Leu Met Ile
             35                  40                 45

Ser Arg Thr Pro Glu Val Thr Cys Val Val Asp Val Ser His Glu
     50                  55                  60

Asp Pro Glu Val Lys Phe Asn Trp Tyr Val Asp Gly Val Glu Val His
 65                  70                  75                  80

Asn Ala Lys Thr Lys Pro Arg Glu Glu Gln Tyr Asn Ser Thr Tyr Arg
                 85                  90                  95

Val Val Ser Val Leu Thr Val Leu His Gln Asp Trp Leu Asn Gly Lys
                 100                 105                 110

Glu Tyr Lys Cys Lys Val Ser Asn Lys Ala Leu Pro Ala Pro Ile Glu
             115                 120                 125

Lys Thr Ile Ser Lys Ala Lys Gly Gln Pro Arg Glu Pro Gln Val Tyr
     130                 135                 140

Thr Leu Pro Pro Ser Arg Asp Glu Leu Thr Lys Asn Gln Val Ser Leu
145                 150                 155                 160

Thr Cys Leu Val Lys Gly Phe Tyr Pro Ser Asp Ile Ala Val Glu Trp
                 165                 170                 175

Glu Ser Asn Gly Gln Pro Glu Asn Asn Tyr Lys Thr Thr Pro Pro Val
             180                 185                 190

Leu Asp Ser Asp Gly Ser Phe Phe Leu Tyr Ser Lys Leu Thr Val Asp
     195                 200                 205

Lys Ser Arg Trp Gln Gln Gly Asn Val Phe Ser Cys Ser Val Met His
210                 215                 220

Glu Ala Leu His Asn His Tyr Thr Gln Lys Ser Leu Ser Leu Ser Pro
225                 230                 235                 240

Gly Gln Gly Gly Ser Gly Gly Ser Ser Gly Gly Pro Gln Arg
                 245                 250                 255

Val Ala Ala His Ile Thr Gly Thr Arg Gly Arg Ser Asn Thr Leu Ser
                 260                 265                 270

Ser Pro Asn Ser Lys Asn Glu Lys Ala Leu Gly Arg Lys Ile Asn Ser
     275                 280                 285

Trp Glu Ser Ser Arg Ser Gly His Ser Phe Leu Ser Asn Leu His Leu
             290                 295                 300

Arg Asn Gly Glu Leu Val Ile His Glu Lys Gly Phe Tyr Tyr Ile Tyr
305                 310                 315                 320

Ser Gln Thr Tyr Phe Arg Phe Gln Glu Glu Ile Lys Glu Asn Thr Lys
                 325                 330                 335

Asn Asp Lys Gln Met Val Gln Tyr Ile Tyr Lys Tyr Thr Ser Tyr Pro
             340                 345                 350

Asp Pro Ile Leu Leu Met Lys Ser Ala Arg Asn Ser Cys Trp Ser Lys
         355                 360                 365

Asp Ala Glu Tyr Gly Leu Tyr Ser Ile Tyr Gln Gly Gly Ile Phe Glu
     370                 375                 380

Leu Lys Glu Asn Asp Arg Ile Phe Val Ser Val Thr Asn Glu His Leu
385                 390                 395                 400

Ile Asp Met Asp His Glu Ala Ser Phe Phe Gly Ala Phe Leu Val Gly
                 405                 410                 415
```

```
Gly Gly Pro Gln Arg Val Ala Ala His Ile Thr Gly Thr Arg Gly Arg
            420                 425                 430

Ser Asn Thr Leu Ser Ser Pro Asn Ser Lys Asn Glu Lys Ala Leu Gly
            435                 440                 445

Arg Lys Ile Asn Ser Trp Glu Ser Ser Arg Ser Gly His Ser Phe Leu
        450                 455                 460

Ser Asn Leu His Leu Arg Asn Gly Glu Leu Val Ile His Glu Lys Gly
465                 470                 475                 480

Phe Tyr Tyr Ile Tyr Ser Gln Thr Tyr Phe Arg Phe Gln Glu Glu Ile
                    485                 490                 495

Lys Glu Asn Thr Lys Asn Asp Lys Gln Met Val Gln Tyr Ile Tyr Lys
            500                 505                 510

Tyr Thr Ser Tyr Pro Asp Pro Ile Leu Leu Met Lys Ser Ala Arg Asn
        515                 520                 525

Ser Cys Trp Ser Lys Asp Ala Glu Tyr Gly Leu Tyr Ser Ile Tyr Gln
        530                 535                 540

Gly Gly Ile Phe Glu Leu Lys Glu Asn Asp Arg Ile Phe Val Ser Val
545                 550                 555                 560

Thr Asn Glu His Leu Ile Asp Met Asp His Glu Ala Ser Phe Phe Gly
                565                 570                 575

Ala Phe Leu Val Gly Gly Pro Gln Arg Val Ala Ala His Ile Thr
            580                 585                 590

Gly Thr Arg Gly Arg Ser Asn Thr Leu Ser Ser Pro Asn Ser Lys Asn
        595                 600                 605

Glu Lys Ala Leu Gly Arg Lys Ile Asn Ser Trp Glu Ser Ser Arg Ser
610                 615                 620

Gly His Ser Phe Leu Ser Asn Leu His Leu Arg Asn Gly Glu Leu Val
625                 630                 635                 640

Ile His Glu Lys Gly Phe Tyr Tyr Ile Tyr Ser Gln Thr Tyr Phe Arg
                645                 650                 655

Phe Gln Glu Glu Ile Lys Glu Asn Thr Lys Asn Asp Lys Gln Met Val
            660                 665                 670

Gln Tyr Ile Tyr Lys Tyr Thr Ser Tyr Pro Asp Pro Ile Leu Leu Met
        675                 680                 685

Lys Ser Ala Arg Asn Ser Cys Trp Ser Lys Asp Ala Glu Tyr Gly Leu
        690                 695                 700

Tyr Ser Ile Tyr Gln Gly Gly Ile Phe Glu Leu Lys Glu Asn Asp Arg
705                 710                 715                 720

Ile Phe Val Ser Val Thr Asn Glu His Leu Ile Asp Met Asp His Glu
                725                 730                 735

Ala Ser Phe Phe Gly Ala Phe Leu Val Gly
            740                 745

<210> SEQ ID NO 211
<211> LENGTH: 997
<212> TYPE: PRT
<213> ORGANISM: Homo sapiens

<400> SEQUENCE: 211

Asp Tyr Lys Asp Asp Asp Asp Lys Gly Gly Gly Gly Ser Gly Thr Glu
1               5                   10                  15

Val Gln Leu Val Glu Ser Gly Gly Gly Leu Val Gln Pro Gly Gly Ser
            20                  25                  30

Leu Arg Leu Ser Cys Ala Ala Ser Gly Phe Asn Ile Lys Asp Thr Tyr
        35                  40                  45
```

```
Ile His Trp Val Arg Gln Ala Pro Gly Lys Gly Leu Glu Trp Val Ala
 50                  55                  60

Arg Ile Tyr Pro Thr Asn Gly Tyr Thr Arg Tyr Ala Asp Ser Val Lys
 65                  70                  75                  80

Gly Arg Phe Thr Ile Ser Ala Asp Thr Ser Lys Asn Thr Ala Tyr Leu
                 85                  90                  95

Gln Met Asn Ser Leu Arg Ala Glu Asp Thr Ala Val Tyr Tyr Cys Ser
                100                 105                 110

Arg Trp Gly Gly Asp Gly Phe Tyr Ala Met Asp Tyr Trp Gly Gln Gly
            115                 120                 125

Thr Leu Val Thr Val Ser Gly Gly Gly Ser Gly Gly Gly Gly
        130                 135                 140

Ser Gly Gly Gly Gly Ser Asp Ile Gln Met Thr Gln Ser Pro Ser Ser
145                 150                 155                 160

Leu Ser Ala Ser Val Gly Asp Arg Val Thr Ile Thr Cys Arg Ala Ser
                165                 170                 175

Gln Asp Val Asn Thr Ala Val Ala Trp Tyr Gln Gln Lys Pro Gly Lys
                180                 185                 190

Ala Pro Lys Leu Leu Ile Tyr Ser Ala Ser Phe Leu Tyr Ser Gly Val
            195                 200                 205

Pro Ser Arg Phe Ser Gly Ser Arg Ser Gly Thr Asp Phe Thr Leu Thr
210                 215                 220

Ile Ser Ser Leu Gln Pro Glu Asp Phe Ala Thr Tyr Tyr Cys Gln Gln
225                 230                 235                 240

His Tyr Thr Thr Pro Pro Thr Phe Gly Gln Gly Thr Lys Val Glu Ile
                245                 250                 255

Lys Arg Ala Ala Ala Gly Gly Ser Gly Gly Asp Lys Thr His Thr Cys
            260                 265                 270

Pro Pro Cys Pro Ala Pro Glu Leu Leu Gly Gly Pro Ser Val Phe Leu
        275                 280                 285

Phe Pro Pro Lys Pro Lys Asp Thr Leu Met Ile Ser Arg Thr Pro Glu
    290                 295                 300

Val Thr Cys Val Val Val Asp Val Ser His Glu Asp Pro Glu Val Lys
305                 310                 315                 320

Phe Asn Trp Tyr Val Asp Gly Val Glu Val His Asn Ala Lys Thr Lys
                325                 330                 335

Pro Arg Glu Glu Gln Tyr Asn Ser Thr Tyr Arg Val Val Ser Val Leu
            340                 345                 350

Thr Val Leu His Gln Asp Trp Leu Asn Gly Lys Glu Tyr Lys Cys Lys
        355                 360                 365

Val Ser Asn Lys Ala Leu Pro Ala Pro Ile Glu Lys Thr Ile Ser Lys
    370                 375                 380

Ala Lys Gly Gln Pro Arg Glu Pro Gln Val Tyr Thr Leu Pro Pro Ser
385                 390                 395                 400

Arg Asp Glu Leu Thr Lys Asn Gln Val Ser Leu Thr Cys Leu Val Lys
                405                 410                 415

Gly Phe Tyr Pro Ser Asp Ile Ala Val Glu Trp Glu Ser Asn Gly Gln
            420                 425                 430

Pro Glu Asn Asn Tyr Lys Thr Thr Pro Pro Val Leu Asp Ser Asp Gly
        435                 440                 445

Ser Phe Phe Leu Tyr Ser Lys Leu Thr Val Asp Lys Ser Arg Trp Gln
450                 455                 460
```

```
Gln Gly Asn Val Phe Ser Cys Ser Val Met His Glu Ala Leu His Asn
465                 470                 475                 480

His Tyr Thr Gln Lys Ser Leu Ser Leu Ser Pro Gly Gln Gly Gly Ser
        485                 490                 495

Gly Gly Gly Ser Ser Gly Gly Gly Pro Gln Arg Val Ala Ala His Ile
            500                 505                 510

Thr Gly Thr Arg Gly Arg Ser Asn Thr Leu Ser Ser Pro Asn Ser Lys
        515                 520                 525

Asn Glu Lys Ala Leu Gly Arg Lys Ile Asn Ser Trp Glu Ser Ser Arg
    530                 535                 540

Ser Gly His Ser Phe Leu Ser Asn Leu His Leu Arg Asn Gly Glu Leu
545                 550                 555                 560

Val Ile His Glu Lys Gly Phe Tyr Tyr Ile Tyr Ser Gln Thr Tyr Phe
            565                 570                 575

Arg Phe Gln Glu Glu Ile Lys Glu Asn Thr Lys Asn Asp Lys Gln Met
        580                 585                 590

Val Gln Tyr Ile Tyr Lys Tyr Thr Ser Tyr Pro Asp Pro Ile Leu Leu
    595                 600                 605

Met Lys Ser Ala Arg Asn Ser Cys Trp Ser Lys Asp Ala Glu Tyr Gly
610                 615                 620

Leu Tyr Ser Ile Tyr Gln Gly Gly Ile Phe Glu Leu Lys Glu Asn Asp
625                 630                 635                 640

Arg Ile Phe Val Ser Val Thr Asn Glu His Leu Ile Asp Met Asp His
            645                 650                 655

Glu Ala Ser Phe Phe Gly Ala Phe Leu Val Gly Gly Pro Gln Arg
            660                 665                 670

Val Ala Ala His Ile Thr Gly Thr Arg Gly Arg Ser Asn Thr Leu Ser
            675                 680                 685

Ser Pro Asn Ser Lys Asn Glu Lys Ala Leu Gly Arg Lys Ile Asn Ser
            690                 695                 700

Trp Glu Ser Ser Arg Ser Gly His Ser Phe Leu Ser Asn Leu His Leu
705                 710                 715                 720

Arg Asn Gly Glu Leu Val Ile His Glu Lys Gly Phe Tyr Tyr Ile Tyr
                725                 730                 735

Ser Gln Thr Tyr Phe Arg Phe Gln Glu Glu Ile Lys Glu Asn Thr Lys
            740                 745                 750

Asn Asp Lys Gln Met Val Gln Tyr Ile Tyr Lys Tyr Thr Ser Tyr Pro
            755                 760                 765

Asp Pro Ile Leu Leu Met Lys Ser Ala Arg Asn Ser Cys Trp Ser Lys
770                 775                 780

Asp Ala Glu Tyr Gly Leu Tyr Ser Ile Tyr Gln Gly Gly Ile Phe Glu
785                 790                 795                 800

Leu Lys Glu Asn Asp Arg Ile Phe Val Ser Val Thr Asn Glu His Leu
            805                 810                 815

Ile Asp Met Asp His Glu Ala Ser Phe Phe Gly Ala Phe Leu Val Gly
            820                 825                 830

Gly Gly Pro Gln Arg Val Ala Ala His Ile Thr Gly Thr Arg Gly Arg
            835                 840                 845

Ser Asn Thr Leu Ser Ser Pro Asn Ser Lys Asn Glu Lys Ala Leu Gly
            850                 855                 860

Arg Lys Ile Asn Ser Trp Glu Ser Ser Arg Ser Gly His Ser Phe Leu
865                 870                 875                 880

Ser Asn Leu His Leu Arg Asn Gly Glu Leu Val Ile His Glu Lys Gly
```

```
                        885                 890                 895
Phe Tyr Tyr Ile Tyr Ser Gln Thr Tyr Phe Arg Phe Gln Glu Glu Ile
                    900                 905                 910

Lys Glu Asn Thr Lys Asn Asp Lys Gln Met Val Gln Tyr Ile Tyr Lys
                915                 920                 925

Tyr Thr Ser Tyr Pro Asp Pro Ile Leu Leu Met Lys Ser Ala Arg Asn
            930                 935                 940

Ser Cys Trp Ser Lys Asp Ala Glu Tyr Gly Leu Tyr Ser Ile Tyr Gln
945                 950                 955                 960

Gly Gly Ile Phe Glu Leu Lys Glu Asn Asp Arg Ile Phe Val Ser Val
                965                 970                 975

Thr Asn Glu His Leu Ile Asp Met Asp His Glu Ala Ser Phe Phe Gly
            980                 985                 990

Ala Phe Leu Val Gly
            995

<210> SEQ ID NO 212
<211> LENGTH: 545
<212> TYPE: PRT
<213> ORGANISM: Artificial Sequence
<220> FEATURE:
<223> OTHER INFORMATION: Fusion protein scTRAIL3-FLVGGGGSVRERGPQRVA

<400> SEQUENCE: 212

Met Asp Trp Thr Trp Arg Val Phe Cys Leu Leu Ala Val Ala Pro Gly
1               5                   10                  15

Ala His Ser Leu Asp Asp Tyr Lys Asp Asp Asp Lys Glu Phe Gly
            20                  25                  30

Gly Val Arg Glu Arg Gly Pro Gln Arg Val Ala Ala His Ile Thr Gly
        35                  40                  45

Thr Arg Gly Arg Ser Asn Thr Leu Ser Ser Pro Asn Ser Lys Asn Glu
    50                  55                  60

Lys Ala Leu Gly Arg Lys Ile Asn Ser Trp Glu Ser Ser Arg Ser Gly
65                  70                  75                  80

His Ser Phe Leu Ser Asn Leu His Leu Arg Asn Gly Glu Leu Val Ile
                85                  90                  95

His Glu Lys Gly Phe Tyr Tyr Ile Tyr Ser Gln Thr Tyr Phe Arg Phe
            100                 105                 110

Gln Glu Glu Ile Lys Glu Asn Thr Lys Asn Asp Lys Gln Met Val Gln
        115                 120                 125

Tyr Ile Tyr Lys Tyr Thr Ser Tyr Pro Asp Pro Ile Leu Leu Met Lys
    130                 135                 140

Ser Ala Arg Asn Ser Cys Trp Ser Lys Asp Ala Glu Tyr Gly Leu Tyr
145                 150                 155                 160

Ser Ile Tyr Gln Gly Gly Ile Phe Glu Leu Lys Glu Asn Asp Arg Ile
                165                 170                 175

Phe Val Ser Val Thr Asn Glu His Leu Ile Asp Met Asp His Glu Ala
            180                 185                 190

Ser Phe Phe Gly Ala Phe Leu Val Gly Gly Gly Ser Val Arg Glu
        195                 200                 205

Arg Gly Pro Gln Arg Val Ala Ala His Ile Thr Gly Thr Arg Gly Arg
    210                 215                 220

Ser Asn Thr Leu Ser Ser Pro Asn Ser Lys Asn Glu Lys Ala Leu Gly
225                 230                 235                 240

Arg Lys Ile Asn Ser Trp Glu Ser Ser Arg Ser Gly His Ser Phe Leu
```

```
                245                 250                 255
Ser Asn Leu His Leu Arg Asn Gly Glu Leu Val Ile His Glu Lys Gly
            260                 265                 270

Phe Tyr Tyr Ile Tyr Ser Gln Thr Tyr Phe Arg Phe Gln Glu Glu Ile
        275                 280                 285

Lys Glu Asn Thr Lys Asn Asp Lys Gln Met Val Gln Tyr Ile Tyr Lys
    290                 295                 300

Tyr Thr Ser Tyr Pro Asp Pro Ile Leu Leu Met Lys Ser Ala Arg Asn
305                 310                 315                 320

Ser Cys Trp Ser Lys Asp Ala Glu Tyr Gly Leu Tyr Ser Ile Tyr Gln
            325                 330                 335

Gly Gly Ile Phe Glu Leu Lys Glu Asn Asp Arg Ile Phe Val Ser Val
        340                 345                 350

Thr Asn Glu His Leu Ile Asp Met Asp His Glu Ala Ser Phe Phe Gly
    355                 360                 365

Ala Phe Leu Val Gly Gly Gly Ser Val Arg Glu Arg Gly Pro Gln
370                 375                 380

Arg Val Ala Ala His Ile Thr Gly Thr Arg Gly Arg Ser Asn Thr Leu
385                 390                 395                 400

Ser Ser Pro Asn Ser Lys Asn Glu Lys Ala Leu Gly Arg Lys Ile Asn
            405                 410                 415

Ser Trp Glu Ser Ser Arg Ser Gly His Ser Phe Leu Ser Asn Leu His
        420                 425                 430

Leu Arg Asn Gly Glu Leu Val Ile His Glu Lys Gly Phe Tyr Tyr Ile
    435                 440                 445

Tyr Ser Gln Thr Tyr Phe Arg Phe Gln Glu Glu Ile Lys Glu Asn Thr
450                 455                 460

Lys Asn Asp Lys Gln Met Val Gln Tyr Ile Tyr Lys Tyr Thr Ser Tyr
465                 470                 475                 480

Pro Asp Pro Ile Leu Leu Met Lys Ser Ala Arg Asn Ser Cys Trp Ser
            485                 490                 495

Lys Asp Ala Glu Tyr Gly Leu Tyr Ser Ile Tyr Gln Gly Gly Ile Phe
        500                 505                 510

Glu Leu Lys Glu Asn Asp Arg Ile Phe Val Ser Val Thr Asn Glu His
    515                 520                 525

Leu Ile Asp Met Asp His Glu Ala Ser Phe Phe Gly Ala Phe Leu Val
    530                 535                 540

Gly
545

<210> SEQ ID NO 213
<211> LENGTH: 553
<212> TYPE: PRT
<213> ORGANISM: Artificial Sequence
<220> FEATURE:
<223> OTHER INFORMATION: fusion protein scTRAIL3-FLVGGGGSGGGSVRERGPQRVA

<400> SEQUENCE: 213

Met Asp Trp Thr Trp Arg Val Phe Cys Leu Leu Ala Val Ala Pro Gly
1               5                   10                  15

Ala His Ser Leu Asp Asp Tyr Lys Asp Asp Asp Lys Glu Phe Gly
            20                  25                  30

Gly Val Arg Glu Arg Gly Pro Gln Arg Val Ala Ala His Ile Thr Gly
        35                  40                  45

Thr Arg Gly Arg Ser Asn Thr Leu Ser Ser Pro Asn Ser Lys Asn Glu
```

-continued

```
                50                  55                  60
Lys Ala Leu Gly Arg Lys Ile Asn Ser Trp Glu Ser Ser Arg Ser Gly
 65                  70                  75                  80

His Ser Phe Leu Ser Asn Leu His Leu Arg Asn Gly Glu Leu Val Ile
                 85                  90                  95

His Glu Lys Gly Phe Tyr Tyr Ile Tyr Ser Gln Thr Tyr Phe Arg Phe
                100                 105                 110

Gln Glu Glu Ile Lys Glu Asn Thr Lys Asn Asp Lys Gln Met Val Gln
                115                 120                 125

Tyr Ile Tyr Lys Tyr Thr Ser Tyr Pro Asp Pro Ile Leu Leu Met Lys
130                 135                 140

Ser Ala Arg Asn Ser Cys Trp Ser Lys Asp Ala Glu Tyr Gly Leu Tyr
145                 150                 155                 160

Ser Ile Tyr Gln Gly Gly Ile Phe Glu Leu Lys Glu Asn Asp Arg Ile
                165                 170                 175

Phe Val Ser Val Thr Asn Glu His Leu Ile Asp Met Asp His Glu Ala
                180                 185                 190

Ser Phe Phe Gly Ala Phe Leu Val Gly Gly Gly Ser Gly Gly Gly
                195                 200                 205

Ser Val Arg Glu Arg Gly Pro Gln Arg Val Ala Ala His Ile Thr Gly
210                 215                 220

Thr Arg Gly Arg Ser Asn Thr Leu Ser Ser Pro Asn Ser Lys Asn Glu
225                 230                 235                 240

Lys Ala Leu Gly Arg Lys Ile Asn Ser Trp Glu Ser Ser Arg Ser Gly
                245                 250                 255

His Ser Phe Leu Ser Asn Leu His Leu Arg Asn Gly Glu Leu Val Ile
                260                 265                 270

His Glu Lys Gly Phe Tyr Tyr Ile Tyr Ser Gln Thr Tyr Phe Arg Phe
                275                 280                 285

Gln Glu Glu Ile Lys Glu Asn Thr Lys Asn Asp Lys Gln Met Val Gln
                290                 295                 300

Tyr Ile Tyr Lys Tyr Thr Ser Tyr Pro Asp Pro Ile Leu Leu Met Lys
305                 310                 315                 320

Ser Ala Arg Asn Ser Cys Trp Ser Lys Asp Ala Glu Tyr Gly Leu Tyr
                325                 330                 335

Ser Ile Tyr Gln Gly Gly Ile Phe Glu Leu Lys Glu Asn Asp Arg Ile
                340                 345                 350

Phe Val Ser Val Thr Asn Glu His Leu Ile Asp Met Asp His Glu Ala
                355                 360                 365

Ser Phe Phe Gly Ala Phe Leu Val Gly Gly Gly Ser Gly Gly Gly
                370                 375                 380

Ser Val Arg Glu Arg Gly Pro Gln Arg Val Ala Ala His Ile Thr Gly
385                 390                 395                 400

Thr Arg Gly Arg Ser Asn Thr Leu Ser Ser Pro Asn Ser Lys Asn Glu
                405                 410                 415

Lys Ala Leu Gly Arg Lys Ile Asn Ser Trp Glu Ser Ser Arg Ser Gly
                420                 425                 430

His Ser Phe Leu Ser Asn Leu His Leu Arg Asn Gly Glu Leu Val Ile
                435                 440                 445

His Glu Lys Gly Phe Tyr Tyr Ile Tyr Ser Gln Thr Tyr Phe Arg Phe
                450                 455                 460

Gln Glu Glu Ile Lys Glu Asn Thr Lys Asn Asp Lys Gln Met Val Gln
465                 470                 475                 480
```

```
Tyr Ile Tyr Lys Tyr Thr Ser Tyr Pro Asp Pro Ile Leu Leu Met Lys
            485                 490                 495

Ser Ala Arg Asn Ser Cys Trp Ser Lys Asp Ala Glu Tyr Gly Leu Tyr
        500                 505                 510

Ser Ile Tyr Gln Gly Gly Ile Phe Glu Leu Lys Glu Asn Asp Arg Ile
        515                 520                 525

Phe Val Ser Val Thr Asn Glu His Leu Ile Asp Met Asp His Glu Ala
        530                 535                 540

Ser Phe Phe Gly Ala Phe Leu Val Gly
545                 550

<210> SEQ ID NO 214
<211> LENGTH: 527
<212> TYPE: PRT
<213> ORGANISM: Artificial Sequence
<220> FEATURE:
<223> OTHER INFORMATION: scTRAIL3-FLVGGGGSQRVA

<400> SEQUENCE: 214

Met Asp Trp Thr Trp Arg Val Phe Cys Leu Leu Ala Val Ala Pro Gly
1               5                   10                  15

Ala His Ser Leu Asp Asp Tyr Lys Asp Asp Asp Lys Glu Phe Gly
            20                  25                  30

Gly Gln Arg Val Ala Ala His Ile Thr Gly Thr Arg Gly Arg Ser Asn
        35                  40                  45

Thr Leu Ser Ser Pro Asn Ser Lys Asn Glu Lys Ala Leu Gly Arg Lys
    50                  55                  60

Ile Asn Ser Trp Glu Ser Ser Arg Ser Gly His Ser Phe Leu Ser Asn
65                  70                  75                  80

Leu His Leu Arg Asn Gly Glu Leu Val Ile His Glu Lys Gly Phe Tyr
                85                  90                  95

Tyr Ile Tyr Ser Gln Thr Tyr Phe Arg Phe Gln Glu Glu Ile Lys Glu
            100                 105                 110

Asn Thr Lys Asn Asp Lys Gln Met Val Gln Tyr Ile Tyr Lys Tyr Thr
        115                 120                 125

Ser Tyr Pro Asp Pro Ile Leu Leu Met Lys Ser Ala Arg Asn Ser Cys
    130                 135                 140

Trp Ser Lys Asp Ala Glu Tyr Gly Leu Tyr Ser Ile Tyr Gln Gly Gly
145                 150                 155                 160

Ile Phe Glu Leu Lys Glu Asn Asp Arg Ile Phe Val Ser Val Thr Asn
                165                 170                 175

Glu His Leu Ile Asp Met Asp His Glu Ala Ser Phe Phe Gly Ala Phe
            180                 185                 190

Leu Val Gly Gly Gly Ser Gln Arg Val Ala Ala His Ile Thr Gly
            195                 200                 205

Thr Arg Gly Arg Ser Asn Thr Leu Ser Ser Pro Asn Ser Lys Asn Glu
    210                 215                 220

Lys Ala Leu Gly Arg Lys Ile Asn Ser Trp Glu Ser Ser Arg Ser Gly
225                 230                 235                 240

His Ser Phe Leu Ser Asn Leu His Leu Arg Asn Gly Glu Leu Val Ile
                245                 250                 255

His Glu Lys Gly Phe Tyr Tyr Ile Tyr Ser Gln Thr Tyr Phe Arg Phe
            260                 265                 270

Gln Glu Glu Ile Lys Glu Asn Thr Lys Asn Asp Lys Gln Met Val Gln
        275                 280                 285
```

Tyr Ile Tyr Lys Tyr Thr Ser Tyr Pro Asp Pro Ile Leu Met Lys
            290                 295                 300

Ser Ala Arg Asn Ser Cys Trp Ser Lys Asp Ala Glu Tyr Gly Leu Tyr
305                 310                 315                 320

Ser Ile Tyr Gln Gly Gly Ile Phe Glu Leu Lys Glu Asn Asp Arg Ile
                325                 330                 335

Phe Val Ser Val Thr Asn Glu His Leu Ile Asp Met Asp His Glu Ala
            340                 345                 350

Ser Phe Phe Gly Ala Phe Leu Val Gly Gly Gly Ser Gln Arg Val
            355                 360                 365

Ala Ala His Ile Thr Gly Thr Arg Gly Arg Ser Asn Thr Leu Ser Ser
            370                 375                 380

Pro Asn Ser Lys Asn Glu Lys Ala Leu Gly Arg Lys Ile Asn Ser Trp
385                 390                 395                 400

Glu Ser Ser Arg Ser Gly His Ser Phe Leu Ser Asn Leu His Leu Arg
                405                 410                 415

Asn Gly Glu Leu Val Ile His Glu Lys Gly Phe Tyr Tyr Ile Tyr Ser
            420                 425                 430

Gln Thr Tyr Phe Arg Phe Gln Glu Glu Ile Lys Glu Asn Thr Lys Asn
            435                 440                 445

Asp Lys Gln Met Val Gln Tyr Ile Tyr Lys Tyr Thr Ser Tyr Pro Asp
450                 455                 460

Pro Ile Leu Leu Met Lys Ser Ala Arg Asn Ser Cys Trp Ser Lys Asp
465                 470                 475                 480

Ala Glu Tyr Gly Leu Tyr Ser Ile Tyr Gln Gly Gly Ile Phe Glu Leu
                485                 490                 495

Lys Glu Asn Asp Arg Ile Phe Val Ser Val Thr Asn Glu His Leu Ile
            500                 505                 510

Asp Met Asp His Glu Ala Ser Phe Phe Gly Ala Phe Leu Val Gly
            515                 520                 525

<210> SEQ ID NO 215
<211> LENGTH: 535
<212> TYPE: PRT
<213> ORGANISM: Artificial Sequence
<220> FEATURE:
<223> OTHER INFORMATION: fusion protein scTRAIL3-FLVGGGGSGGGSQRVA

<400> SEQUENCE: 215

Met Asp Trp Thr Trp Arg Val Phe Cys Leu Leu Ala Val Ala Pro Gly
1               5                   10                  15

Ala His Ser Leu Asp Asp Tyr Lys Asp Asp Asp Lys Glu Phe Gly
            20                  25                  30

Gly Gln Arg Val Ala Ala His Ile Thr Gly Thr Arg Gly Arg Ser Asn
            35                  40                  45

Thr Leu Ser Ser Pro Asn Ser Lys Asn Glu Lys Ala Leu Gly Arg Lys
        50                  55                  60

Ile Asn Ser Trp Glu Ser Ser Arg Ser Gly His Ser Phe Leu Ser Asn
65                  70                  75                  80

Leu His Leu Arg Asn Gly Glu Leu Val Ile His Glu Lys Gly Phe Tyr
                85                  90                  95

Tyr Ile Tyr Ser Gln Thr Tyr Phe Arg Phe Gln Glu Glu Ile Lys Glu
            100                 105                 110

Asn Thr Lys Asn Asp Lys Gln Met Val Gln Tyr Ile Tyr Lys Tyr Thr
        115                 120                 125

-continued

```
Ser Tyr Pro Asp Pro Ile Leu Leu Met Lys Ser Ala Arg Asn Ser Cys
    130                 135                 140

Trp Ser Lys Asp Ala Glu Tyr Gly Leu Tyr Ser Ile Tyr Gln Gly Gly
145                 150                 155                 160

Ile Phe Glu Leu Lys Glu Asn Asp Arg Ile Phe Val Ser Val Thr Asn
                165                 170                 175

Glu His Leu Ile Asp Met Asp His Glu Ala Ser Phe Phe Gly Ala Phe
                180                 185                 190

Leu Val Gly Gly Gly Ser Gly Gly Gly Ser Gln Arg Val Ala Ala
            195                 200                 205

His Ile Thr Gly Thr Arg Gly Arg Ser Asn Thr Leu Ser Ser Pro Asn
    210                 215                 220

Ser Lys Asn Glu Lys Ala Leu Gly Arg Lys Ile Asn Ser Trp Glu Ser
225                 230                 235                 240

Ser Arg Ser Gly His Ser Phe Leu Ser Asn Leu His Leu Arg Asn Gly
                245                 250                 255

Glu Leu Val Ile His Glu Lys Gly Phe Tyr Tyr Ile Tyr Ser Gln Thr
                260                 265                 270

Tyr Phe Arg Phe Gln Glu Glu Ile Lys Glu Asn Thr Lys Asn Asp Lys
            275                 280                 285

Gln Met Val Gln Tyr Ile Tyr Lys Tyr Thr Ser Tyr Pro Asp Pro Ile
    290                 295                 300

Leu Leu Met Lys Ser Ala Arg Asn Ser Cys Trp Ser Lys Asp Ala Glu
305                 310                 315                 320

Tyr Gly Leu Tyr Ser Ile Tyr Gln Gly Gly Ile Phe Glu Leu Lys Glu
                325                 330                 335

Asn Asp Arg Ile Phe Val Ser Val Thr Asn Glu His Leu Ile Asp Met
            340                 345                 350

Asp His Glu Ala Ser Phe Phe Gly Ala Phe Leu Val Gly Gly Gly Gly
    355                 360                 365

Ser Gly Gly Gly Ser Gln Arg Val Ala Ala His Ile Thr Gly Thr Arg
    370                 375                 380

Gly Arg Ser Asn Thr Leu Ser Ser Pro Asn Ser Lys Asn Glu Lys Ala
385                 390                 395                 400

Leu Gly Arg Lys Ile Asn Ser Trp Glu Ser Ser Arg Ser Gly His Ser
                405                 410                 415

Phe Leu Ser Asn Leu His Leu Arg Asn Gly Glu Leu Val Ile His Glu
            420                 425                 430

Lys Gly Phe Tyr Tyr Ile Tyr Ser Gln Thr Tyr Phe Arg Phe Gln Glu
    435                 440                 445

Glu Ile Lys Glu Asn Thr Lys Asn Asp Lys Gln Met Val Gln Tyr Ile
    450                 455                 460

Tyr Lys Tyr Thr Ser Tyr Pro Asp Pro Ile Leu Leu Met Lys Ser Ala
465                 470                 475                 480

Arg Asn Ser Cys Trp Ser Lys Asp Ala Glu Tyr Gly Leu Tyr Ser Ile
                485                 490                 495

Tyr Gln Gly Gly Ile Phe Glu Leu Lys Glu Asn Asp Arg Ile Phe Val
            500                 505                 510

Ser Val Thr Asn Glu His Leu Ile Asp Met Asp His Glu Ala Ser Phe
    515                 520                 525

Phe Gly Ala Phe Leu Val Gly
    530                 535
```

<210> SEQ ID NO 216
<211> LENGTH: 525
<212> TYPE: PRT
<213> ORGANISM: Artificial Sequence
<220> FEATURE:
<223> OTHER INFORMATION: fusion protein scTRAIL3-FLVGGPQRVA

<400> SEQUENCE: 216

```
Met Asp Trp Thr Trp Arg Val Phe Cys Leu Leu Ala Val Ala Pro Gly
1               5                   10                  15

Ala His Ser Leu Asp Asp Tyr Lys Asp Asp Asp Lys Glu Phe Gly
            20                  25                  30

Gly Gly Pro Gln Arg Val Ala Ala His Ile Thr Gly Thr Arg Gly Arg
            35                  40                  45

Ser Asn Thr Leu Ser Ser Pro Asn Ser Lys Asn Glu Lys Ala Leu Gly
50                  55                  60

Arg Lys Ile Asn Ser Trp Glu Ser Ser Arg Ser Gly His Ser Phe Leu
65                  70                  75                  80

Ser Asn Leu His Leu Arg Asn Gly Glu Leu Val Ile His Glu Lys Gly
                85                  90                  95

Phe Tyr Tyr Ile Tyr Ser Gln Thr Tyr Phe Arg Phe Gln Glu Glu Ile
            100                 105                 110

Lys Glu Asn Thr Lys Asn Asp Lys Gln Met Val Gln Tyr Ile Tyr Lys
        115                 120                 125

Tyr Thr Ser Tyr Pro Asp Pro Ile Leu Leu Met Lys Ser Ala Arg Asn
130                 135                 140

Ser Cys Trp Ser Lys Asp Ala Glu Tyr Gly Leu Tyr Ser Ile Tyr Gln
145                 150                 155                 160

Gly Gly Ile Phe Glu Leu Lys Glu Asn Asp Arg Ile Phe Val Ser Val
                165                 170                 175

Thr Asn Glu His Leu Ile Asp Met Asp His Glu Ala Ser Phe Phe Gly
            180                 185                 190

Ala Phe Leu Val Gly Gly Pro Gln Arg Val Ala Ala His Ile Thr Gly
        195                 200                 205

Thr Arg Gly Arg Ser Asn Thr Leu Ser Ser Pro Asn Ser Lys Asn Glu
    210                 215                 220

Lys Ala Leu Gly Arg Lys Ile Asn Ser Trp Glu Ser Ser Arg Ser Gly
225                 230                 235                 240

His Ser Phe Leu Ser Asn Leu His Leu Arg Asn Gly Glu Leu Val Ile
                245                 250                 255

His Glu Lys Gly Phe Tyr Tyr Ile Tyr Ser Gln Thr Tyr Phe Arg Phe
            260                 265                 270

Gln Glu Glu Ile Lys Glu Asn Thr Lys Asn Asp Lys Gln Met Val Gln
        275                 280                 285

Tyr Ile Tyr Lys Tyr Thr Ser Tyr Pro Asp Pro Ile Leu Leu Met Lys
    290                 295                 300

Ser Ala Arg Asn Ser Cys Trp Ser Lys Asp Ala Glu Tyr Gly Leu Tyr
305                 310                 315                 320

Ser Ile Tyr Gln Gly Gly Ile Phe Glu Leu Lys Glu Asn Asp Arg Ile
                325                 330                 335

Phe Val Ser Val Thr Asn Glu His Leu Ile Asp Met Asp His Glu Ala
            340                 345                 350

Ser Phe Phe Gly Ala Phe Leu Val Gly Gly Pro Gln Arg Val Ala Ala
        355                 360                 365
```

His Ile Thr Gly Thr Arg Gly Arg Ser Asn Thr Leu Ser Ser Pro Asn
    370                 375                 380

Ser Lys Asn Glu Lys Ala Leu Gly Arg Lys Ile Asn Ser Trp Glu Ser
385                 390                 395                 400

Ser Arg Ser Gly His Ser Phe Leu Ser Asn Leu His Leu Arg Asn Gly
                405                 410                 415

Glu Leu Val Ile His Glu Lys Gly Phe Tyr Tyr Ile Tyr Ser Gln Thr
            420                 425                 430

Tyr Phe Arg Phe Gln Glu Glu Ile Lys Glu Asn Thr Lys Asn Asp Lys
                435                 440                 445

Gln Met Val Gln Tyr Ile Tyr Lys Tyr Thr Ser Tyr Pro Asp Pro Ile
450                 455                 460

Leu Leu Met Lys Ser Ala Arg Asn Ser Cys Trp Ser Lys Asp Ala Glu
465                 470                 475                 480

Tyr Gly Leu Tyr Ser Ile Tyr Gln Gly Gly Ile Phe Glu Leu Lys Glu
                485                 490                 495

Asn Asp Arg Ile Phe Val Ser Val Thr Asn Glu His Leu Ile Asp Met
                500                 505                 510

Asp His Glu Ala Ser Phe Phe Gly Ala Phe Leu Val Gly
            515                 520                 525

<210> SEQ ID NO 217
<211> LENGTH: 526
<212> TYPE: PRT
<213> ORGANISM: Artificial Sequence
<220> FEATURE:
<223> OTHER INFORMATION: fusion protein scTRAIL3-FLVGGGPQRVA

<400> SEQUENCE: 217

Met Asp Trp Thr Trp Arg Val Phe Cys Leu Leu Ala Val Ala Pro Gly
1               5                   10                  15

Ala His Ser Leu Asp Asp Tyr Lys Asp Asp Asp Lys Glu Phe Gly
            20                  25                  30

Gly Gly Pro Gln Arg Val Ala Ala His Ile Thr Gly Thr Arg Gly Arg
        35                  40                  45

Ser Asn Thr Leu Ser Ser Pro Asn Ser Lys Asn Glu Lys Ala Leu Gly
50                  55                  60

Arg Lys Ile Asn Ser Trp Glu Ser Ser Arg Ser Gly His Ser Phe Leu
65                  70                  75                  80

Ser Asn Leu His Leu Arg Asn Gly Glu Leu Val Ile His Glu Lys Gly
                85                  90                  95

Phe Tyr Tyr Ile Tyr Ser Gln Thr Tyr Phe Arg Phe Gln Glu Glu Ile
            100                 105                 110

Lys Glu Asn Thr Lys Asn Asp Lys Gln Met Val Gln Tyr Ile Tyr Lys
        115                 120                 125

Tyr Thr Ser Tyr Pro Asp Pro Ile Leu Leu Met Lys Ser Ala Arg Asn
130                 135                 140

Ser Cys Trp Ser Lys Asp Ala Glu Tyr Gly Leu Tyr Ser Ile Tyr Gln
145                 150                 155                 160

Gly Gly Ile Phe Glu Leu Lys Glu Asn Asp Arg Ile Phe Val Ser Val
                165                 170                 175

Thr Asn Glu His Leu Ile Asp Met Asp His Glu Ala Ser Phe Phe Gly
            180                 185                 190

Ala Phe Leu Val Gly Gly Gly Pro Gln Arg Val Ala Ala His Ile Thr
        195                 200                 205

Gly Thr Arg Gly Arg Ser Asn Thr Leu Ser Ser Pro Asn Ser Lys Asn
210                 215                 220

Glu Lys Ala Leu Gly Arg Lys Ile Asn Ser Trp Glu Ser Ser Arg Ser
225                 230                 235                 240

Gly His Ser Phe Leu Ser Asn Leu His Leu Arg Asn Gly Glu Leu Val
            245                 250                 255

Ile His Glu Lys Gly Phe Tyr Tyr Ile Tyr Ser Gln Thr Tyr Phe Arg
        260                 265                 270

Phe Gln Glu Glu Ile Lys Glu Asn Thr Lys Asn Asp Lys Gln Met Val
    275                 280                 285

Gln Tyr Ile Tyr Lys Tyr Thr Ser Tyr Pro Asp Pro Ile Leu Leu Met
290                 295                 300

Lys Ser Ala Arg Asn Ser Cys Trp Ser Lys Asp Ala Glu Tyr Gly Leu
305                 310                 315                 320

Tyr Ser Ile Tyr Gln Gly Gly Ile Phe Glu Leu Lys Glu Asn Asp Arg
            325                 330                 335

Ile Phe Val Ser Val Thr Asn Glu His Leu Ile Asp Met Asp His Glu
        340                 345                 350

Ala Ser Phe Phe Gly Ala Phe Leu Val Gly Gly Pro Gln Arg Val
    355                 360                 365

Ala Ala His Ile Thr Gly Thr Arg Gly Arg Ser Asn Thr Leu Ser Ser
370                 375                 380

Pro Asn Ser Lys Asn Glu Lys Ala Leu Gly Arg Lys Ile Asn Ser Trp
385                 390                 395                 400

Glu Ser Ser Arg Ser Gly His Ser Phe Leu Ser Asn Leu His Leu Arg
            405                 410                 415

Asn Gly Glu Leu Val Ile His Glu Lys Gly Phe Tyr Tyr Ile Tyr Ser
        420                 425                 430

Gln Thr Tyr Phe Arg Phe Gln Glu Glu Ile Lys Glu Asn Thr Lys Asn
    435                 440                 445

Asp Lys Gln Met Val Gln Tyr Ile Tyr Lys Tyr Thr Ser Tyr Pro Asp
450                 455                 460

Pro Ile Leu Leu Met Lys Ser Ala Arg Asn Ser Cys Trp Ser Lys Asp
465                 470                 475                 480

Ala Glu Tyr Gly Leu Tyr Ser Ile Tyr Gln Gly Gly Ile Phe Glu Leu
            485                 490                 495

Lys Glu Asn Asp Arg Ile Phe Val Ser Val Thr Asn Glu His Leu Ile
        500                 505                 510

Asp Met Asp His Glu Ala Ser Phe Phe Gly Ala Phe Leu Val
    515                 520                 525

<210> SEQ ID NO 218
<211> LENGTH: 529
<212> TYPE: PRT
<213> ORGANISM: Artificial Sequence
<220> FEATURE:
<223> OTHER INFORMATION: fusion protein scTRAIL3-FLVGGGGPQRVA

<400> SEQUENCE: 218

Met Asp Trp Thr Trp Arg Val Phe Cys Leu Leu Ala Val Ala Pro Gly
1               5                   10                  15

Ala His Ser Leu Asp Asp Tyr Lys Asp Asp Asp Lys Glu Phe Gly
            20                  25                  30

Gly Gly Pro Gln Arg Val Ala Ala His Ile Thr Gly Thr Arg Gly Arg
        35                  40                  45

```
Ser Asn Thr Leu Ser Ser Pro Asn Ser Lys Asn Glu Lys Ala Leu Gly
    50                  55                  60

Arg Lys Ile Asn Ser Trp Glu Ser Ser Arg Ser Gly His Ser Phe Leu
 65                  70                  75                  80

Ser Asn Leu His Leu Arg Asn Gly Glu Leu Val Ile His Glu Lys Gly
                 85                  90                  95

Phe Tyr Tyr Ile Tyr Ser Gln Thr Tyr Phe Arg Phe Gln Glu Glu Ile
                100                 105                 110

Lys Glu Asn Thr Lys Asn Asp Lys Gln Met Val Gln Tyr Ile Tyr Lys
                115                 120                 125

Tyr Thr Ser Tyr Pro Asp Pro Ile Leu Leu Met Lys Ser Ala Arg Asn
130                 135                 140

Ser Cys Trp Ser Lys Asp Ala Glu Tyr Gly Leu Tyr Ser Ile Tyr Gln
145                 150                 155                 160

Gly Gly Ile Phe Glu Leu Lys Glu Asn Asp Arg Ile Phe Val Ser Val
                165                 170                 175

Thr Asn Glu His Leu Ile Asp Met Asp His Glu Ala Ser Phe Phe Gly
                180                 185                 190

Ala Phe Leu Val Gly Gly Gly Pro Gln Arg Val Ala Ala His Ile
                195                 200                 205

Thr Gly Thr Arg Gly Arg Ser Asn Thr Leu Ser Ser Pro Asn Ser Lys
210                 215                 220

Asn Glu Lys Ala Leu Gly Arg Lys Ile Asn Ser Trp Glu Ser Ser Arg
225                 230                 235                 240

Ser Gly His Ser Phe Leu Ser Asn Leu His Leu Arg Asn Gly Glu Leu
                245                 250                 255

Val Ile His Glu Lys Gly Phe Tyr Tyr Ile Tyr Ser Gln Thr Tyr Phe
                260                 265                 270

Arg Phe Gln Glu Glu Ile Lys Glu Asn Thr Lys Asn Asp Lys Gln Met
                275                 280                 285

Val Gln Tyr Ile Tyr Lys Tyr Thr Ser Tyr Pro Asp Pro Ile Leu Leu
                290                 295                 300

Met Lys Ser Ala Arg Asn Ser Cys Trp Ser Lys Asp Ala Glu Tyr Gly
305                 310                 315                 320

Leu Tyr Ser Ile Tyr Gln Gly Gly Ile Phe Glu Leu Lys Glu Asn Asp
                325                 330                 335

Arg Ile Phe Val Ser Val Thr Asn Glu His Leu Ile Asp Met Asp His
                340                 345                 350

Glu Ala Ser Phe Phe Gly Ala Phe Leu Val Gly Gly Gly Pro Gln
                355                 360                 365

Arg Val Ala Ala His Ile Thr Gly Thr Arg Gly Arg Ser Asn Thr Leu
370                 375                 380

Ser Ser Pro Asn Ser Lys Asn Glu Lys Ala Leu Gly Arg Lys Ile Asn
385                 390                 395                 400

Ser Trp Glu Ser Ser Arg Ser Gly His Ser Phe Leu Ser Asn Leu His
                405                 410                 415

Leu Arg Asn Gly Glu Leu Val Ile His Glu Lys Gly Phe Tyr Tyr Ile
                420                 425                 430

Tyr Ser Gln Thr Tyr Phe Arg Phe Gln Glu Glu Ile Lys Glu Asn Thr
                435                 440                 445

Lys Asn Asp Lys Gln Met Val Gln Tyr Ile Tyr Lys Tyr Thr Ser Tyr
450                 455                 460

Pro Asp Pro Ile Leu Leu Met Lys Ser Ala Arg Asn Ser Cys Trp Ser
```

```
465                 470                 475                 480
Lys Asp Ala Glu Tyr Gly Leu Tyr Ser Ile Tyr Gln Gly Gly Ile Phe
                485                 490                 495
Glu Leu Lys Glu Asn Asp Arg Ile Phe Val Ser Val Thr Asn Glu His
                500                 505                 510
Leu Ile Asp Met Asp His Glu Ala Ser Phe Phe Gly Ala Phe Leu Val
                515                 520                 525
Gly

<210> SEQ ID NO 219
<211> LENGTH: 521
<212> TYPE: PRT
<213> ORGANISM: Homo sapiens

<400> SEQUENCE: 219

Met Asp Trp Thr Trp Arg Val Phe Cys Leu Leu Ala Val Ala Pro Gly
1               5                   10                  15
Ala His Ser Leu Asp Asp Tyr Lys Asp Asp Asp Lys Glu Phe Gly
                20                  25                  30
Gly Gln Arg Val Ala Ala His Ile Thr Gly Thr Arg Gly Arg Ser Asn
            35                  40                  45
Thr Leu Ser Ser Pro Asn Ser Lys Asn Glu Lys Ala Leu Gly Arg Lys
    50                  55                  60
Ile Asn Ser Trp Glu Ser Arg Ser Gly His Ser Phe Leu Ser Asn
65                  70                  75                  80
Leu His Leu Arg Asn Gly Glu Leu Val Ile His Glu Lys Gly Phe Tyr
                85                  90                  95
Tyr Ile Tyr Ser Gln Thr Tyr Phe Arg Phe Gln Glu Glu Ile Lys Glu
                100                 105                 110
Asn Thr Lys Asn Asp Lys Gln Met Val Gln Tyr Ile Tyr Lys Tyr Thr
            115                 120                 125
Ser Tyr Pro Asp Pro Ile Leu Leu Met Lys Ser Ala Arg Asn Ser Cys
    130                 135                 140
Trp Ser Lys Asp Ala Glu Tyr Gly Leu Tyr Ser Ile Tyr Gln Gly Gly
145                 150                 155                 160
Ile Phe Glu Leu Lys Glu Asn Asp Arg Ile Phe Val Ser Val Thr Asn
                165                 170                 175
Glu His Leu Ile Asp Met Asp His Glu Ala Ser Phe Phe Gly Ala Phe
                180                 185                 190
Leu Val Gly Gly Gln Arg Val Ala Ala His Ile Thr Gly Thr Arg Gly
            195                 200                 205
Arg Ser Asn Thr Leu Ser Ser Pro Asn Ser Lys Asn Glu Lys Ala Leu
    210                 215                 220
Gly Arg Lys Ile Asn Ser Trp Glu Ser Ser Arg Ser Gly His Ser Phe
225                 230                 235                 240
Leu Ser Asn Leu His Leu Arg Asn Gly Glu Leu Val Ile His Glu Lys
                245                 250                 255
Gly Phe Tyr Tyr Ile Tyr Ser Gln Thr Tyr Phe Arg Phe Gln Glu Glu
                260                 265                 270
Ile Lys Glu Asn Thr Lys Asn Asp Lys Gln Met Val Gln Tyr Ile Tyr
            275                 280                 285
Lys Tyr Thr Ser Tyr Pro Asp Pro Ile Leu Leu Met Lys Ser Ala Arg
    290                 295                 300
Asn Ser Cys Trp Ser Lys Asp Ala Glu Tyr Gly Leu Tyr Ser Ile Tyr
```

```
                    305                 310                 315                 320
Gln Gly Gly Ile Phe Glu Leu Lys Glu Asn Asp Arg Ile Phe Val Ser
                325                 330                 335

Val Thr Asn Glu His Leu Ile Asp Met Asp His Glu Ala Ser Phe Phe
                340                 345                 350

Gly Ala Phe Leu Val Gly Gly Gln Arg Val Ala Ala His Ile Thr Gly
                355                 360                 365

Thr Arg Gly Arg Ser Asn Thr Leu Ser Ser Pro Asn Ser Lys Asn Glu
                370                 375                 380

Lys Ala Leu Gly Arg Lys Ile Asn Ser Trp Glu Ser Ser Arg Ser Gly
385                 390                 395                 400

His Ser Phe Leu Ser Asn Leu His Leu Arg Asn Gly Glu Leu Val Ile
                405                 410                 415

His Glu Lys Gly Phe Tyr Tyr Ile Tyr Ser Gln Thr Tyr Phe Arg Phe
                420                 425                 430

Gln Glu Glu Ile Lys Glu Asn Thr Lys Asn Asp Lys Gln Met Val Gln
                435                 440                 445

Tyr Ile Tyr Lys Tyr Thr Ser Tyr Pro Asp Pro Ile Leu Leu Met Lys
                450                 455                 460

Ser Ala Arg Asn Ser Cys Trp Ser Lys Asp Ala Glu Tyr Gly Leu Tyr
465                 470                 475                 480

Ser Ile Tyr Gln Gly Gly Ile Phe Glu Leu Lys Glu Asn Asp Arg Ile
                485                 490                 495

Phe Val Ser Val Thr Asn Glu His Leu Ile Asp Met Asp His Glu Ala
                500                 505                 510

Ser Phe Phe Gly Ala Phe Leu Val Gly
                515                 520

<210> SEQ ID NO 220
<211> LENGTH: 518
<212> TYPE: PRT
<213> ORGANISM: Artificial Sequence
<220> FEATURE:
<223> OTHER INFORMATION: fusion protein scTRAIL3-FLVGGRVA

<400> SEQUENCE: 220

Met Asp Trp Thr Trp Arg Val Phe Cys Leu Leu Ala Val Ala Pro Gly
1               5                   10                  15

Ala His Ser Leu Asp Asp Tyr Lys Asp Asp Asp Lys Glu Phe Gly
                20                  25                  30

Gly Arg Val Ala Ala His Ile Thr Gly Thr Arg Gly Arg Ser Asn Thr
                35                  40                  45

Leu Ser Ser Pro Asn Ser Lys Asn Glu Lys Ala Leu Gly Arg Lys Ile
            50                  55                  60

Asn Ser Trp Glu Ser Ser Arg Ser Gly His Ser Phe Leu Ser Asn Leu
65                  70                  75                  80

His Leu Arg Asn Gly Glu Leu Val Ile His Glu Lys Gly Phe Tyr Tyr
                85                  90                  95

Ile Tyr Ser Gln Thr Tyr Phe Arg Phe Gln Glu Glu Ile Lys Glu Asn
                100                 105                 110

Thr Lys Asn Asp Lys Gln Met Val Gln Tyr Ile Tyr Lys Tyr Thr Ser
                115                 120                 125

Tyr Pro Asp Pro Ile Leu Leu Met Lys Ser Ala Arg Asn Ser Cys Trp
            130                 135                 140

Ser Lys Asp Ala Glu Tyr Gly Leu Tyr Ser Ile Tyr Gln Gly Gly Ile
```

```
            145                 150                 155                 160

Phe Glu Leu Lys Glu Asn Asp Arg Ile Phe Val Ser Val Thr Asn Glu
                            165                 170                 175

His Leu Ile Asp Met Asp His Glu Ala Ser Phe Phe Gly Ala Phe Leu
                            180                 185                 190

Val Gly Gly Arg Val Ala Ala His Ile Thr Gly Thr Arg Gly Arg Ser
                            195                 200                 205

Asn Thr Leu Ser Ser Pro Asn Ser Lys Asn Glu Lys Ala Leu Gly Arg
                            210                 215                 220

Lys Ile Asn Ser Trp Glu Ser Ser Arg Ser Gly His Ser Phe Leu Ser
        225                 230                 235                 240

Asn Leu His Leu Arg Asn Gly Glu Leu Val Ile His Glu Lys Gly Phe
                            245                 250                 255

Tyr Tyr Ile Tyr Ser Gln Thr Tyr Phe Arg Phe Gln Glu Glu Ile Lys
                            260                 265                 270

Glu Asn Thr Lys Asn Asp Lys Gln Met Val Gln Tyr Ile Tyr Lys Tyr
                            275                 280                 285

Thr Ser Tyr Pro Asp Pro Ile Leu Leu Met Lys Ser Ala Arg Asn Ser
                            290                 295                 300

Cys Trp Ser Lys Asp Ala Glu Tyr Gly Leu Tyr Ser Ile Tyr Gln Gly
        305                 310                 315                 320

Gly Ile Phe Glu Leu Lys Glu Asn Asp Arg Ile Phe Val Ser Val Thr
                            325                 330                 335

Asn Glu His Leu Ile Asp Met Asp His Glu Ala Ser Phe Phe Gly Ala
                            340                 345                 350

Phe Leu Val Gly Gly Arg Val Ala Ala His Ile Thr Gly Thr Arg Gly
                            355                 360                 365

Arg Ser Asn Thr Leu Ser Ser Pro Asn Ser Lys Asn Glu Lys Ala Leu
                            370                 375                 380

Gly Arg Lys Ile Asn Ser Trp Glu Ser Ser Arg Ser Gly His Ser Phe
        385                 390                 395                 400

Leu Ser Asn Leu His Leu Arg Asn Gly Glu Leu Val Ile His Glu Lys
                            405                 410                 415

Gly Phe Tyr Tyr Ile Tyr Ser Gln Thr Tyr Phe Arg Phe Gln Glu Glu
                            420                 425                 430

Ile Lys Glu Asn Thr Lys Asn Asp Lys Gln Met Val Gln Tyr Ile Tyr
                            435                 440                 445

Lys Tyr Thr Ser Tyr Pro Asp Pro Ile Leu Leu Met Lys Ser Ala Arg
                            450                 455                 460

Asn Ser Cys Trp Ser Lys Asp Ala Glu Tyr Gly Leu Tyr Ser Ile Tyr
        465                 470                 475                 480

Gln Gly Gly Ile Phe Glu Leu Lys Glu Asn Asp Arg Ile Phe Val Ser
                            485                 490                 495

Val Thr Asn Glu His Leu Ile Asp Met Asp His Glu Ala Ser Phe Phe
                            500                 505                 510

Gly Ala Phe Leu Val Gly
                            515

<210> SEQ ID NO 221
<211> LENGTH: 515
<212> TYPE: PRT
<213> ORGANISM: Artificial Sequence
<220> FEATURE:
<223> OTHER INFORMATION: scTRAIL3-FLVGGVA
```

<400> SEQUENCE: 221

```
Met Asp Trp Thr Trp Arg Val Phe Cys Leu Leu Ala Val Ala Pro Gly
1               5                   10                  15

Ala His Ser Leu Asp Asp Tyr Lys Asp Asp Asp Lys Glu Phe Gly
            20                  25                  30

Gly Val Ala Ala His Ile Thr Gly Thr Arg Gly Arg Ser Asn Thr Leu
            35                  40                  45

Ser Ser Pro Asn Ser Lys Asn Glu Lys Ala Leu Gly Arg Lys Ile Asn
50                  55                  60

Ser Trp Glu Ser Ser Arg Ser Gly His Ser Phe Leu Ser Asn Leu His
65                  70                  75                  80

Leu Arg Asn Gly Glu Leu Val Ile His Glu Lys Gly Phe Tyr Tyr Ile
                85                  90                  95

Tyr Ser Gln Thr Tyr Phe Arg Phe Gln Glu Glu Ile Lys Glu Asn Thr
            100                 105                 110

Lys Asn Asp Lys Gln Met Val Gln Tyr Ile Tyr Lys Tyr Thr Ser Tyr
            115                 120                 125

Pro Asp Pro Ile Leu Leu Met Lys Ser Ala Arg Asn Ser Cys Trp Ser
130                 135                 140

Lys Asp Ala Glu Tyr Gly Leu Tyr Ser Ile Tyr Gln Gly Gly Ile Phe
145                 150                 155                 160

Glu Leu Lys Glu Asn Asp Arg Ile Phe Val Ser Val Thr Asn Glu His
                165                 170                 175

Leu Ile Asp Met Asp His Glu Ala Ser Phe Phe Gly Ala Phe Leu Val
            180                 185                 190

Gly Gly Val Ala Ala His Ile Thr Gly Thr Arg Gly Arg Ser Asn Thr
            195                 200                 205

Leu Ser Ser Pro Asn Ser Lys Asn Glu Lys Ala Leu Gly Arg Lys Ile
210                 215                 220

Asn Ser Trp Glu Ser Ser Arg Ser Gly His Ser Phe Leu Ser Asn Leu
225                 230                 235                 240

His Leu Arg Asn Gly Glu Leu Val Ile His Glu Lys Gly Phe Tyr Tyr
                245                 250                 255

Ile Tyr Ser Gln Thr Tyr Phe Arg Phe Gln Glu Glu Ile Lys Glu Asn
            260                 265                 270

Thr Lys Asn Asp Lys Gln Met Val Gln Tyr Ile Tyr Lys Tyr Thr Ser
            275                 280                 285

Tyr Pro Asp Pro Ile Leu Leu Met Lys Ser Ala Arg Asn Ser Cys Trp
290                 295                 300

Ser Lys Asp Ala Glu Tyr Gly Leu Tyr Ser Ile Tyr Gln Gly Gly Ile
305                 310                 315                 320

Phe Glu Leu Lys Glu Asn Asp Arg Ile Phe Val Ser Val Thr Asn Glu
                325                 330                 335

His Leu Ile Asp Met Asp His Glu Ala Ser Phe Phe Gly Ala Phe Leu
            340                 345                 350

Val Gly Gly Val Ala Ala His Ile Thr Gly Thr Arg Gly Arg Ser Asn
            355                 360                 365

Thr Leu Ser Ser Pro Asn Ser Lys Asn Glu Lys Ala Leu Gly Arg Lys
370                 375                 380

Ile Asn Ser Trp Glu Ser Ser Arg Ser Gly His Ser Phe Leu Ser Asn
385                 390                 395                 400

Leu His Leu Arg Asn Gly Glu Leu Val Ile His Glu Lys Gly Phe Tyr
                405                 410                 415
```

Tyr Ile Tyr Ser Gln Thr Tyr Phe Arg Phe Gln Glu Ile Lys Glu
            420                 425                 430

Asn Thr Lys Asn Asp Lys Gln Met Val Gln Tyr Ile Tyr Lys Tyr Thr
            435                 440                 445

Ser Tyr Pro Asp Pro Ile Leu Leu Met Lys Ser Ala Arg Asn Ser Cys
450                 455                 460

Trp Ser Lys Asp Ala Glu Tyr Gly Leu Tyr Ser Ile Tyr Gln Gly Gly
465                 470                 475                 480

Ile Phe Glu Leu Lys Glu Asn Asp Arg Ile Phe Val Ser Val Thr Asn
                485                 490                 495

Glu His Leu Ile Asp Met Asp His Glu Ala Ser Phe Phe Gly Ala Phe
            500                 505                 510

Leu Val Gly
        515

<210> SEQ ID NO 222
<211> LENGTH: 515
<212> TYPE: PRT
<213> ORGANISM: Artificial Sequence
<220> FEATURE:
<223> OTHER INFORMATION: fusion protein scTRAIL3-FLVGGGA

<400> SEQUENCE: 222

Met Asp Trp Thr Trp Arg Val Phe Cys Leu Leu Ala Val Ala Pro Gly
1               5                   10                  15

Ala His Ser Leu Asp Asp Tyr Lys Asp Asp Asp Lys Glu Phe Gly
            20                  25                  30

Gly Gly Ala Ala His Ile Thr Gly Thr Arg Gly Arg Ser Asn Thr Leu
        35                  40                  45

Ser Ser Pro Asn Ser Lys Asn Glu Lys Ala Leu Gly Arg Lys Ile Asn
50                  55                  60

Ser Trp Glu Ser Ser Arg Ser Gly His Ser Phe Leu Ser Asn Leu His
65                  70                  75                  80

Leu Arg Asn Gly Glu Leu Val Ile His Glu Lys Gly Phe Tyr Tyr Ile
                85                  90                  95

Tyr Ser Gln Thr Tyr Phe Arg Phe Gln Glu Glu Ile Lys Glu Asn Thr
            100                 105                 110

Lys Asn Asp Lys Gln Met Val Gln Tyr Ile Tyr Lys Tyr Thr Ser Tyr
        115                 120                 125

Pro Asp Pro Ile Leu Leu Met Lys Ser Ala Arg Asn Ser Cys Trp Ser
130                 135                 140

Lys Asp Ala Glu Tyr Gly Leu Tyr Ser Ile Tyr Gln Gly Gly Ile Phe
145                 150                 155                 160

Glu Leu Lys Glu Asn Asp Arg Ile Phe Val Ser Val Thr Asn Glu His
                165                 170                 175

Leu Ile Asp Met Asp His Glu Ala Ser Phe Phe Gly Ala Phe Leu Val
            180                 185                 190

Gly Gly Gly Ala Ala His Ile Thr Gly Thr Arg Gly Arg Ser Asn Thr
        195                 200                 205

Leu Ser Ser Pro Asn Ser Lys Asn Glu Lys Ala Leu Gly Arg Lys Ile
    210                 215                 220

Asn Ser Trp Glu Ser Ser Arg Ser Gly His Ser Phe Leu Ser Asn Leu
225                 230                 235                 240

His Leu Arg Asn Gly Glu Leu Val Ile His Glu Lys Gly Phe Tyr Tyr
                245                 250                 255

```
Ile Tyr Ser Gln Thr Tyr Phe Arg Phe Gln Glu Ile Lys Glu Asn
            260                 265                 270

Thr Lys Asn Asp Lys Gln Met Val Gln Tyr Ile Tyr Lys Tyr Thr Ser
        275                 280                 285

Tyr Pro Asp Pro Ile Leu Leu Met Lys Ser Ala Arg Asn Ser Cys Trp
290                 295                 300

Ser Lys Asp Ala Glu Tyr Gly Leu Tyr Ser Ile Tyr Gln Gly Gly Ile
305                 310                 315                 320

Phe Glu Leu Lys Glu Asn Asp Arg Ile Phe Val Ser Val Thr Asn Glu
                325                 330                 335

His Leu Ile Asp Met Asp His Glu Ala Ser Phe Phe Gly Ala Phe Leu
                340                 345                 350

Val Gly Gly Gly Ala Ala His Ile Thr Gly Thr Arg Gly Arg Ser Asn
                355                 360                 365

Thr Leu Ser Ser Pro Asn Ser Lys Asn Glu Lys Ala Leu Gly Arg Lys
            370                 375                 380

Ile Asn Ser Trp Glu Ser Ser Arg Ser Gly His Ser Phe Leu Ser Asn
385                 390                 395                 400

Leu His Leu Arg Asn Gly Glu Leu Val Ile His Glu Lys Gly Phe Tyr
                405                 410                 415

Tyr Ile Tyr Ser Gln Thr Tyr Phe Arg Phe Gln Glu Ile Lys Glu
                420                 425                 430

Asn Thr Lys Asn Asp Lys Gln Met Val Gln Tyr Ile Tyr Lys Tyr Thr
                435                 440                 445

Ser Tyr Pro Asp Pro Ile Leu Leu Met Lys Ser Ala Arg Asn Ser Cys
450                 455                 460

Trp Ser Lys Asp Ala Glu Tyr Gly Leu Tyr Ser Ile Tyr Gln Gly Gly
465                 470                 475                 480

Ile Phe Glu Leu Lys Glu Asn Asp Arg Ile Phe Val Ser Val Thr Asn
                485                 490                 495

Glu His Leu Ile Asp Met Asp His Glu Ala Ser Phe Phe Gly Ala Phe
                500                 505                 510

Leu Val Gly
        515

<210> SEQ ID NO 223
<211> LENGTH: 512
<212> TYPE: PRT
<213> ORGANISM: Artificial Sequence
<220> FEATURE:
<223> OTHER INFORMATION: fusion protein scTRAIL3-FLGGGA

<400> SEQUENCE: 223

Met Asp Trp Thr Trp Arg Val Phe Cys Leu Leu Ala Val Ala Pro Gly
1               5                   10                  15

Ala His Ser Leu Asp Asp Tyr Lys Asp Asp Asp Lys Glu Phe Gly
            20                  25                  30

Gly Ala Ala His Ile Thr Gly Thr Arg Gly Arg Ser Asn Thr Leu Ser
            35                  40                  45

Ser Pro Asn Ser Lys Asn Glu Lys Ala Leu Gly Arg Lys Ile Asn Ser
        50                  55                  60

Trp Glu Ser Ser Arg Ser Gly His Ser Phe Leu Ser Asn Leu His Leu
65                  70                  75                  80

Arg Asn Gly Glu Leu Val Ile His Glu Lys Gly Phe Tyr Tyr Ile Tyr
                85                  90                  95
```

Ser Gln Thr Tyr Phe Arg Phe Gln Glu Glu Ile Lys Glu Asn Thr Lys
            100                 105                 110

Asn Asp Lys Gln Met Val Gln Tyr Ile Tyr Lys Tyr Thr Ser Tyr Pro
            115                 120                 125

Asp Pro Ile Leu Leu Met Lys Ser Ala Arg Asn Ser Cys Trp Ser Lys
130                 135                 140

Asp Ala Glu Tyr Gly Leu Tyr Ser Ile Tyr Gln Gly Gly Ile Phe Glu
145                 150                 155                 160

Leu Lys Glu Asn Asp Arg Ile Phe Val Ser Val Thr Asn Glu His Leu
                165                 170                 175

Ile Asp Met Asp His Glu Ala Ser Phe Phe Gly Ala Phe Leu Gly Gly
            180                 185                 190

Gly Ala Ala His Ile Thr Gly Thr Arg Gly Arg Ser Asn Thr Leu Ser
            195                 200                 205

Ser Pro Asn Ser Lys Asn Glu Lys Ala Leu Gly Arg Lys Ile Asn Ser
            210                 215                 220

Trp Glu Ser Ser Arg Ser Gly His Ser Phe Leu Ser Asn Leu His Leu
225                 230                 235                 240

Arg Asn Gly Glu Leu Val Ile His Glu Lys Gly Phe Tyr Tyr Ile Tyr
                245                 250                 255

Ser Gln Thr Tyr Phe Arg Phe Gln Glu Glu Ile Lys Glu Asn Thr Lys
            260                 265                 270

Asn Asp Lys Gln Met Val Gln Tyr Ile Tyr Lys Tyr Thr Ser Tyr Pro
            275                 280                 285

Asp Pro Ile Leu Leu Met Lys Ser Ala Arg Asn Ser Cys Trp Ser Lys
290                 295                 300

Asp Ala Glu Tyr Gly Leu Tyr Ser Ile Tyr Gln Gly Gly Ile Phe Glu
305                 310                 315                 320

Leu Lys Glu Asn Asp Arg Ile Phe Val Ser Val Thr Asn Glu His Leu
                325                 330                 335

Ile Asp Met Asp His Glu Ala Ser Phe Phe Gly Ala Phe Leu Gly Gly
            340                 345                 350

Gly Ala Ala His Ile Thr Gly Thr Arg Gly Arg Ser Asn Thr Leu Ser
            355                 360                 365

Ser Pro Asn Ser Lys Asn Glu Lys Ala Leu Gly Arg Lys Ile Asn Ser
            370                 375                 380

Trp Glu Ser Ser Arg Ser Gly His Ser Phe Leu Ser Asn Leu His Leu
385                 390                 395                 400

Arg Asn Gly Glu Leu Val Ile His Glu Lys Gly Phe Tyr Tyr Ile Tyr
                405                 410                 415

Ser Gln Thr Tyr Phe Arg Phe Gln Glu Glu Ile Lys Glu Asn Thr Lys
            420                 425                 430

Asn Asp Lys Gln Met Val Gln Tyr Ile Tyr Lys Tyr Thr Ser Tyr Pro
            435                 440                 445

Asp Pro Ile Leu Leu Met Lys Ser Ala Arg Asn Ser Cys Trp Ser Lys
            450                 455                 460

Asp Ala Glu Tyr Gly Leu Tyr Ser Ile Tyr Gln Gly Gly Ile Phe Glu
465                 470                 475                 480

Leu Lys Glu Asn Asp Arg Ile Phe Val Ser Val Thr Asn Glu His Leu
                485                 490                 495

Ile Asp Met Asp His Glu Ala Ser Phe Phe Gly Ala Phe Leu Val Gly
            500                 505                 510

<210> SEQ ID NO 224
<211> LENGTH: 515
<212> TYPE: PRT
<213> ORGANISM: Artificial Sequence
<220> FEATURE:
<223> OTHER INFORMATION: fusion protein scTRAIL3-FLVGGIA

<400> SEQUENCE: 224

```
Met Asp Trp Thr Trp Arg Val Phe Cys Leu Leu Ala Val Ala Pro Gly
1               5                   10                  15

Ala His Ser Leu Asp Asp Tyr Lys Asp Asp Asp Lys Glu Phe Gly
            20                  25                  30

Gly Ile Ala Ala His Ile Thr Gly Thr Arg Gly Arg Ser Asn Thr Leu
        35                  40                  45

Ser Ser Pro Asn Ser Lys Asn Glu Lys Ala Leu Gly Arg Lys Ile Asn
    50                  55                  60

Ser Trp Glu Ser Ser Arg Ser Gly His Ser Phe Leu Ser Asn Leu His
65                  70                  75                  80

Leu Arg Asn Gly Glu Leu Val Ile His Glu Lys Gly Phe Tyr Tyr Ile
                85                  90                  95

Tyr Ser Gln Thr Tyr Phe Arg Phe Gln Glu Glu Ile Lys Glu Asn Thr
            100                 105                 110

Lys Asn Asp Lys Gln Met Val Gln Tyr Ile Tyr Lys Tyr Thr Ser Tyr
        115                 120                 125

Pro Asp Pro Ile Leu Leu Met Lys Ser Ala Arg Asn Ser Cys Trp Ser
    130                 135                 140

Lys Asp Ala Glu Tyr Gly Leu Tyr Ser Ile Tyr Gln Gly Gly Ile Phe
145                 150                 155                 160

Glu Leu Lys Glu Asn Asp Arg Ile Phe Val Ser Val Thr Asn Glu His
                165                 170                 175

Leu Ile Asp Met Asp His Glu Ala Ser Phe Phe Gly Ala Phe Leu Val
            180                 185                 190

Gly Gly Ile Ala Ala His Ile Thr Gly Thr Arg Gly Arg Ser Asn Thr
        195                 200                 205

Leu Ser Ser Pro Asn Ser Lys Asn Glu Lys Ala Leu Gly Arg Lys Ile
    210                 215                 220

Asn Ser Trp Glu Ser Ser Arg Ser Gly His Ser Phe Leu Ser Asn Leu
225                 230                 235                 240

His Leu Arg Asn Gly Glu Leu Val Ile His Glu Lys Gly Phe Tyr Tyr
                245                 250                 255

Ile Tyr Ser Gln Thr Tyr Phe Arg Phe Gln Glu Glu Ile Lys Glu Asn
            260                 265                 270

Thr Lys Asn Asp Lys Gln Met Val Gln Tyr Ile Tyr Lys Tyr Thr Ser
        275                 280                 285

Tyr Pro Asp Pro Ile Leu Leu Met Lys Ser Ala Arg Asn Ser Cys Trp
    290                 295                 300

Ser Lys Asp Ala Glu Tyr Gly Leu Tyr Ser Ile Tyr Gln Gly Gly Ile
305                 310                 315                 320

Phe Glu Leu Lys Glu Asn Asp Arg Ile Phe Val Ser Val Thr Asn Glu
                325                 330                 335

His Leu Ile Asp Met Asp His Glu Ala Ser Phe Phe Gly Ala Phe Leu
            340                 345                 350

Val Gly Gly Ile Ala Ala His Ile Thr Gly Thr Arg Gly Arg Ser Asn
        355                 360                 365
```

```
Thr Leu Ser Ser Pro Asn Ser Lys Asn Glu Lys Ala Leu Gly Arg Lys
    370                 375                 380

Ile Asn Ser Trp Glu Ser Ser Arg Ser Gly His Ser Phe Leu Ser Asn
385                 390                 395                 400

Leu His Leu Arg Asn Gly Glu Leu Val Ile His Glu Lys Gly Phe Tyr
                405                 410                 415

Tyr Ile Tyr Ser Gln Thr Tyr Phe Arg Phe Gln Glu Glu Ile Lys Glu
            420                 425                 430

Asn Thr Lys Asn Asp Lys Gln Met Val Gln Tyr Ile Tyr Lys Tyr Thr
        435                 440                 445

Ser Tyr Pro Asp Pro Ile Leu Leu Met Lys Ser Ala Arg Asn Ser Cys
    450                 455                 460

Trp Ser Lys Asp Ala Glu Tyr Gly Leu Tyr Ser Ile Tyr Gln Gly Gly
465                 470                 475                 480

Ile Phe Glu Leu Lys Glu Asn Asp Arg Ile Phe Val Ser Val Thr Asn
                485                 490                 495

Glu His Leu Ile Asp Met Asp His Glu Ala Ser Phe Phe Gly Ala Phe
                500                 505                 510

Leu Val Gly
        515
```

<210> SEQ ID NO 225
<211> LENGTH: 515
<212> TYPE: PRT
<213> ORGANISM: Artificial Sequence
<220> FEATURE:
<223> OTHER INFORMATION: fusion protein scTRAIL3-FLVGGAA

<400> SEQUENCE: 225

```
Met Asp Trp Thr Trp Arg Val Phe Cys Leu Leu Ala Val Ala Pro Gly
1               5                   10                  15

Ala His Ser Leu Asp Asp Tyr Lys Asp Asp Asp Lys Glu Phe Gly Gly
            20                  25                  30

Gly Ala Ala Ala His Ile Thr Gly Thr Arg Gly Arg Ser Asn Thr Leu
        35                  40                  45

Ser Ser Pro Asn Ser Lys Asn Glu Lys Ala Leu Gly Arg Lys Ile Asn
    50                  55                  60

Ser Trp Glu Ser Ser Arg Ser Gly His Ser Phe Leu Ser Asn Leu His
65                  70                  75                  80

Leu Arg Asn Gly Glu Leu Val Ile His Glu Lys Gly Phe Tyr Tyr Ile
                85                  90                  95

Tyr Ser Gln Thr Tyr Phe Arg Phe Gln Glu Glu Ile Lys Glu Asn Thr
            100                 105                 110

Lys Asn Asp Lys Gln Met Val Gln Tyr Ile Tyr Lys Tyr Thr Ser Tyr
        115                 120                 125

Pro Asp Pro Ile Leu Leu Met Lys Ser Ala Arg Asn Ser Cys Trp Ser
    130                 135                 140

Lys Asp Ala Glu Tyr Gly Leu Tyr Ser Ile Tyr Gln Gly Gly Ile Phe
145                 150                 155                 160

Glu Leu Lys Glu Asn Asp Arg Ile Phe Val Ser Val Thr Asn Glu His
                165                 170                 175

Leu Ile Asp Met Asp His Glu Ala Ser Phe Phe Gly Ala Phe Leu Val
            180                 185                 190

Gly Gly Ala Ala Ala His Ile Thr Gly Thr Arg Gly Arg Ser Asn Thr
        195                 200                 205
```

Leu Ser Ser Pro Asn Ser Lys Asn Glu Lys Ala Leu Gly Arg Lys Ile
    210             215                 220

Asn Ser Trp Glu Ser Ser Arg Ser Gly His Ser Phe Leu Ser Asn Leu
225             230                 235                 240

His Leu Arg Asn Gly Glu Leu Val Ile His Glu Lys Gly Phe Tyr Tyr
            245                 250                 255

Ile Tyr Ser Gln Thr Tyr Phe Arg Phe Gln Glu Ile Lys Glu Asn
        260                 265                 270

Thr Lys Asn Asp Lys Gln Met Val Gln Tyr Ile Tyr Lys Tyr Thr Ser
            275                 280                 285

Tyr Pro Asp Pro Ile Leu Leu Met Lys Ser Ala Arg Asn Ser Cys Trp
    290                 295                 300

Ser Lys Asp Ala Glu Tyr Gly Leu Tyr Ser Ile Tyr Gln Gly Gly Ile
305             310                 315                 320

Phe Glu Leu Lys Glu Asn Asp Arg Ile Phe Val Ser Val Thr Asn Glu
            325                 330                 335

His Leu Ile Asp Met Asp His Glu Ala Ser Phe Phe Gly Ala Phe Leu
            340                 345                 350

Val Gly Gly Ala Ala His Ile Thr Gly Thr Arg Gly Arg Ser Asn
    355                 360                 365

Thr Leu Ser Ser Pro Asn Ser Lys Asn Glu Lys Ala Leu Gly Arg Lys
    370                 375                 380

Ile Asn Ser Trp Glu Ser Ser Arg Ser Gly His Ser Phe Leu Ser Asn
385                 390                 395                 400

Leu His Leu Arg Asn Gly Glu Leu Val Ile His Glu Lys Gly Phe Tyr
                405                 410                 415

Tyr Ile Tyr Ser Gln Thr Tyr Phe Arg Phe Gln Glu Glu Ile Lys Glu
                420                 425                 430

Asn Thr Lys Asn Asp Lys Gln Met Val Gln Tyr Ile Tyr Lys Tyr Thr
                435                 440                 445

Ser Tyr Pro Asp Pro Ile Leu Leu Met Lys Ser Ala Arg Asn Ser Cys
    450                 455                 460

Trp Ser Lys Asp Ala Glu Tyr Gly Leu Tyr Ser Ile Tyr Gln Gly Gly
465                 470                 475                 480

Ile Phe Glu Leu Lys Glu Asn Asp Arg Ile Phe Val Ser Val Thr Asn
                485                 490                 495

Glu His Leu Ile Asp Met Asp His Glu Ala Ser Phe Phe Gly Ala Phe
                500                 505                 510

Leu Val Gly
    515

<210> SEQ ID NO 226
<211> LENGTH: 515
<212> TYPE: PRT
<213> ORGANISM: Artificial Sequence
<220> FEATURE:
<223> OTHER INFORMATION: fusion protein scTRAIL3-FAVGGAA

<400> SEQUENCE: 226

Met Asp Trp Thr Trp Arg Val Phe Cys Leu Leu Ala Val Ala Pro Gly
1               5                   10                  15

Ala His Ser Leu Asp Asp Tyr Lys Asp Asp Asp Lys Glu Phe Gly
            20                  25                  30

Gly Ala Ala Ala His Ile Thr Gly Thr Arg Gly Arg Ser Asn Thr Leu
            35                  40                  45

```
Ser Ser Pro Asn Ser Lys Asn Glu Lys Ala Leu Gly Arg Lys Ile Asn
    50                  55                  60
Ser Trp Glu Ser Ser Arg Ser Gly His Ser Phe Leu Ser Asn Leu His
65                  70                  75                  80
Leu Arg Asn Gly Glu Leu Val Ile His Glu Lys Gly Phe Tyr Tyr Ile
                85                  90                  95
Tyr Ser Gln Thr Tyr Phe Arg Phe Gln Glu Ile Lys Glu Asn Thr
            100                 105                 110
Lys Asn Asp Lys Gln Met Val Gln Tyr Ile Tyr Lys Tyr Thr Ser Tyr
            115                 120                 125
Pro Asp Pro Ile Leu Leu Met Lys Ser Ala Arg Asn Ser Cys Trp Ser
    130                 135                 140
Lys Asp Ala Glu Tyr Gly Leu Tyr Ser Ile Tyr Gln Gly Gly Ile Phe
145                 150                 155                 160
Glu Leu Lys Glu Asn Asp Arg Ile Phe Val Ser Val Thr Asn Glu His
                165                 170                 175
Leu Ile Asp Met Asp His Glu Ala Ser Phe Phe Gly Ala Phe Ala Val
            180                 185                 190
Gly Gly Ala Ala Ala His Ile Thr Gly Thr Arg Gly Arg Ser Asn Thr
            195                 200                 205
Leu Ser Ser Pro Asn Ser Lys Asn Glu Lys Ala Leu Gly Arg Lys Ile
    210                 215                 220
Asn Ser Trp Glu Ser Ser Arg Ser Gly His Ser Phe Leu Ser Asn Leu
225                 230                 235                 240
His Leu Arg Asn Gly Glu Leu Val Ile His Glu Lys Gly Phe Tyr Tyr
                245                 250                 255
Ile Tyr Ser Gln Thr Tyr Phe Arg Phe Gln Glu Ile Lys Glu Asn
            260                 265                 270
Thr Lys Asn Asp Lys Gln Met Val Gln Tyr Ile Tyr Lys Tyr Thr Ser
            275                 280                 285
Tyr Pro Asp Pro Ile Leu Leu Met Lys Ser Ala Arg Asn Ser Cys Trp
    290                 295                 300
Ser Lys Asp Ala Glu Tyr Gly Leu Tyr Ser Ile Tyr Gln Gly Gly Ile
305                 310                 315                 320
Phe Glu Leu Lys Glu Asn Asp Arg Ile Phe Val Ser Val Thr Asn Glu
                325                 330                 335
His Leu Ile Asp Met Asp His Glu Ala Ser Phe Phe Gly Ala Phe Ala
            340                 345                 350
Val Gly Gly Ala Ala Ala His Ile Thr Gly Thr Arg Gly Arg Ser Asn
            355                 360                 365
Thr Leu Ser Ser Pro Asn Ser Lys Asn Glu Lys Ala Leu Gly Arg Lys
    370                 375                 380
Ile Asn Ser Trp Glu Ser Ser Arg Ser Gly His Ser Phe Leu Ser Asn
385                 390                 395                 400
Leu His Leu Arg Asn Gly Glu Leu Val Ile His Glu Lys Gly Phe Tyr
                405                 410                 415
Tyr Ile Tyr Ser Gln Thr Tyr Phe Arg Phe Gln Glu Ile Lys Glu
            420                 425                 430
Asn Thr Lys Asn Asp Lys Gln Met Val Gln Tyr Ile Tyr Lys Tyr Thr
            435                 440                 445
Ser Tyr Pro Asp Pro Ile Leu Leu Met Lys Ser Ala Arg Asn Ser Cys
    450                 455                 460
Trp Ser Lys Asp Ala Glu Tyr Gly Leu Tyr Ser Ile Tyr Gln Gly Gly
```

```
               465                 470                 475                 480
Ile Phe Glu Leu Lys Glu Asn Asp Arg Ile Phe Val Ser Val Thr Asn
                    485                 490                 495
Glu His Leu Ile Asp Met Asp His Glu Ala Ser Phe Phe Gly Ala Phe
                    500                 505                 510
Ala Val Gly
        515

<210> SEQ ID NO 227
<211> LENGTH: 515
<212> TYPE: PRT
<213> ORGANISM: Artificial Sequence
<220> FEATURE:
<223> OTHER INFORMATION: fusion protein scTRAIL3-FAVSGAA

<400> SEQUENCE: 227

Met Asp Trp Thr Trp Arg Val Phe Cys Leu Leu Ala Val Ala Pro Gly
1               5                   10                  15
Ala His Ser Leu Asp Asp Tyr Lys Asp Asp Asp Lys Glu Phe Gly
            20                  25                  30
Gly Ala Ala His Ile Thr Gly Thr Arg Gly Arg Ser Asn Thr Leu
        35                  40                  45
Ser Ser Pro Asn Ser Lys Asn Glu Lys Ala Leu Gly Arg Lys Ile Asn
50                  55                  60
Ser Trp Glu Ser Ser Arg Ser Gly His Ser Phe Leu Ser Asn Leu His
65                  70                  75                  80
Leu Arg Asn Gly Glu Leu Val Ile His Glu Lys Gly Phe Tyr Tyr Ile
                    85                  90                  95
Tyr Ser Gln Thr Tyr Phe Arg Phe Gln Glu Glu Ile Lys Glu Asn Thr
                    100                 105                 110
Lys Asn Asp Lys Gln Met Val Gln Tyr Ile Tyr Lys Tyr Thr Ser Tyr
            115                 120                 125
Pro Asp Pro Ile Leu Leu Met Lys Ser Ala Arg Asn Ser Cys Trp Ser
        130                 135                 140
Lys Asp Ala Glu Tyr Gly Leu Tyr Ser Ile Tyr Gln Gly Gly Ile Phe
145                 150                 155                 160
Glu Leu Lys Glu Asn Asp Arg Ile Phe Val Ser Val Thr Asn Glu His
                    165                 170                 175
Leu Ile Asp Met Asp His Glu Ala Ser Phe Phe Gly Ala Phe Ala Val
                    180                 185                 190
Ser Gly Ala Ala Ala His Ile Thr Gly Thr Arg Gly Arg Ser Asn Thr
            195                 200                 205
Leu Ser Ser Pro Asn Ser Lys Asn Glu Lys Ala Leu Gly Arg Lys Ile
        210                 215                 220
Asn Ser Trp Glu Ser Ser Arg Ser Gly His Ser Phe Leu Ser Asn Leu
225                 230                 235                 240
His Leu Arg Asn Gly Glu Leu Val Ile His Glu Lys Gly Phe Tyr Tyr
                    245                 250                 255
Ile Tyr Ser Gln Thr Tyr Phe Arg Phe Gln Glu Glu Ile Lys Glu Asn
                    260                 265                 270
Thr Lys Asn Asp Lys Gln Met Val Gln Tyr Ile Tyr Lys Tyr Thr Ser
            275                 280                 285
Tyr Pro Asp Pro Ile Leu Leu Met Lys Ser Ala Arg Asn Ser Cys Trp
        290                 295                 300
Ser Lys Asp Ala Glu Tyr Gly Leu Tyr Ser Ile Tyr Gln Gly Gly Ile
```

```
             305                 310                 315                 320
    Phe Glu Leu Lys Glu Asn Asp Arg Ile Phe Val Ser Val Thr Asn Glu
                    325                 330                 335

His Leu Ile Asp Met Asp His Glu Ala Ser Phe Phe Gly Ala Phe Ala
                    340                 345                 350

Val Ser Gly Ala Ala His Ile Thr Gly Thr Arg Gly Arg Ser Asn
                    355                 360                 365

Thr Leu Ser Ser Pro Asn Ser Lys Asn Glu Lys Ala Leu Gly Arg Lys
                    370                 375                 380

Ile Asn Ser Trp Glu Ser Ser Arg Ser Gly His Ser Phe Leu Ser Asn
    385                 390                 395                 400

Leu His Leu Arg Asn Gly Glu Leu Val Ile His Glu Lys Gly Phe Tyr
                    405                 410                 415

Tyr Ile Tyr Ser Gln Thr Tyr Phe Arg Phe Gln Glu Glu Ile Lys Glu
                    420                 425                 430

Asn Thr Lys Asn Asp Lys Gln Met Val Gln Tyr Ile Tyr Lys Tyr Thr
                    435                 440                 445

Ser Tyr Pro Asp Pro Ile Leu Leu Met Lys Ser Ala Arg Asn Ser Cys
                    450                 455                 460

Trp Ser Lys Asp Ala Glu Tyr Gly Leu Tyr Ser Ile Tyr Gln Gly Gly
    465                 470                 475                 480

Ile Phe Glu Leu Lys Glu Asn Asp Arg Ile Phe Val Ser Val Thr Asn
                    485                 490                 495

Glu His Leu Ile Asp Met Asp His Glu Ala Ser Phe Phe Gly Ala Phe
                    500                 505                 510

Ala Val Ser
            515

<210> SEQ ID NO 228
<211> LENGTH: 515
<212> TYPE: PRT
<213> ORGANISM: Artificial Sequence
<220> FEATURE:
<223> OTHER INFORMATION: fusion protein scTRAIL3-FAVGGIA

<400> SEQUENCE: 228

Met Asp Trp Thr Trp Arg Val Phe Cys Leu Leu Ala Val Ala Pro Gly
1               5                   10                  15

Ala His Ser Leu Asp Asp Tyr Lys Asp Asp Asp Lys Glu Phe Gly
                20                  25                  30

Gly Ile Ala Ala His Ile Thr Gly Thr Arg Gly Arg Ser Asn Thr Leu
                35                  40                  45

Ser Ser Pro Asn Ser Lys Asn Glu Lys Ala Leu Gly Arg Lys Ile Asn
            50                  55                  60

Ser Trp Glu Ser Ser Arg Ser Gly His Ser Phe Leu Ser Asn Leu His
65                  70                  75                  80

Leu Arg Asn Gly Glu Leu Val Ile His Glu Lys Gly Phe Tyr Tyr Ile
                85                  90                  95

Tyr Ser Gln Thr Tyr Phe Arg Phe Gln Glu Glu Ile Lys Glu Asn Thr
                100                 105                 110

Lys Asn Asp Lys Gln Met Val Gln Tyr Ile Tyr Lys Tyr Thr Ser Tyr
                115                 120                 125

Pro Asp Pro Ile Leu Leu Met Lys Ser Ala Arg Asn Ser Cys Trp Ser
                130                 135                 140

Lys Asp Ala Glu Tyr Gly Leu Tyr Ser Ile Tyr Gln Gly Gly Ile Phe
```

```
            145                 150                 155                 160
        Glu Leu Lys Glu Asn Asp Arg Ile Phe Val Ser Val Thr Asn Glu His
                        165                 170                 175
        Leu Ile Asp Met Asp His Glu Ala Ser Phe Phe Gly Ala Phe Ala Val
                        180                 185                 190
        Gly Gly Ile Ala Ala His Ile Thr Gly Thr Arg Gly Arg Ser Asn Thr
                        195                 200                 205
        Leu Ser Ser Pro Asn Ser Lys Asn Glu Lys Ala Leu Gly Arg Lys Ile
        210                 215                 220
        Asn Ser Trp Glu Ser Ser Arg Ser Gly His Ser Phe Leu Ser Asn Leu
        225                 230                 235                 240
        His Leu Arg Asn Gly Glu Leu Val Ile His Glu Lys Gly Phe Tyr Tyr
                        245                 250                 255
        Ile Tyr Ser Gln Thr Tyr Phe Arg Phe Gln Glu Ile Lys Glu Asn
                        260                 265                 270
        Thr Lys Asn Asp Lys Gln Met Val Gln Tyr Ile Tyr Lys Tyr Thr Ser
                        275                 280                 285
        Tyr Pro Asp Pro Ile Leu Leu Met Lys Ser Ala Arg Asn Ser Cys Trp
                        290                 295                 300
        Ser Lys Asp Ala Glu Tyr Gly Leu Tyr Ser Ile Tyr Gln Gly Gly Ile
        305                 310                 315                 320
        Phe Glu Leu Lys Glu Asn Asp Arg Ile Phe Val Ser Val Thr Asn Glu
                        325                 330                 335
        His Leu Ile Asp Met Asp His Glu Ala Ser Phe Phe Gly Ala Phe Ala
                        340                 345                 350
        Val Gly Gly Ile Ala Ala His Ile Thr Gly Thr Arg Gly Arg Ser Asn
                        355                 360                 365
        Thr Leu Ser Ser Pro Asn Ser Lys Asn Glu Lys Ala Leu Gly Arg Lys
                        370                 375                 380
        Ile Asn Ser Trp Glu Ser Ser Arg Ser Gly His Ser Phe Leu Ser Asn
        385                 390                 395                 400
        Leu His Leu Arg Asn Gly Glu Leu Val Ile His Glu Lys Gly Phe Tyr
                        405                 410                 415
        Tyr Ile Tyr Ser Gln Thr Tyr Phe Arg Phe Gln Glu Ile Lys Glu
                        420                 425                 430
        Asn Thr Lys Asn Asp Lys Gln Met Val Gln Tyr Ile Tyr Lys Tyr Thr
                        435                 440                 445
        Ser Tyr Pro Asp Pro Ile Leu Leu Met Lys Ser Ala Arg Asn Ser Cys
                        450                 455                 460
        Trp Ser Lys Asp Ala Glu Tyr Gly Leu Tyr Ser Ile Tyr Gln Gly Gly
        465                 470                 475                 480
        Ile Phe Glu Leu Lys Glu Asn Asp Arg Ile Phe Val Ser Val Thr Asn
                        485                 490                 495
        Glu His Leu Ile Asp Met Asp His Glu Ala Ser Phe Phe Gly Ala Phe
                        500                 505                 510
        Ala Val Gly
                515

<210> SEQ ID NO 229
<211> LENGTH: 515
<212> TYPE: PRT
<213> ORGANISM: Artificial Sequence
<220> FEATURE:
<223> OTHER INFORMATION: fusion protein scTRAIL3-FIVGGIA
```

```
<400> SEQUENCE: 229

Met Asp Trp Thr Trp Arg Val Phe Cys Leu Leu Ala Val Ala Pro Gly
1               5                   10                  15

Ala His Ser Leu Asp Asp Tyr Lys Asp Asp Asp Asp Lys Glu Phe Gly
            20                  25                  30

Gly Ile Ala Ala His Ile Thr Gly Thr Arg Gly Arg Ser Asn Thr Leu
        35                  40                  45

Ser Ser Pro Asn Ser Lys Asn Glu Lys Ala Leu Gly Arg Lys Ile Asn
    50                  55                  60

Ser Trp Glu Ser Ser Arg Ser Gly His Ser Phe Leu Ser Asn Leu His
65                  70                  75                  80

Leu Arg Asn Gly Glu Leu Val Ile His Glu Lys Gly Phe Tyr Tyr Ile
                85                  90                  95

Tyr Ser Gln Thr Tyr Phe Arg Phe Gln Glu Glu Ile Lys Glu Asn Thr
            100                 105                 110

Lys Asn Asp Lys Gln Met Val Gln Tyr Ile Tyr Lys Tyr Thr Ser Tyr
            115                 120                 125

Pro Asp Pro Ile Leu Leu Met Lys Ser Ala Arg Asn Ser Cys Trp Ser
130                 135                 140

Lys Asp Ala Glu Tyr Gly Leu Tyr Ser Ile Tyr Gln Gly Gly Ile Phe
145                 150                 155                 160

Glu Leu Lys Glu Asn Asp Arg Ile Phe Val Ser Val Thr Asn Glu His
                165                 170                 175

Leu Ile Asp Met Asp His Glu Ala Ser Phe Phe Gly Ala Phe Ile Val
            180                 185                 190

Gly Gly Ile Ala Ala His Ile Thr Gly Thr Arg Gly Arg Ser Asn Thr
        195                 200                 205

Leu Ser Ser Pro Asn Ser Lys Asn Glu Lys Ala Leu Gly Arg Lys Ile
    210                 215                 220

Asn Ser Trp Glu Ser Ser Arg Ser Gly His Ser Phe Leu Ser Asn Leu
225                 230                 235                 240

His Leu Arg Asn Gly Glu Leu Val Ile His Glu Lys Gly Phe Tyr Tyr
                245                 250                 255

Ile Tyr Ser Gln Thr Tyr Phe Arg Phe Gln Glu Glu Ile Lys Glu Asn
            260                 265                 270

Thr Lys Asn Asp Lys Gln Met Val Gln Tyr Ile Tyr Lys Tyr Thr Ser
            275                 280                 285

Tyr Pro Asp Pro Ile Leu Leu Met Lys Ser Ala Arg Asn Ser Cys Trp
290                 295                 300

Ser Lys Asp Ala Glu Tyr Gly Leu Tyr Ser Ile Tyr Gln Gly Gly Ile
305                 310                 315                 320

Phe Glu Leu Lys Glu Asn Asp Arg Ile Phe Val Ser Val Thr Asn Glu
                325                 330                 335

His Leu Ile Asp Met Asp His Glu Ala Ser Phe Phe Gly Ala Phe Ile
            340                 345                 350

Val Gly Gly Ile Ala Ala His Ile Thr Gly Thr Arg Gly Arg Ser Asn
        355                 360                 365

Thr Leu Ser Ser Pro Asn Ser Lys Asn Glu Lys Ala Leu Gly Arg Lys
    370                 375                 380

Ile Asn Ser Trp Glu Ser Ser Arg Ser Gly His Ser Phe Leu Ser Asn
385                 390                 395                 400

Leu His Leu Arg Asn Gly Glu Leu Val Ile His Glu Lys Gly Phe Tyr
                405                 410                 415
```

Tyr Ile Tyr Ser Gln Thr Tyr Phe Arg Phe Gln Glu Glu Ile Lys Glu
              420                 425                 430

Asn Thr Lys Asn Asp Lys Gln Met Val Gln Tyr Ile Tyr Lys Tyr Thr
              435                 440                 445

Ser Tyr Pro Asp Pro Ile Leu Leu Met Lys Ser Ala Arg Asn Ser Cys
              450                 455                 460

Trp Ser Lys Asp Ala Glu Tyr Gly Leu Tyr Ser Ile Tyr Gln Gly Gly
465                 470                 475                 480

Ile Phe Glu Leu Lys Glu Asn Asp Arg Ile Phe Val Ser Val Thr Asn
                  485                 490                 495

Glu His Leu Ile Asp Met Asp His Glu Ala Ser Phe Phe Gly Ala Phe
              500                 505                 510

Ile Val Gly
        515

<210> SEQ ID NO 230
<211> LENGTH: 515
<212> TYPE: PRT
<213> ORGANISM: Artificial Sequence
<220> FEATURE:
<223> OTHER INFORMATION: fusion protein scTRAIL3-FLVSGIA

<400> SEQUENCE: 230

Met Asp Trp Thr Trp Arg Val Phe Cys Leu Leu Ala Val Ala Pro Gly
1               5                   10                  15

Ala His Ser Leu Asp Asp Tyr Lys Asp Asp Asp Lys Glu Phe Gly
              20                  25                  30

Gly Ile Ala Ala His Ile Thr Gly Thr Arg Gly Arg Ser Asn Thr Leu
              35                  40                  45

Ser Ser Pro Asn Ser Lys Asn Glu Lys Ala Leu Gly Arg Lys Ile Asn
        50                  55                  60

Ser Trp Glu Ser Ser Arg Ser Gly His Ser Phe Leu Ser Asn Leu His
65                  70                  75                  80

Leu Arg Asn Gly Glu Leu Val Ile His Glu Lys Gly Phe Tyr Tyr Ile
                85                  90                  95

Tyr Ser Gln Thr Tyr Phe Arg Phe Gln Glu Glu Ile Lys Glu Asn Thr
              100                 105                 110

Lys Asn Asp Lys Gln Met Val Gln Tyr Ile Tyr Lys Tyr Thr Ser Tyr
              115                 120                 125

Pro Asp Pro Ile Leu Leu Met Lys Ser Ala Arg Asn Ser Cys Trp Ser
              130                 135                 140

Lys Asp Ala Glu Tyr Gly Leu Tyr Ser Ile Tyr Gln Gly Gly Ile Phe
145                 150                 155                 160

Glu Leu Lys Glu Asn Asp Arg Ile Phe Val Ser Val Thr Asn Glu His
                  165                 170                 175

Leu Ile Asp Met Asp His Glu Ala Ser Phe Phe Gly Ala Phe Leu Val
              180                 185                 190

Ser Gly Ile Ala Ala His Ile Thr Gly Thr Arg Gly Arg Ser Asn Thr
              195                 200                 205

Leu Ser Ser Pro Asn Ser Lys Asn Glu Lys Ala Leu Gly Arg Lys Ile
              210                 215                 220

Asn Ser Trp Glu Ser Ser Arg Ser Gly His Ser Phe Leu Ser Asn Leu
225                 230                 235                 240

His Leu Arg Asn Gly Glu Leu Val Ile His Glu Lys Gly Phe Tyr Tyr
                  245                 250                 255

-continued

```
Ile Tyr Ser Gln Thr Tyr Phe Arg Phe Gln Glu Ile Lys Glu Asn
            260                 265                 270

Thr Lys Asn Asp Lys Gln Met Val Gln Tyr Ile Tyr Lys Tyr Thr Ser
        275                 280                 285

Tyr Pro Asp Pro Ile Leu Leu Met Lys Ser Ala Arg Asn Ser Cys Trp
    290                 295                 300

Ser Lys Asp Ala Glu Tyr Gly Leu Tyr Ser Ile Tyr Gln Gly Gly Ile
305                 310                 315                 320

Phe Glu Leu Lys Glu Asn Asp Arg Ile Phe Val Ser Val Thr Asn Glu
                325                 330                 335

His Leu Ile Asp Met Asp His Glu Ala Ser Phe Phe Gly Ala Phe Leu
            340                 345                 350

Val Ser Gly Ile Ala Ala His Ile Thr Gly Thr Arg Gly Arg Ser Asn
        355                 360                 365

Thr Leu Ser Ser Pro Asn Ser Lys Asn Glu Lys Ala Leu Gly Arg Lys
    370                 375                 380

Ile Asn Ser Trp Glu Ser Ser Arg Ser Gly His Ser Phe Leu Ser Asn
385                 390                 395                 400

Leu His Leu Arg Asn Gly Glu Leu Val Ile His Glu Lys Gly Phe Tyr
                405                 410                 415

Tyr Ile Tyr Ser Gln Thr Tyr Phe Arg Phe Gln Glu Ile Lys Glu
            420                 425                 430

Asn Thr Lys Asn Asp Lys Gln Met Val Gln Tyr Ile Tyr Lys Tyr Thr
        435                 440                 445

Ser Tyr Pro Asp Pro Ile Leu Leu Met Lys Ser Ala Arg Asn Ser Cys
    450                 455                 460

Trp Ser Lys Asp Ala Glu Tyr Gly Leu Tyr Ser Ile Tyr Gln Gly Gly
465                 470                 475                 480

Ile Phe Glu Leu Lys Glu Asn Asp Arg Ile Phe Val Ser Val Thr Asn
                485                 490                 495

Glu His Leu Ile Asp Met Asp His Glu Ala Ser Phe Phe Gly Ala Phe
            500                 505                 510

Leu Val Ser
        515

<210> SEQ ID NO 231
<211> LENGTH: 515
<212> TYPE: PRT
<213> ORGANISM: Artificial Sequence
<220> FEATURE:
<223> OTHER INFORMATION: fusion protein scTRAIL3-FIVSGIA

<400> SEQUENCE: 231

Met Asp Trp Thr Trp Arg Val Phe Cys Leu Leu Ala Val Ala Pro Gly
1               5                   10                  15

Ala His Ser Leu Asp Asp Tyr Lys Asp Asp Asp Lys Glu Phe Gly
            20                  25                  30

Gly Ile Ala Ala His Ile Thr Gly Thr Arg Gly Arg Ser Asn Thr Leu
        35                  40                  45

Ser Ser Pro Asn Ser Lys Asn Glu Lys Ala Leu Gly Arg Lys Ile Asn
    50                  55                  60

Ser Trp Glu Ser Ser Arg Ser Gly His Ser Phe Leu Ser Asn Leu His
65                  70                  75                  80

Leu Arg Asn Gly Glu Leu Val Ile His Glu Lys Gly Phe Tyr Tyr Ile
                85                  90                  95
```

```
Tyr Ser Gln Thr Tyr Phe Arg Phe Gln Glu Glu Ile Lys Glu Asn Thr
            100                 105                 110

Lys Asn Asp Lys Gln Met Val Gln Tyr Ile Tyr Lys Tyr Thr Ser Tyr
            115                 120                 125

Pro Asp Pro Ile Leu Leu Met Lys Ser Ala Arg Asn Ser Cys Trp Ser
130             135                 140

Lys Asp Ala Glu Tyr Gly Leu Tyr Ser Ile Tyr Gln Gly Gly Ile Phe
145             150                 155                 160

Glu Leu Lys Glu Asn Asp Arg Ile Phe Val Ser Val Thr Asn Glu His
                165                 170                 175

Leu Ile Asp Met Asp His Glu Ala Ser Phe Phe Gly Ala Phe Ile Val
            180                 185                 190

Ser Gly Ile Ala Ala His Ile Thr Gly Thr Arg Gly Arg Ser Asn Thr
        195                 200                 205

Leu Ser Ser Pro Asn Ser Lys Asn Glu Lys Ala Leu Gly Arg Lys Ile
        210                 215                 220

Asn Ser Trp Glu Ser Ser Arg Ser Gly His Ser Phe Leu Ser Asn Leu
225                 230                 235                 240

His Leu Arg Asn Gly Glu Leu Val Ile His Glu Lys Gly Phe Tyr Tyr
            245                 250                 255

Ile Tyr Ser Gln Thr Tyr Phe Arg Phe Gln Glu Glu Ile Lys Glu Asn
            260                 265                 270

Thr Lys Asn Asp Lys Gln Met Val Gln Tyr Ile Tyr Lys Tyr Thr Ser
            275                 280                 285

Tyr Pro Asp Pro Ile Leu Leu Met Lys Ser Ala Arg Asn Ser Cys Trp
        290                 295                 300

Ser Lys Asp Ala Glu Tyr Gly Leu Tyr Ser Ile Tyr Gln Gly Gly Ile
305                 310                 315                 320

Phe Glu Leu Lys Glu Asn Asp Arg Ile Phe Val Ser Val Thr Asn Glu
                325                 330                 335

His Leu Ile Asp Met Asp His Glu Ala Ser Phe Phe Gly Ala Phe Ile
            340                 345                 350

Val Ser Gly Ile Ala Ala His Ile Thr Gly Thr Arg Gly Arg Ser Asn
            355                 360                 365

Thr Leu Ser Ser Pro Asn Ser Lys Asn Glu Lys Ala Leu Gly Arg Lys
        370                 375                 380

Ile Asn Ser Trp Glu Ser Ser Arg Ser Gly His Ser Phe Leu Ser Asn
385                 390                 395                 400

Leu His Leu Arg Asn Gly Glu Leu Val Ile His Glu Lys Gly Phe Tyr
                405                 410                 415

Tyr Ile Tyr Ser Gln Thr Tyr Phe Arg Phe Gln Glu Glu Ile Lys Glu
            420                 425                 430

Asn Thr Lys Asn Asp Lys Gln Met Val Gln Tyr Ile Tyr Lys Tyr Thr
            435                 440                 445

Ser Tyr Pro Asp Pro Ile Leu Leu Met Lys Ser Ala Arg Asn Ser Cys
        450                 455                 460

Trp Ser Lys Asp Ala Glu Tyr Gly Leu Tyr Ser Ile Tyr Gln Gly Gly
465                 470                 475                 480

Ile Phe Glu Leu Lys Glu Asn Asp Arg Ile Phe Val Ser Val Thr Asn
                485                 490                 495

Glu His Leu Ile Asp Met Asp His Glu Ala Ser Phe Phe Gly Ala Phe
            500                 505                 510
```

Ile Val Ser
        515

<210> SEQ ID NO 232
<211> LENGTH: 515
<212> TYPE: PRT
<213> ORGANISM: Artificial Sequence
<220> FEATURE:
<223> OTHER INFORMATION: fusion protein scTRAIL3-FAVSGIA

<400> SEQUENCE: 232

Met Asp Trp Thr Trp Arg Val Phe Cys Leu Leu Ala Val Ala Pro Gly
1               5                   10                  15

Ala His Ser Leu Asp Asp Tyr Lys Asp Asp Asp Lys Glu Phe Gly
            20                  25                  30

Gly Ile Ala Ala His Ile Thr Gly Thr Arg Gly Arg Ser Asn Thr Leu
        35                  40                  45

Ser Ser Pro Asn Ser Lys Asn Glu Lys Ala Leu Gly Arg Lys Ile Asn
    50                  55                  60

Ser Trp Glu Ser Ser Arg Ser Gly His Ser Phe Leu Ser Asn Leu His
65                  70                  75                  80

Leu Arg Asn Gly Glu Leu Val Ile His Glu Lys Gly Phe Tyr Tyr Ile
                85                  90                  95

Tyr Ser Gln Thr Tyr Phe Arg Phe Gln Glu Glu Ile Lys Glu Asn Thr
            100                 105                 110

Lys Asn Asp Lys Gln Met Val Gln Tyr Ile Tyr Lys Tyr Thr Ser Tyr
        115                 120                 125

Pro Asp Pro Ile Leu Leu Met Lys Ser Ala Arg Asn Ser Cys Trp Ser
130                 135                 140

Lys Asp Ala Glu Tyr Gly Leu Tyr Ser Ile Tyr Gln Gly Gly Ile Phe
145                 150                 155                 160

Glu Leu Lys Glu Asn Asp Arg Ile Phe Val Ser Val Thr Asn Glu His
                165                 170                 175

Leu Ile Asp Met Asp His Glu Ala Ser Phe Phe Gly Ala Phe Ala Val
            180                 185                 190

Ser Gly Ile Ala Ala His Ile Thr Gly Thr Arg Gly Arg Ser Asn Thr
        195                 200                 205

Leu Ser Ser Pro Asn Ser Lys Asn Glu Lys Ala Leu Gly Arg Lys Ile
    210                 215                 220

Asn Ser Trp Glu Ser Ser Arg Ser Gly His Ser Phe Leu Ser Asn Leu
225                 230                 235                 240

His Leu Arg Asn Gly Glu Leu Val Ile His Glu Lys Gly Phe Tyr Tyr
                245                 250                 255

Ile Tyr Ser Gln Thr Tyr Phe Arg Phe Gln Glu Glu Ile Lys Glu Asn
            260                 265                 270

Thr Lys Asn Asp Lys Gln Met Val Gln Tyr Ile Tyr Lys Tyr Thr Ser
        275                 280                 285

Tyr Pro Asp Pro Ile Leu Leu Met Lys Ser Ala Arg Asn Ser Cys Trp
    290                 295                 300

Ser Lys Asp Ala Glu Tyr Gly Leu Tyr Ser Ile Tyr Gln Gly Gly Ile
305                 310                 315                 320

Phe Glu Leu Lys Glu Asn Asp Arg Ile Phe Val Ser Val Thr Asn Glu
                325                 330                 335

His Leu Ile Asp Met Asp His Glu Ala Ser Phe Phe Gly Ala Phe Ala
            340                 345                 350

Val Ser Gly Ile Ala Ala His Ile Thr Gly Thr Arg Gly Arg Ser Asn
            355                 360                 365

Thr Leu Ser Ser Pro Asn Ser Lys Asn Glu Lys Ala Leu Gly Arg Lys
    370                 375                 380

Ile Asn Ser Trp Glu Ser Ser Arg Ser Gly His Ser Phe Leu Ser Asn
385                 390                 395                 400

Leu His Leu Arg Asn Gly Glu Leu Val Ile His Glu Lys Gly Phe Tyr
                405                 410                 415

Tyr Ile Tyr Ser Gln Thr Tyr Phe Arg Phe Gln Glu Glu Ile Lys Glu
            420                 425                 430

Asn Thr Lys Asn Asp Lys Gln Met Val Gln Tyr Ile Tyr Lys Tyr Thr
    435                 440                 445

Ser Tyr Pro Asp Pro Ile Leu Leu Met Lys Ser Ala Arg Asn Ser Cys
450                 455                 460

Trp Ser Lys Asp Ala Glu Tyr Gly Leu Tyr Ser Ile Tyr Gln Gly Gly
465                 470                 475                 480

Ile Phe Glu Leu Lys Glu Asn Asp Arg Ile Phe Val Ser Val Thr Asn
                485                 490                 495

Glu His Leu Ile Asp Met Asp His Glu Ala Ser Phe Phe Gly Ala Phe
            500                 505                 510

Ala Val Ser
        515

<210> SEQ ID NO 233
<211> LENGTH: 515
<212> TYPE: PRT
<213> ORGANISM: Artificial Sequence
<220> FEATURE:
<223> OTHER INFORMATION: fusion protein scTRAIL3-FLVGGVA

<400> SEQUENCE: 233

Met Asp Trp Thr Trp Arg Val Phe Cys Leu Leu Ala Val Ala Pro Gly
1               5                   10                  15

Ala His Ser Leu Asp Asp Tyr Lys Asp Asp Asp Lys Glu Phe Gly
            20                  25                  30

Gly Val Ala Ala His Ile Thr Gly Thr Arg Gly Arg Ser Asn Thr Leu
            35                  40                  45

Ser Ser Pro Asn Ser Lys Asn Glu Lys Ala Leu Gly Arg Lys Ile Asn
    50                  55                  60

Ser Trp Glu Ser Ser Arg Ser Gly His Ser Phe Leu Ser Asn Leu His
65                  70                  75                  80

Leu Arg Asn Gly Glu Leu Val Ile His Glu Lys Gly Phe Tyr Tyr Ile
                85                  90                  95

Tyr Ser Gln Thr Tyr Phe Arg Phe Gln Glu Glu Ile Lys Glu Asn Thr
            100                 105                 110

Lys Asn Asp Lys Gln Met Val Gln Tyr Ile Tyr Lys Tyr Thr Ser Tyr
        115                 120                 125

Pro Asp Pro Ile Leu Leu Met Lys Ser Ala Arg Asn Ser Cys Trp Ser
    130                 135                 140

Lys Asp Ala Glu Tyr Gly Leu Tyr Ser Ile Tyr Gln Gly Gly Ile Phe
145                 150                 155                 160

Glu Leu Lys Glu Asn Asp Arg Ile Phe Val Ser Val Thr Asn Glu His
                165                 170                 175

Leu Ile Asp Met Asp His Glu Ala Ser Phe Phe Gly Ala Phe Leu Val
            180                 185                 190

```
Gly Gly Val Ala Ala His Ile Thr Gly Thr Arg Gly Arg Ser Asn Thr
            195                 200                 205
Leu Ser Ser Pro Asn Ser Lys Asn Glu Lys Ala Leu Gly Arg Lys Ile
210                 215                 220
Asn Ser Trp Glu Ser Ser Arg Ser Gly His Ser Phe Leu Ser Asn Leu
225                 230                 235                 240
His Leu Arg Asn Gly Glu Leu Val Ile His Glu Lys Gly Phe Tyr Tyr
                245                 250                 255
Ile Tyr Ser Gln Thr Tyr Phe Arg Phe Gln Glu Ile Lys Glu Asn
            260                 265                 270
Thr Lys Asn Asp Lys Gln Met Val Gln Tyr Ile Tyr Lys Tyr Thr Ser
    275                 280                 285
Tyr Pro Asp Pro Ile Leu Leu Met Lys Ser Ala Arg Asn Ser Cys Trp
290                 295                 300
Ser Lys Asp Ala Glu Tyr Gly Leu Tyr Ser Ile Tyr Gln Gly Gly Ile
305                 310                 315                 320
Phe Glu Leu Lys Glu Asn Asp Arg Ile Phe Val Ser Val Thr Asn Glu
                325                 330                 335
His Leu Ile Asp Met Asp His Glu Ala Ser Phe Phe Gly Ala Phe Leu
            340                 345                 350
Val Gly Gly Val Ala Ala His Ile Thr Gly Thr Arg Gly Arg Ser Asn
    355                 360                 365
Thr Leu Ser Ser Pro Asn Ser Lys Asn Glu Lys Ala Leu Gly Arg Lys
370                 375                 380
Ile Asn Ser Trp Glu Ser Ser Arg Ser Gly His Ser Phe Leu Ser Asn
385                 390                 395                 400
Leu His Leu Arg Asn Gly Glu Leu Val Ile His Glu Lys Gly Phe Tyr
                405                 410                 415
Tyr Ile Tyr Ser Gln Thr Tyr Phe Arg Phe Gln Glu Ile Lys Glu
            420                 425                 430
Asn Thr Lys Asn Asp Lys Gln Met Val Gln Tyr Ile Tyr Lys Tyr Thr
    435                 440                 445
Ser Tyr Pro Asp Pro Ile Leu Leu Met Lys Ser Ala Arg Asn Ser Cys
450                 455                 460
Trp Ser Lys Asp Ala Glu Tyr Gly Leu Tyr Ser Ile Tyr Gln Gly Gly
465                 470                 475                 480
Ile Phe Glu Leu Lys Glu Asn Asp Arg Ile Phe Val Ser Val Thr Asn
                485                 490                 495
Glu His Leu Ile Asp Met Asp His Glu Ala Ser Phe Phe Gly Ala Phe
            500                 505                 510
Leu Val Gly
        515

<210> SEQ ID NO 234
<211> LENGTH: 749
<212> TYPE: PRT
<213> ORGANISM: Artificial Sequence
<220> FEATURE:
<223> OTHER INFORMATION: fusion protein Db-scTRAIL3

<400> SEQUENCE: 234

Asp Tyr Lys Asp Asp Asp Lys Gly Gly Gly Gly Ser Gly Thr Glu
1               5                   10                  15
Val Gln Leu Val Glu Ser Gly Gly Gly Leu Val Gln Pro Gly Gly Ser
            20                  25                  30
```

-continued

```
Leu Arg Leu Ser Cys Ala Ala Ser Gly Phe Ser Leu Thr Asn Tyr Gly
             35                  40                  45

Val His Trp Val Arg Gln Ala Pro Gly Lys Gly Leu Glu Trp Leu Gly
     50                  55                  60

Val Ile Trp Ser Gly Gly Asn Thr Asp Tyr Asn Thr Pro Phe Thr Ser
 65                  70                  75                  80

Arg Phe Thr Ile Ser Arg Asp Asn Ser Lys Asn Thr Leu Tyr Leu Gln
                 85                  90                  95

Met Asn Ser Leu Arg Ala Glu Asp Thr Ala Val Tyr Tyr Cys Ala Arg
            100                 105                 110

Ala Leu Thr Tyr Tyr Asp Tyr Glu Phe Ala Tyr Trp Gly Gln Gly Thr
        115                 120                 125

Thr Val Thr Val Ser Ser Gly Gly Gly Ser Asp Ile Gln Leu Thr
    130                 135                 140

Gln Ser Pro Ser Phe Leu Ser Ala Ser Val Gly Asp Arg Val Thr Ile
145                 150                 155                 160

Thr Cys Arg Ala Ser Gln Ser Ile Gly Thr Asn Ile His Trp Tyr Gln
                165                 170                 175

Gln Lys Pro Gly Lys Ala Pro Lys Leu Leu Ile Lys Tyr Ala Ser Glu
            180                 185                 190

Ser Ile Ser Gly Val Pro Ser Arg Phe Ser Gly Ser Gly Ser Gly Thr
        195                 200                 205

Glu Phe Thr Leu Thr Ile Ser Ser Leu Gln Pro Glu Asp Phe Ala Thr
    210                 215                 220

Tyr Tyr Cys Gln Gln Asn Asn Asn Trp Pro Thr Thr Phe Gly Ala Gly
225                 230                 235                 240

Thr Lys Leu Glu Ile Lys Arg Ala Ala Ala Gly Gly Ser Gly Gly Gly
                245                 250                 255

Pro Gln Arg Val Ala Ala His Ile Thr Gly Thr Arg Gly Arg Ser Asn
            260                 265                 270

Thr Leu Ser Ser Pro Asn Ser Lys Asn Glu Lys Ala Leu Gly Arg Lys
        275                 280                 285

Ile Asn Ser Trp Glu Ser Ser Arg Ser Gly His Ser Phe Leu Ser Asn
    290                 295                 300

Leu His Leu Arg Asn Gly Glu Leu Val Ile His Glu Lys Gly Phe Tyr
305                 310                 315                 320

Tyr Ile Tyr Ser Gln Thr Tyr Phe Arg Phe Gln Glu Glu Ile Lys Glu
                325                 330                 335

Asn Thr Lys Asn Asp Lys Gln Met Val Gln Tyr Ile Tyr Lys Tyr Thr
            340                 345                 350

Ser Tyr Pro Asp Pro Ile Leu Leu Met Lys Ser Ala Arg Asn Ser Cys
        355                 360                 365

Trp Ser Lys Asp Ala Glu Tyr Gly Leu Tyr Ser Ile Tyr Gln Gly Gly
    370                 375                 380

Ile Phe Glu Leu Lys Glu Asn Asp Arg Ile Phe Val Ser Val Thr Asn
385                 390                 395                 400

Glu His Leu Ile Asp Met Asp His Glu Ala Ser Phe Phe Gly Ala Phe
                405                 410                 415

Leu Val Gly Gly Gly Pro Gln Arg Val Ala Ala His Ile Thr Gly Thr
            420                 425                 430

Arg Gly Arg Ser Asn Thr Leu Ser Ser Pro Asn Ser Lys Asn Glu Lys
        435                 440                 445

Ala Leu Gly Arg Lys Ile Asn Ser Trp Glu Ser Ser Arg Ser Gly His
```

```
                    450                 455                 460
Ser Phe Leu Ser Asn Leu His Leu Arg Asn Gly Glu Leu Val Ile His
465                 470                 475                 480

Glu Lys Gly Phe Tyr Tyr Ile Tyr Ser Gln Thr Tyr Phe Arg Phe Gln
                485                 490                 495

Glu Glu Ile Lys Glu Asn Thr Lys Asn Asp Lys Gln Met Val Gln Tyr
                500                 505                 510

Ile Tyr Lys Tyr Thr Ser Tyr Pro Asp Pro Ile Leu Leu Met Lys Ser
            515                 520                 525

Ala Arg Asn Ser Cys Trp Ser Lys Asp Ala Glu Tyr Gly Leu Tyr Ser
        530                 535                 540

Ile Tyr Gln Gly Gly Ile Phe Glu Leu Lys Glu Asn Asp Arg Ile Phe
545                 550                 555                 560

Val Ser Val Thr Asn Glu His Leu Ile Asp Met Asp His Glu Ala Ser
                565                 570                 575

Phe Phe Gly Ala Phe Leu Val Gly Gly Pro Gln Arg Val Ala Ala
                580                 585                 590

His Ile Thr Gly Thr Arg Gly Arg Ser Asn Thr Leu Ser Ser Pro Asn
            595                 600                 605

Ser Lys Asn Glu Lys Ala Leu Gly Arg Lys Ile Asn Ser Trp Glu Ser
        610                 615                 620

Ser Arg Ser Gly His Ser Phe Leu Ser Asn Leu His Leu Arg Asn Gly
625                 630                 635                 640

Glu Leu Val Ile His Glu Lys Gly Phe Tyr Tyr Ile Tyr Ser Gln Thr
                645                 650                 655

Tyr Phe Arg Phe Gln Glu Glu Ile Lys Glu Asn Thr Lys Asn Asp Lys
                660                 665                 670

Gln Met Val Gln Tyr Ile Tyr Lys Tyr Thr Ser Tyr Pro Asp Pro Ile
            675                 680                 685

Leu Leu Met Lys Ser Ala Arg Asn Ser Cys Trp Ser Lys Asp Ala Glu
        690                 695                 700

Tyr Gly Leu Tyr Ser Ile Tyr Gln Gly Gly Ile Phe Glu Leu Lys Glu
705                 710                 715                 720

Asn Asp Arg Ile Phe Val Ser Val Thr Asn Glu His Leu Ile Asp Met
                725                 730                 735

Asp His Glu Ala Ser Phe Phe Gly Ala Phe Leu Val Gly
                740                 745

<210> SEQ ID NO 235
<211> LENGTH: 749
<212> TYPE: PRT
<213> ORGANISM: Artificial Sequence
<220> FEATURE:
<223> OTHER INFORMATION: fusion protein dsDb-scTRAIL3

<400> SEQUENCE: 235

Asp Tyr Lys Asp Asp Asp Lys Gly Gly Gly Ser Gly Thr Glu
1               5                   10                  15

Val Gln Leu Val Glu Ser Gly Gly Gly Leu Val Gln Pro Gly Gly Ser
                20                  25                  30

Leu Arg Leu Ser Cys Ala Ala Ser Gly Phe Ser Leu Thr Asn Tyr Gly
            35                  40                  45

Val His Trp Val Arg Gln Ala Pro Gly Lys Cys Leu Glu Trp Leu Gly
        50                  55                  60

Val Ile Trp Ser Gly Gly Asn Thr Asp Tyr Asn Thr Pro Phe Thr Ser
```

```
            65                  70                  75                  80
Arg Phe Thr Ile Ser Arg Asp Asn Ser Lys Asn Thr Leu Tyr Leu Gln
                    85                  90                  95

Met Asn Ser Leu Arg Ala Glu Asp Thr Ala Val Tyr Tyr Cys Ala Arg
            100                 105                 110

Ala Leu Thr Tyr Tyr Asp Tyr Glu Phe Ala Tyr Trp Gly Gln Gly Thr
            115                 120                 125

Thr Val Thr Val Ser Ser Gly Gly Gly Ser Asp Ile Gln Leu Thr
        130                 135                 140

Gln Ser Pro Ser Phe Leu Ser Ala Ser Val Gly Asp Arg Val Thr Ile
145                 150                 155                 160

Thr Cys Arg Ala Ser Gln Ser Ile Gly Thr Asn Ile His Trp Tyr Gln
                165                 170                 175

Gln Lys Pro Gly Lys Ala Pro Lys Leu Leu Ile Lys Tyr Ala Ser Glu
            180                 185                 190

Ser Ile Ser Gly Val Pro Ser Arg Phe Ser Gly Ser Gly Ser Gly Thr
            195                 200                 205

Glu Phe Thr Leu Thr Ile Ser Ser Leu Gln Pro Glu Asp Phe Ala Thr
        210                 215                 220

Tyr Tyr Cys Gln Gln Asn Asn Asn Trp Pro Thr Thr Phe Gly Cys Gly
225                 230                 235                 240

Thr Lys Leu Glu Ile Lys Arg Ala Ala Gly Gly Ser Gly Gly Gly
                245                 250                 255

Pro Gln Arg Val Ala Ala His Ile Thr Gly Thr Arg Gly Arg Ser Asn
            260                 265                 270

Thr Leu Ser Ser Pro Asn Ser Lys Asn Glu Lys Ala Leu Gly Arg Lys
        275                 280                 285

Ile Asn Ser Trp Glu Ser Ser Arg Ser Gly His Ser Phe Leu Ser Asn
        290                 295                 300

Leu His Leu Arg Asn Gly Glu Leu Val Ile His Glu Lys Gly Phe Tyr
305                 310                 315                 320

Tyr Ile Tyr Ser Gln Thr Tyr Phe Arg Phe Gln Glu Glu Ile Lys Glu
                325                 330                 335

Asn Thr Lys Asn Asp Lys Gln Met Val Gln Tyr Ile Tyr Lys Tyr Thr
            340                 345                 350

Ser Tyr Pro Asp Pro Ile Leu Leu Met Lys Ser Ala Arg Asn Ser Cys
        355                 360                 365

Trp Ser Lys Asp Ala Glu Tyr Gly Leu Tyr Ser Ile Tyr Gln Gly Gly
        370                 375                 380

Ile Phe Glu Leu Lys Glu Asn Asp Arg Ile Phe Val Ser Val Thr Asn
385                 390                 395                 400

Glu His Leu Ile Asp Met Asp His Glu Ala Ser Phe Phe Gly Ala Phe
                405                 410                 415

Leu Val Gly Gly Gly Pro Gln Arg Val Ala Ala His Ile Thr Gly Thr
            420                 425                 430

Arg Gly Arg Ser Asn Thr Leu Ser Ser Pro Asn Ser Lys Asn Glu Lys
        435                 440                 445

Ala Leu Gly Arg Lys Ile Asn Ser Trp Glu Ser Ser Arg Ser Gly His
        450                 455                 460

Ser Phe Leu Ser Asn Leu His Leu Arg Asn Gly Glu Leu Val Ile His
465                 470                 475                 480

Glu Lys Gly Phe Tyr Tyr Ile Tyr Ser Gln Thr Tyr Phe Arg Phe Gln
                485                 490                 495
```

```
Glu Glu Ile Lys Glu Asn Thr Lys Asn Asp Lys Gln Met Val Gln Tyr
                500                 505                 510

Ile Tyr Lys Tyr Thr Ser Tyr Pro Asp Pro Ile Leu Leu Met Lys Ser
        515                 520                 525

Ala Arg Asn Ser Cys Trp Ser Lys Asp Ala Glu Tyr Gly Leu Tyr Ser
    530                 535                 540

Ile Tyr Gln Gly Gly Ile Phe Glu Leu Lys Glu Asn Asp Arg Ile Phe
545                 550                 555                 560

Val Ser Val Thr Asn Glu His Leu Ile Asp Met Asp His Glu Ala Ser
                565                 570                 575

Phe Phe Gly Ala Phe Leu Val Gly Gly Pro Gln Arg Val Ala Ala
            580                 585                 590

His Ile Thr Gly Thr Arg Gly Arg Ser Asn Thr Leu Ser Ser Pro Asn
                595                 600                 605

Ser Lys Asn Glu Lys Ala Leu Gly Arg Lys Ile Asn Ser Trp Glu Ser
        610                 615                 620

Ser Arg Ser Gly His Ser Phe Leu Ser Asn Leu His Leu Arg Asn Gly
625                 630                 635                 640

Glu Leu Val Ile His Glu Lys Gly Phe Tyr Tyr Ile Tyr Ser Gln Thr
                645                 650                 655

Tyr Phe Arg Phe Gln Glu Glu Ile Lys Glu Asn Thr Lys Asn Asp Lys
            660                 665                 670

Gln Met Val Gln Tyr Ile Tyr Lys Tyr Thr Ser Tyr Pro Asp Pro Ile
        675                 680                 685

Leu Leu Met Lys Ser Ala Arg Asn Ser Cys Trp Ser Lys Asp Ala Glu
690                 695                 700

Tyr Gly Leu Tyr Ser Ile Tyr Gln Gly Gly Ile Phe Glu Leu Lys Glu
705                 710                 715                 720

Asn Asp Arg Ile Phe Val Ser Val Thr Asn Glu His Leu Ile Asp Met
                725                 730                 735

Asp His Glu Ala Ser Phe Phe Gly Ala Phe Leu Val Gly
            740                 745
```

<210> SEQ ID NO 236
<211> LENGTH: 875
<212> TYPE: PRT
<213> ORGANISM: Artificial Sequence
<220> FEATURE:
<223> OTHER INFORMATION: fusion protein scFv-EHD2-scTRAIL3

<400> SEQUENCE: 236

```
Asp Tyr Lys Asp Asp Asp Asp Lys Gly Gly Gly Gly Ser Gly Thr Glu
1               5                   10                  15

Val Gln Leu Val Glu Ser Gly Gly Gly Leu Val Gln Pro Gly Gly Ser
                20                  25                  30

Leu Arg Leu Ser Cys Ala Ala Ser Gly Phe Ser Leu Thr Asn Tyr Gly
            35                  40                  45

Val His Trp Val Arg Gln Ala Pro Gly Lys Gly Leu Glu Trp Leu Gly
    50                  55                  60

Val Ile Trp Ser Gly Gly Asn Thr Asp Tyr Asn Thr Pro Phe Thr Ser
65                  70                  75                  80

Arg Phe Thr Ile Ser Arg Asp Asn Ser Lys Asn Thr Leu Tyr Leu Gln
                85                  90                  95

Met Asn Ser Leu Arg Ala Glu Asp Thr Ala Val Tyr Tyr Cys Ala Arg
            100                 105                 110
```

```
Ala Leu Thr Tyr Tyr Asp Tyr Glu Phe Ala Tyr Trp Gly Gln Gly Thr
            115                 120                 125

Thr Val Thr Val Ser Ser Gly Gly Gly Gly Ser Gly Gly Gly Gly Ser
        130                 135                 140

Gly Gly Gly Gly Ser Asp Ile Gln Leu Thr Gln Ser Pro Ser Phe Leu
145                 150                 155                 160

Ser Ala Ser Val Gly Asp Arg Val Thr Ile Thr Cys Arg Ala Ser Gln
                165                 170                 175

Ser Ile Gly Thr Asn Ile His Trp Tyr Gln Gln Lys Pro Gly Lys Ala
            180                 185                 190

Pro Lys Leu Leu Ile Lys Tyr Ala Ser Glu Ser Ile Ser Gly Val Pro
        195                 200                 205

Ser Arg Phe Ser Gly Ser Gly Ser Gly Thr Glu Phe Thr Leu Thr Ile
    210                 215                 220

Ser Ser Leu Gln Pro Glu Asp Phe Ala Thr Tyr Tyr Cys Gln Gln Asn
225                 230                 235                 240

Asn Asn Trp Pro Thr Thr Phe Gly Ala Gly Thr Lys Leu Glu Ile Lys
            245                 250                 255

Arg Ala Ala Ala Gly Gly Ser Gly Gly Asp Phe Thr Pro Pro Thr Val
        260                 265                 270

Lys Ile Leu Gln Ser Ser Cys Asp Gly Gly Gly His Phe Pro Pro Thr
    275                 280                 285

Ile Gln Leu Leu Cys Leu Val Ser Gly Tyr Thr Pro Gly Thr Ile Asn
        290                 295                 300

Ile Thr Trp Leu Glu Asp Gly Gln Val Met Asp Val Asp Leu Ser Thr
305                 310                 315                 320

Ala Ser Thr Thr Gln Glu Gly Glu Leu Ala Ser Thr Gln Ser Glu Leu
                325                 330                 335

Thr Leu Ser Gln Lys His Trp Leu Ser Asp Arg Thr Tyr Thr Cys Gln
            340                 345                 350

Val Thr Tyr Gln Gly His Thr Phe Glu Asp Ser Thr Lys Lys Cys Ala
        355                 360                 365

Asp Ser Asn Gly Gly Ser Gly Gly Ala Ser Ser Gly Gly Gly Pro Gln
    370                 375                 380

Arg Val Ala Ala His Ile Thr Gly Thr Arg Gly Arg Ser Asn Thr Leu
385                 390                 395                 400

Ser Ser Pro Asn Ser Lys Asn Glu Lys Ala Leu Gly Arg Lys Ile Asn
                405                 410                 415

Ser Trp Glu Ser Ser Arg Ser Gly His Ser Phe Leu Ser Asn Leu His
            420                 425                 430

Leu Arg Asn Gly Glu Leu Val Ile His Glu Lys Gly Phe Tyr Tyr Ile
        435                 440                 445

Tyr Ser Gln Thr Tyr Phe Arg Phe Gln Glu Glu Ile Lys Glu Asn Thr
    450                 455                 460

Lys Asn Asp Lys Gln Met Val Gln Tyr Ile Tyr Lys Tyr Thr Ser Tyr
465                 470                 475                 480

Pro Asp Pro Ile Leu Leu Met Lys Ser Ala Arg Asn Ser Cys Trp Ser
                485                 490                 495

Lys Asp Ala Glu Tyr Gly Leu Tyr Ser Ile Tyr Gln Gly Gly Ile Phe
            500                 505                 510

Glu Leu Lys Glu Asn Asp Arg Ile Phe Val Ser Val Thr Asn Glu His
        515                 520                 525
```

Leu Ile Asp Met Asp His Glu Ala Ser Phe Phe Gly Ala Phe Leu Val
530                 535                 540

Gly Gly Gly Pro Gln Arg Val Ala Ala His Ile Thr Gly Thr Arg Gly
545                 550                 555                 560

Arg Ser Asn Thr Leu Ser Ser Pro Asn Ser Lys Asn Glu Lys Ala Leu
                565                 570                 575

Gly Arg Lys Ile Asn Ser Trp Glu Ser Ser Arg Ser Gly His Ser Phe
                580                 585                 590

Leu Ser Asn Leu His Leu Arg Asn Gly Glu Leu Val Ile His Glu Lys
                595                 600                 605

Gly Phe Tyr Tyr Ile Tyr Ser Gln Thr Tyr Phe Arg Phe Gln Glu Glu
610                 615                 620

Ile Lys Glu Asn Thr Lys Asn Asp Lys Gln Met Val Gln Tyr Ile Tyr
625                 630                 635                 640

Lys Tyr Thr Ser Tyr Pro Asp Pro Ile Leu Leu Met Lys Ser Ala Arg
                645                 650                 655

Asn Ser Cys Trp Ser Lys Asp Ala Glu Tyr Gly Leu Tyr Ser Ile Tyr
                660                 665                 670

Gln Gly Gly Ile Phe Glu Leu Lys Glu Asn Asp Arg Ile Phe Val Ser
                675                 680                 685

Val Thr Asn Glu His Leu Ile Asp Met Asp His Glu Ala Ser Phe Phe
690                 695                 700

Gly Ala Phe Leu Val Gly Gly Gly Pro Gln Arg Val Ala Ala His Ile
705                 710                 715                 720

Thr Gly Thr Arg Gly Arg Ser Asn Thr Leu Ser Ser Pro Asn Ser Lys
                725                 730                 735

Asn Glu Lys Ala Leu Gly Arg Lys Ile Asn Ser Trp Glu Ser Ser Arg
                740                 745                 750

Ser Gly His Ser Phe Leu Ser Asn Leu His Leu Arg Asn Gly Glu Leu
                755                 760                 765

Val Ile His Glu Lys Gly Phe Tyr Tyr Ile Tyr Ser Gln Thr Tyr Phe
770                 775                 780

Arg Phe Gln Glu Glu Ile Lys Glu Asn Thr Lys Asn Asp Lys Gln Met
785                 790                 795                 800

Val Gln Tyr Ile Tyr Lys Tyr Thr Ser Tyr Pro Asp Pro Ile Leu Leu
                805                 810                 815

Met Lys Ser Ala Arg Asn Ser Cys Trp Ser Lys Asp Ala Glu Tyr Gly
                820                 825                 830

Leu Tyr Ser Ile Tyr Gln Gly Gly Ile Phe Glu Leu Lys Glu Asn Asp
                835                 840                 845

Arg Ile Phe Val Ser Val Thr Asn Glu His Leu Ile Asp Met Asp His
850                 855                 860

Glu Ala Ser Phe Phe Gly Ala Phe Leu Val Gly
865                 870                 875

<210> SEQ ID NO 237
<211> LENGTH: 119
<212> TYPE: PRT
<213> ORGANISM: Artificial Sequence
<220> FEATURE:
<223> OTHER INFORMATION: fusion of scTRAIL3-FAVSGAA

<400> SEQUENCE: 237

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Asn Tyr
            20                  25                  30

Gly Val His Trp Val Arg Gln Ala Pro Gly Lys Gly Leu Glu Trp Leu
            35                  40                  45

Gly Val Ile Trp Ser Gly Gly Asn Thr Asp Tyr Asn Thr Pro Phe Thr
50                      55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Ala Leu Thr Tyr Tyr Asp Tyr Glu Phe Ala Tyr Trp Gly Gln Gly
                100                 105                 110

Thr Thr Val Thr Val Ser Ser
            115

<210> SEQ ID NO 238
<211> LENGTH: 108
<212> TYPE: PRT
<213> ORGANISM: Homo sapiens

<400> SEQUENCE: 238

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg
                100                 105

<210> SEQ ID NO 239
<211> LENGTH: 120
<212> TYPE: PRT
<213> ORGANISM: Homo sapiens

<400> SEQUENCE: 239

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
            35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
                100                 105                 110

Gly Thr Leu Val Thr Val Ser Ser
        115                 120

<210> SEQ ID NO 240
<211> LENGTH: 111
<212> TYPE: PRT
<213> ORGANISM: Homo sapiens

<400> SEQUENCE: 240

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Val Val Ser Trp Tyr Gln Gln His Pro Gly Lys Ala Pro Lys Leu
        35                  40                  45

Ile Ile Tyr Glu Val Ser Gln Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Thr Glu Asp Glu Ala Asp Tyr Tyr Cys Ser Ser Tyr Ala Gly Ser
                85                  90                  95

Ser Ile Phe Val Ile Phe Gly Gly Gly Thr Lys Val Thr Val Leu
            100                 105                 110

<210> SEQ ID NO 241
<211> LENGTH: 119
<212> TYPE: PRT
<213> ORGANISM: Homo sapiens

<400> SEQUENCE: 241

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

Val Met Ala Trp Val Arg Gln Ala Pro Gly Lys Gly Leu Glu Trp Val
        35                  40                  45

Ser Ser Ile Ser Ser Ser Gly Trp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gly Leu Lys Met Ala Thr Ile Phe Asp Tyr Trp Gly Gln Gly
            100                 105                 110

Thr Leu Val Thr Val Ser Ser
        115

<210> SEQ ID NO 242
<211> LENGTH: 480
<212> TYPE: PRT
<213> ORGANISM: Homo sapiens

<400> SEQUENCE: 242

Met Glu Thr Asp Thr Leu Leu Leu Trp Val Leu Leu Trp Val Pro
1               5                   10                  15

Gly Ser Thr Gly Ala Ser Asp Tyr Lys Asp Asp Asp Lys Gly Ala
            20                  25                  30

Glu Val Gln Leu Val Glu Ser Gly Gly Gly Leu Val Gln Pro Gly Gly

```
                35                  40                  45
Ser Leu Arg Leu Ser Cys Ala Ala Ser Gly Phe Ser Leu Thr Asn Tyr
 50                  55                  60
Gly Val His Trp Val Arg Gln Ala Pro Gly Lys Gly Leu Glu Trp Leu
 65                  70                  75                  80
Gly Val Ile Trp Ser Gly Gly Asn Thr Asp Tyr Asn Thr Pro Phe Thr
                 85                  90                  95
Ser Arg Phe Thr Ile Ser Arg Asp Asn Ser Lys Asn Thr Leu Tyr Leu
                100                 105                 110
Gln Met Asn Ser Leu Arg Ala Glu Asp Thr Ala Val Tyr Tyr Cys Ala
                115                 120                 125
Arg Ala Leu Thr Tyr Tyr Asp Tyr Glu Phe Ala Tyr Trp Gly Gln Gly
                130                 135                 140
Thr Thr Val Thr Val Ser Ser Ala Ser Thr Lys Gly Pro Ser Val Phe
145                 150                 155                 160
Pro Leu Ala Pro Ser Ser Lys Ser Thr Ser Gly Gly Thr Ala Ala Leu
                165                 170                 175
Gly Cys Leu Val Lys Asp Tyr Phe Pro Glu Pro Val Thr Val Ser Trp
                180                 185                 190
Asn Ser Gly Ala Leu Thr Ser Gly Val His Thr Phe Pro Ala Val Leu
                195                 200                 205
Gln Ser Ser Gly Leu Tyr Ser Leu Ser Ser Val Val Thr Val Pro Ser
                210                 215                 220
Ser Ser Leu Gly Thr Gln Thr Tyr Ile Cys Asn Val Asn His Lys Pro
225                 230                 235                 240
Ser Asn Thr Lys Val Asp Lys Lys Val Glu Pro Lys Ser Cys Asp Lys
                245                 250                 255
Thr His Thr Cys Pro Pro Cys Pro Ala Pro Val Ala Gly Pro Ser
                260                 265                 270
Val Phe Leu Phe Pro Pro Lys Pro Lys Asp Thr Leu Met Ile Ser Arg
                275                 280                 285
Thr Pro Glu Val Thr Cys Val Val Val Asp Val Ser His Glu Asp Pro
290                 295                 300
Glu Val Lys Phe Asn Trp Tyr Val Asp Gly Val Glu Val His Asn Ala
305                 310                 315                 320
Lys Thr Lys Pro Arg Glu Glu Gln Tyr Asn Ser Thr Tyr Arg Val Val
                325                 330                 335
Ser Val Leu Thr Val Leu His Gln Asp Trp Leu Asn Gly Lys Glu Tyr
                340                 345                 350
Lys Cys Lys Val Ser Asn Lys Gly Leu Pro Ser Ser Ile Glu Lys Thr
                355                 360                 365
Ile Ser Lys Ala Lys Gly Gln Pro Arg Glu Pro Gln Val Tyr Thr Leu
                370                 375                 380
Pro Pro Ser Arg Asp Glu Leu Thr Lys Asn Gln Val Ser Leu Thr Cys
385                 390                 395                 400
Leu Val Lys Gly Phe Tyr Pro Ser Asp Ile Ala Val Glu Trp Glu Ser
                405                 410                 415
Asn Gly Gln Pro Glu Asn Asn Tyr Lys Thr Thr Pro Pro Val Leu Asp
                420                 425                 430
Ser Asp Gly Ser Phe Phe Leu Tyr Ser Lys Leu Thr Val Asp Lys Ser
                435                 440                 445
Arg Trp Gln Gln Gly Asn Val Phe Ser Cys Ser Val Met His Glu Ala
450                 455                 460
```

```
Leu His Asn His Tyr Thr Gln Lys Ser Leu Ser Leu Ser Pro Gly Lys
465                 470                 475                 480
```

<210> SEQ ID NO 243
<211> LENGTH: 234
<212> TYPE: PRT
<213> ORGANISM: Homo sapiens

<400> SEQUENCE: 243

```
Met Glu Thr Asp Thr Leu Leu Leu Trp Val Leu Leu Leu Trp Val Pro
1               5                   10                  15

Gly Ser Thr Gly Asp Ile Gln Leu Thr Gln Ser Pro Ser Phe Leu Ser
            20                  25                  30

Ala Ser Val Gly Asp Arg Val Thr Ile Thr Cys Arg Ala Ser Gln Ser
        35                  40                  45

Ile Gly Thr Asn Ile His Trp Tyr Gln Gln Lys Pro Gly Lys Ala Pro
    50                  55                  60

Lys Leu Leu Ile Lys Tyr Ala Ser Glu Ser Ile Ser Gly Val Pro Ser
65                  70                  75                  80

Arg Phe Ser Gly Ser Gly Ser Gly Thr Glu Phe Thr Leu Thr Ile Ser
                85                  90                  95

Ser Leu Gln Pro Glu Asp Phe Ala Thr Tyr Tyr Cys Gln Gln Asn Asn
            100                 105                 110

Asn Trp Pro Thr Thr Phe Gly Ala Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 244
<211> LENGTH: 731
<212> TYPE: PRT
<213> ORGANISM: Artificial Sequence
<220> FEATURE:
<223> OTHER INFORMATION: fusion protein hu225 IgG light
      chain-scTRAIL3-FAVSGAA

<400> SEQUENCE: 244

```
Met Glu Thr Asp Thr Leu Leu Leu Trp Val Leu Leu Leu Trp Val Pro
1               5                   10                  15

Gly Ser Thr Gly Asp Ile Gln Leu Thr Gln Ser Pro Ser Phe Leu Ser
            20                  25                  30

Ala Ser Val Gly Asp Arg Val Thr Ile Thr Cys Arg Ala Ser Gln Ser
        35                  40                  45

Ile Gly Thr Asn Ile His Trp Tyr Gln Gln Lys Pro Gly Lys Ala Pro
    50                  55                  60
```

```
Lys Leu Leu Ile Lys Tyr Ala Ser Glu Ser Ile Ser Gly Val Pro Ser
 65                  70                  75                  80

Arg Phe Ser Gly Ser Gly Ser Gly Thr Glu Phe Thr Leu Thr Ile Ser
                 85                  90                  95

Ser Leu Gln Pro Glu Asp Phe Ala Thr Tyr Tyr Cys Gln Gln Asn Asn
            100                 105                 110

Asn Trp Pro Thr Thr Phe Gly Ala Gly Thr Lys Leu Glu Ile Lys Arg
            115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
            195                 200                 205

His Lys Val Tyr Ala Cys Glu Val Thr His Gln Gly Leu Ser Ser Pro
210                 215                 220

Val Thr Lys Ser Phe Asn Arg Gly Glu Cys Ala Ala Gly Asn Gly Thr
225                 230                 235                 240

Ser Asn Gly Thr Ser Glu Phe Gly Ala Ala Ala His Ile Thr Gly Thr
            245                 250                 255

Thr Arg Gly Arg Ser Asn Thr Leu Ser Ser Pro Asn Ser Lys Asn Glu
            260                 265                 270

Lys Ala Leu Gly Arg Lys Ile Asn Ser Trp Glu Ser Ser Arg Ser Gly
            275                 280                 285

His Ser Phe Leu Ser Asn Leu His Leu Arg Asn Gly Glu Leu Val Ile
            290                 295                 300

His Glu Lys Gly Phe Tyr Tyr Ile Tyr Ser Gln Thr Tyr Phe Arg Phe
305                 310                 315                 320

Gln Glu Glu Ile Lys Glu Asn Thr Lys Asn Asp Lys Gln Met Val Gln
                325                 330                 335

Tyr Ile Tyr Lys Tyr Thr Ser Tyr Pro Asp Pro Ile Leu Leu Met Lys
            340                 345                 350

Ser Ala Arg Asn Ser Cys Trp Ser Lys Asp Ala Glu Tyr Gly Leu Tyr
            355                 360                 365

Ser Ile Tyr Gln Gly Gly Ile Phe Glu Leu Lys Glu Asn Asp Arg Ile
            370                 375                 380

Phe Val Ser Val Thr Asn Glu His Leu Ile Asp Met Asp His Glu Ala
385                 390                 395                 400

Ser Phe Phe Gly Ala Phe Ala Val Ser Gly Ala Ala His Ile Thr
                405                 410                 415

Gly Thr Arg Gly Arg Ser Asn Thr Leu Ser Ser Pro Asn Ser Lys Asn
            420                 425                 430

Glu Lys Ala Leu Gly Arg Lys Ile Asn Ser Trp Glu Ser Ser Arg Ser
            435                 440                 445

Gly His Ser Phe Leu Ser Asn Leu His Leu Arg Asn Gly Glu Leu Val
            450                 455                 460

Ile His Glu Lys Gly Phe Tyr Tyr Ile Tyr Ser Gln Thr Tyr Phe Arg
465                 470                 475                 480
```

```
Phe Gln Glu Glu Ile Lys Glu Asn Thr Lys Asn Asp Lys Gln Met Val
                485                 490                 495

Gln Tyr Ile Tyr Lys Tyr Thr Ser Tyr Pro Asp Pro Ile Leu Leu Met
            500                 505                 510

Lys Ser Ala Arg Asn Ser Cys Trp Ser Lys Asp Ala Glu Tyr Gly Leu
            515                 520                 525

Tyr Ser Ile Tyr Gln Gly Gly Ile Phe Glu Leu Lys Glu Asn Asp Arg
            530                 535                 540

Ile Phe Val Ser Val Thr Asn Glu His Leu Ile Asp Met Asp His Glu
545                 550                 555                 560

Ala Ser Phe Phe Gly Ala Phe Ala Val Ser Gly Ala Ala His Ile
                565                 570                 575

Thr Gly Thr Arg Gly Arg Ser Asn Thr Leu Ser Ser Pro Asn Ser Lys
            580                 585                 590

Asn Glu Lys Ala Leu Gly Arg Lys Ile Asn Ser Trp Glu Ser Ser Arg
            595                 600                 605

Ser Gly His Ser Phe Leu Ser Asn Leu His Leu Arg Asn Gly Glu Leu
            610                 615                 620

Val Ile His Glu Lys Gly Phe Tyr Tyr Ile Tyr Ser Gln Thr Tyr Phe
625                 630                 635                 640

Arg Phe Gln Glu Glu Ile Lys Glu Asn Thr Lys Asn Asp Lys Gln Met
                645                 650                 655

Val Gln Tyr Ile Tyr Lys Tyr Thr Ser Tyr Pro Asp Pro Ile Leu Leu
            660                 665                 670

Met Lys Ser Ala Arg Asn Ser Cys Trp Ser Lys Asp Ala Glu Tyr Gly
            675                 680                 685

Leu Tyr Ser Ile Tyr Gln Gly Gly Ile Phe Glu Leu Lys Glu Asn Asp
            690                 695                 700

Arg Ile Phe Val Ser Val Thr Asn Glu His Leu Ile Asp Met Asp His
705                 710                 715                 720

Glu Ala Ser Phe Phe Gly Ala Phe Ala Val Ser
                725                 730

<210> SEQ ID NO 245
<211> LENGTH: 762
<212> TYPE: PRT
<213> ORGANISM: Artificial Sequence
<220> FEATURE:
<223> OTHER INFORMATION: scTRAIL3-FAVSGAA-Fc

<400> SEQUENCE: 245

Met Glu Thr Asp Thr Leu Leu Leu Trp Val Leu Leu Leu Trp Val Pro
1               5                   10                  15

Gly Ser Thr Gly Asp Tyr Lys Asp Asp Asp Lys Gly Gly Gly Gly
            20                  25                  30

Ser Gly Thr Gly Gly Ala Ala Ala His Ile Thr Gly Thr Arg Gly Arg
            35                  40                  45

Ser Asn Thr Leu Ser Ser Pro Asn Ser Lys Asn Glu Lys Ala Leu Gly
            50                  55                  60

Arg Lys Ile Asn Ser Trp Glu Ser Ser Arg Ser Gly His Ser Phe Leu
65                  70                  75                  80

Ser Asn Leu His Leu Arg Asn Gly Glu Leu Val Ile His Glu Lys Gly
                85                  90                  95

Phe Tyr Tyr Ile Tyr Ser Gln Thr Tyr Phe Arg Phe Gln Glu Glu Ile
            100                 105                 110
```

-continued

Lys Glu Asn Thr Lys Asn Asp Lys Gln Met Val Gln Tyr Ile Tyr Lys
            115                 120                 125

Tyr Thr Ser Tyr Pro Asp Pro Ile Leu Leu Met Lys Ser Ala Arg Asn
        130                 135                 140

Ser Cys Trp Ser Lys Asp Ala Glu Tyr Gly Leu Tyr Ser Ile Tyr Gln
145                 150                 155                 160

Gly Gly Ile Phe Glu Leu Lys Glu Asn Asp Arg Ile Phe Val Ser Val
                165                 170                 175

Thr Asn Glu His Leu Ile Asp Met Asp His Glu Ala Ser Phe Phe Gly
            180                 185                 190

Ala Phe Ala Val Ser Gly Ala Ala His Ile Thr Gly Thr Arg Gly
        195                 200                 205

Arg Ser Asn Thr Leu Ser Ser Pro Asn Ser Lys Asn Glu Lys Ala Leu
210                 215                 220

Gly Arg Lys Ile Asn Ser Trp Glu Ser Ser Arg Ser Gly His Ser Phe
225                 230                 235                 240

Leu Ser Asn Leu His Leu Arg Asn Gly Glu Leu Val Ile His Glu Lys
            245                 250                 255

Gly Phe Tyr Tyr Ile Tyr Ser Gln Thr Tyr Phe Arg Phe Gln Glu Glu
        260                 265                 270

Ile Lys Glu Asn Thr Lys Asn Asp Lys Gln Met Val Gln Tyr Ile Tyr
            275                 280                 285

Lys Tyr Thr Ser Tyr Pro Asp Pro Ile Leu Leu Met Lys Ser Ala Arg
        290                 295                 300

Asn Ser Cys Trp Ser Lys Asp Ala Glu Tyr Gly Leu Tyr Ser Ile Tyr
305                 310                 315                 320

Gln Gly Gly Ile Phe Glu Leu Lys Glu Asn Asp Arg Ile Phe Val Ser
                325                 330                 335

Val Thr Asn Glu His Leu Ile Asp Met Asp His Glu Ala Ser Phe Phe
            340                 345                 350

Gly Ala Phe Ala Val Ser Gly Ala Ala Ala His Ile Thr Gly Thr Arg
        355                 360                 365

Gly Arg Ser Asn Thr Leu Ser Ser Pro Asn Ser Lys Asn Glu Lys Ala
        370                 375                 380

Leu Gly Arg Lys Ile Asn Ser Trp Glu Ser Ser Arg Ser Gly His Ser
385                 390                 395                 400

Phe Leu Ser Asn Leu His Leu Arg Asn Gly Glu Leu Val Ile His Glu
                405                 410                 415

Lys Gly Phe Tyr Tyr Ile Tyr Ser Gln Thr Tyr Phe Arg Phe Gln Glu
            420                 425                 430

Glu Ile Lys Glu Asn Thr Lys Asn Asp Lys Gln Met Val Gln Tyr Ile
            435                 440                 445

Tyr Lys Tyr Thr Ser Tyr Pro Asp Pro Ile Leu Leu Met Lys Ser Ala
        450                 455                 460

Arg Asn Ser Cys Trp Ser Lys Asp Ala Glu Tyr Gly Leu Tyr Ser Ile
465                 470                 475                 480

Tyr Gln Gly Gly Ile Phe Glu Leu Lys Glu Asn Asp Arg Ile Phe Val
                485                 490                 495

Ser Val Thr Asn Glu His Leu Ile Asp Met Asp His Glu Ala Ser Phe
            500                 505                 510

Phe Gly Ala Phe Ala Val Ser Gly Ser Gly Asn Gly Thr Ser Asn Gly
        515                 520                 525

Thr Ser Gly Ser Ser Gly Gly Asp Lys Thr His Thr Cys Pro Pro Cys

```
            530                 535                 540
Pro Ala Pro Glu Leu Leu Gly Gly Pro Ser Val Phe Leu Phe Pro Pro
545                 550                 555                 560

Lys Pro Lys Asp Thr Leu Met Ile Ser Arg Thr Pro Glu Val Thr Cys
                565                 570                 575

Val Val Val Asp Val Ser His Glu Asp Pro Glu Val Lys Phe Asn Trp
            580                 585                 590

Tyr Val Asp Gly Val Glu Val His Asn Ala Lys Thr Lys Pro Arg Glu
        595                 600                 605

Glu Gln Tyr Asn Ser Thr Tyr Arg Val Val Ser Val Leu Thr Val Leu
    610                 615                 620

His Gln Asp Trp Leu Asn Gly Lys Glu Tyr Lys Cys Lys Val Ser Asn
625                 630                 635                 640

Lys Ala Leu Pro Ala Pro Ile Glu Lys Thr Ile Ser Lys Ala Lys Gly
                645                 650                 655

Gln Pro Arg Glu Pro Gln Val Tyr Thr Leu Pro Pro Ser Arg Asp Glu
            660                 665                 670

Leu Thr Lys Asn Gln Val Ser Leu Thr Cys Leu Val Lys Gly Phe Tyr
        675                 680                 685

Pro Ser Asp Ile Ala Val Glu Trp Glu Ser Asn Gly Gln Pro Glu Asn
    690                 695                 700

Asn Tyr Lys Thr Thr Pro Pro Val Leu Asp Ser Asp Gly Ser Phe Phe
705                 710                 715                 720

Leu Tyr Ser Lys Leu Thr Val Asp Lys Ser Arg Trp Gln Gln Gly Asn
                725                 730                 735

Val Phe Ser Cys Ser Val Met His Glu Ala Leu His Asn His Tyr Thr
            740                 745                 750

Gln Lys Ser Leu Ser Leu Ser Pro Gly Lys
        755                 760

<210> SEQ ID NO 246
<211> LENGTH: 760
<212> TYPE: PRT
<213> ORGANISM: Artificial Sequence
<220> FEATURE:
<223> OTHER INFORMATION: Fc-scTRAIL3-FAVSGAA

<400> SEQUENCE: 246

Met Glu Thr Asp Thr Leu Leu Leu Trp Val Leu Leu Leu Trp Val Pro
1               5                   10                  15

Gly Ser Thr Gly Asp Tyr Lys Asp Asp Asp Asp Lys Gly Gly Gly Gly
                20                  25                  30

Ser Gly Thr Asp Lys Thr His Thr Cys Pro Pro Cys Pro Ala Pro Glu
            35                  40                  45

Leu Leu Gly Gly Pro Ser Val Phe Leu Phe Pro Pro Lys Pro Lys Asp
        50                  55                  60

Thr Leu Met Ile Ser Arg Thr Pro Glu Val Thr Cys Val Val Val Asp
65                  70                  75                  80

Val Ser His Glu Asp Pro Glu Val Lys Phe Asn Trp Tyr Val Asp Gly
                85                  90                  95

Val Glu Val His Asn Ala Lys Thr Lys Pro Arg Glu Glu Gln Tyr Asn
            100                 105                 110

Ser Thr Tyr Arg Val Val Ser Val Leu Thr Val Leu His Gln Asp Trp
        115                 120                 125

Leu Asn Gly Lys Glu Tyr Lys Cys Lys Val Ser Asn Lys Ala Leu Pro
```

```
            130                 135                 140
Ala Pro Ile Glu Lys Thr Ile Ser Lys Ala Lys Gly Gln Pro Arg Glu
145                 150                 155                 160

Pro Gln Val Tyr Thr Leu Pro Pro Ser Arg Asp Glu Leu Thr Lys Asn
                    165                 170                 175

Gln Val Ser Leu Thr Cys Leu Val Lys Gly Phe Tyr Pro Ser Asp Ile
                180                 185                 190

Ala Val Glu Trp Glu Ser Asn Gly Gln Pro Glu Asn Asn Tyr Lys Thr
            195                 200                 205

Thr Pro Pro Val Leu Asp Ser Asp Gly Ser Phe Phe Leu Tyr Ser Lys
210                 215                 220

Leu Thr Val Asp Lys Ser Arg Trp Gln Gln Gly Asn Val Phe Ser Cys
225                 230                 235                 240

Ser Val Met His Glu Ala Leu His Asn His Tyr Thr Gln Lys Ser Leu
                245                 250                 255

Ser Leu Ser Pro Gly Gln Gly Ser Gly Asn Gly Thr Ser Asn Gly Thr
                260                 265                 270

Ser Gly Ser Ser Gly Gly Ala Ala His Ile Thr Gly Thr Arg Gly
            275                 280                 285

Arg Ser Asn Thr Leu Ser Ser Pro Asn Ser Lys Asn Glu Lys Ala Leu
            290                 295                 300

Gly Arg Lys Ile Asn Ser Trp Glu Ser Ser Arg Ser Gly His Ser Phe
305                 310                 315                 320

Leu Ser Asn Leu His Leu Arg Asn Gly Glu Leu Val Ile His Glu Lys
                325                 330                 335

Gly Phe Tyr Tyr Ile Tyr Ser Gln Thr Tyr Phe Arg Phe Gln Glu Glu
                340                 345                 350

Ile Lys Glu Asn Thr Lys Asn Asp Lys Gln Met Val Gln Tyr Ile Tyr
                355                 360                 365

Lys Tyr Thr Ser Tyr Pro Asp Pro Ile Leu Leu Met Lys Ser Ala Arg
            370                 375                 380

Asn Ser Cys Trp Ser Lys Asp Ala Glu Tyr Gly Leu Tyr Ser Ile Tyr
385                 390                 395                 400

Gln Gly Gly Ile Phe Glu Leu Lys Glu Asn Asp Arg Ile Phe Val Ser
                405                 410                 415

Val Thr Asn Glu His Leu Ile Asp Met Asp His Glu Ala Ser Phe Phe
                420                 425                 430

Gly Ala Phe Ala Val Ser Gly Ala Ala His Ile Thr Gly Thr Arg
            435                 440                 445

Gly Arg Ser Asn Thr Leu Ser Ser Pro Asn Ser Lys Asn Glu Lys Ala
450                 455                 460

Leu Gly Arg Lys Ile Asn Ser Trp Glu Ser Ser Arg Ser Gly His Ser
465                 470                 475                 480

Phe Leu Ser Asn Leu His Leu Arg Asn Gly Glu Leu Val Ile His Glu
                485                 490                 495

Lys Gly Phe Tyr Tyr Ile Tyr Ser Gln Thr Tyr Phe Arg Phe Gln Glu
                500                 505                 510

Glu Ile Lys Glu Asn Thr Lys Asn Asp Lys Gln Met Val Gln Tyr Ile
                515                 520                 525

Tyr Lys Tyr Thr Ser Tyr Pro Asp Pro Ile Leu Leu Met Lys Ser Ala
            530                 535                 540

Arg Asn Ser Cys Trp Ser Lys Asp Ala Glu Tyr Gly Leu Tyr Ser Ile
545                 550                 555                 560
```

```
Tyr Gln Gly Gly Ile Phe Glu Leu Lys Glu Asn Asp Arg Ile Phe Val
                565                 570                 575

Ser Val Thr Asn Glu His Leu Ile Asp Met Asp His Glu Ala Ser Phe
            580                 585                 590

Phe Gly Ala Phe Ala Val Ser Gly Ala Ala His Ile Thr Gly Thr
        595                 600                 605

Arg Gly Arg Ser Asn Thr Leu Ser Ser Pro Asn Ser Lys Asn Glu Lys
    610                 615                 620

Ala Leu Gly Arg Lys Ile Asn Ser Trp Glu Ser Ser Arg Ser Gly His
625                 630                 635                 640

Ser Phe Leu Ser Asn Leu His Leu Arg Asn Gly Glu Leu Val Ile His
                645                 650                 655

Glu Lys Gly Phe Tyr Tyr Ile Tyr Ser Gln Thr Tyr Phe Arg Phe Gln
                660                 665                 670

Glu Glu Ile Lys Glu Asn Thr Lys Asn Asp Lys Gln Met Val Gln Tyr
                675                 680                 685

Ile Tyr Lys Tyr Thr Ser Tyr Pro Asp Pro Ile Leu Leu Met Lys Ser
                690                 695                 700

Ala Arg Asn Ser Cys Trp Ser Lys Asp Ala Glu Tyr Gly Leu Tyr Ser
705                 710                 715                 720

Ile Tyr Gln Gly Gly Ile Phe Glu Leu Lys Glu Asn Asp Arg Ile Phe
                725                 730                 735

Val Ser Val Thr Asn Glu His Leu Ile Asp Met Asp His Glu Ala Ser
                740                 745                 750

Phe Phe Gly Ala Phe Ala Val Ser
                755                 760

<210> SEQ ID NO 247
<211> LENGTH: 1260
<212> TYPE: PRT
<213> ORGANISM: Artificial Sequence
<220> FEATURE:
<223> OTHER INFORMATION: scTRAIL3-FAVSGAA-Fc-scTRAIL3-FAVSGAA

<400> SEQUENCE: 247

Met Glu Thr Asp Thr Leu Leu Leu Trp Val Leu Leu Leu Trp Val Pro
1               5                   10                  15

Gly Ser Thr Gly Asp Tyr Lys Asp Asp Asp Asp Lys Gly Gly Gly Gly
                20                  25                  30

Ser Gly Thr Gly Gly Ala Ala Ala His Ile Thr Gly Thr Arg Gly Arg
            35                  40                  45

Ser Asn Thr Leu Ser Ser Pro Asn Ser Lys Asn Glu Lys Ala Leu Gly
    50                  55                  60

Arg Lys Ile Asn Ser Trp Glu Ser Ser Arg Ser Gly His Ser Phe Leu
65                  70                  75                  80

Ser Asn Leu His Leu Arg Asn Gly Glu Leu Val Ile His Glu Lys Gly
                85                  90                  95

Phe Tyr Tyr Ile Tyr Ser Gln Thr Tyr Phe Arg Phe Gln Glu Glu Ile
                100                 105                 110

Lys Glu Asn Thr Lys Asn Asp Lys Gln Met Val Gln Tyr Ile Tyr Lys
            115                 120                 125

Tyr Thr Ser Tyr Pro Asp Pro Ile Leu Leu Met Lys Ser Ala Arg Asn
    130                 135                 140

Ser Cys Trp Ser Lys Asp Ala Glu Tyr Gly Leu Tyr Ser Ile Tyr Gln
145                 150                 155                 160
```

```
Gly Gly Ile Phe Glu Leu Lys Glu Asn Asp Arg Ile Phe Val Ser Val
            165                 170                 175

Thr Asn Glu His Leu Ile Asp Met Asp His Glu Ala Ser Phe Phe Gly
            180                 185                 190

Ala Phe Ala Val Ser Gly Ala Ala His Ile Thr Gly Thr Arg Gly
        195                 200                 205

Arg Ser Asn Thr Leu Ser Ser Pro Asn Ser Lys Asn Glu Lys Ala Leu
        210                 215                 220

Gly Arg Lys Ile Asn Ser Trp Glu Ser Ser Arg Ser Gly His Ser Phe
225                 230                 235                 240

Leu Ser Asn Leu His Leu Arg Asn Gly Glu Leu Val Ile His Glu Lys
            245                 250                 255

Gly Phe Tyr Tyr Ile Tyr Ser Gln Thr Tyr Phe Arg Phe Gln Glu Glu
            260                 265                 270

Ile Lys Glu Asn Thr Lys Asn Asp Lys Gln Met Val Gln Tyr Ile Tyr
            275                 280                 285

Lys Tyr Thr Ser Tyr Pro Asp Pro Ile Leu Leu Met Lys Ser Ala Arg
            290                 295                 300

Asn Ser Cys Trp Ser Lys Asp Ala Glu Tyr Gly Leu Tyr Ser Ile Tyr
305                 310                 315                 320

Gln Gly Gly Ile Phe Glu Leu Lys Glu Asn Asp Arg Ile Phe Val Ser
                325                 330                 335

Val Thr Asn Glu His Leu Ile Asp Met Asp His Glu Ala Ser Phe Phe
            340                 345                 350

Gly Ala Phe Ala Val Ser Gly Ala Ala His Ile Thr Gly Thr Arg
        355                 360                 365

Gly Arg Ser Asn Thr Leu Ser Ser Pro Asn Ser Lys Asn Glu Lys Ala
        370                 375                 380

Leu Gly Arg Lys Ile Asn Ser Trp Glu Ser Ser Arg Ser Gly His Ser
385                 390                 395                 400

Phe Leu Ser Asn Leu His Leu Arg Asn Gly Glu Leu Val Ile His Glu
            405                 410                 415

Lys Gly Phe Tyr Tyr Ile Tyr Ser Gln Thr Tyr Phe Arg Phe Gln Glu
            420                 425                 430

Glu Ile Lys Glu Asn Thr Lys Asn Asp Lys Gln Met Val Gln Tyr Ile
            435                 440                 445

Tyr Lys Tyr Thr Ser Tyr Pro Asp Pro Ile Leu Leu Met Lys Ser Ala
            450                 455                 460

Arg Asn Ser Cys Trp Ser Lys Asp Ala Glu Tyr Gly Leu Tyr Ser Ile
465                 470                 475                 480

Tyr Gln Gly Gly Ile Phe Glu Leu Lys Glu Asn Asp Arg Ile Phe Val
                485                 490                 495

Ser Val Thr Asn Glu His Leu Ile Asp Met Asp His Glu Ala Ser Phe
            500                 505                 510

Phe Gly Ala Phe Ala Val Ser Gly Ser Gly Asn Gly Thr Ser Asn Gly
        515                 520                 525

Thr Ser Gly Ser Ser Arg Thr Asp Lys Thr His Thr Cys Pro Pro Cys
        530                 535                 540

Pro Ala Pro Glu Leu Leu Gly Gly Pro Ser Val Phe Leu Phe Pro Pro
545                 550                 555                 560

Lys Pro Lys Asp Thr Leu Met Ile Ser Arg Thr Pro Glu Val Thr Cys
                565                 570                 575
```

```
Val Val Val Asp Val Ser His Glu Asp Pro Glu Val Lys Phe Asn Trp
            580                 585                 590

Tyr Val Asp Gly Val Glu Val His Asn Ala Lys Thr Lys Pro Arg Glu
        595                 600                 605

Glu Gln Tyr Asn Ser Thr Tyr Arg Val Val Ser Val Leu Thr Val Leu
    610                 615                 620

His Gln Asp Trp Leu Asn Gly Lys Glu Tyr Lys Cys Lys Val Ser Asn
625                 630                 635                 640

Lys Ala Leu Pro Ala Pro Ile Glu Lys Thr Ile Ser Lys Ala Lys Gly
                645                 650                 655

Gln Pro Arg Glu Pro Gln Val Tyr Thr Leu Pro Pro Ser Arg Asp Glu
            660                 665                 670

Leu Thr Lys Asn Gln Val Ser Leu Thr Cys Leu Val Lys Gly Phe Tyr
        675                 680                 685

Pro Ser Asp Ile Ala Val Glu Trp Glu Ser Asn Gly Gln Pro Glu Asn
    690                 695                 700

Asn Tyr Lys Thr Thr Pro Pro Val Leu Asp Ser Asp Gly Ser Phe Phe
705                 710                 715                 720

Leu Tyr Ser Lys Leu Thr Val Asp Lys Ser Arg Trp Gln Gln Gly Asn
                725                 730                 735

Val Phe Ser Cys Ser Val Met His Glu Ala Leu His Asn His Tyr Thr
            740                 745                 750

Gln Lys Ser Leu Ser Leu Ser Pro Gly Gln Gly Ser Gly Asn Gly Thr
        755                 760                 765

Ser Asn Gly Thr Ser Gly Ser Ser Gly Ala Ala Ala His Ile Thr
    770                 775                 780

Gly Thr Arg Gly Arg Ser Asn Thr Leu Ser Ser Pro Asn Ser Lys Asn
785                 790                 795                 800

Glu Lys Ala Leu Gly Arg Lys Ile Asn Ser Trp Glu Ser Ser Arg Ser
                805                 810                 815

Gly His Ser Phe Leu Ser Asn Leu His Leu Arg Asn Gly Glu Leu Val
            820                 825                 830

Ile His Glu Lys Gly Phe Tyr Tyr Ile Tyr Ser Gln Thr Tyr Phe Arg
        835                 840                 845

Phe Gln Glu Glu Ile Lys Glu Asn Thr Lys Asn Asp Lys Gln Met Val
    850                 855                 860

Gln Tyr Ile Tyr Lys Tyr Thr Ser Tyr Pro Asp Pro Ile Leu Leu Met
865                 870                 875                 880

Lys Ser Ala Arg Asn Ser Cys Trp Ser Lys Asp Ala Glu Tyr Gly Leu
                885                 890                 895

Tyr Ser Ile Tyr Gln Gly Gly Ile Phe Glu Leu Lys Glu Asn Asp Arg
            900                 905                 910

Ile Phe Val Ser Val Thr Asn Glu His Leu Ile Asp Met Asp His Glu
        915                 920                 925

Ala Ser Phe Phe Gly Ala Phe Ala Val Ser Gly Ala Ala Ala His Ile
    930                 935                 940

Thr Gly Thr Arg Gly Arg Ser Asn Thr Leu Ser Ser Pro Asn Ser Lys
945                 950                 955                 960

Asn Glu Lys Ala Leu Gly Arg Lys Ile Asn Ser Trp Glu Ser Ser Arg
                965                 970                 975

Ser Gly His Ser Phe Leu Ser Asn Leu His Leu Arg Asn Gly Glu Leu
            980                 985                 990

Val Ile His Glu Lys Gly Phe Tyr  Tyr Ile Tyr Ser Gln  Thr Tyr Phe
```

```
                995           1000           1005
Arg Phe Gln Glu Glu Ile Lys Glu Asn Thr Lys Asn Asp Lys Gln
    1010           1015           1020

Met Val Gln Tyr Ile Tyr Lys Tyr Thr Ser Tyr Pro Asp Pro Ile
    1025           1030           1035

Leu Leu Met Lys Ser Ala Arg Asn Ser Cys Trp Ser Lys Asp Ala
    1040           1045           1050

Glu Tyr Gly Leu Tyr Ser Ile Tyr Gln Gly Gly Ile Phe Glu Leu
    1055           1060           1065

Lys Glu Asn Asp Arg Ile Phe Val Ser Val Thr Asn Glu His Leu
    1070           1075           1080

Ile Asp Met Asp His Glu Ala Ser Phe Phe Gly Ala Phe Ala Val
    1085           1090           1095

Ser Gly Ala Ala Ala His Ile Thr Gly Thr Arg Gly Arg Ser Asn
    1100           1105           1110

Thr Leu Ser Ser Pro Asn Ser Lys Asn Glu Lys Ala Leu Gly Arg
    1115           1120           1125

Lys Ile Asn Ser Trp Glu Ser Ser Arg Ser Gly His Ser Phe Leu
    1130           1135           1140

Ser Asn Leu His Leu Arg Asn Gly Glu Leu Val Ile His Glu Lys
    1145           1150           1155

Gly Phe Tyr Tyr Ile Tyr Ser Gln Thr Tyr Phe Arg Phe Gln Glu
    1160           1165           1170

Glu Ile Lys Glu Asn Thr Lys Asn Asp Lys Gln Met Val Gln Tyr
    1175           1180           1185

Ile Tyr Lys Tyr Thr Ser Tyr Pro Asp Pro Ile Leu Leu Met Lys
    1190           1195           1200

Ser Ala Arg Asn Ser Cys Trp Ser Lys Asp Ala Glu Tyr Gly Leu
    1205           1210           1215

Tyr Ser Ile Tyr Gln Gly Gly Ile Phe Glu Leu Lys Glu Asn Asp
    1220           1225           1230

Arg Ile Phe Val Ser Val Thr Asn Glu His Leu Ile Asp Met Asp
    1235           1240           1245

His Glu Ala Ser Phe Phe Gly Ala Phe Ala Val Ser
    1250           1255           1260

<210> SEQ ID NO 248
<211> LENGTH: 746
<212> TYPE: PRT
<213> ORGANISM: Artificial Sequence
<220> FEATURE:
<223> OTHER INFORMATION: scTRAIL3-FAVSGAA-0-Fc

<400> SEQUENCE: 248

Met Glu Thr Asp Thr Leu Leu Leu Trp Val Leu Leu Leu Trp Val Pro
1               5                   10                  15

Gly Ser Thr Gly Asp Tyr Lys Asp Asp Asp Lys Gly Gly Gly Gly
                20                  25                  30

Ser Gly Thr Gly Gly Ala Ala Ala His Ile Thr Gly Thr Arg Gly Arg
        35                  40                  45

Ser Asn Thr Leu Ser Ser Pro Asn Ser Lys Asn Glu Lys Ala Leu Gly
    50                  55                  60

Arg Lys Ile Asn Ser Trp Glu Ser Ser Arg Ser Gly His Ser Phe Leu
65                  70                  75                  80

Ser Asn Leu His Leu Arg Asn Gly Glu Leu Val Ile His Glu Lys Gly
```

```
                   85                  90                  95
Phe Tyr Tyr Ile Tyr Ser Gln Thr Tyr Phe Arg Phe Gln Glu Glu Ile
                  100                 105                 110
Lys Glu Asn Thr Lys Asn Asp Lys Gln Met Val Gln Tyr Ile Tyr Lys
                  115                 120                 125
Tyr Thr Ser Tyr Pro Asp Pro Ile Leu Leu Met Lys Ser Ala Arg Asn
                  130                 135                 140
Ser Cys Trp Ser Lys Asp Ala Glu Tyr Gly Leu Tyr Ser Ile Tyr Gln
145                 150                 155                 160
Gly Gly Ile Phe Glu Leu Lys Glu Asn Asp Arg Ile Phe Val Ser Val
                  165                 170                 175
Thr Asn Glu His Leu Ile Asp Met Asp His Glu Ala Ser Phe Phe Gly
                  180                 185                 190
Ala Phe Ala Val Ser Gly Ala Ala His Ile Thr Gly Thr Arg Gly
                  195                 200                 205
Arg Ser Asn Thr Leu Ser Ser Pro Asn Ser Lys Asn Glu Lys Ala Leu
                  210                 215                 220
Gly Arg Lys Ile Asn Ser Trp Glu Ser Ser Arg Ser Gly His Ser Phe
225                 230                 235                 240
Leu Ser Asn Leu His Leu Arg Asn Gly Glu Leu Val Ile His Glu Lys
                  245                 250                 255
Gly Phe Tyr Tyr Ile Tyr Ser Gln Thr Tyr Phe Arg Phe Gln Glu Glu
                  260                 265                 270
Ile Lys Glu Asn Thr Lys Asn Asp Lys Gln Met Val Gln Tyr Ile Tyr
                  275                 280                 285
Lys Tyr Thr Ser Tyr Pro Asp Pro Ile Leu Leu Met Lys Ser Ala Arg
                  290                 295                 300
Asn Ser Cys Trp Ser Lys Asp Ala Glu Tyr Gly Leu Tyr Ser Ile Tyr
305                 310                 315                 320
Gln Gly Gly Ile Phe Glu Leu Lys Glu Asn Asp Arg Ile Phe Val Ser
                  325                 330                 335
Val Thr Asn Glu His Leu Ile Asp Met Asp His Glu Ala Ser Phe Phe
                  340                 345                 350
Gly Ala Phe Ala Val Ser Gly Ala Ala His Ile Thr Gly Thr Arg
                  355                 360                 365
Gly Arg Ser Asn Thr Leu Ser Ser Pro Asn Ser Lys Asn Glu Lys Ala
                  370                 375                 380
Leu Gly Arg Lys Ile Asn Ser Trp Glu Ser Ser Arg Ser Gly His Ser
385                 390                 395                 400
Phe Leu Ser Asn Leu His Leu Arg Asn Gly Glu Leu Val Ile His Glu
                  405                 410                 415
Lys Gly Phe Tyr Tyr Ile Tyr Ser Gln Thr Tyr Phe Arg Phe Gln Glu
                  420                 425                 430
Glu Ile Lys Glu Asn Thr Lys Asn Asp Lys Gln Met Val Gln Tyr Ile
                  435                 440                 445
Tyr Lys Tyr Thr Ser Tyr Pro Asp Pro Ile Leu Leu Met Lys Ser Ala
                  450                 455                 460
Arg Asn Ser Cys Trp Ser Lys Asp Ala Glu Tyr Gly Leu Tyr Ser Ile
465                 470                 475                 480
Tyr Gln Gly Gly Ile Phe Glu Leu Lys Glu Asn Asp Arg Ile Phe Val
                  485                 490                 495
Ser Val Thr Asn Glu His Leu Ile Asp Met Asp His Glu Ala Ser Phe
                  500                 505                 510
```

```
Phe Gly Ala Phe Ala Val Ser Asp Lys Thr His Thr Cys Pro Pro Cys
            515                 520                 525

Pro Ala Pro Glu Leu Leu Gly Gly Pro Ser Val Phe Leu Phe Pro Pro
    530                 535                 540

Lys Pro Lys Asp Thr Leu Met Ile Ser Arg Thr Pro Glu Val Thr Cys
545                 550                 555                 560

Val Val Val Asp Val Ser His Glu Asp Pro Glu Val Lys Phe Asn Trp
                565                 570                 575

Tyr Val Asp Gly Val Glu Val His Asn Ala Lys Thr Lys Pro Arg Glu
            580                 585                 590

Glu Gln Tyr Asn Ser Thr Tyr Arg Val Val Ser Val Leu Thr Val Leu
        595                 600                 605

His Gln Asp Trp Leu Asn Gly Lys Glu Tyr Lys Cys Lys Val Ser Asn
    610                 615                 620

Lys Ala Leu Pro Ala Pro Ile Glu Lys Thr Ile Ser Lys Ala Lys Gly
625                 630                 635                 640

Gln Pro Arg Glu Pro Gln Val Tyr Thr Leu Pro Pro Ser Arg Asp Glu
                645                 650                 655

Leu Thr Lys Asn Gln Val Ser Leu Thr Cys Leu Val Lys Gly Phe Tyr
            660                 665                 670

Pro Ser Asp Ile Ala Val Glu Trp Glu Ser Asn Gly Gln Pro Glu Asn
        675                 680                 685

Asn Tyr Lys Thr Thr Pro Pro Val Leu Asp Ser Asp Gly Ser Phe Phe
    690                 695                 700

Leu Tyr Ser Lys Leu Thr Val Asp Lys Ser Arg Trp Gln Gln Gly Asn
705                 710                 715                 720

Val Phe Ser Cys Ser Val Met His Glu Ala Leu His Asn His Tyr Thr
                725                 730                 735

Gln Lys Ser Leu Ser Leu Ser Pro Gly Lys
            740                 745

<210> SEQ ID NO 249
<211> LENGTH: 751
<212> TYPE: PRT
<213> ORGANISM: Artificial Sequence
<220> FEATURE:
<223> OTHER INFORMATION: scTRAIL3-FAVSGAA-5 G/S-Fc

<400> SEQUENCE: 249

Met Glu Thr Asp Thr Leu Leu Leu Trp Val Leu Leu Leu Trp Val Pro
1               5                   10                  15

Gly Ser Thr Gly Asp Tyr Lys Asp Asp Asp Asp Lys Gly Gly Gly Gly
            20                  25                  30

Ser Gly Thr Gly Gly Ala Ala His Ile Thr Gly Thr Arg Gly Arg
        35                  40                  45

Ser Asn Thr Leu Ser Ser Pro Asn Ser Lys Asn Glu Lys Ala Leu Gly
    50                  55                  60

Arg Lys Ile Asn Ser Trp Glu Ser Ser Arg Ser Gly His Ser Phe Leu
65                  70                  75                  80

Ser Asn Leu His Leu Arg Asn Gly Glu Leu Val Ile His Glu Lys Gly
                85                  90                  95

Phe Tyr Tyr Ile Tyr Ser Gln Thr Tyr Phe Arg Phe Gln Glu Glu Ile
            100                 105                 110

Lys Glu Asn Thr Lys Asn Asp Lys Gln Met Val Gln Tyr Ile Tyr Lys
        115                 120                 125
```

```
Tyr Thr Ser Tyr Pro Asp Pro Ile Leu Leu Met Lys Ser Ala Arg Asn
    130                 135                 140

Ser Cys Trp Ser Lys Asp Ala Glu Tyr Gly Leu Tyr Ser Ile Tyr Gln
145                 150                 155                 160

Gly Gly Ile Phe Glu Leu Lys Glu Asn Asp Arg Ile Phe Val Ser Val
                165                 170                 175

Thr Asn Glu His Leu Ile Asp Met Asp His Glu Ala Ser Phe Phe Gly
            180                 185                 190

Ala Phe Ala Val Ser Gly Ala Ala His Ile Thr Gly Thr Arg Gly
        195                 200                 205

Arg Ser Asn Thr Leu Ser Ser Pro Asn Ser Lys Asn Glu Lys Ala Leu
    210                 215                 220

Gly Arg Lys Ile Asn Ser Trp Glu Ser Ser Arg Ser Gly His Ser Phe
225                 230                 235                 240

Leu Ser Asn Leu His Leu Arg Asn Gly Glu Leu Val Ile His Glu Lys
                245                 250                 255

Gly Phe Tyr Tyr Ile Tyr Ser Gln Thr Tyr Phe Arg Phe Gln Glu Glu
                260                 265                 270

Ile Lys Glu Asn Thr Lys Asn Asp Lys Gln Met Val Gln Tyr Ile Tyr
            275                 280                 285

Lys Tyr Thr Ser Tyr Pro Asp Pro Ile Leu Leu Met Lys Ser Ala Arg
    290                 295                 300

Asn Ser Cys Trp Ser Lys Asp Ala Glu Tyr Gly Leu Tyr Ser Ile Tyr
305                 310                 315                 320

Gln Gly Gly Ile Phe Glu Leu Lys Glu Asn Asp Arg Ile Phe Val Ser
                325                 330                 335

Val Thr Asn Glu His Leu Ile Asp Met Asp His Glu Ala Ser Phe Phe
            340                 345                 350

Gly Ala Phe Ala Val Ser Gly Ala Ala His Ile Thr Gly Thr Arg
        355                 360                 365

Gly Arg Ser Asn Thr Leu Ser Ser Pro Asn Ser Lys Asn Glu Lys Ala
    370                 375                 380

Leu Gly Arg Lys Ile Asn Ser Trp Glu Ser Ser Arg Ser Gly His Ser
385                 390                 395                 400

Phe Leu Ser Asn Leu His Leu Arg Asn Gly Glu Leu Val Ile His Glu
                405                 410                 415

Lys Gly Phe Tyr Tyr Ile Tyr Ser Gln Thr Tyr Phe Arg Phe Gln Glu
                420                 425                 430

Glu Ile Lys Glu Asn Thr Lys Asn Asp Lys Gln Met Val Gln Tyr Ile
        435                 440                 445

Tyr Lys Tyr Thr Ser Tyr Pro Asp Pro Ile Leu Leu Met Lys Ser Ala
    450                 455                 460

Arg Asn Ser Cys Trp Ser Lys Asp Ala Glu Tyr Gly Leu Tyr Ser Ile
465                 470                 475                 480

Tyr Gln Gly Gly Ile Phe Glu Leu Lys Glu Asn Asp Arg Ile Phe Val
                485                 490                 495

Ser Val Thr Asn Glu His Leu Ile Asp Met Asp His Glu Ala Ser Phe
            500                 505                 510

Phe Gly Ala Phe Ala Val Ser Gly Gly Ser Gly Gly Asp Lys Thr His
        515                 520                 525

Thr Cys Pro Pro Cys Pro Ala Pro Glu Leu Leu Gly Gly Pro Ser Val
    530                 535                 540
```

Phe Leu Phe Pro Pro Lys Pro Lys Asp Thr Leu Met Ile Ser Arg Thr
545                 550                 555                 560

Pro Glu Val Thr Cys Val Val Val Asp Val Ser His Glu Asp Pro Glu
                565                 570                 575

Val Lys Phe Asn Trp Tyr Val Asp Gly Val Glu Val His Asn Ala Lys
            580                 585                 590

Thr Lys Pro Arg Glu Glu Gln Tyr Asn Ser Thr Tyr Arg Val Val Ser
        595                 600                 605

Val Leu Thr Val Leu His Gln Asp Trp Leu Asn Gly Lys Glu Tyr Lys
    610                 615                 620

Cys Lys Val Ser Asn Lys Ala Leu Pro Ala Pro Ile Glu Lys Thr Ile
625                 630                 635                 640

Ser Lys Ala Lys Gly Gln Pro Arg Glu Pro Gln Val Tyr Thr Leu Pro
                645                 650                 655

Pro Ser Arg Asp Glu Leu Thr Lys Asn Gln Val Ser Leu Thr Cys Leu
            660                 665                 670

Val Lys Gly Phe Tyr Pro Ser Asp Ile Ala Val Glu Trp Glu Ser Asn
        675                 680                 685

Gly Gln Pro Glu Asn Asn Tyr Lys Thr Thr Pro Pro Val Leu Asp Ser
    690                 695                 700

Asp Gly Ser Phe Phe Leu Tyr Ser Lys Leu Thr Val Asp Lys Ser Arg
705                 710                 715                 720

Trp Gln Gln Gly Asn Val Phe Ser Cys Ser Val Met His Glu Ala Leu
                725                 730                 735

His Asn His Tyr Thr Gln Lys Ser Leu Ser Leu Ser Pro Gly Lys
            740                 745                 750

<210> SEQ ID NO 250
<211> LENGTH: 756
<212> TYPE: PRT
<213> ORGANISM: Artificial Sequence
<220> FEATURE:
<223> OTHER INFORMATION: scTRAIL3-FAVSGAA-10 G/S-Fc

<400> SEQUENCE: 250

Met Glu Thr Asp Thr Leu Leu Leu Trp Val Leu Leu Leu Trp Val Pro
1               5                   10                  15

Gly Ser Thr Gly Asp Tyr Lys Asp Asp Asp Asp Lys Gly Gly Gly Gly
                20                  25                  30

Ser Gly Thr Gly Gly Ala Ala Ala His Ile Thr Gly Thr Arg Gly Arg
            35                  40                  45

Ser Asn Thr Leu Ser Ser Pro Asn Ser Lys Asn Glu Lys Ala Leu Gly
        50                  55                  60

Arg Lys Ile Asn Ser Trp Glu Ser Ser Arg Ser Gly His Ser Phe Leu
65                  70                  75                  80

Ser Asn Leu His Leu Arg Asn Gly Glu Leu Val Ile His Glu Lys Gly
                85                  90                  95

Phe Tyr Tyr Ile Tyr Ser Gln Thr Tyr Phe Arg Phe Gln Glu Glu Ile
            100                 105                 110

Lys Glu Asn Thr Lys Asn Asp Lys Gln Met Val Gln Tyr Ile Tyr Lys
        115                 120                 125

Tyr Thr Ser Tyr Pro Asp Pro Ile Leu Leu Met Lys Ser Ala Arg Asn
    130                 135                 140

Ser Cys Trp Ser Lys Asp Ala Glu Tyr Gly Leu Tyr Ser Ile Tyr Gln
145                 150                 155                 160

```
Gly Gly Ile Phe Glu Leu Lys Glu Asn Asp Arg Ile Phe Val Ser Val
                165                 170                 175
Thr Asn Glu His Leu Ile Asp Met Asp His Glu Ala Ser Phe Phe Gly
            180                 185                 190
Ala Phe Ala Val Ser Gly Ala Ala His Ile Thr Gly Thr Arg Gly
        195                 200                 205
Arg Ser Asn Thr Leu Ser Ser Pro Asn Ser Lys Asn Glu Lys Ala Leu
        210                 215                 220
Gly Arg Lys Ile Asn Ser Trp Glu Ser Ser Arg Ser Gly His Ser Phe
225                 230                 235                 240
Leu Ser Asn Leu His Leu Arg Asn Gly Glu Leu Val Ile His Glu Lys
                245                 250                 255
Gly Phe Tyr Tyr Ile Tyr Ser Gln Thr Tyr Phe Arg Phe Gln Glu Glu
                260                 265                 270
Ile Lys Glu Asn Thr Lys Asn Asp Lys Gln Met Val Gln Tyr Ile Tyr
            275                 280                 285
Lys Tyr Thr Ser Tyr Pro Asp Pro Ile Leu Leu Met Lys Ser Ala Arg
        290                 295                 300
Asn Ser Cys Trp Ser Lys Asp Ala Glu Tyr Gly Leu Tyr Ser Ile Tyr
305                 310                 315                 320
Gln Gly Gly Ile Phe Glu Leu Lys Glu Asn Asp Arg Ile Phe Val Ser
                325                 330                 335
Val Thr Asn Glu His Leu Ile Asp Met Asp His Glu Ala Ser Phe Phe
            340                 345                 350
Gly Ala Phe Ala Val Ser Gly Ala Ala Ala His Ile Thr Gly Thr Arg
        355                 360                 365
Gly Arg Ser Asn Thr Leu Ser Ser Pro Asn Ser Lys Asn Glu Lys Ala
        370                 375                 380
Leu Gly Arg Lys Ile Asn Ser Trp Glu Ser Ser Arg Ser Gly His Ser
385                 390                 395                 400
Phe Leu Ser Asn Leu His Leu Arg Asn Gly Glu Leu Val Ile His Glu
                405                 410                 415
Lys Gly Phe Tyr Tyr Ile Tyr Ser Gln Thr Tyr Phe Arg Phe Gln Glu
            420                 425                 430
Glu Ile Lys Glu Asn Thr Lys Asn Asp Lys Gln Met Val Gln Tyr Ile
        435                 440                 445
Tyr Lys Tyr Thr Ser Tyr Pro Asp Pro Ile Leu Leu Met Lys Ser Ala
        450                 455                 460
Arg Asn Ser Cys Trp Ser Lys Asp Ala Glu Tyr Gly Leu Tyr Ser Ile
465                 470                 475                 480
Tyr Gln Gly Gly Ile Phe Glu Leu Lys Glu Asn Asp Arg Ile Phe Val
                485                 490                 495
Ser Val Thr Asn Glu His Leu Ile Asp Met Asp His Glu Ala Ser Phe
            500                 505                 510
Phe Gly Ala Phe Ala Val Ser Gly Gly Ser Gly Gly Gly Gly Ser Gly
        515                 520                 525
Gly Asp Lys Thr His Thr Cys Pro Pro Cys Pro Ala Pro Glu Leu Leu
        530                 535                 540
Gly Gly Pro Ser Val Phe Leu Phe Pro Pro Lys Pro Lys Asp Thr Leu
545                 550                 555                 560
Met Ile Ser Arg Thr Pro Glu Val Thr Cys Val Val Val Asp Val Ser
                565                 570                 575
His Glu Asp Pro Glu Val Lys Phe Asn Trp Tyr Val Asp Gly Val Glu
```

```
                    580                585                590
Val His Asn Ala Lys Thr Lys Pro Arg Glu Glu Gln Tyr Asn Ser Thr
            595                600                605

Tyr Arg Val Val Ser Val Leu Thr Val Leu His Gln Asp Trp Leu Asn
610                615                620

Gly Lys Glu Tyr Lys Cys Lys Val Ser Asn Lys Ala Leu Pro Ala Pro
625                630                635                640

Ile Glu Lys Thr Ile Ser Lys Ala Lys Gly Gln Pro Arg Glu Pro Gln
            645                650                655

Val Tyr Thr Leu Pro Pro Ser Arg Asp Glu Leu Thr Lys Asn Gln Val
            660                665                670

Ser Leu Thr Cys Leu Val Lys Gly Phe Tyr Pro Ser Asp Ile Ala Val
            675                680                685

Glu Trp Glu Ser Asn Gly Gln Pro Glu Asn Asn Tyr Lys Thr Thr Pro
            690                695                700

Pro Val Leu Asp Ser Asp Gly Ser Phe Phe Leu Tyr Ser Lys Leu Thr
705                710                715                720

Val Asp Lys Ser Arg Trp Gln Gln Gly Asn Val Phe Ser Cys Ser Val
            725                730                735

Met His Glu Ala Leu His Asn His Tyr Thr Gln Lys Ser Leu Ser Leu
            740                745                750

Ser Pro Gly Lys
            755

<210> SEQ ID NO 251
<211> LENGTH: 761
<212> TYPE: PRT
<213> ORGANISM: Artificial Sequence
<220> FEATURE:
<223> OTHER INFORMATION: scTRAIL3-FAVSGAA-15 G/S-Fc

<400> SEQUENCE: 251

Met Glu Thr Asp Thr Leu Leu Leu Trp Val Leu Leu Leu Trp Val Pro
1               5                  10                 15

Gly Ser Thr Gly Asp Tyr Lys Asp Asp Asp Lys Gly Gly Gly Gly Gly
            20                 25                 30

Ser Gly Thr Gly Gly Ala Ala Ala His Ile Thr Gly Thr Arg Gly Arg
            35                 40                 45

Ser Asn Thr Leu Ser Ser Pro Asn Ser Lys Asn Glu Lys Ala Leu Gly
            50                 55                 60

Arg Lys Ile Asn Ser Trp Glu Ser Ser Arg Ser Gly His Ser Phe Leu
65              70                 75                 80

Ser Asn Leu His Leu Arg Asn Gly Glu Leu Val Ile His Glu Lys Gly
            85                 90                 95

Phe Tyr Tyr Ile Tyr Ser Gln Thr Tyr Phe Arg Phe Gln Glu Glu Ile
            100                105                110

Lys Glu Asn Thr Lys Asn Asp Lys Gln Met Val Gln Tyr Ile Tyr Lys
            115                120                125

Tyr Thr Ser Tyr Pro Asp Pro Ile Leu Leu Met Lys Ser Ala Arg Asn
            130                135                140

Ser Cys Trp Ser Lys Asp Ala Glu Tyr Gly Leu Tyr Ser Ile Tyr Gln
145             150                155                160

Gly Gly Ile Phe Glu Leu Lys Glu Asn Asp Arg Ile Phe Val Ser Val
            165                170                175

Thr Asn Glu His Leu Ile Asp Met Asp His Glu Ala Ser Phe Phe Gly
```

```
                180                 185                 190
Ala Phe Ala Val Ser Gly Ala Ala His Ile Thr Gly Thr Arg Gly
            195                 200                 205

Arg Ser Asn Thr Leu Ser Ser Pro Asn Ser Lys Asn Glu Lys Ala Leu
        210                 215                 220

Gly Arg Lys Ile Asn Ser Trp Glu Ser Ser Arg Ser Gly His Ser Phe
225                 230                 235                 240

Leu Ser Asn Leu His Leu Arg Asn Gly Glu Leu Val Ile His Glu Lys
                245                 250                 255

Gly Phe Tyr Tyr Ile Tyr Ser Gln Thr Tyr Phe Arg Phe Gln Glu Glu
            260                 265                 270

Ile Lys Glu Asn Thr Lys Asn Asp Lys Gln Met Val Gln Tyr Ile Tyr
        275                 280                 285

Lys Tyr Thr Ser Tyr Pro Asp Pro Ile Leu Leu Met Lys Ser Ala Arg
    290                 295                 300

Asn Ser Cys Trp Ser Lys Asp Ala Glu Tyr Gly Leu Tyr Ser Ile Tyr
305                 310                 315                 320

Gln Gly Gly Ile Phe Glu Leu Lys Glu Asn Asp Arg Ile Phe Val Ser
                325                 330                 335

Val Thr Asn Glu His Leu Ile Asp Met Asp His Glu Ala Ser Phe Phe
            340                 345                 350

Gly Ala Phe Ala Val Ser Gly Ala Ala His Ile Thr Gly Thr Arg
        355                 360                 365

Gly Arg Ser Asn Thr Leu Ser Ser Pro Asn Ser Lys Asn Glu Lys Ala
    370                 375                 380

Leu Gly Arg Lys Ile Asn Ser Trp Glu Ser Ser Arg Ser Gly His Ser
385                 390                 395                 400

Phe Leu Ser Asn Leu His Leu Arg Asn Gly Glu Leu Val Ile His Glu
                405                 410                 415

Lys Gly Phe Tyr Tyr Ile Tyr Ser Gln Thr Tyr Phe Arg Phe Gln Glu
            420                 425                 430

Glu Ile Lys Glu Asn Thr Lys Asn Asp Lys Gln Met Val Gln Tyr Ile
        435                 440                 445

Tyr Lys Tyr Thr Ser Tyr Pro Asp Pro Ile Leu Leu Met Lys Ser Ala
    450                 455                 460

Arg Asn Ser Cys Trp Ser Lys Asp Ala Glu Tyr Gly Leu Tyr Ser Ile
465                 470                 475                 480

Tyr Gln Gly Gly Ile Phe Glu Leu Lys Glu Asn Asp Arg Ile Phe Val
                485                 490                 495

Ser Val Thr Asn Glu His Leu Ile Asp Met Asp His Glu Ala Ser Phe
            500                 505                 510

Phe Gly Ala Phe Ala Val Ser Gly Gly Ser Gly Gly Gly Ser Gly
        515                 520                 525

Gly Gly Gly Ser Gly Gly Asp Lys Thr His Thr Cys Pro Pro Cys Pro
    530                 535                 540

Ala Pro Glu Leu Leu Gly Gly Pro Ser Val Phe Leu Phe Pro Pro Lys
545                 550                 555                 560

Pro Lys Asp Thr Leu Met Ile Ser Arg Thr Pro Glu Val Thr Cys Val
                565                 570                 575

Val Val Asp Val Ser His Glu Asp Pro Glu Val Lys Phe Asn Trp Tyr
            580                 585                 590

Val Asp Gly Val Glu Val His Asn Ala Lys Thr Lys Pro Arg Glu Glu
        595                 600                 605
```

```
Gln Tyr Asn Ser Thr Tyr Arg Val Val Ser Val Leu Thr Val Leu His
        610                 615                 620

Gln Asp Trp Leu Asn Gly Lys Glu Tyr Lys Cys Lys Val Ser Asn Lys
625                 630                 635                 640

Ala Leu Pro Ala Pro Ile Glu Lys Thr Ile Ser Lys Ala Lys Gly Gln
                645                 650                 655

Pro Arg Glu Pro Gln Val Tyr Thr Leu Pro Pro Ser Arg Asp Glu Leu
                660                 665                 670

Thr Lys Asn Gln Val Ser Leu Thr Cys Leu Val Lys Gly Phe Tyr Pro
            675                 680                 685

Ser Asp Ile Ala Val Glu Trp Glu Ser Asn Gly Gln Pro Glu Asn Asn
        690                 695                 700

Tyr Lys Thr Thr Pro Pro Val Leu Asp Ser Asp Gly Ser Phe Phe Leu
705                 710                 715                 720

Tyr Ser Lys Leu Thr Val Asp Lys Ser Arg Trp Gln Gln Gly Asn Val
                725                 730                 735

Phe Ser Cys Ser Val Met His Glu Ala Leu His Asn His Tyr Thr Gln
                740                 745                 750

Lys Ser Leu Ser Leu Ser Pro Gly Lys
            755                 760

<210> SEQ ID NO 252
<211> LENGTH: 766
<212> TYPE: PRT
<213> ORGANISM: Artificial Sequence
<220> FEATURE:
<223> OTHER INFORMATION: scTRAIL3-FAVSGAA-20 G/S-Fc

<400> SEQUENCE: 252

Met Glu Thr Asp Thr Leu Leu Leu Trp Val Leu Leu Leu Trp Val Pro
1               5                   10                  15

Gly Ser Thr Gly Asp Tyr Lys Asp Asp Asp Asp Lys Gly Gly Gly Gly
                20                  25                  30

Ser Gly Thr Gly Gly Ala Ala Ala His Ile Thr Gly Thr Arg Gly Arg
            35                  40                  45

Ser Asn Thr Leu Ser Ser Pro Asn Ser Lys Asn Glu Lys Ala Leu Gly
50                  55                  60

Arg Lys Ile Asn Ser Trp Glu Ser Ser Arg Ser Gly His Ser Phe Leu
65                  70                  75                  80

Ser Asn Leu His Leu Arg Asn Gly Glu Leu Val Ile His Glu Lys Gly
                85                  90                  95

Phe Tyr Tyr Ile Tyr Ser Gln Thr Tyr Phe Arg Phe Gln Glu Glu Ile
            100                 105                 110

Lys Glu Asn Thr Lys Asn Asp Lys Gln Met Val Gln Tyr Ile Tyr Lys
        115                 120                 125

Tyr Thr Ser Tyr Pro Asp Pro Ile Leu Leu Met Lys Ser Ala Arg Asn
    130                 135                 140

Ser Cys Trp Ser Lys Asp Ala Glu Tyr Gly Leu Tyr Ser Ile Tyr Gln
145                 150                 155                 160

Gly Gly Ile Phe Glu Leu Lys Glu Asn Asp Arg Ile Phe Val Ser Val
                165                 170                 175

Thr Asn Glu His Leu Ile Asp Met Asp His Glu Ala Ser Phe Phe Gly
            180                 185                 190

Ala Phe Ala Val Ser Gly Ala Ala Ala His Ile Thr Gly Thr Arg Gly
        195                 200                 205
```

```
Arg Ser Asn Thr Leu Ser Ser Pro Asn Ser Lys Asn Glu Lys Ala Leu
    210                 215                 220

Gly Arg Lys Ile Asn Ser Trp Glu Ser Ser Arg Ser Gly His Ser Phe
225                 230                 235                 240

Leu Ser Asn Leu His Leu Arg Asn Gly Glu Leu Val Ile His Glu Lys
                245                 250                 255

Gly Phe Tyr Tyr Ile Tyr Ser Gln Thr Tyr Phe Arg Phe Gln Glu Glu
                260                 265                 270

Ile Lys Glu Asn Thr Lys Asn Asp Lys Gln Met Val Gln Tyr Ile Tyr
        275                 280                 285

Lys Tyr Thr Ser Tyr Pro Asp Pro Ile Leu Leu Met Lys Ser Ala Arg
    290                 295                 300

Asn Ser Cys Trp Ser Lys Asp Ala Glu Tyr Gly Leu Tyr Ser Ile Tyr
305                 310                 315                 320

Gln Gly Gly Ile Phe Glu Leu Lys Glu Asn Asp Arg Ile Phe Val Ser
                325                 330                 335

Val Thr Asn Glu His Leu Ile Asp Met Asp His Glu Ala Ser Phe Phe
                340                 345                 350

Gly Ala Phe Ala Val Ser Gly Ala Ala Ala His Ile Thr Gly Thr Arg
                355                 360                 365

Gly Arg Ser Asn Thr Leu Ser Ser Pro Asn Ser Lys Asn Glu Lys Ala
370                 375                 380

Leu Gly Arg Lys Ile Asn Ser Trp Glu Ser Ser Arg Ser Gly His Ser
385                 390                 395                 400

Phe Leu Ser Asn Leu His Leu Arg Asn Gly Glu Leu Val Ile His Glu
                405                 410                 415

Lys Gly Phe Tyr Tyr Ile Tyr Ser Gln Thr Tyr Phe Arg Phe Gln Glu
                420                 425                 430

Glu Ile Lys Glu Asn Thr Lys Asn Asp Lys Gln Met Val Gln Tyr Ile
        435                 440                 445

Tyr Lys Tyr Thr Ser Tyr Pro Asp Pro Ile Leu Leu Met Lys Ser Ala
    450                 455                 460

Arg Asn Ser Cys Trp Ser Lys Asp Ala Glu Tyr Gly Leu Tyr Ser Ile
465                 470                 475                 480

Tyr Gln Gly Gly Ile Phe Glu Leu Lys Glu Asn Asp Arg Ile Phe Val
                485                 490                 495

Ser Val Thr Asn Glu His Leu Ile Asp Met Asp His Glu Ala Ser Phe
                500                 505                 510

Phe Gly Ala Phe Ala Val Ser Gly Gly Ser Gly Gly Gly Ser Gly
        515                 520                 525

Gly Gly Gly Ser Gly Gly Gly Gly Ser Gly Gly Asp Lys Thr His Thr
    530                 535                 540

Cys Pro Pro Cys Pro Ala Pro Glu Leu Leu Gly Gly Pro Ser Val Phe
545                 550                 555                 560

Leu Phe Pro Pro Lys Pro Lys Asp Thr Leu Met Ile Ser Arg Thr Pro
                565                 570                 575

Glu Val Thr Cys Val Val Val Asp Val Ser His Glu Asp Pro Glu Val
                580                 585                 590

Lys Phe Asn Trp Tyr Val Asp Gly Val Glu Val His Asn Ala Lys Thr
                595                 600                 605

Lys Pro Arg Glu Glu Gln Tyr Asn Ser Thr Tyr Arg Val Val Ser Val
    610                 615                 620
```

-continued

Leu Thr Val Leu His Gln Asp Trp Leu Asn Gly Lys Glu Tyr Lys Cys
625                 630                 635                 640

Lys Val Ser Asn Lys Ala Leu Pro Ala Pro Ile Glu Lys Thr Ile Ser
            645                 650                 655

Lys Ala Lys Gly Gln Pro Arg Glu Pro Gln Val Tyr Thr Leu Pro Pro
            660                 665                 670

Ser Arg Asp Glu Leu Thr Lys Asn Gln Val Ser Leu Thr Cys Leu Val
            675                 680                 685

Lys Gly Phe Tyr Pro Ser Asp Ile Ala Val Glu Trp Glu Ser Asn Gly
            690                 695                 700

Gln Pro Glu Asn Asn Tyr Lys Thr Thr Pro Pro Val Leu Asp Ser Asp
705                 710                 715                 720

Gly Ser Phe Phe Leu Tyr Ser Lys Leu Thr Val Asp Lys Ser Arg Trp
            725                 730                 735

Gln Gln Gly Asn Val Phe Ser Cys Ser Val Met His Glu Ala Leu His
            740                 745                 750

Asn His Tyr Thr Gln Lys Ser Leu Ser Leu Ser Pro Gly Lys
            755                 760                 765

<210> SEQ ID NO 253
<211> LENGTH: 771
<212> TYPE: PRT
<213> ORGANISM: Artificial Sequence
<220> FEATURE:
<223> OTHER INFORMATION: scTRAIL3-FAVSGAA-25 G/S-Fc

<400> SEQUENCE: 253

Met Glu Thr Asp Thr Leu Leu Leu Trp Val Leu Leu Leu Trp Val Pro
1               5                   10                  15

Gly Ser Thr Gly Asp Tyr Lys Asp Asp Asp Lys Gly Gly Gly Gly Gly
            20                  25                  30

Ser Gly Thr Gly Gly Ala Ala Ala His Ile Thr Gly Thr Arg Gly Arg
            35                  40                  45

Ser Asn Thr Leu Ser Ser Pro Asn Ser Lys Asn Glu Lys Ala Leu Gly
50                  55                  60

Arg Lys Ile Asn Ser Trp Glu Ser Ser Arg Ser Gly His Ser Phe Leu
65                  70                  75                  80

Ser Asn Leu His Leu Arg Asn Gly Glu Leu Val Ile His Glu Lys Gly
            85                  90                  95

Phe Tyr Tyr Ile Tyr Ser Gln Thr Tyr Phe Arg Phe Gln Glu Glu Ile
            100                 105                 110

Lys Glu Asn Thr Lys Asn Asp Lys Gln Met Val Gln Tyr Ile Tyr Lys
            115                 120                 125

Tyr Thr Ser Tyr Pro Asp Pro Ile Leu Leu Met Lys Ser Ala Arg Asn
            130                 135                 140

Ser Cys Trp Ser Lys Asp Ala Glu Tyr Gly Leu Tyr Ser Ile Tyr Gln
145                 150                 155                 160

Gly Gly Ile Phe Glu Leu Lys Glu Asn Asp Arg Ile Phe Val Ser Val
            165                 170                 175

Thr Asn Glu His Leu Ile Asp Met Asp His Glu Ala Ser Phe Phe Gly
            180                 185                 190

Ala Phe Ala Val Ser Gly Ala Ala Ala His Ile Thr Gly Thr Arg Gly
            195                 200                 205

Arg Ser Asn Thr Leu Ser Ser Pro Asn Ser Lys Asn Glu Lys Ala Leu
            210                 215                 220

-continued

```
Gly Arg Lys Ile Asn Ser Trp Glu Ser Ser Arg Ser Gly His Ser Phe
225                 230                 235                 240

Leu Ser Asn Leu His Leu Arg Asn Gly Glu Leu Val Ile His Glu Lys
            245                 250                 255

Gly Phe Tyr Tyr Ile Tyr Ser Gln Thr Tyr Phe Arg Phe Gln Glu Glu
                260                 265                 270

Ile Lys Glu Asn Thr Lys Asn Asp Lys Gln Met Val Gln Tyr Ile Tyr
        275                 280                 285

Lys Tyr Thr Ser Tyr Pro Asp Pro Ile Leu Leu Met Lys Ser Ala Arg
    290                 295                 300

Asn Ser Cys Trp Ser Lys Asp Ala Glu Tyr Gly Leu Tyr Ser Ile Tyr
305                 310                 315                 320

Gln Gly Gly Ile Phe Glu Leu Lys Glu Asn Asp Arg Ile Phe Val Ser
                325                 330                 335

Val Thr Asn Glu His Leu Ile Asp Met Asp His Glu Ala Ser Phe Phe
            340                 345                 350

Gly Ala Phe Ala Val Ser Gly Ala Ala Ala His Ile Thr Gly Thr Arg
        355                 360                 365

Gly Arg Ser Asn Thr Leu Ser Ser Pro Asn Ser Lys Asn Glu Lys Ala
    370                 375                 380

Leu Gly Arg Lys Ile Asn Ser Trp Glu Ser Ser Arg Ser Gly His Ser
385                 390                 395                 400

Phe Leu Ser Asn Leu His Leu Arg Asn Gly Glu Leu Val Ile His Glu
                405                 410                 415

Lys Gly Phe Tyr Tyr Ile Tyr Ser Gln Thr Tyr Phe Arg Phe Gln Glu
            420                 425                 430

Glu Ile Lys Glu Asn Thr Lys Asn Asp Lys Gln Met Val Gln Tyr Ile
        435                 440                 445

Tyr Lys Tyr Thr Ser Tyr Pro Asp Pro Ile Leu Leu Met Lys Ser Ala
    450                 455                 460

Arg Asn Ser Cys Trp Ser Lys Asp Ala Glu Tyr Gly Leu Tyr Ser Ile
465                 470                 475                 480

Tyr Gln Gly Gly Ile Phe Glu Leu Lys Glu Asn Asp Arg Ile Phe Val
                485                 490                 495

Ser Val Thr Asn Glu His Leu Ile Asp Met Asp His Glu Ala Ser Phe
            500                 505                 510

Phe Gly Ala Phe Ala Val Ser Gly Gly Ser Gly Gly Gly Gly Ser Gly
        515                 520                 525

Gly Gly Gly Ser Gly Gly Gly Gly Ser Gly Gly Gly Ser Gly Gly
    530                 535                 540

Asp Lys Thr His Thr Cys Pro Pro Cys Pro Ala Pro Glu Leu Leu Gly
545                 550                 555                 560

Gly Pro Ser Val Phe Leu Phe Pro Pro Lys Pro Lys Asp Thr Leu Met
                565                 570                 575

Ile Ser Arg Thr Pro Glu Val Thr Cys Val Val Val Asp Val Ser His
            580                 585                 590

Glu Asp Pro Glu Val Lys Phe Asn Trp Tyr Val Asp Gly Val Glu Val
        595                 600                 605

His Asn Ala Lys Thr Lys Pro Arg Glu Glu Gln Tyr Asn Ser Thr Tyr
    610                 615                 620

Arg Val Val Ser Val Leu Thr Val Leu His Gln Asp Trp Leu Asn Gly
625                 630                 635                 640

Lys Glu Tyr Lys Cys Lys Val Ser Asn Lys Ala Leu Pro Ala Pro Ile
```

```
                    645                 650                 655
Glu Lys Thr Ile Ser Lys Ala Lys Gly Gln Pro Arg Glu Pro Gln Val
                660                 665                 670

Tyr Thr Leu Pro Pro Ser Arg Asp Glu Leu Thr Lys Asn Gln Val Ser
            675                 680                 685

Leu Thr Cys Leu Val Lys Gly Phe Tyr Pro Ser Asp Ile Ala Val Glu
        690                 695                 700

Trp Glu Ser Asn Gly Gln Pro Glu Asn Tyr Lys Thr Thr Pro Pro
705                 710                 715                 720

Val Leu Asp Ser Asp Gly Ser Phe Phe Leu Tyr Ser Lys Leu Thr Val
                725                 730                 735

Asp Lys Ser Arg Trp Gln Gln Gly Asn Val Phe Ser Cys Ser Val Met
                740                 745                 750

His Glu Ala Leu His Asn His Tyr Thr Gln Lys Ser Leu Ser Leu Ser
            755                 760                 765

Pro Gly Lys
    770

<210> SEQ ID NO 254
<211> LENGTH: 779
<212> TYPE: PRT
<213> ORGANISM: Artificial Sequence
<220> FEATURE:
<223> OTHER INFORMATION: scTRAIL3-FAVSGAA-"W"-Fc

<400> SEQUENCE: 254

Met Glu Thr Asp Thr Leu Leu Leu Trp Val Leu Leu Leu Trp Val Pro
1               5                   10                  15

Gly Ser Thr Gly Asp Tyr Lys Asp Asp Asp Lys Gly Gly Gly Gly
            20                  25                  30

Ser Gly Thr Gly Gly Ala Ala Ala His Ile Thr Gly Thr Arg Gly Arg
        35                  40                  45

Ser Asn Thr Leu Ser Ser Pro Asn Ser Lys Asn Glu Lys Ala Leu Gly
    50                  55                  60

Arg Lys Ile Asn Ser Trp Glu Ser Ser Arg Ser Gly His Ser Phe Leu
65                  70                  75                  80

Ser Asn Leu His Leu Arg Asn Gly Glu Leu Val Ile His Glu Lys Gly
                85                  90                  95

Phe Tyr Tyr Ile Tyr Ser Gln Thr Tyr Phe Arg Phe Gln Glu Glu Ile
            100                 105                 110

Lys Glu Asn Thr Lys Asn Asp Lys Gln Met Val Gln Tyr Ile Tyr Lys
        115                 120                 125

Tyr Thr Ser Tyr Pro Asp Pro Ile Leu Leu Met Lys Ser Ala Arg Asn
    130                 135                 140

Ser Cys Trp Ser Lys Asp Ala Glu Tyr Gly Leu Tyr Ser Ile Tyr Gln
145                 150                 155                 160

Gly Gly Ile Phe Glu Leu Lys Glu Asn Asp Arg Ile Phe Val Ser Val
                165                 170                 175

Thr Asn Glu His Leu Ile Asp Met Asp His Glu Ala Ser Phe Phe Gly
            180                 185                 190

Ala Phe Ala Val Ser Gly Ala Ala His Ile Thr Gly Thr Arg Gly
        195                 200                 205

Arg Ser Asn Thr Leu Ser Ser Pro Asn Ser Lys Asn Glu Lys Ala Leu
    210                 215                 220

Gly Arg Lys Ile Asn Ser Trp Glu Ser Ser Arg Ser Gly His Ser Phe
```

```
                225                 230                 235                 240
Leu Ser Asn Leu His Leu Arg Asn Gly Glu Leu Val Ile His Glu Lys
                245                 250                 255
Gly Phe Tyr Tyr Ile Tyr Ser Gln Thr Tyr Phe Arg Phe Gln Glu Glu
                260                 265                 270
Ile Lys Glu Asn Thr Lys Asn Asp Lys Gln Met Val Gln Tyr Ile Tyr
                275                 280                 285
Lys Tyr Thr Ser Tyr Pro Asp Pro Ile Leu Leu Met Lys Ser Ala Arg
                290                 295                 300
Asn Ser Cys Trp Ser Lys Asp Ala Glu Tyr Gly Leu Tyr Ser Ile Tyr
305                 310                 315                 320
Gln Gly Gly Ile Phe Glu Leu Lys Glu Asn Asp Arg Ile Phe Val Ser
                325                 330                 335
Val Thr Asn Glu His Leu Ile Asp Met Asp His Glu Ala Ser Phe Phe
                340                 345                 350
Gly Ala Phe Ala Val Ser Gly Ala Ala Ala His Ile Thr Gly Thr Arg
                355                 360                 365
Gly Arg Ser Asn Thr Leu Ser Ser Pro Asn Ser Lys Asn Glu Lys Ala
370                 375                 380
Leu Gly Arg Lys Ile Asn Ser Trp Glu Ser Ser Arg Ser Gly His Ser
385                 390                 395                 400
Phe Leu Ser Asn Leu His Leu Arg Asn Gly Glu Leu Val Ile His Glu
                405                 410                 415
Lys Gly Phe Tyr Tyr Ile Tyr Ser Gln Thr Tyr Phe Arg Phe Gln Glu
                420                 425                 430
Glu Ile Lys Glu Asn Thr Lys Asn Asp Lys Gln Met Val Gln Tyr Ile
                435                 440                 445
Tyr Lys Tyr Thr Ser Tyr Pro Asp Pro Ile Leu Leu Met Lys Ser Ala
                450                 455                 460
Arg Asn Ser Cys Trp Ser Lys Asp Ala Glu Tyr Gly Leu Tyr Ser Ile
465                 470                 475                 480
Tyr Gln Gly Gly Ile Phe Glu Leu Lys Glu Asn Asp Arg Ile Phe Val
                485                 490                 495
Ser Val Thr Asn Glu His Leu Ile Asp Met Asp His Glu Ala Ser Phe
                500                 505                 510
Phe Gly Ala Phe Ala Val Ser Gly Gly Ser Gly Glu Ala Ala Ala Lys
                515                 520                 525
Glu Ala Ala Ala Lys Glu Ala Ala Ala Lys Glu Ala Ala Ala Lys Glu
                530                 535                 540
Ala Ala Ala Lys Gly Ser Gly Gly Asp Lys Thr His Thr Cys Pro Pro
545                 550                 555                 560
Cys Pro Ala Pro Glu Leu Leu Gly Gly Pro Ser Val Phe Leu Phe Pro
                565                 570                 575
Pro Lys Pro Lys Asp Thr Leu Met Ile Ser Arg Thr Pro Glu Val Thr
                580                 585                 590
Cys Val Val Val Asp Val Ser His Glu Asp Pro Glu Val Lys Phe Asn
                595                 600                 605
Trp Tyr Val Asp Gly Val Glu Val His Asn Ala Lys Thr Lys Pro Arg
                610                 615                 620
Glu Glu Gln Tyr Asn Ser Thr Tyr Arg Val Val Ser Val Leu Thr Val
625                 630                 635                 640
Leu His Gln Asp Trp Leu Asn Gly Lys Glu Tyr Lys Cys Lys Val Ser
                645                 650                 655
```

```
Asn Lys Ala Leu Pro Ala Pro Ile Glu Lys Thr Ile Ser Lys Ala Lys
            660                 665                 670

Gly Gln Pro Arg Glu Pro Gln Val Tyr Thr Leu Pro Pro Ser Arg Asp
        675                 680                 685

Glu Leu Thr Lys Asn Gln Val Ser Leu Thr Cys Leu Val Lys Gly Phe
    690                 695                 700

Tyr Pro Ser Asp Ile Ala Val Glu Trp Glu Ser Asn Gly Gln Pro Glu
705                 710                 715                 720

Asn Asn Tyr Lys Thr Thr Pro Pro Val Leu Asp Ser Asp Gly Ser Phe
                725                 730                 735

Phe Leu Tyr Ser Lys Leu Thr Val Asp Lys Ser Arg Trp Gln Gln Gly
            740                 745                 750

Asn Val Phe Ser Cys Ser Val Met His Glu Ala Leu His Asn His Tyr
        755                 760                 765

Thr Gln Lys Ser Leu Ser Leu Ser Pro Gly Lys
    770                 775

<210> SEQ ID NO 255
<211> LENGTH: 769
<212> TYPE: PRT
<213> ORGANISM: Artificial Sequence
<220> FEATURE:
<223> OTHER INFORMATION: Db anti-FAP-Glyco-scTRAIL3-FAVSGAA

<400> SEQUENCE: 255

Met Asp Trp Thr Trp Arg Val Phe Cys Leu Leu Ala Val Ala Pro Gly
1               5                   10                  15

Ala His Ser Leu Glu Ala Ser Asp Tyr Lys Asp Asp Asp Asp Lys Gly
            20                  25                  30

Thr Gly Gln Val Gln Leu Val Gln Ser Gly Ala Glu Val Lys Lys Pro
        35                  40                  45

Gly Ala Ser Val Lys Val Ser Cys Lys Ala Ser Gly Tyr Thr Phe Thr
    50                  55                  60

Glu Asn Ile Ile His Trp Val Arg Gln Ala Pro Gly Gln Gly Leu Glu
65                  70                  75                  80

Trp Met Gly Trp Phe His Pro Gly Ser Gly Ser Ile Lys Tyr Asn Glu
                85                  90                  95

Lys Phe Lys Asp Arg Val Thr Met Thr Ala Asp Thr Ser Thr Ser Thr
            100                 105                 110

Val Tyr Met Glu Leu Ser Ser Leu Arg Ser Glu Asp Thr Ala Val Tyr
        115                 120                 125

Tyr Cys Ala Arg His Gly Gly Thr Gly Arg Gly Ala Met Asp Tyr Trp
    130                 135                 140

Gly Gln Gly Thr Leu Val Thr Val Ser Ser Gly Gly Gly Gly Ser Asp
145                 150                 155                 160

Ile Gln Met Thr Gln Ser Pro Ser Ser Leu Ser Ala Ser Val Gly Asp
                165                 170                 175

Arg Val Thr Ile Thr Cys Arg Ala Ser Lys Ser Val Ser Thr Ser Ala
            180                 185                 190

Tyr Ser Tyr Met His Trp Tyr Gln Gln Lys Pro Gly Lys Ala Pro Lys
        195                 200                 205

Leu Leu Ile Tyr Leu Ala Ser Asn Leu Glu Ser Gly Val Pro Ser Arg
    210                 215                 220

Phe Ser Gly Ser Gly Ser Gly Thr Asp Phe Thr Leu Thr Ile Ser Ser
225                 230                 235                 240
```

```
Leu Gln Pro Glu Asp Phe Ala Thr Tyr Tyr Cys Gln His Ser Arg Glu
            245                 250                 255

Leu Pro Tyr Thr Phe Gly Gln Gly Thr Lys Leu Glu Ile Lys Arg Ala
            260                 265                 270

Ala Ala Gly Asn Gly Thr Ser Asn Gly Thr Ser Glu Phe Gly Gly Ala
            275                 280                 285

Ala Ala His Ile Thr Gly Thr Arg Gly Arg Ser Asn Thr Leu Ser Ser
        290                 295                 300

Pro Asn Ser Lys Asn Glu Lys Ala Leu Gly Arg Lys Ile Asn Ser Trp
305                 310                 315                 320

Glu Ser Ser Arg Ser Gly His Ser Phe Leu Ser Asn Leu His Leu Arg
                325                 330                 335

Asn Gly Glu Leu Val Ile His Glu Lys Gly Phe Tyr Tyr Ile Tyr Ser
            340                 345                 350

Gln Thr Tyr Phe Arg Phe Gln Glu Glu Ile Lys Glu Asn Thr Lys Asn
            355                 360                 365

Asp Lys Gln Met Val Gln Tyr Ile Tyr Lys Tyr Thr Ser Tyr Pro Asp
        370                 375                 380

Pro Ile Leu Leu Met Lys Ser Ala Arg Asn Ser Cys Trp Ser Lys Asp
385                 390                 395                 400

Ala Glu Tyr Gly Leu Tyr Ser Ile Tyr Gln Gly Gly Ile Phe Glu Leu
                405                 410                 415

Lys Glu Asn Asp Arg Ile Phe Val Ser Val Thr Asn Glu His Leu Ile
            420                 425                 430

Asp Met Asp His Glu Ala Ser Phe Phe Gly Ala Phe Ala Val Ser Gly
        435                 440                 445

Ala Ala Ala His Ile Thr Gly Thr Arg Gly Arg Ser Asn Thr Leu Ser
450                 455                 460

Ser Pro Asn Ser Lys Asn Glu Lys Ala Leu Gly Arg Lys Ile Asn Ser
465                 470                 475                 480

Trp Glu Ser Ser Arg Ser Gly His Ser Phe Leu Ser Asn Leu His Leu
                485                 490                 495

Arg Asn Gly Glu Leu Val Ile His Glu Lys Gly Phe Tyr Tyr Ile Tyr
            500                 505                 510

Ser Gln Thr Tyr Phe Arg Phe Gln Glu Glu Ile Lys Glu Asn Thr Lys
            515                 520                 525

Asn Asp Lys Gln Met Val Gln Tyr Ile Tyr Lys Tyr Thr Ser Tyr Pro
        530                 535                 540

Asp Pro Ile Leu Leu Met Lys Ser Ala Arg Asn Ser Cys Trp Ser Lys
545                 550                 555                 560

Asp Ala Glu Tyr Gly Leu Tyr Ser Ile Tyr Gln Gly Gly Ile Phe Glu
                565                 570                 575

Leu Lys Glu Asn Asp Arg Ile Phe Val Ser Val Thr Asn Glu His Leu
            580                 585                 590

Ile Asp Met Asp His Glu Ala Ser Phe Phe Gly Ala Phe Ala Val Ser
        595                 600                 605

Gly Ala Ala Ala His Ile Thr Gly Thr Arg Gly Arg Ser Asn Thr Leu
610                 615                 620

Ser Ser Pro Asn Ser Lys Asn Glu Lys Ala Leu Gly Arg Lys Ile Asn
625                 630                 635                 640

Ser Trp Glu Ser Ser Arg Ser Gly His Ser Phe Leu Ser Asn Leu His
                645                 650                 655
```

Leu Arg Asn Gly Glu Leu Val Ile His Glu Lys Gly Phe Tyr Tyr Ile
                660                 665                 670

Tyr Ser Gln Thr Tyr Phe Arg Phe Gln Glu Glu Ile Lys Glu Asn Thr
        675                 680                 685

Lys Asn Asp Lys Gln Met Val Gln Tyr Ile Tyr Lys Tyr Thr Ser Tyr
        690                 695                 700

Pro Asp Pro Ile Leu Leu Met Lys Ser Ala Arg Asn Ser Cys Trp Ser
705                 710                 715                 720

Lys Asp Ala Glu Tyr Gly Leu Tyr Ser Ile Tyr Gln Gly Gly Ile Phe
                725                 730                 735

Glu Leu Lys Glu Asn Asp Arg Ile Phe Val Ser Val Thr Asn Glu His
                740                 745                 750

Leu Ile Asp Met Asp His Glu Ala Ser Phe Phe Gly Ala Phe Ala Val
        755                 760                 765

Ser

<210> SEQ ID NO 256
<211> LENGTH: 1020
<212> TYPE: PRT
<213> ORGANISM: Artificial Sequence
<220> FEATURE:
<223> OTHER INFORMATION: scFv36-Fc- scTRAIL3-FLVGGGPQRVA

<400> SEQUENCE: 256

Met Glu Thr Asp Thr Leu Leu Leu Trp Val Leu Leu Leu Trp Val Pro
1               5                   10                  15

Gly Ser Thr Gly Asp Tyr Lys Asp Asp Asp Asp Lys Gly Gly Gly Gly
                20                  25                  30

Ser Gly Thr Gln Val Gln Leu Lys Gln Ser Gly Ala Glu Leu Val Lys
        35                  40                  45

Pro Gly Ala Ser Val Lys Leu Ser Cys Lys Thr Ser Gly Tyr Thr Phe
    50                  55                  60

Thr Glu Asn Ile Ile His Trp Val Lys Gln Arg Ser Gly Gln Gly Leu
65                  70                  75                  80

Glu Trp Ile Gly Trp Phe His Pro Gly Ser Gly Ser Ile Lys Tyr Asn
                85                  90                  95

Glu Lys Phe Lys Asp Lys Ala Thr Leu Thr Ala Asp Lys Ser Ser Ser
                100                 105                 110

Thr Val Tyr Met Glu Leu Ser Arg Leu Thr Ser Glu Asp Ser Ala Val
        115                 120                 125

Tyr Phe Cys Ala Arg His Gly Gly Thr Gly Arg Gly Ala Met Asp Tyr
    130                 135                 140

Trp Gly Gln Gly Thr Ser Val Thr Val Ser Ser Gly Gly Gly Gly Ser
145                 150                 155                 160

Gly Gly Gly Gly Ser Gly Gly Ser Ala Gln Ile Leu Met Thr Gln Ser
                165                 170                 175

Pro Ala Ser Ser Val Val Ser Leu Gly Gln Arg Ala Thr Ile Ser Cys
        180                 185                 190

Arg Ala Ser Lys Ser Val Ser Thr Ser Ala Tyr Ser Tyr Met His Trp
    195                 200                 205

Tyr Gln Gln Lys Pro Gly Gln Pro Pro Lys Leu Leu Ile Tyr Leu Ala
        210                 215                 220

Ser Asn Leu Glu Ser Gly Val Pro Pro Arg Phe Ser Gly Ser Gly Ser
225                 230                 235                 240

Gly Thr Asp Phe Thr Leu Asn Ile His Pro Val Glu Glu Glu Asp Ala

-continued

```
                245                 250                 255
Ala Thr Tyr Tyr Cys Gln His Ser Arg Glu Leu Pro Tyr Thr Phe Gly
            260                 265                 270

Gly Gly Thr Lys Leu Glu Ile Lys Arg Ala Ala Gly Gly Ser Gly
            275                 280                 285

Gly Asp Lys Thr His Thr Cys Pro Pro Cys Pro Ala Pro Glu Leu Leu
290                 295                 300

Gly Gly Pro Ser Val Phe Leu Phe Pro Pro Lys Pro Lys Asp Thr Leu
305                 310                 315                 320

Met Ile Ser Arg Thr Pro Glu Val Thr Cys Val Val Val Asp Val Ser
                325                 330                 335

His Glu Asp Pro Glu Val Lys Phe Asn Trp Tyr Val Asp Gly Val Glu
                340                 345                 350

Val His Asn Ala Lys Thr Lys Pro Arg Glu Glu Gln Tyr Asn Ser Thr
                355                 360                 365

Tyr Arg Val Val Ser Val Leu Thr Val Leu His Gln Asp Trp Leu Asn
            370                 375                 380

Gly Lys Glu Tyr Lys Cys Lys Val Ser Asn Lys Ala Leu Pro Ala Pro
385                 390                 395                 400

Ile Glu Lys Thr Ile Ser Lys Ala Lys Gly Gln Pro Arg Glu Pro Gln
                    405                 410                 415

Val Tyr Thr Leu Pro Pro Ser Arg Asp Glu Leu Thr Lys Asn Gln Val
                420                 425                 430

Ser Leu Thr Cys Leu Val Lys Gly Phe Tyr Pro Ser Asp Ile Ala Val
                435                 440                 445

Glu Trp Glu Ser Asn Gly Gln Pro Glu Asn Asn Tyr Lys Thr Thr Pro
            450                 455                 460

Pro Val Leu Asp Ser Asp Gly Ser Phe Phe Leu Tyr Ser Lys Leu Thr
465                 470                 475                 480

Val Asp Lys Ser Arg Trp Gln Gln Gly Asn Val Phe Ser Cys Ser Val
                485                 490                 495

Met His Glu Ala Leu His Asn His Tyr Thr Gln Lys Ser Leu Ser Leu
                500                 505                 510

Ser Pro Gly Gln Gly Gly Ser Gly Gly Ser Ser Gly Gly Pro
            515                 520                 525

Gln Arg Val Ala Ala His Ile Thr Gly Thr Arg Gly Arg Ser Asn Thr
                530                 535                 540

Leu Ser Ser Pro Asn Ser Lys Asn Glu Lys Ala Leu Gly Arg Lys Ile
545                 550                 555                 560

Asn Ser Trp Glu Ser Ser Arg Ser Gly His Ser Phe Leu Ser Asn Leu
                565                 570                 575

His Leu Arg Asn Gly Glu Leu Val Ile His Glu Lys Gly Phe Tyr Tyr
            580                 585                 590

Ile Tyr Ser Gln Thr Tyr Phe Arg Phe Gln Glu Glu Ile Lys Glu Asn
                595                 600                 605

Thr Lys Asn Asp Lys Gln Met Val Gln Tyr Ile Tyr Lys Tyr Thr Ser
            610                 615                 620

Tyr Pro Asp Pro Ile Leu Leu Met Lys Ser Ala Arg Asn Ser Cys Trp
625                 630                 635                 640

Ser Lys Asp Ala Glu Tyr Gly Leu Tyr Ser Ile Tyr Gln Gly Gly Ile
                645                 650                 655

Phe Glu Leu Lys Glu Asn Asp Arg Ile Phe Val Ser Val Thr Asn Glu
                660                 665                 670
```

His Leu Ile Asp Met Asp His Glu Ala Ser Phe Phe Gly Ala Phe Leu
                675                 680                 685

Val Gly Gly Pro Gln Arg Val Ala Ala His Ile Thr Gly Thr Arg
690             695                 700

Gly Arg Ser Asn Thr Leu Ser Ser Pro Asn Ser Lys Asn Glu Lys Ala
705                 710                 715                 720

Leu Gly Arg Lys Ile Asn Ser Trp Glu Ser Ser Arg Ser Gly His Ser
                725                 730                 735

Phe Leu Ser Asn Leu His Leu Arg Asn Gly Glu Leu Val Ile His Glu
                740                 745                 750

Lys Gly Phe Tyr Tyr Ile Tyr Ser Gln Thr Tyr Phe Arg Phe Gln Glu
                755                 760                 765

Glu Ile Lys Glu Asn Thr Lys Asn Asp Lys Gln Met Val Gln Tyr Ile
770                 775                 780

Tyr Lys Tyr Thr Ser Tyr Pro Asp Pro Ile Leu Leu Met Lys Ser Ala
785                 790                 795                 800

Arg Asn Ser Cys Trp Ser Lys Asp Ala Glu Tyr Gly Leu Tyr Ser Ile
                805                 810                 815

Tyr Gln Gly Gly Ile Phe Glu Leu Lys Glu Asn Asp Arg Ile Phe Val
                820                 825                 830

Ser Val Thr Asn Glu His Leu Ile Asp Met Asp His Glu Ala Ser Phe
                835                 840                 845

Phe Gly Ala Phe Leu Val Gly Gly Pro Gln Arg Val Ala Ala His
850                 855                 860

Ile Thr Gly Thr Arg Gly Arg Ser Asn Thr Leu Ser Ser Pro Asn Ser
865                 870                 875                 880

Lys Asn Glu Lys Ala Leu Gly Arg Lys Ile Asn Ser Trp Glu Ser Ser
                885                 890                 895

Arg Ser Gly His Ser Phe Leu Ser Asn Leu His Leu Arg Asn Gly Glu
                900                 905                 910

Leu Val Ile His Glu Lys Gly Phe Tyr Tyr Ile Tyr Ser Gln Thr Tyr
                915                 920                 925

Phe Arg Phe Gln Glu Glu Ile Lys Glu Asn Thr Lys Asn Asp Lys Gln
                930                 935                 940

Met Val Gln Tyr Ile Tyr Lys Tyr Thr Ser Tyr Pro Asp Pro Ile Leu
945                 950                 955                 960

Leu Met Lys Ser Ala Arg Asn Ser Cys Trp Ser Lys Asp Ala Glu Tyr
                965                 970                 975

Gly Leu Tyr Ser Ile Tyr Gln Gly Gly Ile Phe Glu Leu Lys Glu Asn
                980                 985                 990

Asp Arg Ile Phe Val Ser Val Thr Asn Glu His Leu Ile Asp Met Asp
                995                 1000                1005

His Glu Ala Ser Phe Phe Gly Ala Phe Leu Val Gly
        1010            1015            1020

<210> SEQ ID NO 257
<211> LENGTH: 5
<212> TYPE: PRT
<213> ORGANISM: Artificial Sequence
<220> FEATURE:
<223> OTHER INFORMATION: flexible peptide

<400> SEQUENCE: 257

Gly Gly Ser Gly Gly
1               5

<210> SEQ ID NO 258
<211> LENGTH: 16
<212> TYPE: PRT
<213> ORGANISM: Artificial Sequence
<220> FEATURE:
<223> OTHER INFORMATION: Flexibel linker with glycosylation motif

<400> SEQUENCE: 258

Gly Ser Gly Asn Gly Thr Ser Asn Gly Thr Ser Gly Ser Ser Gly Gly
1               5                   10                  15

<210> SEQ ID NO 259
<211> LENGTH: 16
<212> TYPE: PRT
<213> ORGANISM: Artificial Sequence
<220> FEATURE:
<223> OTHER INFORMATION: Flexible peptide with glycosylation motif

<400> SEQUENCE: 259

Gly Ser Gly Asn Gly Thr Ser Asn Gly Thr Ser Gly Ser Ser Arg Thr
1               5                   10                  15

<210> SEQ ID NO 260
<211> LENGTH: 5
<212> TYPE: PRT
<213> ORGANISM: Artificial Sequence
<220> FEATURE:
<223> OTHER INFORMATION: flexible peptide

<400> SEQUENCE: 260

Gly Gly Gly Gly Ser
1               5

<210> SEQ ID NO 261
<211> LENGTH: 8
<212> TYPE: PRT
<213> ORGANISM: Artificial Sequence
<220> FEATURE:
<223> OTHER INFORMATION: flexible peptide

<400> SEQUENCE: 261

Gly Gly Gly Ser Gly Gly Gly Ser
1               5

<210> SEQ ID NO 262
<211> LENGTH: 15
<212> TYPE: PRT
<213> ORGANISM: Artificial Sequence
<220> FEATURE:
<223> OTHER INFORMATION: intervening peptide

<400> SEQUENCE: 262

Leu Val Gly Gly Gly Gly Ser Val Arg Glu Arg Gly Pro Gln Arg
1               5                   10                  15

<210> SEQ ID NO 263
<211> LENGTH: 4
<212> TYPE: PRT
<213> ORGANISM: Artificial Sequence
<220> FEATURE:
<223> OTHER INFORMATION: flexible polypeptide

<400> SEQUENCE: 263

Gly Gly Gly Ser
1

```
<210> SEQ ID NO 264
<211> LENGTH: 4
<212> TYPE: PRT
<213> ORGANISM: Artificial Sequence
<220> FEATURE:
<223> OTHER INFORMATION: synthetic peptide

<400> SEQUENCE: 264

Phe Leu Val Gly
1

<210> SEQ ID NO 265
<211> LENGTH: 4
<212> TYPE: PRT
<213> ORGANISM: Artificial Sequence
<220> FEATURE:
<223> OTHER INFORMATION: synthetic peptide

<400> SEQUENCE: 265

Thr Ser Glu Glu
1

<210> SEQ ID NO 266
<211> LENGTH: 8
<212> TYPE: PRT
<213> ORGANISM: Artificial Sequence
<220> FEATURE:
<223> OTHER INFORMATION: synthetic peptide

<400> SEQUENCE: 266

Val Arg Glu Arg Gly Pro Gln Arg
1               5

<210> SEQ ID NO 267
<211> LENGTH: 5
<212> TYPE: PRT
<213> ORGANISM: Artificial Sequence
<220> FEATURE:
<223> OTHER INFORMATION: synthetic peptide

<400> SEQUENCE: 267

Phe Phe Gly Ala Phe
1               5

<210> SEQ ID NO 268
<211> LENGTH: 5
<212> TYPE: PRT
<213> ORGANISM: Artificial Sequence
<220> FEATURE:
<223> OTHER INFORMATION: synthetic peptide

<400> SEQUENCE: 268

Leu Val Gly Gly Arg
1               5

<210> SEQ ID NO 269
<211> LENGTH: 4
<212> TYPE: PRT
<213> ORGANISM: Artificial Sequence
<220> FEATURE:
<223> OTHER INFORMATION: synthetic peptide

<400> SEQUENCE: 269

Gly Val Gly Gly
1
```

```
<210> SEQ ID NO 270
<211> LENGTH: 5
<212> TYPE: PRT
<213> ORGANISM: Artificial Sequence
<220> FEATURE:
<223> OTHER INFORMATION: synthetic peptide

<400> SEQUENCE: 270

Gly Ala Ala His Ile
1               5

<210> SEQ ID NO 271
<211> LENGTH: 5
<212> TYPE: PRT
<213> ORGANISM: Artificial Sequence
<220> FEATURE:
<223> OTHER INFORMATION: synthetic peptide

<400> SEQUENCE: 271

Ile Ala Ala His Ile
1               5

<210> SEQ ID NO 272
<211> LENGTH: 5
<212> TYPE: PRT
<213> ORGANISM: Artificial Sequence
<220> FEATURE:
<223> OTHER INFORMATION: synthetic peptide

<400> SEQUENCE: 272

Leu Ala Ala His Ile
1               5

<210> SEQ ID NO 273
<211> LENGTH: 5
<212> TYPE: PRT
<213> ORGANISM: Artificial Sequence
<220> FEATURE:
<223> OTHER INFORMATION: synthetic peptide

<400> SEQUENCE: 273

Met Ala Ala His Ile
1               5

<210> SEQ ID NO 274
<211> LENGTH: 5
<212> TYPE: PRT
<213> ORGANISM: Artificial Sequence
<220> FEATURE:
<223> OTHER INFORMATION: synthetic peptide

<400> SEQUENCE: 274

Ala Ala Ala His Ile
1               5

<210> SEQ ID NO 275
<211> LENGTH: 8
<212> TYPE: PRT
<213> ORGANISM: Artificial Sequence
<220> FEATURE:
<223> OTHER INFORMATION: polypeptide linker

<400> SEQUENCE: 275

Ala Ala Ala Gly Gly Ser Gly Gly
1               5
```